United States Patent
Fader et al.

(10) Patent No.: US 7,098,011 B1
(45) Date of Patent: Aug. 29, 2006

(54) NUCLEIC ACID SEQUENCES ENCODING ISOFLAVONE SYNTHASE

(75) Inventors: Gary M. Fader, Landenberg, PA (US); Woosuk Jung, Greenville, DE (US); Brian McGonigle, Wilmington, DE (US); Joan T. Odell, Unionville, PA (US); Xiaodan Yu, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/857,581

(22) PCT Filed: Jan. 26, 2000

(86) PCT No.: PCT/US00/01772

§ 371 (c)(1),
(2), (4) Date: Jun. 5, 2001

(87) PCT Pub. No.: WO00/44909

PCT Pub. Date: Aug. 3, 2000

Related U.S. Application Data

(60) Provisional application No. 60/117,769, filed on Jan. 27, 1999, provisional application No. 60/144,783, filed on Jul. 20, 1999, provisional application No. 60/156,094, filed on Sep. 24, 1999.

(51) Int. Cl.
| | |
|---|---|
| C12N 15/00 | (2006.01) |
| C12N 5/02 | (2006.01) |
| C12N 5/04 | (2006.01) |
| C12N 1/14 | (2006.01) |
| C12N 5/00 | (2006.01) |
| C12P 21/06 | (2006.01) |
| C07H 21/04 | (2006.01) |
| C12N 9/02 | (2006.01) |
| C12N 9/04 | (2006.01) |
| C12N 1/20 | (2006.01) |
| C12Q 1/26 | (2006.01) |
| C07K 1/00 | (2006.01) |

(52) U.S. Cl. .................. 435/189; 435/190; 435/25; 435/419; 435/415; 435/412; 435/252.3; 435/254.2; 435/320.1; 435/69.1; 435/325; 435/410; 536/23.2; 536/23.6; 530/350

(58) Field of Classification Search ................ 435/189, 435/25, 410, 415, 412, 252.3, 254.2, 320.1, 435/69.1, 190, 325, 419; 536/23.2, 23.6; 530/350

See application file for complete search history.

(56) References Cited

U.S. PATENT DOCUMENTS 5,846,784 A 12/1998 Hitz

FOREIGN PATENT DOCUMENTS

| AU | 776161 | 9/2000 |
|---|---|---|
| WO | WO 99/19493 A2 | 4/1999 |
| WO | WO 00/46356 A1 | 8/2000 |
| WO | WO 00/53771 A1 | 9/2000 |

OTHER PUBLICATIONS

Bork , Genome Research, 10:398-400, 2000.*
Broun et al. , Science 282:1315-1317, 1998.*
Seffernick et al. , J. Bacteriol. 183(8):2405-2410, 2001.*
Van de Loo et al. , Proc. Natl. Acad. Sci. 92:6743-6747, 1995.*
Witkowski et al. , Biochemistry 38:11643-11650, 1999.*
EMBL Sequence Library Data Accession No. : AF022462, Jan. 8, 1998, B. Siminsky et al., Expression of a Soybean Cytochrome P450 Monooxygenase cDNA tobacco enhances the metabolism of phenylurea herbicides.
C. R. Schopfer et al., Mol. Gen. Genet., vol. 258:315-322, 1998, Identification of elicitor-induced cytochrome P450s of soybean (*Glycine max* L.) using differential display of mRNA.
Tomoyoshi Akashi et al., Plant Science, vol. 126:39-47, 1997, Cloning of cytochrome P450 cDNAs from cultured *Glycymhiza echinata* L. cells and their transcriptional activation by elicitor-treatment.
Takashi Hakamatsuka et al., Chem. Pharm. Bull., vol. 37(1):249-252, 1989, Isoflavone synthase from cell suspension cultures of Pueraria Lobata.
S. P. Colliver et al., Plant Mol. Biol., vol. 35:509-522, 1997 , Differential modification of flavonoid and isoflavonoid biosynthesis with an antisense chalcone synthase construct in transgenic *Lotus comiculatus* .
Christopher L. Steele et al., Arch. of Biochem. & Biophys., vol. 367(1):146-150, 1999, Molecular characterization of the enzyme catalyzing the aryl migration reaction of Isoflavonoid Biosynthesis in Soybean.
Tomoyoshi Akashi et al., Plant Phys., vol. 121:821-828, 1999, Cloning and functional expression of a cytochrome P450 cDNA encoding 2-Hydroxyisoflavone Synthase involved in biosynthesis of the isoflavonoid skeleton in licorice.
Donald A. Phillips, Phenolic Metabolism in Plants, edited y H. A. Stafford et al., 1992, pp. 201-231, Flavonoids: Plant signals to soil microbes.
Michael Naim et al., J. Agric. Food Chem., vol. 24(6):1174-1177, 1976, Antioxidative and Antihemolytic activities of soybean isoflavones.
Michael Naim et al., J. Agric. Food Chem., vol. 22(5):806-810, 1974, Soybean isoflavones, characterization, determination, and antifungal activity.

(Continued)

*Primary Examiner*—Rebecca E. Prouty
*Assistant Examiner*—Delia M. Ramirez

(57) ABSTRACT

This invention relates to an isolated nucleic acid sequence encoding isoflavone synthase. The invention also relates to the construction of chimeric sequences encoding all or a substantial portion of the enzymes, in sense or antisense orientation, wherein expression of the chimeric sequence results in production of altered levels of the enzyme in a transformed host cell.

35 Claims, 29 Drawing Sheets

OTHER PUBLICATIONS

K. R. Price et al., Food Add & Cont., vol. 2(2):73-106, 1985, Naturally occurring oestrogens in foods—A review.

Mark Messina et al., J. Natl. Cancer Inst., vol. 83(8):541-545, The role of soy products in reducing risk of cancer.

Greg Peterson et al., Biochem. and Biophys. Res. Comm., vol. 179(1):661-667, 1991, Genistein inhibition of the growth of human breast cancer cells: Independence from estrogen receptors and the multi-drug resistance gene.

K. S. Mathur et la., J. Nutrition, vol. 84:201-204, 1964, Effect of bengal gram on experimentally induced high levels of cholesterol in tissues and serum in albino rats.

R. D. Sharma, Lipids, vol. 14(6):535-540, Isoflavones and hypercholesterolemia in rats.

Chigen Tsukamoto et al., J. Agric. Food Chem., vol. 43:1184-1192, 1995, Factors affecting isoflavone content in soybean seeds: Changes in isoflavones, saponins, and Composition of fatty acids at different temperatures during seed development.

Huei-Ju Wang et al., J. Agric. Food Chem., vol. 42:1674-1677, 1994, Isoflavone composition of American and Japanese soybeans in Iowa: Effects of variety, crop year, and location.

Richard A. Dixon et al., Plant Cell, vol. 7:1085-1097, 1995, Stress-Induced Phenylpropanoid Metabolism.

J. Rowell M. Potts et al., J. of Biol. Chem., vol. 249(16):5019-5026, 1974, The 4-Hydroxylation of cinnamic acid by Sorghum Microsomes and the requirement for cytochrome P450.

Tomoyoshi Akashi et al., Biochem & Biophys. Res. Comm., vol. 251:67-70, 1998, CYP81E1, a cytochrome P450 cDNA of licorice (*Glycrmhiza echinata* L. ), encodes Isoflavone 2'-Hydroxylase.

Christel R. Schopfer et al., FEBS Lett., vol. 432:182-186, 1998, Molecular characterization and functional expression of dihydroxypterocarpan 6a-hydroxylase, an enzyme specific for pterocarpanoid phytoalexin biosynthesis in soybean (*Glycine max.* L.).

M. Hagmann et al., FEBS, vol. 175(2):199-202, 1984, Enzymatic rearrangement of flavonone to isoflavone.

Georg Kochs et al., Eur. J. Biochem., vol. 155:311-318, 1986, Enzymic synthesis of isoflavones.

Clint Chapple, Annu. Rev. Plant Physiol. Plant Mol. Biol., vol. 49:311-343, 1998, Molecular-Genetic analysis of plant cytochrome P450-dependent monooxygenases.

Erich Grotewold et al., Plant Cell, vol. 10:721-740, 1998, Engineering secondary meatbolism in maize cells by ectopic expression on transcription factors..

Robert W. M. Sablowski et al., Embo J., vol. 13(1):128-137, 1994, A flower-specific Myb protein activates transcription of phenylpropanoid biosynthetic genes.

Mark D. Adams et al., Science, vol. 252:1651-1656, 1991, Complementary DNA Sequencing: Expressed sequence tags and human genome project.

Stephen F. Altschul et al., J. Mol. Biol., vol. 215:403-410, 1990, Basic Local Alignment Search Tool.

Warren Gish et al., Nature genetics, vol. 3:266-272, 1993, Identification of protein coding regions by database similarity search.

National Center for Biotechnology Information General Identifier No. 2739005, Mar. 2, 1999, B. Siminszky et al., Expression of a soybean cytochrome P450 monooxygenase cDNA in yeast and tobacco enhances the metabolism of phenhylurea herbicides.

Balazs Siminszky et al., PNAS, vol. 96:1750-1755, 1999, Expression of a soybean cytochrome P450 monooxygenase cDNA in yeast and tobacco enhances the metabolism of phenhylurea herbicides.

Muhammed Faisal Hashim et al., FEBS Lett., vol. 271(1,2):219-222, 1990, Reaction mechanism of oxidative rearrangement of flavanone in isoflavone biosynthesis.

National Center for Biotechnology Information General Identification No. 1359894, Oct. 7, 1996, M. Hasenfratz et al., Multiple forms of NADPH-cytochrome P450 reductase in higher plants.

Denis Pompon et al., Methods in Enzymol., vol. 272:51-64, 1996, Yeast expression of animal and plant P450s in Optimized redox environments.

National Center for Biotechnology Information General Identifier No. 984798, Sep. 14, 1995, R. S. Sikorski et al., A system of shuttle vectors and yeast host strains designed for efficient manipulation of DNA in *Saccharomyces cerevisiale* .

Robert S. Sikorski et al., Genetics, vol. 122:19-27, 1989, A system of shuttle vectors and yeast host strains designed for efficient manipulation of DNA in *Saccharomyces cerevisiaie*.

Shao-Bing Hua et al., Plasmid, vol. 38:91-96, 1997, Minimum length of sequence homology required for in vivo cloning by homologous recombination in yeast.

J. Geigert et al., Tetrahedron, vol. 29:2703-2706, 1973, Two phytoalexins from sugarbeet (*beta vulgaris* ) leaves.

Desmond G. Higgins et al., Cabios Comm, vol. 5(2):151-153, 1989, Fast and sensitive multiple sequence alignments on a microcomputer.

Mark H. Harpster et al., Mol. Gen. Genet., vol. 212:182-190, 1988, Relative strengths of the 35S califlower mosaic virus, 1', 2', and nopaline synthase promoters in transformed tobacco sugarbeet and oilseed rape callus tissue.

A. Depicker et al., J. Mol. & Appl. Genet., vol. 1(6):561-573, 1982, Nopaline synthase: Transcript mapping and DNA sequence.

Peter Hajdukiewicz et al., Plant Mol. Biol., vol. 25:989-994, 1994, The small, versatile pPZP family of Agrobacterium binary vectors for plant transformation.

R. Deblaere et al., Methods in Enzymol., vol. 153:277-292, 1987, Vectors for Cloning in Plant Cells.

Pauline A. Bariola et al., Plant Phys., vol. 119:331-342, 1999, Regulation of S-like ribonuclease levels in arabidopsis. Antisense inhibition of RNS1 or RNS2 elevates Anthocyanin accumulation.

G. Murray Balance et al., Plant Phys., vol. 107:1027-1028, 1995, Medicago sativa cDNAs encoding chalcone reductase.

T. M. Klein et al., Nature, vol. 327:70-73, 1987, High-velocity microprojectiles for delivering nucleic acids into living cells.

Wesley Bruce et al., Plant Cell, vol. 12:65-79, 2000, Expression Profiling of the Maize Flavonoid Pathway Genes Controlled by Estradiol-Inducible Transcription Factors CRC and P.

Desmond Mascarenhas et al., Plant Mol. Biol., vol. 15:913-920, 1990, Intron-mediated enhancement of heterologous gene expression in maize.

Loc Phi-Van et al., Embo J. vol. 7(3):655-664, 1988, The matrix attachment regions of the chicken lysozyme gene co-map with the boundaries of the chromatin domain.

M. De Block et al., Embo J., vol. 6(9):2513-2518, 1987, Engineering herbicide resistance in plants by expression of a detoxifying enzyme.

\* cited by examiner

Figure 2A-B
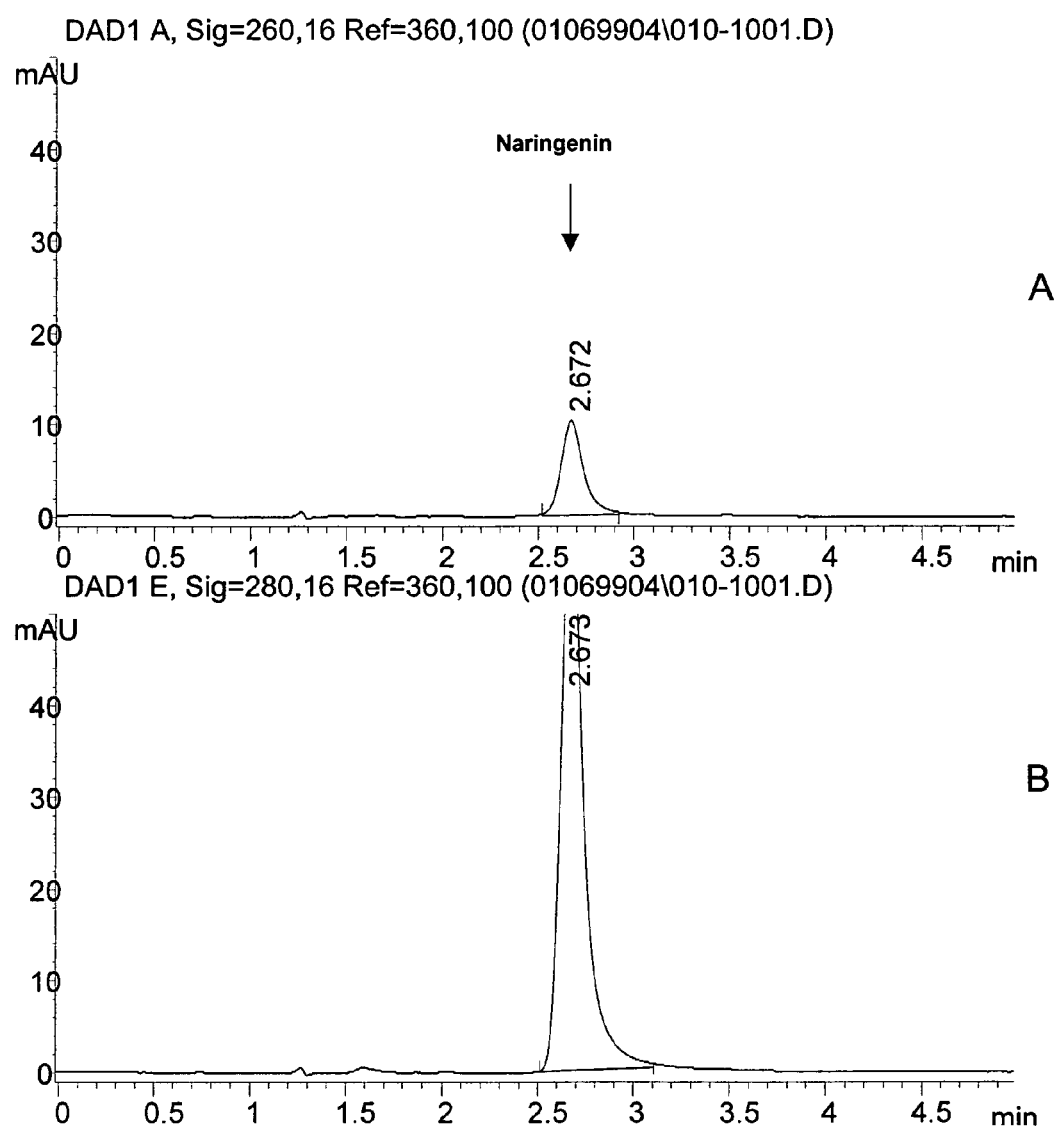

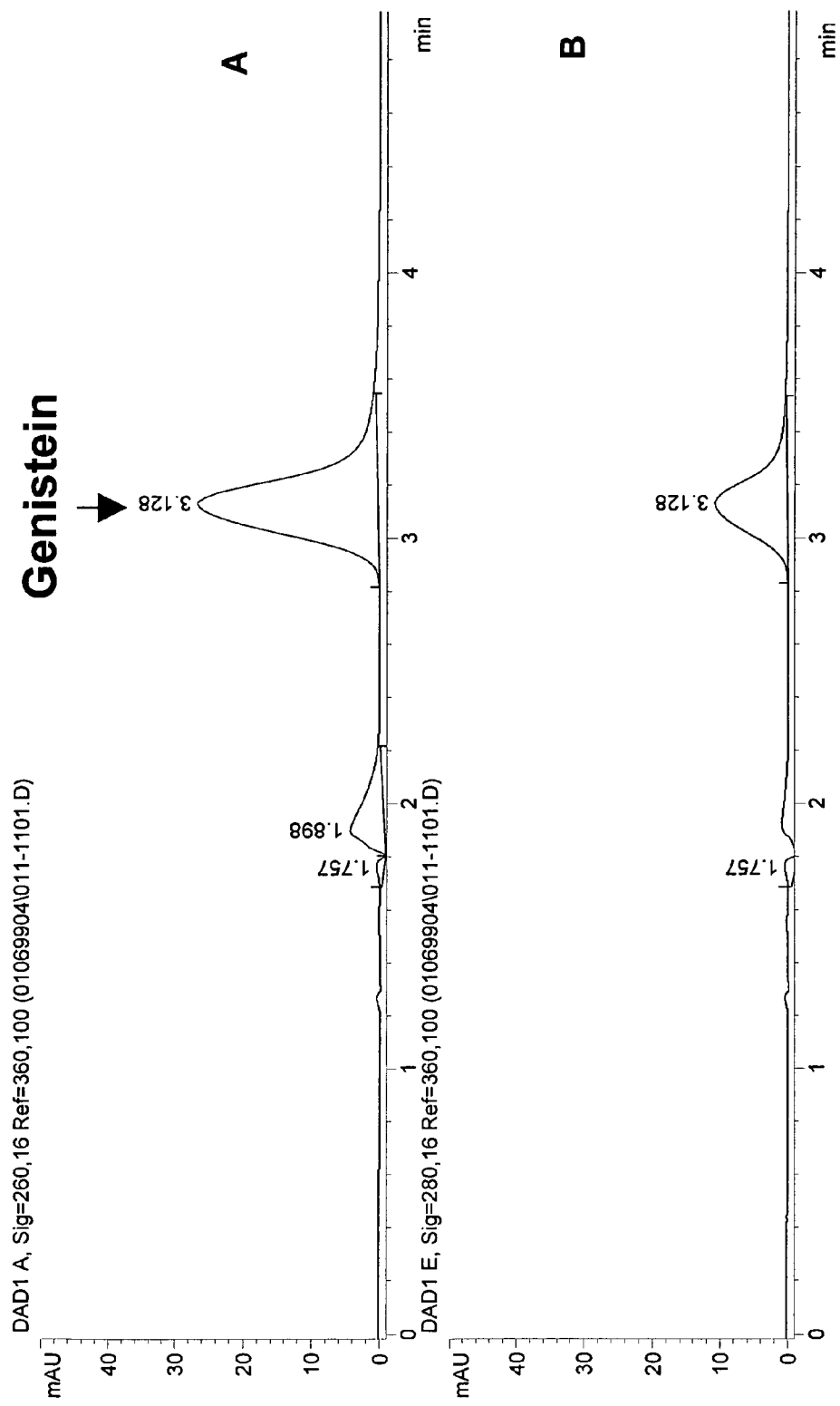
Figure 3A-B

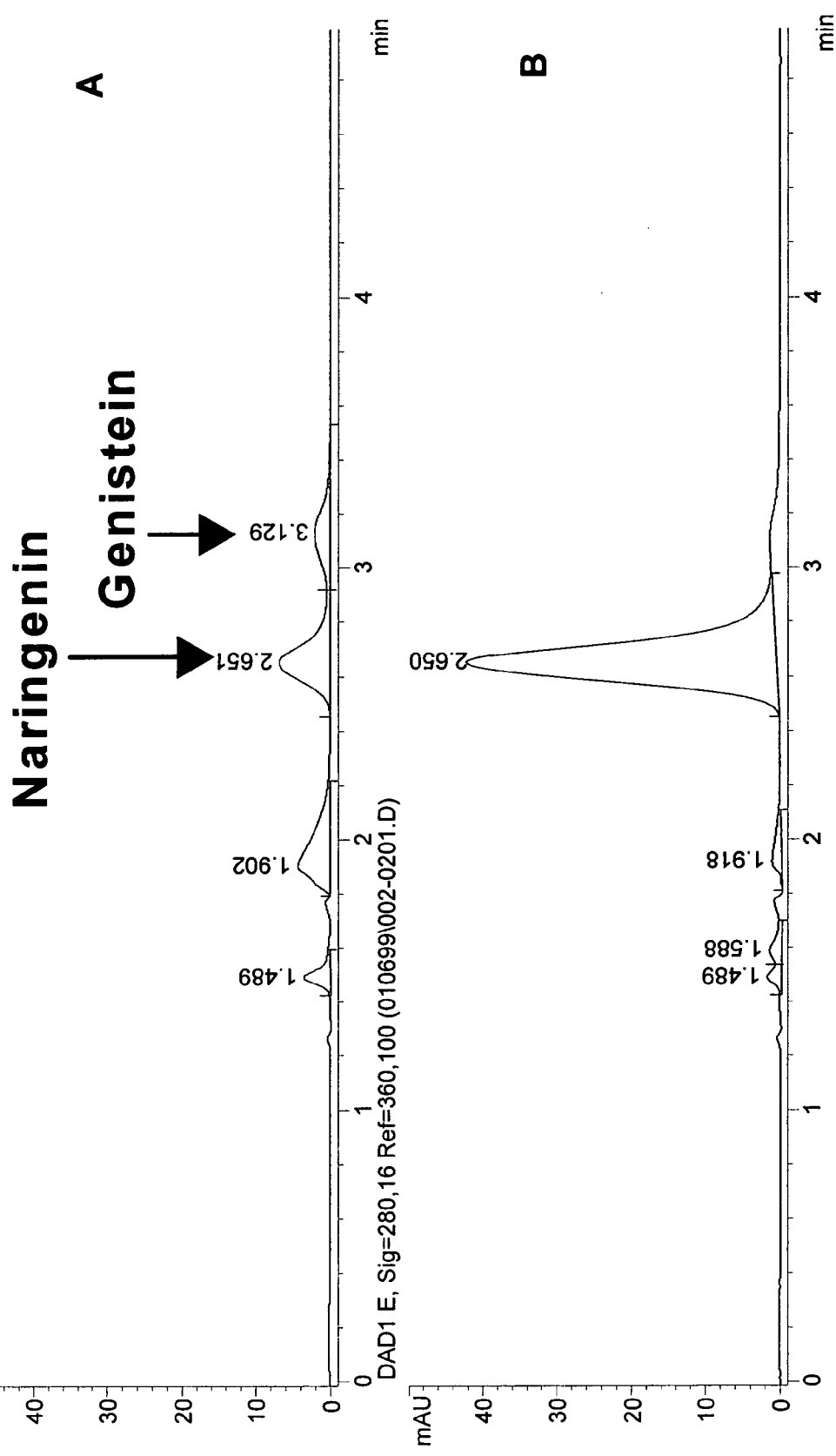
Figure 4A-B

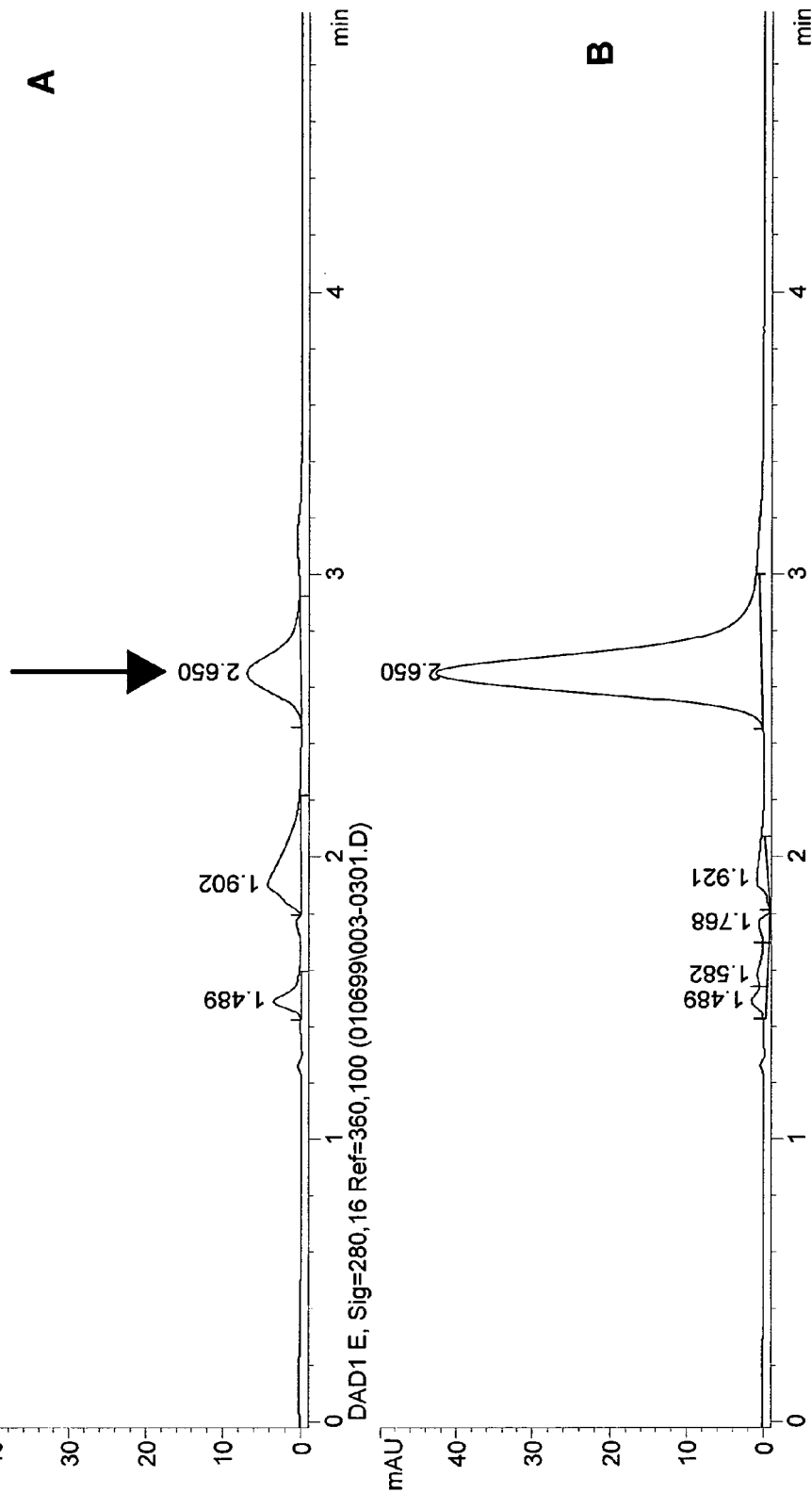
Figure 5A-B

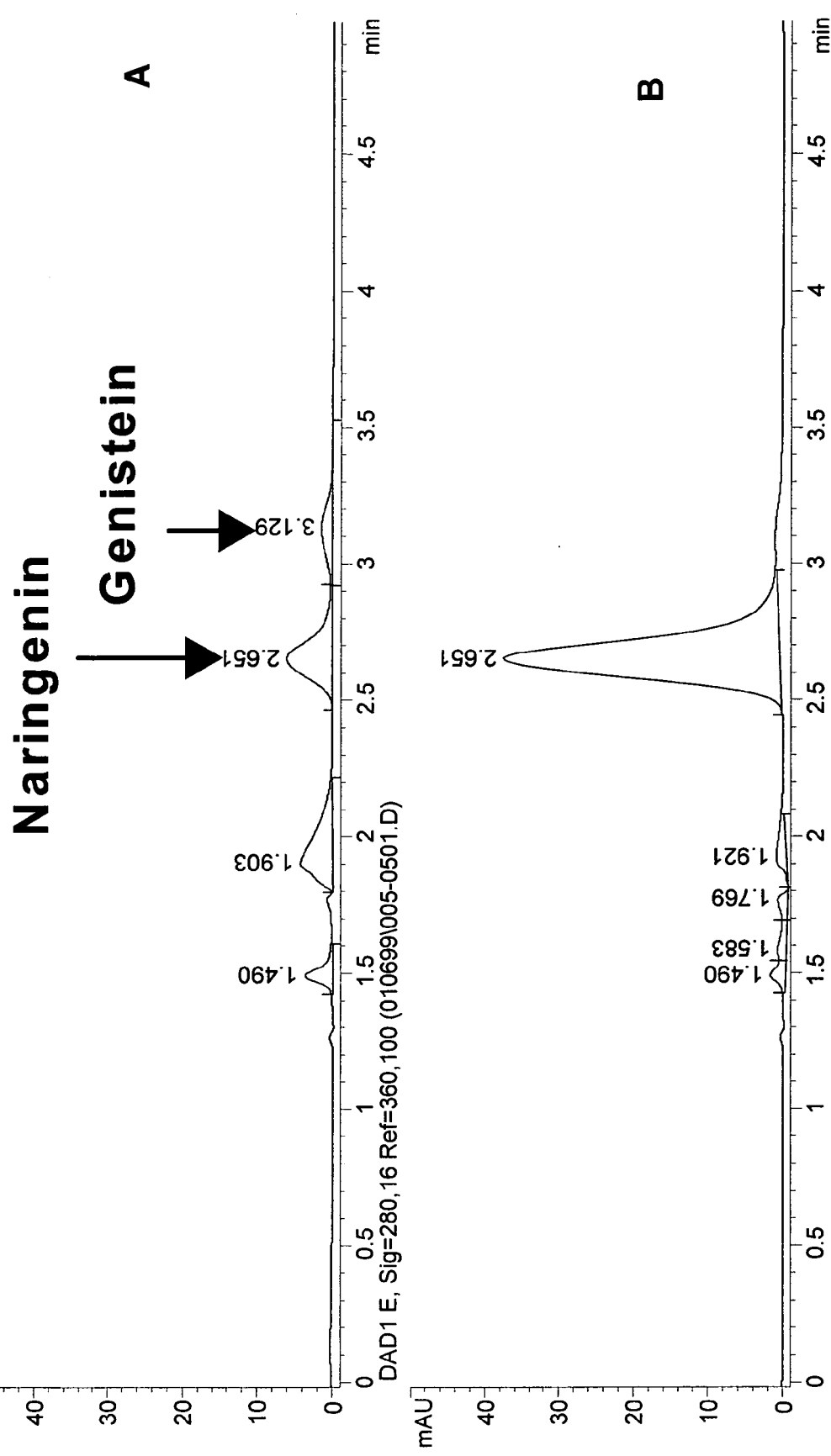
Figure 6A-B

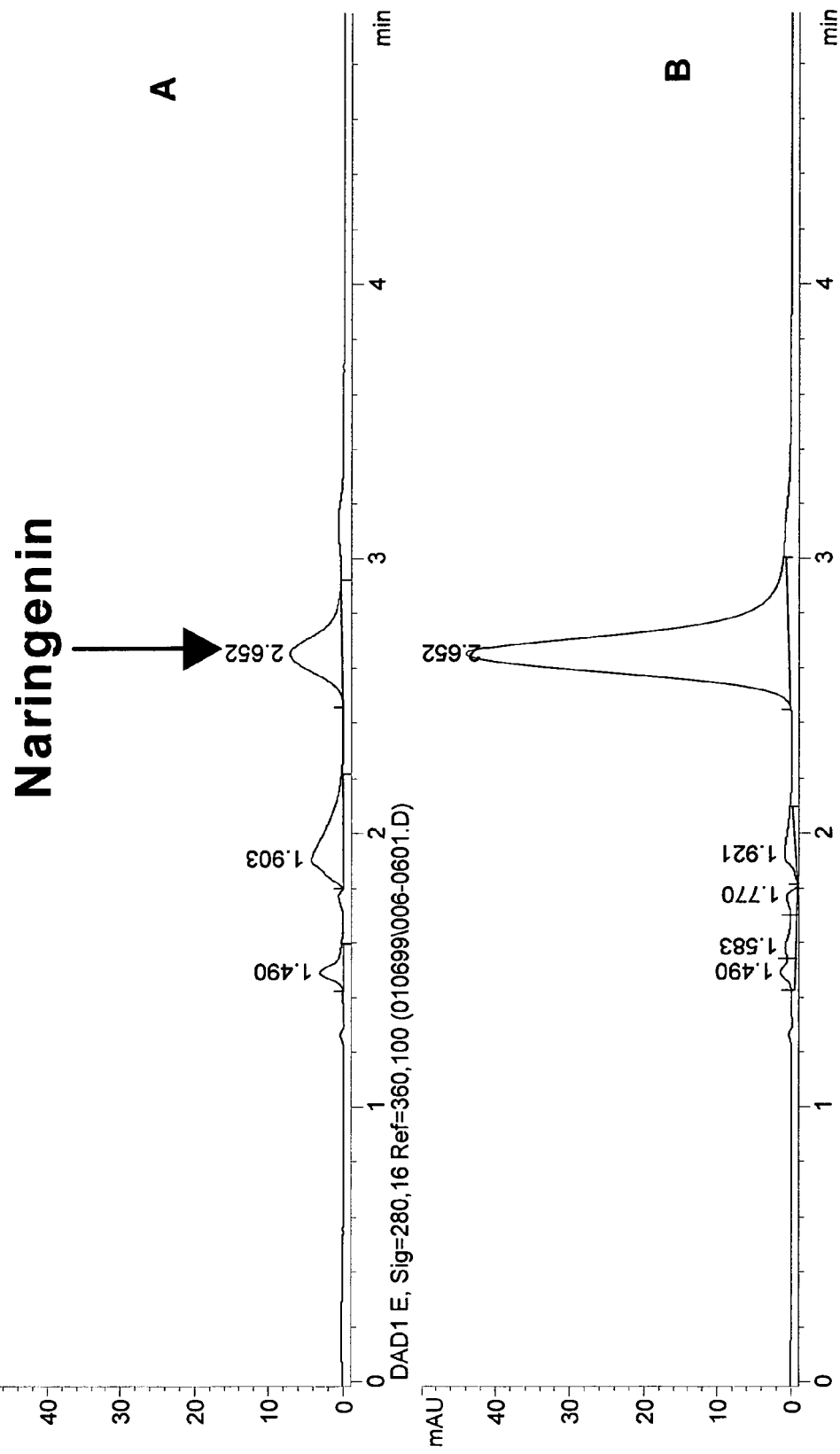
Figure 7A-B

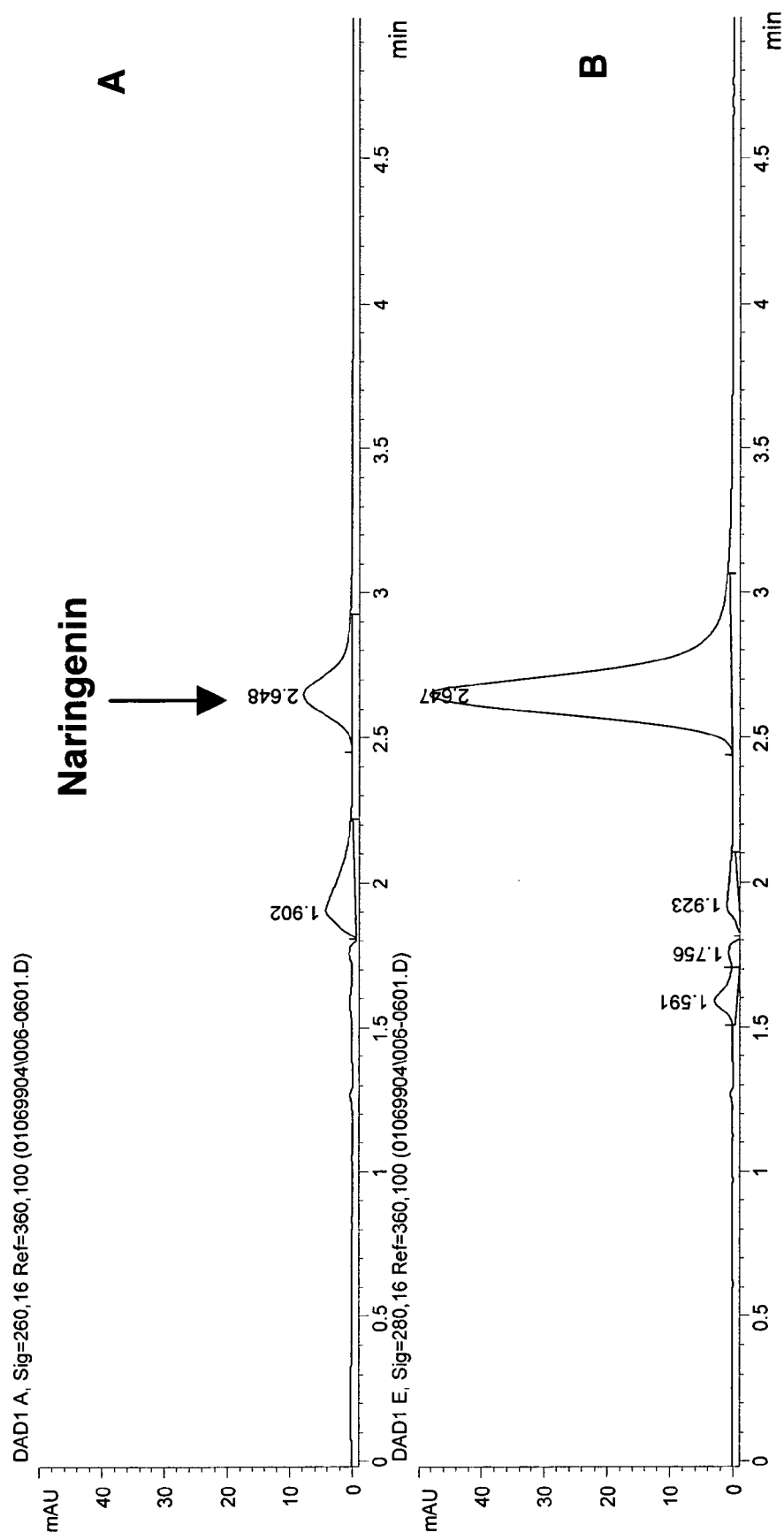
Figure 8A-B

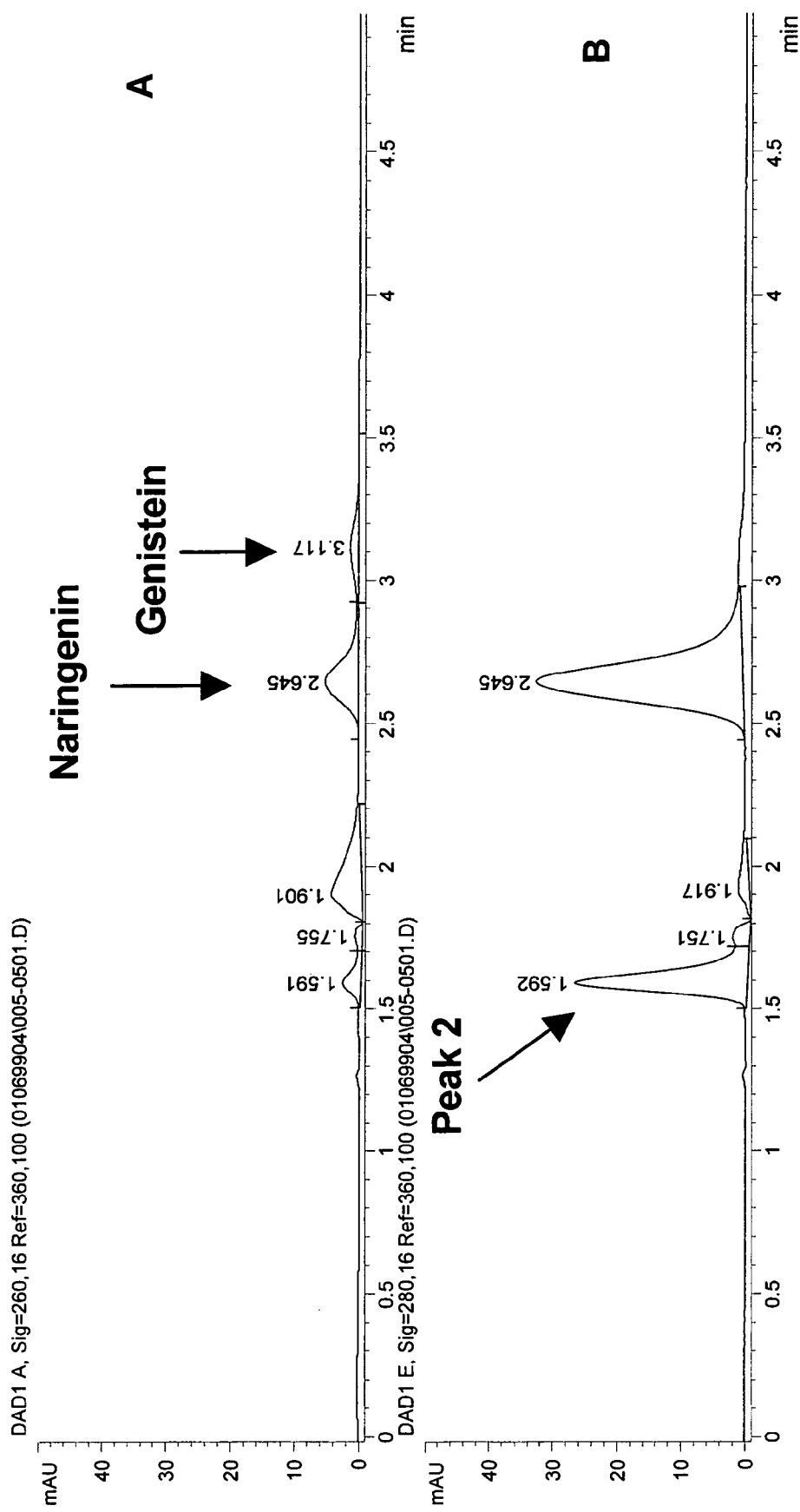
Figure 9A-B

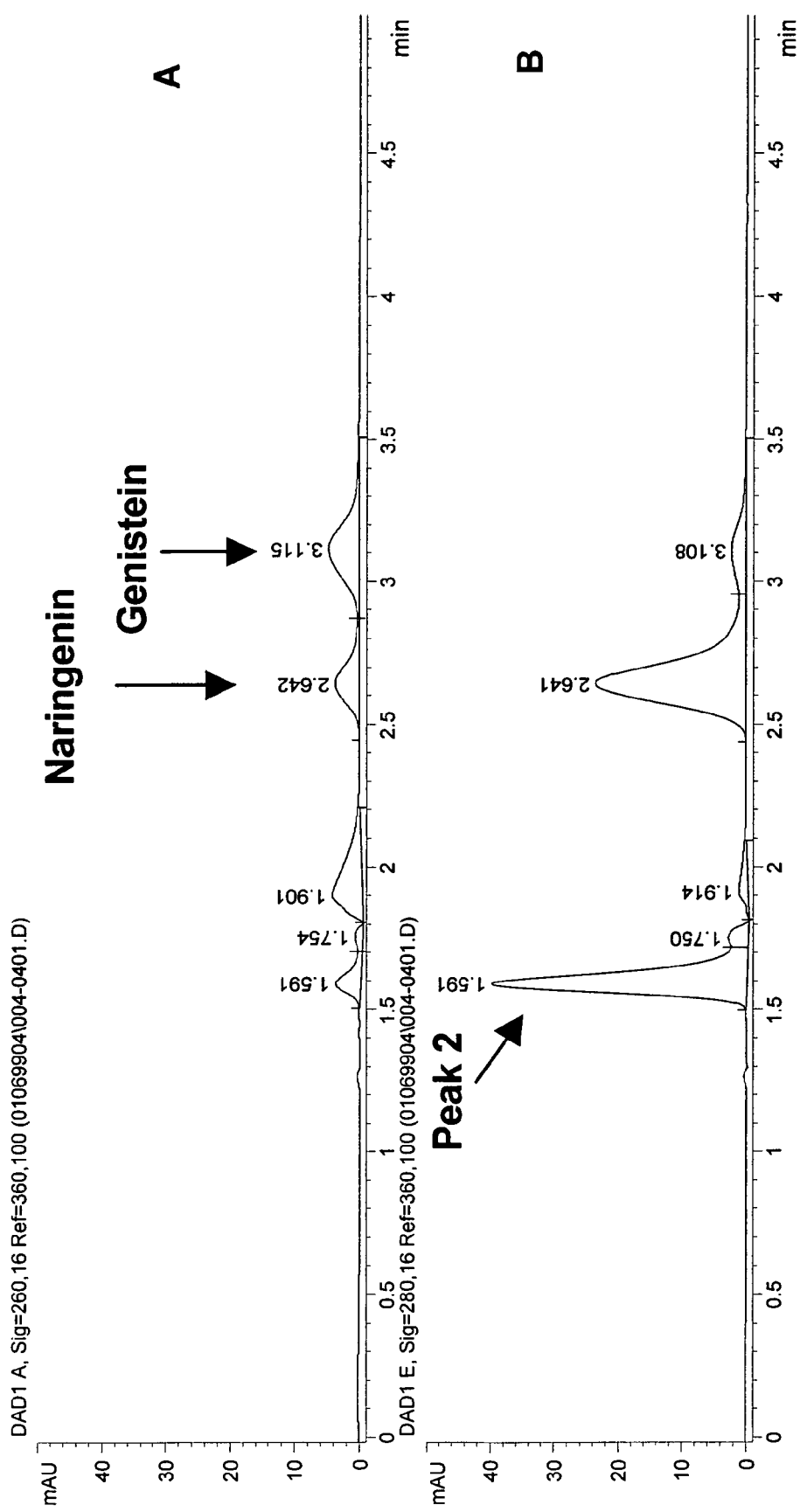
Figure 10A-B

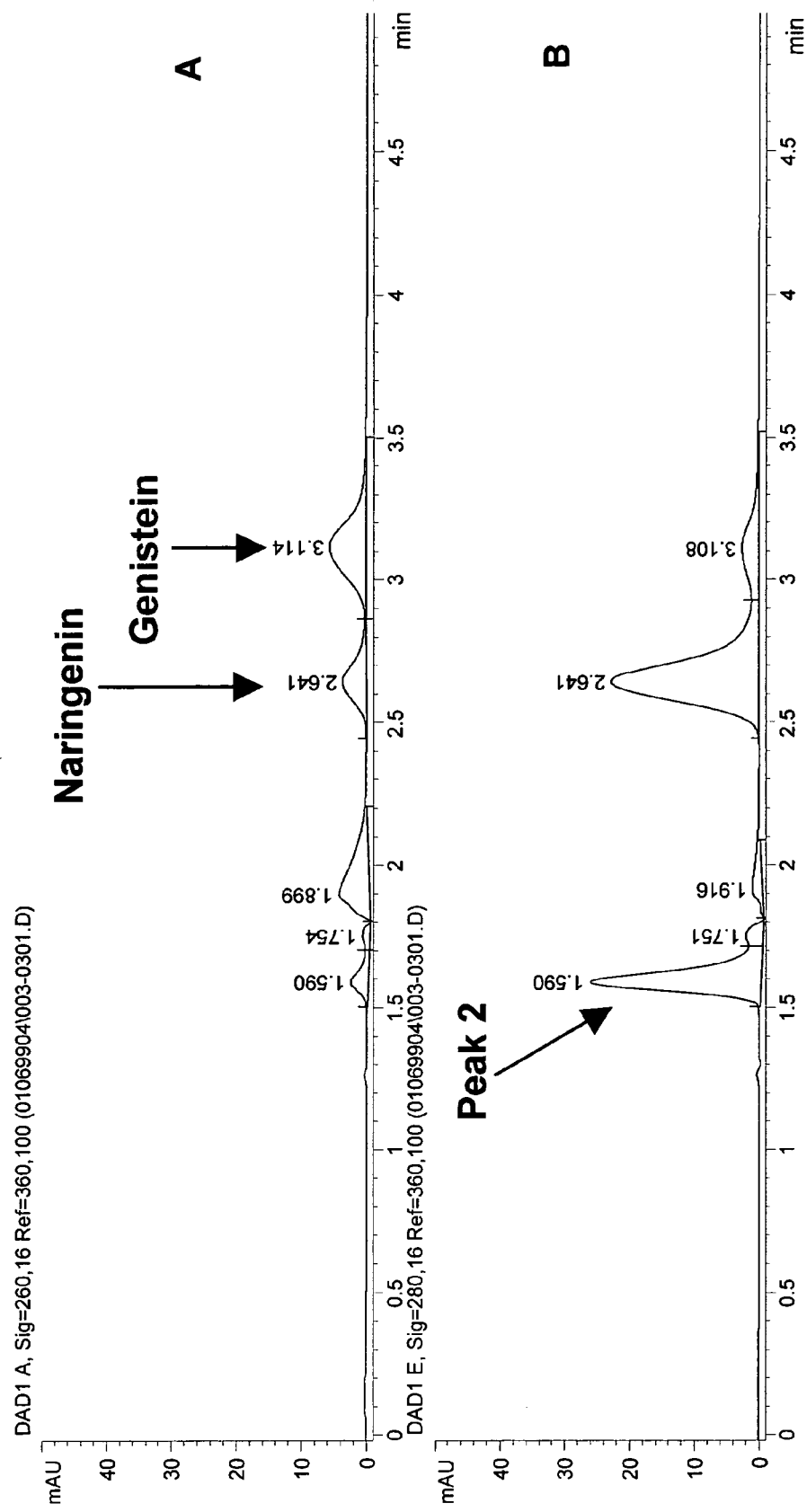
Figure 11A-B

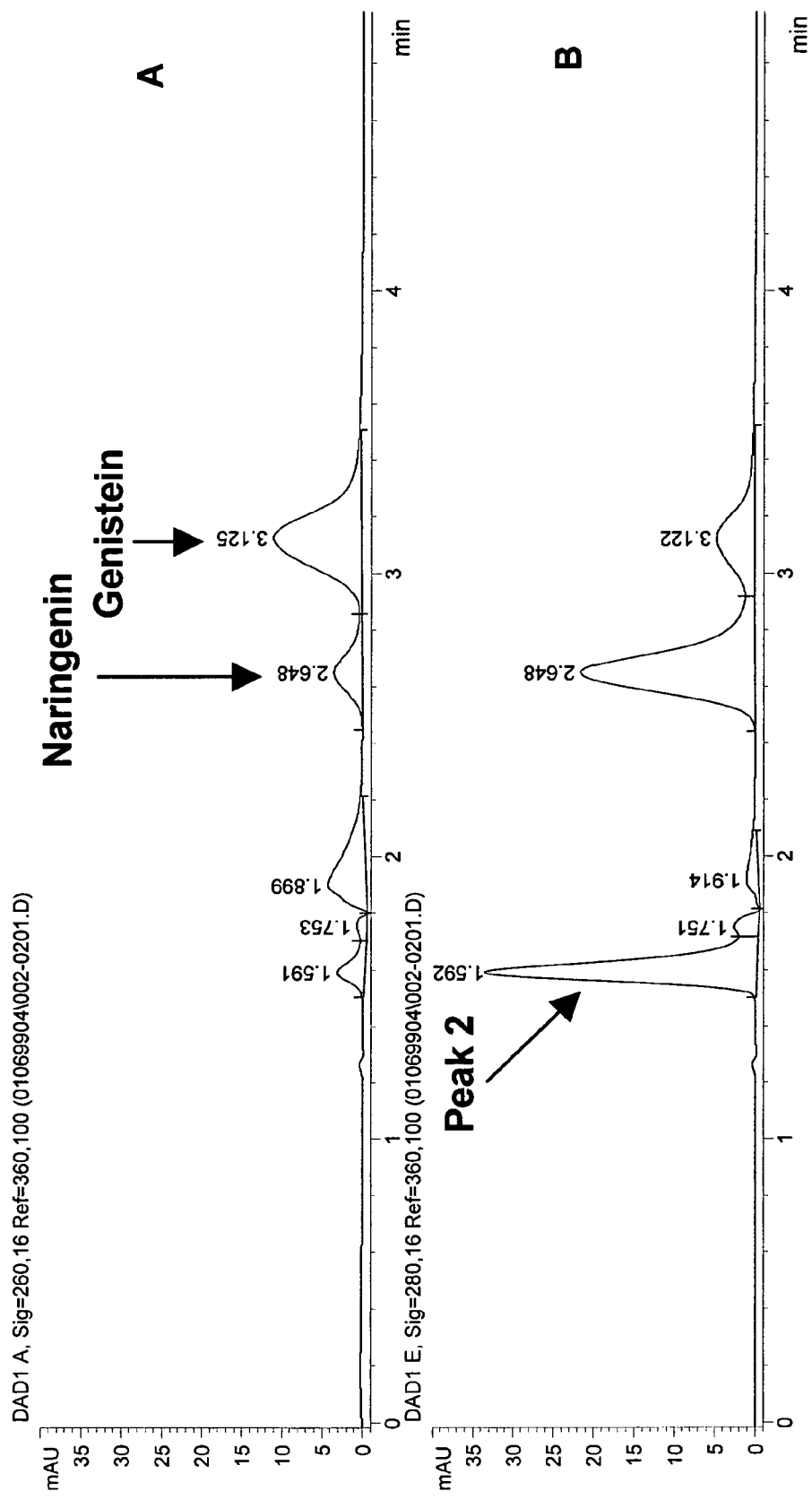
Figure 12A-B

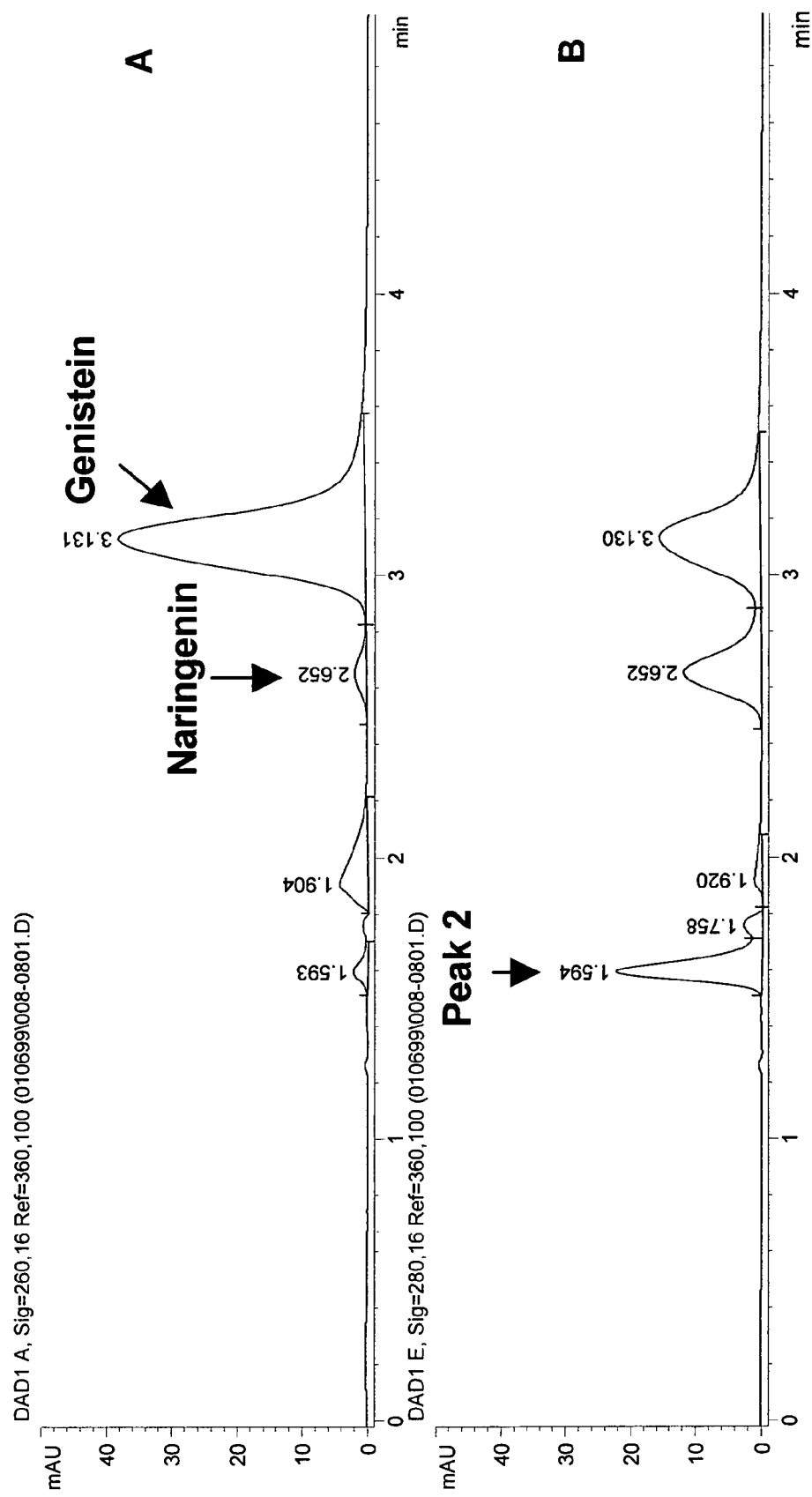
Figure 13A-B

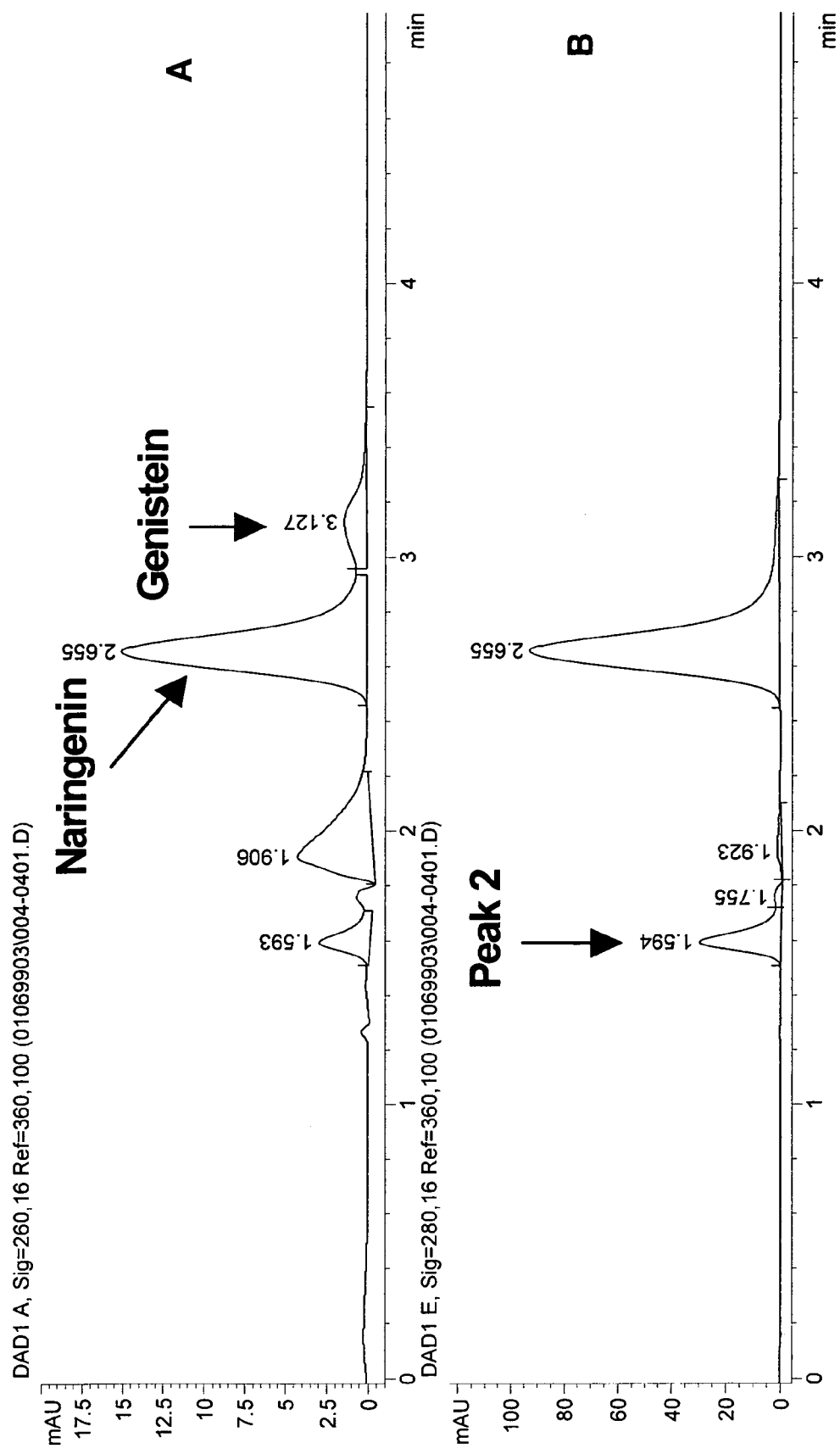
Figure 14A-B

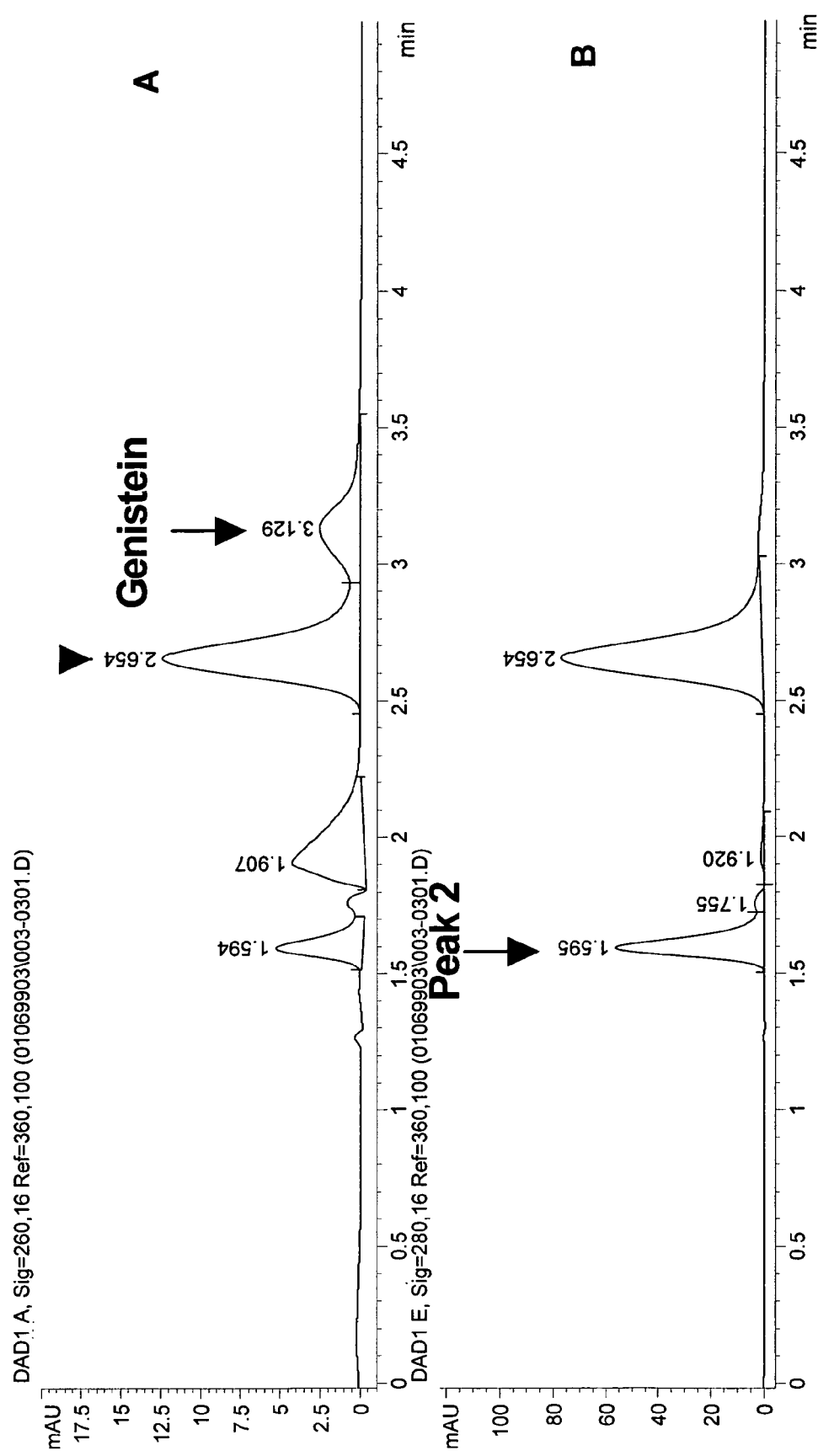
Figure 15A-B

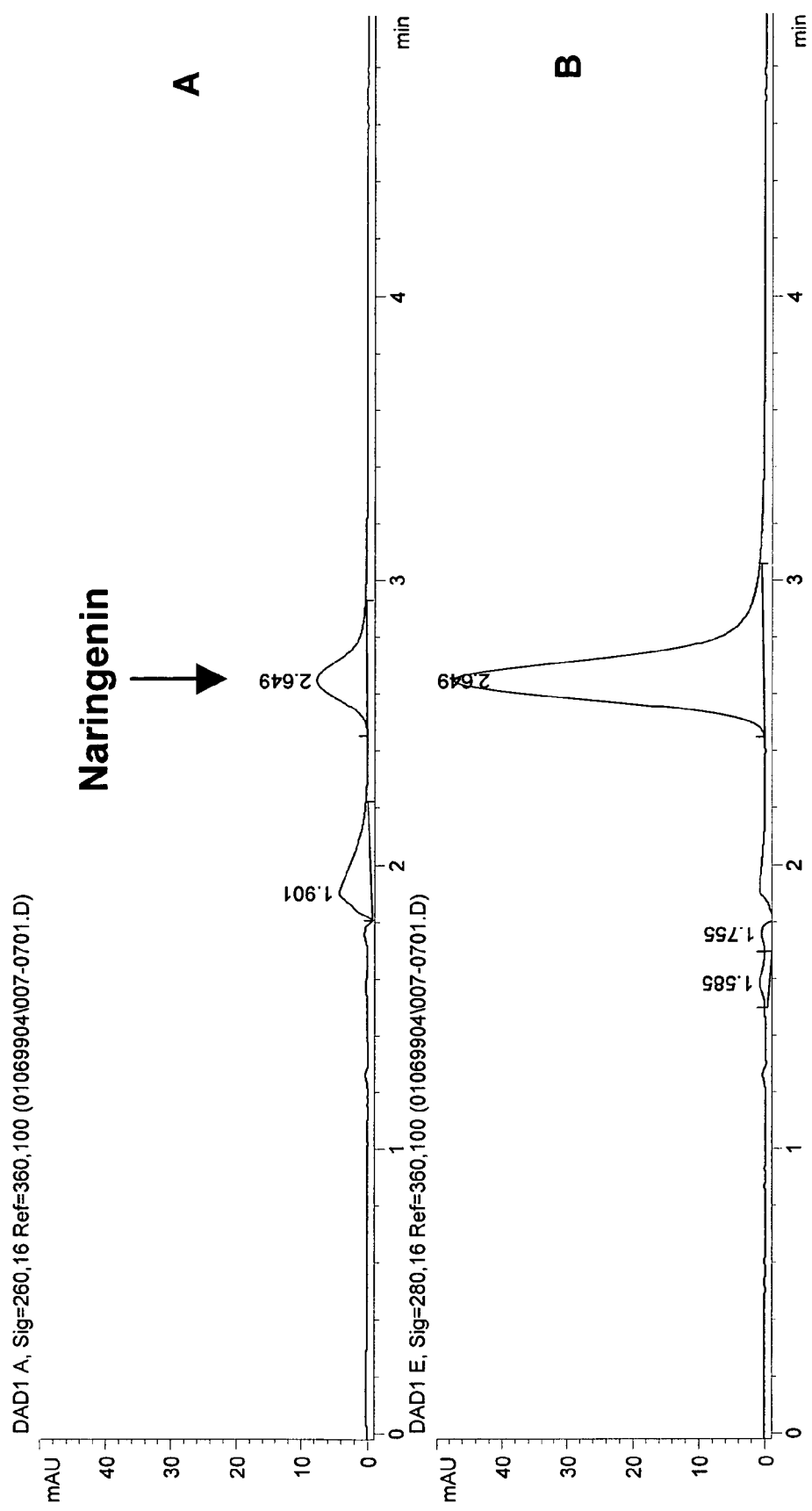
Figure 16A-B

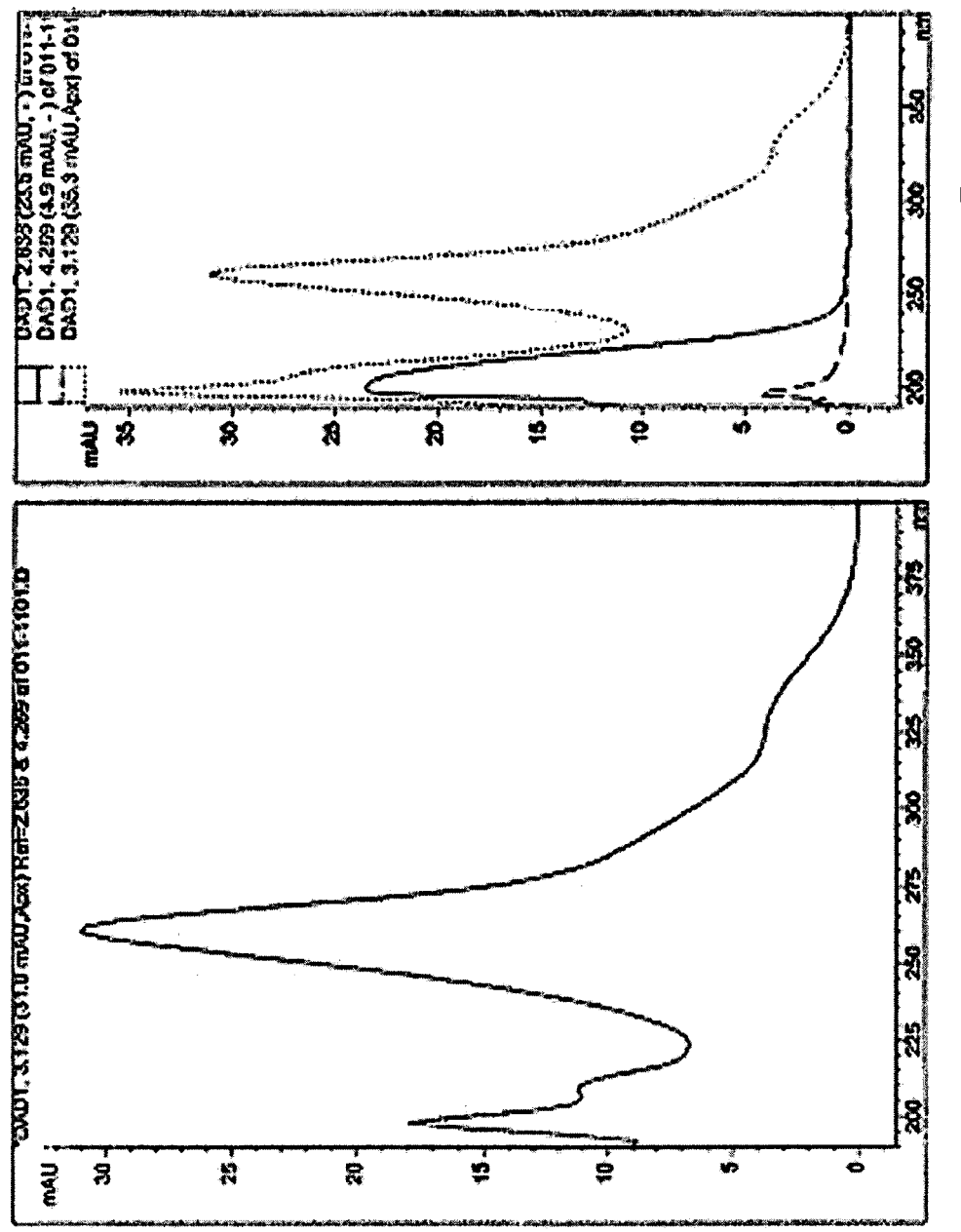
Figure 17A-B

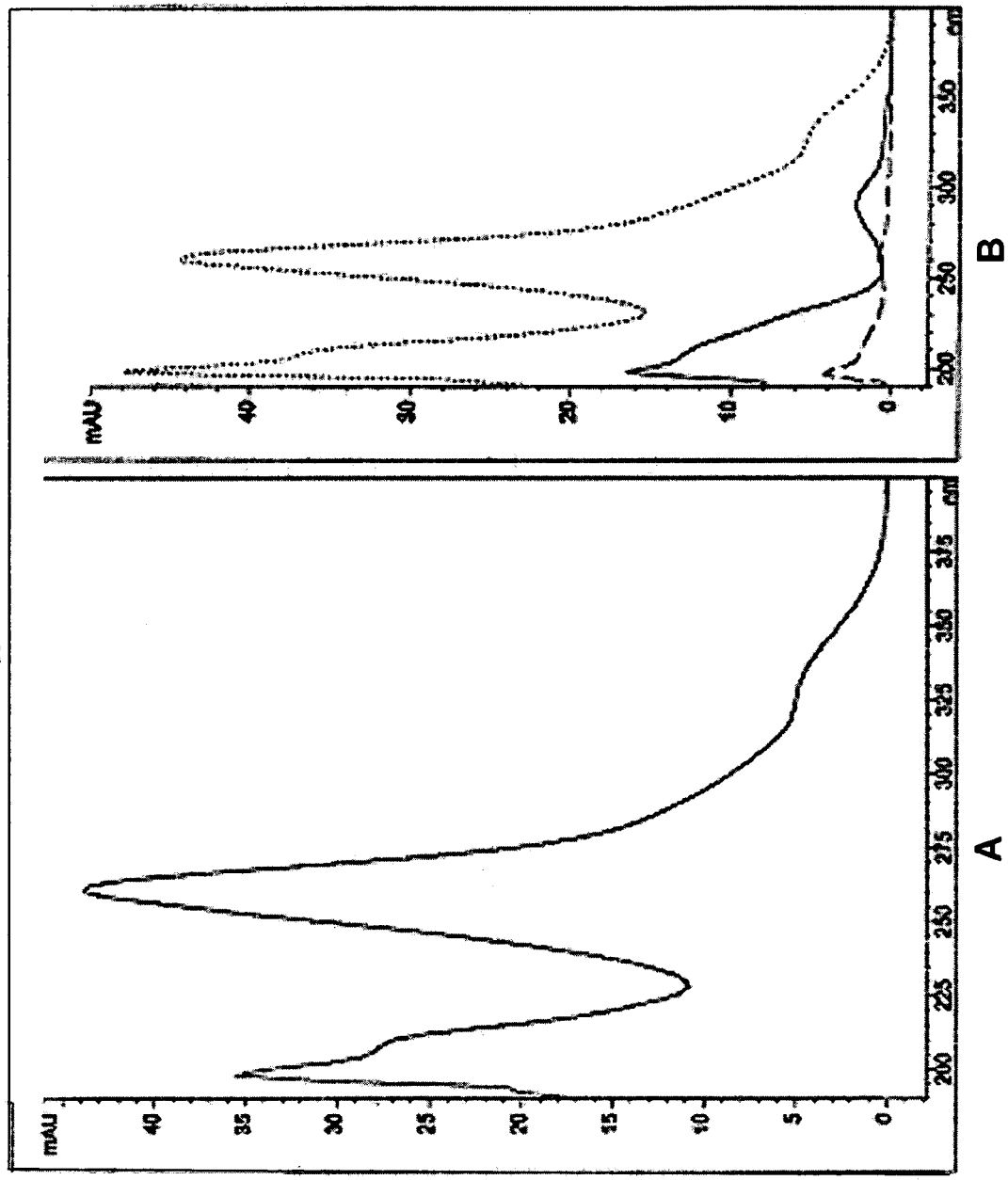
Figure 18 A-B

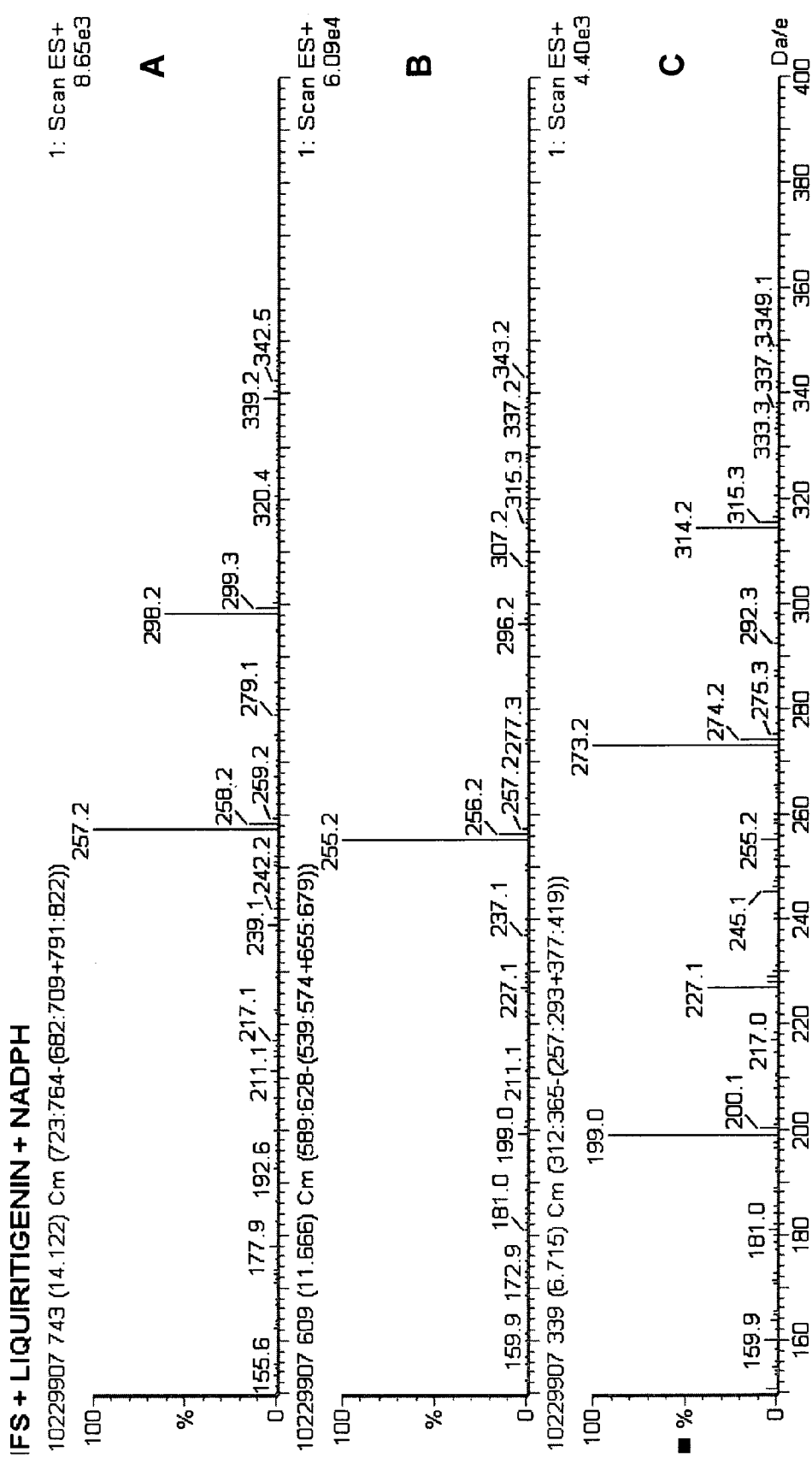
Figure 19 A-C

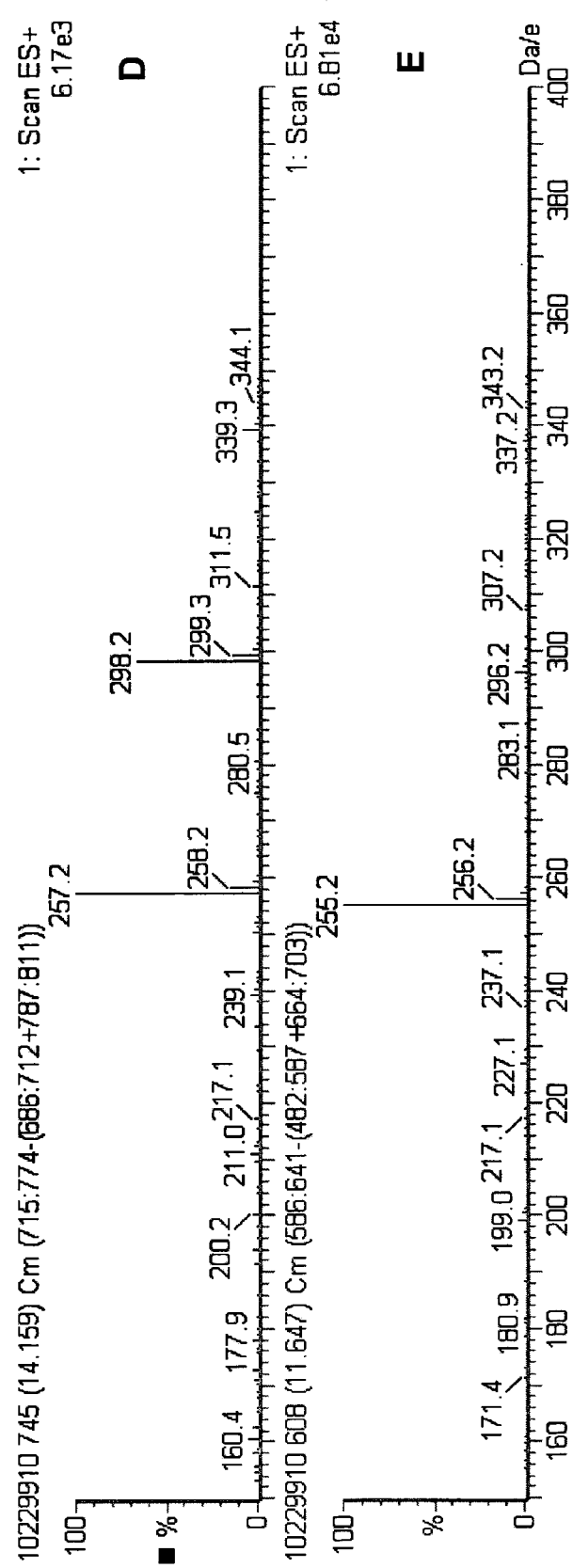
Figure 19D-E

SEQUENCE LISTING

```
<160> NUMBER OF SEQ ID NOS: 66

<210> SEQ ID NO 1
<211> LENGTH: 1756
<212> TYPE: DNA
<213> ORGANISM: Glycine max

<400> SEQUENCE: 1
gtaattaacc tcactcaaac tcgggatcac agaaaccaac aacagttctt gcactgaggt      60
ttcacgatgt tgctggaact tgcacttggt ttgtttgtgt tagctttgtt tctgcacttg     120
cgtcccacac caagtgcaaa atcaaaagca cttcgccacc tcccaaaccc tccaagccca     180
aagcctcgtc ttcccttcat tggccacctt cacctcttaa aagataaact tctccactat     240
gcactcatcg atctctccaa aaagcatggc cccttattct ctctctcctt cggctccatg     300
ccaaccgtcg ttgcctccac ccctgagttg ttcaagctct tcctccaaac ccacgaggca     360
acttccttca acacaaggtt ccaaacctct gccataagac gcctcactta cgacaactct     420
gtggccatgg ttccattcgg accttactgg aagttcgtga ggaagctcat catgaacgac     480
cttctcaacg ccaccaccgt caacaagctc aggcctttga ggacccaaca gatccgcaag     540
ttccttaggg ttatggccca aagcgcagag gcccagaagc cccttgacgt caccgaggag     600
cttctcaaat ggaccaacag caccatctcc atgatgatgc tcggcgaggc tgaggagatc     660
```

-continued

```
agagacatcg ctcgcgaggt tcttaagatc ttcggcgaat acagcctcac tgacttcatc    720
tggcctttga agtatctcaa ggttggaaag tatgagaaga ggattgatga catcttgaac    780
aagttcgacc ctgtcgttga aagggtcatc aagaagcgcc gtgagatcgt cagaaggaga    840
aagaacggag aagttgttga gggcgaggcc agcggcgtct tcctcgacac tttgcttgaa    900
ttcgctgagg acgagaccat ggagatcaaa attaccaagg agcaaatcaa gggccttgtt    960
gtcgactttt tctctgcagg gacagattcc acagcggtgg caacagagtg ggcattggca   1020
gagctcatca acaatcccag ggtgttgcaa aaggctcgtg aggaggtcta cagtgttgtg   1080
ggcaaagata gactcgttga cgaagttgac actcaaaacc ttccttacat tagggccatt   1140
gtgaaggaga cattccgaat gcacccacca ctcccagtgg tcaaaagaaa gtgcacagaa   1200
gagtgtgaga ttaatgggta tgtgatccca gagggagcat tggttctttt caatgtttgg   1260
caagtaggaa gggaccccaa atactgggac agaccatcag aattccgtcc cgagaggttc   1320
ttagaaactg gtgctgaagg ggaagcaggg cctcttgatc ttaggggcca gcatttccaa   1380
ctcctcccat ttgggtctgg gaggagaatg tgccctggtg tcaatttggc tacttcagga   1440
atggcaacac ttcttgcatc tcttatccaa tgctttgacc tgcaagtgct gggccctcaa   1500
ggacaaatat tgaaaggtga tgatgccaaa gttagcatgg aagagagagc tggcctcaca   1560
gttccaaggg cacatagtct cgtttgtgtt ccacttgcaa ggatcggcgt tgcatctaaa   1620
ctcctttctt aattaagata atcatcatat acaatagtag tgtcttgcca tcgcagttgc   1680
tttttatgta ttcataatca tcatttcaat aaggtgtgac tggtacttaa tcaagtaatt   1740
aaggttacat acatgc                                                  1756
```

<210> SEQ ID NO 2
<211> LENGTH: 521
<212> TYPE: PRT
<213> ORGANISM: Glycine max

<400> SEQUENCE: 2

```
Met Leu Leu Glu Leu Ala Leu Gly Leu Phe Val Leu Ala Leu Phe Leu
1               5                   10                  15

His Leu Arg Pro Thr Pro Ser Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Ser Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Thr Ser Phe Asn Thr Arg Phe Gln Thr Ser Ala Ile Arg Arg
            100                 105                 110

Leu Thr Tyr Asp Asn Ser Val Ala Met Val Pro Phe Gly Pro Tyr Trp
        115                 120                 125

Lys Phe Val Arg Lys Leu Ile Met Asn Asp Leu Leu Asn Ala Thr Thr
    130                 135                 140

Val Asn Lys Leu Arg Pro Leu Arg Thr Gln Gln Ile Arg Lys Phe Leu
145                 150                 155                 160

Arg Val Met Ala Gln Ser Ala Glu Ala Gln Lys Pro Leu Asp Val Thr
                165                 170                 175
```

```
Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
            195                 200                 205

Phe Gly Glu Tyr Ser Leu Thr Asp Phe Ile Trp Pro Leu Lys Tyr Leu
            210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Glu Ala Ser Gly Val Phe
                260                 265                 270

Leu Asp Thr Leu Leu Glu Phe Ala Glu Asp Glu Thr Met Glu Ile Lys
            275                 280                 285

Ile Thr Lys Glu Gln Ile Lys Gly Leu Val Val Asp Phe Phe Ser Ala
            290                 295                 300

Gly Thr Asp Ser Thr Ala Val Ala Thr Glu Trp Ala Leu Ala Glu Leu
305                 310                 315                 320

Ile Asn Asn Pro Arg Val Leu Gln Lys Ala Arg Glu Glu Val Tyr Ser
                325                 330                 335

Val Val Gly Lys Asp Arg Leu Val Asp Glu Val Asp Thr Gln Asn Leu
                340                 345                 350

Pro Tyr Ile Arg Ala Ile Val Lys Glu Thr Phe Arg Met His Pro Pro
            355                 360                 365

Leu Pro Val Val Lys Arg Lys Cys Thr Glu Glu Cys Glu Ile Asn Gly
            370                 375                 380

Tyr Val Ile Pro Glu Gly Ala Leu Val Leu Phe Asn Val Trp Gln Val
385                 390                 395                 400

Gly Arg Asp Pro Lys Tyr Trp Asp Arg Pro Ser Glu Phe Arg Pro Glu
                405                 410                 415

Arg Phe Leu Glu Thr Gly Ala Glu Gly Glu Ala Gly Pro Leu Asp Leu
            420                 425                 430

Arg Gly Gln His Phe Gln Leu Leu Pro Phe Gly Ser Gly Arg Arg Met
            435                 440                 445

Cys Pro Gly Val Asn Leu Ala Thr Ser Gly Met Ala Thr Leu Leu Ala
            450                 455                 460

Ser Leu Ile Gln Cys Phe Asp Leu Gln Val Leu Gly Pro Gln Gly Gln
465                 470                 475                 480

Ile Leu Lys Gly Asp Asp Ala Lys Val Ser Met Glu Glu Arg Ala Gly
                485                 490                 495

Leu Thr Val Pro Arg Ala His Ser Leu Val Cys Val Pro Leu Ala Arg
            500                 505                 510

Ile Gly Val Ala Ser Lys Leu Leu Ser
            515                 520

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide primer used in construction of
      WHT1

<400> SEQUENCE: 3
cgggatccat gcaaccggaa accgtcg                                      27
```

<210> SEQ ID NO 4
<211> LENGTH: 32
<212> TYPE: DNA
<213> ORGANISM: Artificial Sequence
<220> FEATURE:
<223> OTHER INFORMATION: Oligonucleotide primer used in construction of
      yeast strain WHT1

<400> SEQUENCE: 4
ccggaattct caccaaacat cacggaggta tc                                32

<210> SEQ ID NO 5
<211> LENGTH: 47
<212> TYPE: DNA
<213> ORGANISM: Artificial Sequence
<220> FEATURE:
<223> OTHER INFORMATION: Oligonucleotide primer

<400> SEQUENCE: 5
tcaaggagaa aaaccccgg atccatgttg ctggaacttg cacttgg                 47

<210> SEQ ID NO 6
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 6
ggccagtgaa ttgtaatacg actcactata gggcg                             35

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 7
aaaattagcc tcacaaaagc aaag                                         24

<210> SEQ ID NO 8
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 8
atataaggat tgatagttta tagtagg                                      27

<210> SEQ ID NO 9
<211> LENGTH: 1824
<212> TYPE: DNA
<213> ORGANISM: Glycine max

<400> SEQUENCE: 9
ggaaaattag cctcacaaaa gcaaagatca acaaaccaa ggacgagaac acgatgttgc    60
ttgaacttgc acttggttta ttggttttgg ctctgtttct gcacttgcgt cccacaccca  120
ctgcaaaatc aaaagcactt cgccatctcc caaacccacc aagcccaaag cctcgtcttc  180
ccttcatagg acaccttcat ctcttaaaag acaaacttct ccactacgca ctcatcgacc  240
tctccaaaaa acatggtccc ttattctctc tctactttgg ctccatgcca accgttgttg  300

-continued

```
cctccacacc agaattgttc aagctcttcc tccaaacgca cgaggcaact tccttcaaca      360
caaggttcca aacctcagcc ataagacgcc tcacctatga tagctcagtg ccatggttc       420 ccttcggacc ttactggaag ttcgtgagga agctcatcat gaacgacctt cccaacgcca      480
ccactgtaaa caagttgagg cctttgagga cccaacagac ccgcaagttc cttagggtta      540
tggcccaagg cgcagaggca cagaagcccc ttgacttgac cgaggagctt ctgaaatgga      600
ccaacagcac catctccatg atgatgctcg gcgaggctga ggagatcaga gacatcgctc      660
gcgaggttct taagatcttt ggcgaataca gcctcactga cttcatctgg ccattgaagc      720
atctcaaggt tggaaagtat gagaagagga tcgacgacat cttgaacaag ttcgaccctg      780
tcgttgaaag ggtcatcaag aagcgccgtg agatcgtgag gaggagaaag aacggagagg      840
ttgttgaggg tgaggtcagc ggggttttcc ttgacacttt gcttgaattc gctgaggatg      900
agaccatgga gatcaaaatc accaaggacc acatcgaggg tcttgttgtc gactttttct      960
cggcaggaac agactccaca gcggtggcaa cagagtgggc attggcagaa ctcatcaaca     1020
atcctaaggt gttggaaaag gctcgtgagg aggtctacag tgttgtggga aggacagac      1080 ttgtggacga agttgacact caaaaccttc cttacattag agcaatcgtg aaggagacat     1140
tccgcatgca cccgccactc ccagtggtca aaagaaagtg cacagaagag tgtgagatta     1200
atggatatgt gatcccagag ggagcattga ttctcttcaa tgtatggcaa gtaggaagag     1260
accccaaata ctgggacaga ccatcggagt tccgtcctga gaggttccta gagacagggg     1320
ctgaagggga agcagggcct cttgatctta ggggacaaca ttttcaactt ctcccatttg     1380
ggtctgggag gagaatgtgc cctggagtca atctggctac ttcgggaatg caacacttc      1440 ttgcatctct tattcagtgc ttcgacttgc aagtgctggg tccacaagga cagatattga     1500
agggtggtga cgccaaagtt agcatggaag agagagccgg cctcactgtt ccaagggcac     1560
atagtcttgt ctgtgttcca cttgcaagga tcggcgttgc atctaaactc ctttcttaat     1620
taagatcatc atcatatata atatttactt tttgtgtgtt gataatcatc atttcaataa     1680
ggtctcgttc atctactttt tatgaagtat ataagccctt ccatgcacat tgtatcatct     1740
cccatttgtc ttcgtttgct acctaaggca atcttttttt ttttagaatc acatcatcct     1800
actataaact atcaatcctt atat                                             1824
```

<210> SEQ ID NO 10
<211> LENGTH: 521
<212> TYPE: PRT
<213> ORGANISM: Glycine max

<400> SEQUENCE: 10

```
Met Leu Leu Glu Leu Ala Leu Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu His Tyr Ala Leu Ile Asp Leu Ser
    50                  55                  60

Lys Lys His Gly Pro Leu Phe Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95
```

```
Glu Ala Thr Ser Phe Asn Thr Arg Phe Gln Thr Ser Ala Ile Arg Arg
            100                 105                 110

Leu Thr Tyr Asp Ser Ser Val Ala Met Val Pro Phe Gly Pro Tyr Trp
            115                 120                 125

Lys Phe Val Arg Lys Leu Ile Met Asn Asp Leu Pro Asn Ala Thr Thr
            130                 135                 140

Val Asn Lys Leu Arg Pro Leu Arg Thr Gln Thr Arg Lys Phe Leu
145                 150                 155                 160

Arg Val Met Ala Gln Gly Ala Glu Ala Gln Lys Pro Leu Asp Leu Thr
            165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
            195                 200                 205

Phe Gly Glu Tyr Ser Leu Thr Asp Phe Ile Trp Pro Leu Lys His Leu
            210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Glu Ile Val Arg
            245                 250                 255

Arg Arg Lys Asn Gly Glu Val Val Glu Gly Glu Val Ser Gly Val Phe
            260                 265                 270

Leu Asp Thr Leu Leu Glu Phe Ala Glu Asp Glu Thr Met Glu Ile Lys
            275                 280                 285

Ile Thr Lys Asp His Ile Glu Gly Leu Val Val Asp Phe Phe Ser Ala
            290                 295                 300

Gly Thr Asp Ser Thr Ala Val Ala Thr Glu Trp Ala Leu Ala Glu Leu
305                 310                 315                 320

Ile Asn Asn Pro Lys Val Leu Glu Lys Ala Arg Glu Glu Val Tyr Ser
            325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
            355                 360                 365

Leu Pro Val Val Lys Arg Lys Cys Thr Glu Glu Cys Glu Ile Asn Gly
            370                 375                 380

Tyr Val Ile Pro Glu Gly Ala Leu Ile Leu Phe Asn Val Trp Gln Val
385                 390                 395                 400

Gly Arg Asp Pro Lys Tyr Trp Asp Arg Pro Ser Glu Phe Arg Pro Glu
            405                 410                 415

Arg Phe Leu Glu Thr Gly Ala Glu Gly Glu Ala Gly Pro Leu Asp Leu
            420                 425                 430

Arg Gly Gln His Phe Gln Leu Leu Pro Phe Gly Ser Gly Arg Arg Met
            435                 440                 445

Cys Pro Gly Val Asn Leu Ala Thr Ser Gly Met Ala Thr Leu Leu Ala
            450                 455                 460

Ser Leu Ile Gln Cys Phe Asp Leu Gln Val Leu Gly Pro Gln Gly Gln
465                 470                 475                 480

Ile Leu Lys Gly Gly Asp Ala Lys Val Ser Met Glu Glu Arg Ala Gly
            485                 490                 495

Leu Thr Val Pro Arg Ala His Ser Leu Val Cys Val Pro Leu Ala Arg
            500                 505                 510

Ile Gly Val Ala Ser Lys Leu Leu Ser
```

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 11
atgttgctgg aacttgcact t                                              21

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 12
ttaagaaagg agtttagatg caacg                                          25

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 13
tgtttctgca cttgcgtccc ac                                             22

<210> SEQ ID NO 14
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 14
ccgatccttg caagtggaac ac                                             22

<210> SEQ ID NO 15
<211> LENGTH: 1501
<212> TYPE: DNA
<213> ORGANISM: Medicago sativa

<400> SEQUENCE: 15
tgtttctgca cttgcgtccc acaccaagtg caaaatcaaa agcacttcgc cacctcccaa      60
acccccaag cccaaagcct cgtcttccct tcattggcca ccttcacctc ttaaaagata      120
aacttctcca ctatgcactc atcgatctct ccaaaaagca tggcccctta ttctctctct      180
ccttcggctc catgccaacc gtcgttgcct ccacccctga gttgttcaag ctcttcctcc      240
aaacccacga ggcaacttcc ttcaacacaa ggttccaaac ctctgccaca agacgcctca      300
cttacgacaa ctctgtggcc atggttccat tcggacctta ctggaggttc gtgaggaagc      360
tcatcatgaa cgaccttctc aacgccacca ccgtcaacaa gctcaggcct ttgaggaccc      420
aacagatccg caagttcctt agggttatgg cccaaagcgc agaggcccag aagcccctt g      480
acgtcaccga ggagcttctc aaatggacca acagcaccat ctccatgatg atgctcggcg      540
aggctgagga gatcagagac atcgctcgcg aggttcttaa gatcttcggc gaatacagcc      600
tcactgactt catctggcct ttgaagtatc tcaaggttgg aaagtatgag aagaggattg      660

```
atgacatctt gaacaagttc gaccctgtcg ttgaaagggt catcaagaag cgccgtggga    720
tcgtcagaag gagagagaac ggagaagttg ttgagggcga ggccagcggc gtcttcctcg    780
acactttgct tgaattcgct gaggacgaga ccatggagat caaaattacc aaggagcaaa    840
tcaagggcct tgttgtcgac cttttctctg cagggacaga ttccacagcg gtggcaacag    900
agtgggcatt ggcagagctc atcaacaatc ccagggtgtt gcaaaaggct cgtgaggagg    960
tctacagtgt tgtgggcaaa gatagactcg ttgacgaagt tgacactcaa aaccttcctt   1020
acattagggc cattgtgaag gagacattcc gaatgcaccc accactccca gtggtcaaaa   1080
gaaagtgcac agaagagtgt gagattaatg ggtatgtgat cccagaggga gcattggttc   1140
ttttcaatgt ttggcaagta ggaagggacc ccaaatactg ggacagacca tccgaattcc   1200
gtcccgagag gttcttagaa actggtgctg aaggggaagc agggcctctt gatcttaggg   1260
gccagcattt ccaactcctc ccatttgggt ctgggaggag aatgtgccct ggtgtcaatt   1320
tggctacttc aggaatggca acacttcttg catctcttat ccaatgcttt gacctgcaag   1380
tgctgggccc tcaaggacaa atattgaaag gtgatgatgc caaagttagc atggaagaga   1440
gagctggcct cacagttcca agggcacata gtctcgtttg tgttccactt gcaaggatcg   1500
g                                                                   1501

<210> SEQ ID NO 16
<211> LENGTH: 499
<212> TYPE: PRT
<213> ORGANISM: Medicago sativa

<400> SEQUENCE: 16

Phe Leu His Leu Arg Pro Thr Pro Ser Ala Lys Ser Lys Ala Leu Arg
1               5                   10                  15

His Leu Pro Asn Pro Pro Ser Pro Lys Pro Arg Leu Pro Phe Ile Gly
            20                  25                  30

His Leu His Leu Leu Lys Asp Lys Leu Leu His Tyr Ala Leu Ile Asp
        35                  40                  45

Leu Ser Lys Lys His Gly Pro Leu Phe Ser Leu Ser Phe Gly Ser Met
    50                  55                  60

Pro Thr Val Val Ala Ser Thr Pro Glu Leu Phe Lys Leu Phe Leu Gln
65                  70                  75                  80

Thr His Glu Ala Thr Ser Phe Asn Thr Arg Phe Gln Thr Ser Ala Thr
                85                  90                  95

Arg Arg Leu Thr Tyr Asp Asn Ser Val Ala Met Val Pro Phe Gly Pro
            100                 105                 110

Tyr Trp Arg Phe Val Arg Lys Leu Ile Met Asn Asp Leu Leu Asn Ala
        115                 120                 125

Thr Thr Val Asn Lys Leu Arg Pro Leu Arg Thr Gln Gln Ile Arg Lys
    130                 135                 140

Phe Leu Arg Val Met Ala Gln Ser Ala Glu Ala Gln Lys Pro Leu Asp
145                 150                 155                 160

Val Thr Glu Glu Leu Leu Lys Trp Thr Asn Ser Thr Ile Ser Met Met
                165                 170                 175

Met Leu Gly Glu Ala Glu Glu Ile Arg Asp Ile Ala Arg Glu Val Leu
            180                 185                 190

Lys Ile Phe Gly Glu Tyr Ser Leu Thr Asp Phe Ile Trp Pro Leu Lys
        195                 200                 205

Tyr Leu Lys Val Gly Lys Tyr Glu Lys Arg Ile Asp Asp Ile Leu Asn
```

```
          210                 215                 220
Lys Phe Asp Pro Val Val Glu Arg Val Ile Lys Arg Arg Gly Ile
225                 230                 235                 240

Val Arg Arg Arg Glu Asn Gly Glu Val Val Glu Gly Glu Ala Ser Gly
                245                 250                 255

Val Phe Leu Asp Thr Leu Leu Glu Phe Ala Glu Asp Glu Thr Met Glu
                260                 265                 270

Ile Lys Ile Thr Lys Glu Gln Ile Lys Gly Leu Val Val Asp Leu Phe
                275                 280                 285

Ser Ala Gly Thr Asp Ser Thr Ala Val Ala Thr Glu Trp Ala Leu Ala
290                 295                 300

Glu Leu Ile Asn Asn Pro Arg Val Leu Gln Lys Ala Arg Glu Glu Val
305                 310                 315                 320

Tyr Ser Val Val Gly Lys Asp Arg Leu Val Asp Glu Val Asp Thr Gln
                325                 330                 335

Asn Leu Pro Tyr Ile Arg Ala Ile Val Lys Glu Thr Phe Arg Met His
                340                 345                 350

Pro Pro Leu Pro Val Val Lys Arg Lys Cys Thr Glu Glu Cys Glu Ile
                355                 360                 365

Asn Gly Tyr Val Ile Pro Glu Gly Ala Leu Val Leu Phe Asn Val Trp
370                 375                 380

Gln Val Gly Arg Asp Pro Lys Tyr Trp Asp Arg Pro Ser Glu Phe Arg
385                 390                 395                 400

Pro Glu Arg Phe Leu Glu Thr Gly Ala Glu Gly Glu Ala Gly Pro Leu
                405                 410                 415

Asp Leu Arg Gly Gln His Phe Gln Leu Leu Pro Phe Gly Ser Gly Arg
                420                 425                 430

Arg Met Cys Pro Gly Val Asn Leu Ala Thr Ser Gly Met Ala Thr Leu
                435                 440                 445

Leu Ala Ser Leu Ile Gln Cys Phe Asp Leu Gln Val Leu Gly Pro Gln
                450                 455                 460

Gly Gln Ile Leu Lys Gly Asp Asp Ala Lys Val Ser Met Glu Glu Arg
465                 470                 475                 480

Ala Gly Leu Thr Val Pro Arg Ala His Ser Leu Val Cys Val Pro Leu
                485                 490                 495

Ala Arg Ile

<210> SEQ ID NO 17
<211> LENGTH: 1501
<212> TYPE: DNA
<213> ORGANISM: Vicia villosa

<400> SEQUENCE: 17
tgtttctgca cttgcgtccc acacccactg caaaatcaaa agcacttcgc catctcccaa      60
acccaccaag cccaaagcct cgtcttccct tcataggaca ccttcatctc ttaaaagaca     120
aacttctcca ctacgcactc atcgacctct ccaaaaaaca tggtccctta ttctctctct     180
actttggctc catgccaacc gttgttgcct ccacaccaga attgttcaag ctcttcctcc     240
aaacgcacga ggcaacttcc ttcaacacaa ggttccaaac ctcagccata agacgcctca     300
cctatgatag cttagtggcc atggttccct tcggacctta ctggaagttc gtgaggaagc     360
tcatcatgaa cgaccttctc aacgccacca ctgtaaacaa gttgaggcct ttgaggaccc     420
aacagatccg caagttcctt agggttatgg cccaaggcgc agaggcacag aagccccttg     480
```

-continued

```
acttgaccga ggagcttctg aaatggacca acagcaccat ctctatgatg atgctcggcg      540
aggctgagga gatcagagac atcgctcgcg aggttcttaa gatctatggc gaatacagcc      600
tcactgactt catctggcca ttgaagcatc tcaaggttgg aaagtatgag aagaggatcg      660
acgacatctt gaacaagttc gaccctgtcg ttgaaagagt catcaagaag cgccgtgaga      720
tcgtgaggag gagaaagaac ggagaggttg ttgagggtga ggtcagcggg gttttccttg      780
acactttgct tgaattcgct gaggatgaga ccacggagat caaaatcacc aaggaccaca      840
tcaagggtct tgttgtcgac ttttttctcgg caggaataga ctccacagcg gtggcaacag      900
agtgggcatt ggcagaactc atcaacaatc ctaaggtgtt ggaaaaggct cgtgaggagg      960
tctacagtgt tgtgggaaag gacagacttg tggacgaagt tgacactcaa aaccttcctt     1020
acattagagc aatcgtgaag gagacattcc gcatgcaccc gccactccca gtggtcaaaa     1080
gaaagtgcac agaagagtgt gagattaatg gatatgtgat cccagaggga gcattgattc     1140
tcttcaatgt atggcaagta ggaagggacc ccaaatactg ggacagacca tcggagttcc     1200
gtcctgagag gttcctagag acaggggctg aaggggaagc aaggcctctt gatcttaggg     1260
gacaacattt tcaacttctc ccatttgggt ctgggagggg aatgtgccct ggagtcaatc     1320
tggctacttc gggaatggca acacttcttg catctcttat tcagtgcttt gacttgcaag     1380
tgctgggtcc acaaggacag atattgaagg gtggtgacgc aaagttagc atggaagaga     1440
gggccggcct cactgttcca aggcacata gtcttgtctg tgttccactt gcaaggatcg     1500
g                                                                    1501
```

<210> SEQ ID NO 18
<211> LENGTH: 499
<212> TYPE: PRT
<213> ORGANISM: Vicia villosa

<400> SEQUENCE: 18

```
Phe Leu His Leu Arg Pro Thr Pro Thr Ala Lys Ser Lys Ala Leu Arg
1               5                  10                  15

His Leu Pro Asn Pro Pro Ser Pro Lys Pro Arg Leu Pro Phe Ile Gly
            20                  25                  30

His Leu His Leu Lys Asp Lys Leu Leu His Tyr Ala Leu Ile Asp
        35                  40                  45

Leu Ser Lys Lys His Gly Pro Leu Phe Ser Leu Tyr Phe Gly Ser Met
    50                  55                  60

Pro Thr Val Val Ala Ser Thr Pro Glu Leu Phe Lys Leu Phe Leu Gln
65                  70                  75                  80

Thr His Glu Ala Thr Ser Phe Asn Thr Arg Phe Gln Thr Ser Ala Ile
                85                  90                  95

Arg Arg Leu Thr Tyr Asp Ser Leu Val Ala Met Val Pro Phe Gly Pro
            100                 105                 110

Tyr Trp Lys Phe Val Arg Lys Leu Ile Met Asn Asp Leu Leu Asn Ala
        115                 120                 125

Thr Thr Val Asn Lys Leu Arg Pro Leu Arg Thr Gln Gln Ile Arg Lys
    130                 135                 140

Phe Leu Arg Val Met Ala Gln Gly Ala Glu Ala Gln Lys Pro Leu Asp
145                 150                 155                 160

Leu Thr Glu Glu Leu Leu Lys Trp Thr Asn Ser Thr Ile Ser Met Met
                165                 170                 175

Met Leu Gly Glu Ala Glu Glu Ile Arg Asp Ile Ala Arg Glu Val Leu
            180                 185                 190
```

```
Lys Ile Tyr Gly Glu Tyr Ser Leu Thr Asp Phe Ile Trp Pro Leu Lys
            195                 200                 205

His Leu Lys Val Gly Lys Tyr Glu Lys Arg Ile Asp Asp Ile Leu Asn
        210                 215                 220

Lys Phe Asp Pro Val Val Glu Arg Val Ile Lys Lys Arg Arg Glu Ile
225                 230                 235                 240

Val Arg Arg Lys Asn Gly Glu Val Val Glu Gly Glu Val Ser Gly
                245                 250                 255

Val Phe Leu Asp Thr Leu Leu Glu Phe Ala Glu Asp Glu Thr Thr Glu
            260                 265                 270

Ile Lys Ile Thr Lys Asp His Ile Lys Gly Leu Val Val Asp Phe Phe
        275                 280                 285

Ser Ala Gly Ile Asp Ser Thr Ala Val Ala Thr Glu Trp Ala Leu Ala
        290                 295                 300

Glu Leu Ile Asn Asn Pro Lys Val Leu Glu Lys Ala Arg Glu Glu Val
305                 310                 315                 320

Tyr Ser Val Val Gly Lys Asp Arg Leu Val Asp Glu Val Asp Thr Gln
                325                 330                 335

Asn Leu Pro Tyr Ile Arg Ala Ile Val Lys Glu Thr Phe Arg Met His
            340                 345                 350

Pro Pro Leu Pro Val Val Lys Arg Lys Cys Thr Glu Glu Cys Glu Ile
            355                 360                 365

Asn Gly Tyr Val Ile Pro Glu Gly Ala Leu Ile Leu Phe Asn Val Trp
        370                 375                 380

Gln Val Gly Arg Asp Pro Lys Tyr Trp Asp Arg Pro Ser Glu Phe Arg
385                 390                 395                 400

Pro Glu Arg Phe Leu Glu Thr Gly Ala Glu Gly Glu Ala Arg Pro Leu
                405                 410                 415

Asp Leu Arg Gly Gln His Phe Gln Leu Leu Pro Phe Gly Ser Gly Arg
            420                 425                 430

Gly Met Cys Pro Gly Val Asn Leu Ala Thr Ser Gly Met Ala Thr Leu
        435                 440                 445

Leu Ala Ser Leu Ile Gln Cys Phe Asp Leu Gln Val Leu Gly Pro Gln
    450                 455                 460

Gly Gln Ile Leu Lys Gly Gly Asp Ala Lys Val Ser Met Glu Glu Arg
465                 470                 475                 480

Ala Gly Leu Thr Val Pro Arg Ala His Ser Leu Val Cys Val Pro Leu
            485                 490                 495

Ala Arg Ile

<210> SEQ ID NO 19
<211> LENGTH: 1501
<212> TYPE: DNA
<213> ORGANISM: Lens culinaris

<400> SEQUENCE: 19
tgtttctgca cttgcgtccc acacccactg caaaatcaaa agcacttcgc catctcccaa      60
acccaccaag cccaaagcct cgtcttccct tcataggaca ccctcatctc ttaaaagaca     120
aacttctcca ctacgcactc atcgacctct ccaaaaaaca tggtccctta ttctccctct     180
actttggctc catgccaacc gttgttgcct ccacaccaga attgttcaag ctcttcctcc     240
aaacgcacga ggcaacttcc ttcaacacaa ggttccaaac ctcagccata agacgcctca     300
cctatgatag ctcagtggcc atggttccat tcggacctta ctggaagttc gtgaggaagc     360
```

-continued

```
tcatcatgaa cgaccttctc aacgccacca ccgtcaacaa gctcaggcct ttgaggaccc      420
aacagatccg caagttcctt agggttatgg cccaaagcgc agaggcccag aagcccttg      480 acgtcaccga ggagcttctc aaatggacca acagcaccat ctccatgatg atgctcggcg      540
aggctgagga gatcagagac atcgctcgcg aggttcttaa gatcttcggc gaatacagcc      600
tcactgactt catctggcct ttgaagtatc tcaaggttgg aaagtatgag aagaggattg      660
atgacatctt gaacaagttc gaccctgtcg ttgaagggt catcaagaag cgccgtgaga       720
tcgtcagaag gagaaagaac ggagaagttg tgagggcga ggccagcggc gtcttcctcg       780
acactttgct tgaattcgct gaggacgaga ccatggagat caaaattacc aaggagcaaa      840
tcaagggcct tgttgtcgac tttttctctg cagggacaga ttccacagcg gtggcaacag      900
agtgggcatt ggcagagctc atcaacaatc ccagggtgtt gcaaaaggct cgtgaggagg      960
tctacagtgt tgtgggcaaa gatatactcg ttgacgaagt tgacactcaa aaccttcctt     1020
acattagggc cattgtgaag gagacattcc gaatgcaccc accactccca gtggtcaaaa     1080
gaaagtgcac agaagagtgt gagattaatg ggcatgtgat cccagaggga gcattggttc     1140
ttttcaatgt ttggcaagta ggaagggacc ccaaatactg ggacagacca tcagaattcc     1200
gtcccgagag gttcttagaa actggtgctg aaggggaagc agggcctctt gatcttaggg     1260
gccagcattt ccaactcctc ccatttgggt ctggagggag aatgtgccct ggtgtcaatt     1320
tggctacttc aggaatggca acacttcttg catctcttat ccaatgcttt gacctgcaag     1380
tgctgggccc tcaaggacaa atattgaaag gtgatgatgc caaagttagc atggaagaga     1440
gagctggcct cacagttcca agggcacata gtctcgtttg tgttccactt gcaaggatcg     1500
g                                                                     1501
```

<210> SEQ ID NO 20
<211> LENGTH: 499
<212> TYPE: PRT
<213> ORGANISM: Lens culinaris

<400> SEQUENCE: 20

```
Phe Leu His Leu Arg Pro Thr Pro Thr Ala Lys Ser Lys Ala Leu Arg
1               5                  10                  15

His Leu Pro Asn Pro Pro Ser Pro Lys Pro Arg Leu Pro Phe Ile Gly
            20                  25                  30

His Pro His Leu Leu Lys Asp Lys Leu Leu His Tyr Ala Leu Ile Asp
        35                  40                  45

Leu Ser Lys Lys His Gly Pro Leu Phe Ser Leu Tyr Phe Gly Ser Met
    50                  55                  60

Pro Thr Val Val Ala Ser Thr Pro Glu Leu Phe Lys Leu Phe Leu Gln
65                  70                  75                  80

Thr His Glu Ala Thr Ser Phe Asn Thr Arg Phe Gln Thr Ser Ala Ile
                85                  90                  95

Arg Arg Leu Thr Tyr Asp Ser Ser Val Ala Met Val Pro Phe Gly Pro
            100                 105                 110

Tyr Trp Lys Phe Val Arg Lys Leu Ile Met Asn Asp Leu Leu Asn Ala
        115                 120                 125

Thr Thr Val Asn Lys Leu Arg Pro Leu Arg Thr Gln Gln Ile Arg Lys
    130                 135                 140

Phe Leu Arg Val Met Ala Gln Ser Ala Glu Ala Gln Lys Pro Leu Asp
145                 150                 155                 160
```

Val Thr Glu Glu Leu Leu Lys Trp Thr Asn Ser Thr Ile Ser Met Met
            165                 170                 175
Met Leu Gly Glu Ala Glu Ile Arg Asp Ile Ala Arg Glu Val Leu
            180                 185                 190
Lys Ile Phe Gly Glu Tyr Ser Leu Thr Asp Phe Ile Trp Pro Leu Lys
            195                 200                 205
Tyr Leu Lys Val Gly Lys Tyr Glu Lys Arg Ile Asp Asp Ile Leu Asn
210                 215                     220
Lys Phe Asp Pro Val Glu Arg Val Ile Lys Arg Arg Glu Ile
225                 230                 235                 240
Val Arg Arg Lys Asn Gly Glu Val Glu Gly Glu Ala Ser Gly
            245                 250                 255
Val Phe Leu Asp Thr Leu Leu Glu Phe Ala Glu Asp Glu Thr Met Glu
            260                 265                 270
Ile Lys Ile Thr Lys Glu Gln Ile Lys Gly Leu Val Val Asp Phe Phe
            275                 280                 285
Ser Ala Gly Thr Asp Ser Thr Ala Val Ala Thr Glu Trp Ala Leu Ala
            290                 295                 300
Glu Leu Ile Asn Asn Pro Arg Val Leu Gln Lys Ala Arg Glu Glu Val
305                 310                 315                 320
Tyr Ser Val Val Gly Lys Asp Ile Leu Val Asp Glu Val Asp Thr Gln
            325                 330                 335
Asn Leu Pro Tyr Ile Arg Ala Ile Val Lys Glu Thr Phe Arg Met His
            340                 345                 350
Pro Pro Leu Pro Val Val Lys Arg Lys Cys Thr Glu Glu Cys Glu Ile
            355                 360                 365
Asn Gly His Val Ile Pro Glu Gly Ala Leu Val Leu Phe Asn Val Trp
            370                 375                 380
Gln Val Gly Arg Asp Pro Lys Tyr Trp Asp Arg Pro Ser Glu Phe Arg
385                 390                 395                 400
Pro Glu Arg Phe Leu Glu Thr Gly Ala Glu Gly Glu Ala Gly Pro Leu
            405                 410                 415
Asp Leu Arg Gly Gln His Phe Gln Leu Leu Pro Phe Gly Ser Gly Arg
            420                 425                 430
Arg Met Cys Pro Gly Val Asn Leu Ala Thr Ser Gly Met Ala Thr Leu
            435                 440                 445
Leu Ala Ser Leu Ile Gln Cys Phe Asp Leu Gln Val Leu Gly Pro Gln
450                 455                 460
Gly Gln Ile Leu Lys Gly Asp Asp Ala Lys Val Ser Met Glu Glu Arg
465                 470                 475                 480
Ala Gly Leu Thr Val Pro Arg Ala His Ser Leu Val Cys Val Pro Leu
            485                 490                 495
Ala Arg Ile

<210> SEQ ID NO 21
<211> LENGTH: 1501
<212> TYPE: DNA
<213> ORGANISM: Lens culinaris

<400> SEQUENCE: 21
tgtttctgca cttgcgtccc acacccactg caaaatcaaa agcacttcgc catctcccaa    60
acccaccaag cccaaagcct cgtcttccct tcataggaca ccttcatctc ttaaaagaca   120
aacttctcca ctacgcactc atcgacctct ccaaaaaaca tggtccctta ttctctctct   180

-continued

```
actttggctc catgccaacc gttgttgcct ccacaccaga attgttcaag ctcttcctcc      240
aaacgcacga ggcaacttcc ttcaacacaa ggttccaaac ctcagccata agacgcctca      300
cctatgatag ctcagtggcc atggttccct tcggacctta ctggaagttc gtgaggaagc      360
tcatcatgaa cgaccttctc aacgccacca ctgtaaacaa gttgaggcct ttgaggaccc      420
aacagatccg caagttcctt agggttatgg cccaaggcgc agaggcacag aagcccttg       480 acttgaccga ggagcttctg aaatggacca acagcaccat ctccatgatg gtgctcggcg      540
aggctgagga gatcagagac atcgctcgcg aggttcttaa gatctttggc gaatacagcc      600
tcactgactt catctggcca ttgaagcatc tcaaggttgg aaagtatgag aagaggatcg      660
acgacatctt gaacaagttc gaccctgtcg ttgaaagagt catcaagaag cgccgtgaga      720
tcgtgaggag gagaaagaac ggagaggttg ttgagggtga ggtcagcggg gttttccttg      780
acactttgct tgaattcgct gaggatgaga ccatggagat caaaatcacc aaggaccaca      840
tcaagggtct tgttgtcgac tttttctcgg caggaacaga ctccacagcg gtggcaacag      900
agtgggcatt ggcagaactc atcaacaatc ctaaggtgtt ggaaaaggct cgtgaggagg      960
tctacagtgt tgtgggaaag gacagacttg tggacgaagt tgacactcaa aaccttcctt     1020
acattagagc aatcgtgaag gagacattcc gcatgcaccc gccactccca gtggtcaaaa     1080
gaaagtgcac agaagagtgt gagattaatg gatgtgtgac cccagaggga gcattgattc     1140
tcttcaatgt atggcaagta ggaagagacc ccaaatactg ggacagacca tcggagttcc     1200
gtcctgagag gttcctagag acaggggctg aaggggaagc aaggcctctt gatcttaggg     1260
gacgacattt tcaacttctc ccatttgggt ctgggaggag aatgtgccct ggagtcaatc     1320
tggctacttc gggaatggca acacttcttg catctcttat tcagtgcttt gacttgcagg     1380
tgctgggtcc acaaggacag atattgaagg gtggtgacgc caaagttagc atggaagaga     1440
gagccggcct cactgttcca agggcacata gtcttgtctg tgttccactt gcaaggatcg     1500
g                                                                    1501
```

<210> SEQ ID NO 22
<211> LENGTH: 499
<212> TYPE: PRT
<213> ORGANISM: Lens culinaris

<400> SEQUENCE: 22

```
Phe Leu His Leu Arg Pro Thr Pro Thr Ala Lys Ser Lys Ala Leu Arg
1               5                  10                  15

His Leu Pro Asn Pro Pro Ser Pro Lys Pro Arg Leu Pro Phe Ile Gly
                20                  25                  30

His Leu His Leu Leu Lys Asp Lys Leu His Tyr Ala Leu Ile Asp
        35                  40                  45

Leu Ser Lys Lys His Gly Pro Leu Phe Ser Leu Tyr Phe Gly Ser Met
    50                  55                  60

Pro Thr Val Val Ala Ser Thr Pro Glu Leu Phe Lys Leu Phe Leu Gln
65                  70                  75                  80

Thr His Glu Ala Thr Ser Phe Asn Thr Arg Phe Gln Thr Ser Ala Ile
                85                  90                  95

Arg Arg Leu Thr Tyr Asp Ser Ser Val Ala Met Val Pro Phe Gly Pro
                100                 105                 110

Tyr Trp Lys Phe Val Arg Lys Leu Ile Met Asn Asp Leu Leu Asn Ala
                115                 120                 125

Thr Thr Val Asn Lys Leu Arg Pro Leu Arg Thr Gln Gln Ile Arg Lys
```

```
            130                 135                 140
Phe Leu Arg Val Met Ala Gln Gly Ala Glu Ala Gln Lys Pro Leu Asp
145                 150                 155                 160

Leu Thr Glu Glu Leu Leu Lys Trp Thr Asn Ser Thr Ile Ser Met Met
                165                 170                 175

Val Leu Gly Glu Ala Glu Ile Arg Asp Ile Ala Arg Glu Val Leu
            180                 185                 190

Lys Ile Phe Gly Glu Tyr Ser Leu Thr Asp Phe Ile Trp Pro Leu Lys
                195                 200                 205

His Leu Lys Val Gly Lys Tyr Glu Lys Arg Ile Asp Asp Ile Leu Asn
            210                 215                 220

Lys Phe Asp Pro Val Val Glu Arg Val Ile Lys Arg Arg Glu Ile
225                 230                 235                 240

Val Arg Arg Lys Asn Gly Glu Val Val Glu Gly Glu Val Ser Gly
                245                 250                 255

Val Phe Leu Asp Thr Leu Leu Glu Phe Ala Glu Asp Glu Thr Met Glu
            260                 265                 270

Ile Lys Ile Thr Lys Asp His Ile Lys Gly Leu Val Val Asp Phe Phe
                275                 280                 285

Ser Ala Gly Thr Asp Ser Thr Ala Val Ala Thr Glu Trp Ala Leu Ala
            290                 295                 300

Glu Leu Ile Asn Asn Pro Lys Val Leu Glu Lys Ala Arg Glu Glu Val
305                 310                 315                 320

Tyr Ser Val Val Gly Lys Asp Arg Leu Val Asp Glu Val Asp Thr Gln
                325                 330                 335

Asn Leu Pro Tyr Ile Arg Ala Ile Val Lys Glu Thr Phe Arg Met His
                340                 345                 350

Pro Pro Leu Pro Val Val Lys Arg Cys Thr Glu Glu Cys Glu Ile
            355                 360                 365

Asn Gly Cys Val Thr Pro Glu Gly Ala Leu Ile Leu Phe Asn Val Trp
            370                 375                 380

Gln Val Gly Arg Asp Pro Lys Tyr Trp Asp Arg Pro Ser Glu Phe Arg
385                 390                 395                 400

Pro Glu Arg Phe Leu Glu Thr Gly Ala Glu Gly Glu Ala Arg Pro Leu
                405                 410                 415

Asp Leu Arg Gly Arg His Phe Gln Leu Leu Pro Phe Gly Ser Gly Arg
                420                 425                 430

Arg Met Cys Pro Gly Val Asn Leu Ala Thr Ser Gly Met Ala Thr Leu
                435                 440                 445

Leu Ala Ser Leu Ile Gln Cys Phe Asp Leu Gln Val Leu Gly Pro Gln
450                 455                 460

Gly Gln Ile Leu Lys Gly Gly Asp Ala Lys Val Ser Met Glu Glu Arg
465                 470                 475                 480

Ala Gly Leu Thr Val Pro Arg Ala His Ser Leu Val Cys Val Pro Leu
                485                 490                 495

Ala Arg Ile

<210> SEQ ID NO 23
<211> LENGTH: 1566
<212> TYPE: DNA
<213> ORGANISM: Phaseolus aureus

<400> SEQUENCE: 23
atgttgctgg aacttgcact tggttttattg gttttggctc tgtttctgca cttgcgtccc      60
```

-continued

```
actcccactg caaaatcaaa agcacttcgc catctcccaa acccaccaag cccaaagcct      120
cgtcttccct tcataggaca ccttcatctc ttaaaagaca aacttctcca ctacgcactc      180
atcgacctct ccaaaaaaca tggtccctta ttctctctct actttggctc catgccaacc      240
gttgttgcct ccacaccaga attgttcaag ctcttcctcc aaacgcacga ggcaacttcc      300
ttcaacacaa ggttccaaac ctcagccata agacgcctca cctatgatag ctcagtggcc      360
atggttccct tcggacctta ctggaagttc gtgaggaagc tcatcatgaa cgaccttctc      420
aacgccacca ctgtaaacaa gttgaggcct tgaggaccc aacagatccg caagttcctt       480
agggttatgg cccaaggcgc agaggcacag aagccccttg acttgaccga ggagcttctg      540
aaatggacca acagcaccat ctccatgatg atgctcggcg aggctgagga gatcagagac      600
atcgctcgcg aggttcttaa gatctttggc gaatacagcc tcactgactt catctggcca      660
ttgaagcatc tcaaggttgg aaagtatgag aagaggatcg acgacatctt gaacaagttc      720
gaccctgtcg ttgaaagagt catcaagaag cgccgtgaga tcgtgaggag gagaaagaac      780
ggagaggttg ttgagggtga ggtcagcggg gttttccttg cactttgct tgaattcgct       840 gaggatgaga ccatggagat caaaatcacc aaggaccaca tcaagggtct tgttgtcgac      900
tttttctcgg caggaacaga ctccacagcg gtggcaacag agtgggcatt ggcagaactc      960
atcaacaatc ctaaggtgtt ggaaaaggct cgtgaggagg cctacagtgt tgtgggaaag     1020
gacagacttg tggacgaagt tgacactcaa aaccttcctt acattagagc aatcgtgaag     1080
gagacattcc gcatgcaccc gccactccca gtggtcaaaa gaaagtgcac agaagagtgt     1140
gagattaatg gatatgtgat cccagaggga gcattgattc tcttcaatgt atggcaagta     1200
ggaagagacc ccaaatactg ggacagacca tcggagttcc gtcctgagag gttcctagag     1260 acagggctg aagggaagc aaggcctctt gatcttaggg gacaacattt tcaacttctc       1320
ccatttgggt ctgggaggag aatgtgccct ggagtcaatc tggctacttc gggaatggca     1380
acacttctcg catctcttat tcagtgcttt gacttgcaag tgctgggtcc acaaggacag     1440
atattgaagg gtggtgacgc caaagttagc atggaagaga gagccggcct cactgttcca     1500
agggcacata gtcttgtctg tgttccactt gcaaggatcg gcgttgcatc taaactcctt     1560
tctaaa                                                                1566
```

<210> SEQ ID NO 24
<211> LENGTH: 522
<212> TYPE: PRT
<213> ORGANISM: Phaseolus aureus

<400> SEQUENCE: 24

```
Met Leu Leu Glu Leu Ala Leu Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Ser Pro Lys Pro Arg Leu Pro Phe Ile Gly His Leu
        35                  40                  45

His Leu Leu Lys Asp Lys Leu His Tyr Ala Leu Ile Asp Leu Ser
    50                  55                  60

Lys Lys His Gly Pro Leu Phe Ser Leu Tyr Phe Gly Ser Met Pro Thr
65                  70                  75                  80

Val Val Ala Ser Thr Pro Glu Leu Phe Lys Leu Phe Leu Gln Thr His
            85                  90                  95
```

-continued

```
Glu Ala Thr Ser Phe Asn Thr Arg Phe Gln Thr Ser Ala Ile Arg Arg
            100                 105                 110
Leu Thr Tyr Asp Ser Ser Val Ala Met Val Pro Phe Gly Pro Tyr Trp
            115                 120                 125
Lys Phe Val Arg Lys Leu Ile Met Asn Asp Leu Leu Asn Ala Thr Thr
            130                 135                 140
Val Asn Lys Leu Arg Pro Leu Arg Thr Gln Gln Ile Arg Lys Phe Leu
145                 150                 155                 160
Arg Val Met Ala Gln Gly Ala Glu Ala Gln Lys Pro Leu Asp Leu Thr
                165                 170                 175
Glu Glu Leu Leu Lys Trp Thr Asn Ser Thr Ile Ser Met Met Met Leu
            180                 185                 190
Gly Glu Ala Glu Glu Ile Arg Asp Ile Ala Arg Glu Val Leu Lys Ile
            195                 200                 205
Phe Gly Glu Tyr Ser Leu Thr Asp Phe Ile Trp Pro Leu Lys His Leu
            210                 215                 220
Lys Val Gly Lys Tyr Glu Lys Arg Ile Asp Asp Ile Leu Asn Lys Phe
225                 230                 235                 240
Asp Pro Val Val Glu Arg Val Ile Lys Lys Arg Glu Ile Val Arg
                245                 250                 255
Arg Arg Lys Asn Gly Glu Val Val Glu Gly Glu Val Ser Gly Val Phe
            260                 265                 270
Leu Asp Thr Leu Leu Glu Phe Ala Glu Asp Glu Thr Met Glu Ile Lys
            275                 280                 285
Ile Thr Lys Asp His Ile Lys Gly Leu Val Val Asp Phe Phe Ser Ala
            290                 295                 300
Gly Thr Asp Ser Thr Ala Val Ala Thr Glu Trp Ala Leu Ala Glu Leu
305                 310                 315                 320
Ile Asn Asn Pro Lys Val Leu Glu Lys Ala Arg Glu Glu Ala Tyr Ser
                325                 330                 335
Val Val Gly Lys Asp Arg Leu Val Asp Glu Val Asp Thr Gln Asn Leu
            340                 345                 350
Pro Tyr Ile Arg Ala Ile Val Lys Glu Thr Phe Arg Met His Pro Pro
            355                 360                 365
Leu Pro Val Val Lys Arg Lys Cys Thr Glu Glu Cys Glu Ile Asn Gly
            370                 375                 380
Tyr Val Ile Pro Glu Gly Ala Leu Ile Leu Phe Asn Val Trp Gln Val
385                 390                 395                 400
Gly Arg Asp Pro Lys Tyr Trp Asp Arg Pro Ser Glu Phe Arg Pro Glu
                405                 410                 415
Arg Phe Leu Glu Thr Gly Ala Glu Gly Glu Ala Arg Pro Leu Asp Leu
            420                 425                 430
Arg Gly Gln His Phe Gln Leu Leu Pro Phe Gly Ser Gly Arg Arg Met
            435                 440                 445
Cys Pro Gly Val Asn Leu Ala Thr Ser Gly Met Ala Thr Leu Leu Ala
            450                 455                 460
Ser Leu Ile Gln Cys Phe Asp Leu Gln Val Leu Gly Pro Gln Gly Gln
465                 470                 475                 480
Ile Leu Lys Gly Gly Asp Ala Lys Val Ser Met Glu Glu Arg Ala Gly
                485                 490                 495
Leu Thr Val Pro Arg Ala His Ser Leu Val Cys Val Pro Leu Ala Arg
            500                 505                 510
Ile Gly Val Ala Ser Lys Leu Leu Ser Lys
```

```
          515             520
```

<210> SEQ ID NO 25
<211> LENGTH: 1566
<212> TYPE: DNA
<213> ORGANISM: Phaseolus aureus

<400> SEQUENCE: 25

| | | | | | |
|---|---|---|---|---|---|
| atgttgctgg | aacttgcact | tggtttattg | gttttggctc | tgtttctgca | cttgcgtccc | 60 |
| acacccactg | caaaatcaaa | agcacttcgc | catctcccaa | acccaccaag | cccaaagcct | 120 |
| cgtcttccct | tcataggaca | ccttcatctc | ttaaaagaca | aacttctcca | ctacgcgctc | 180 |
| atcgacctct | ccaaaaaaca | tggtccctta | ttctctctct | actttggctc | catgccaacc | 240 |
| gttgttgcct | ccacaccaga | attgttcaag | ctcttcctcc | aaacgcacga | ggcaacttcc | 300 |
| ttcaacacaa | ggttccaaac | ctcagccata | agacgcctca | cctatgatag | ctcagtggcc | 360 |
| atggttccct | tcggacctta | ctggaagttc | gtgaggaagc | tcatcatgaa | cgaccttctc | 420 |
| aacgccacca | ctgtaaacaa | gttgaggcct | tgaggaccc | aacagatccg | caagttcctt | 480 |
| agggctatgg | cccaaggcgc | agaggcacag | aagccccttg | acttgaccga | ggagcttctg | 540 |
| aaatggacca | acagcaccat | ctccatgatg | atgctcggcg | aggctgagga | gatcagagac | 600 |
| atcgctcgcg | aggttcttaa | gatctttggc | gaatacagcc | tcactgactt | catctggcca | 660 |
| ttgaagcatc | tcaaggttgg | aaagtatgag | aagaggatcg | acgacatctt | gaacaagttc | 720 |
| gaccctgtcg | ttgaaagagt | catcaagaag | cgccgtgaga | tcgtgaggag | agaaagaac | 780 |
| ggagaggttg | ttgagggtga | ggtcagcggg | gttttccttg | acactttgct | tgaattcgct | 840 |
| gaggatgaga | ccatggagat | caaaatcacc | aaggaccaca | tcaagggtct | tgttgtcgac | 900 |
| tttttctcgg | caggaacaga | ctccacagcg | gtggcaacag | agtgggcatt | ggcagaactc | 960 |
| atcaacaatc | ctaaggtgtt | ggaaaaggct | cgtgaggagg | tctacagtgt | tgtgggaaag | 1020 |
| gacagacttg | tggacgaagt | tgacactcaa | aaccttcctt | acattagagc | aatcgtgaag | 1080 |
| gagacattcc | gcatgcaccc | gccactccca | gtggtcaaaa | gaaagtgcac | ggaagagtgt | 1140 |
| gagattaatg | gatatgtgat | cccagaggga | gcattgattc | tcttcaatgt | atggcaagta | 1200 |
| ggaagagacc | ccaaatactg | ggacagacca | tcggagttcc | gtcctgagag | gttcctagag | 1260 |
| acagggctg | aagggaagc | aaggcctctt | gatcttaggg | gacaacattt | tcaacttctc | 1320 |
| ccatttgggt | ctgggaggag | aatgtgccct | ggagtcaatc | tggctacttc | gggaatggca | 1380 |
| acacttcttg | catctcttat | tcagtgcttt | gacttgcaag | tgctgggtcc | acaaggacag | 1440 |
| atattgaagg | gtggtgacgc | caaagttagc | atggaagaga | gagccggcct | cactgttcca | 1500 |
| agggcacata | gtcttgtctg | tgttccactt | gcaaggatcg | gcgttgcatc | taaactcctt | 1560 |
| tcttaa | | | | | | 1566 |

<210> SEQ ID NO 26
<211> LENGTH: 521
<212> TYPE: PRT
<213> ORGANISM: Phaseolus aureus

<400> SEQUENCE: 26

```
Met Leu Leu Glu Leu Ala Leu Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
```

-continued

```
                35                  40                  45
His Leu Leu Lys Asp Lys Leu Leu His Tyr Ala Leu Ile Asp Leu Ser
 50                  55                  60

Lys Lys His Gly Pro Leu Phe Ser Leu Tyr Phe Gly Ser Met Pro Thr
 65                  70                  75                  80

Val Val Ala Ser Thr Pro Glu Leu Phe Lys Leu Phe Leu Gln Thr His
                 85                  90                  95

Glu Ala Thr Ser Phe Asn Thr Arg Phe Gln Thr Ser Ala Ile Arg Arg
                100                 105                 110

Leu Thr Tyr Asp Ser Ser Val Ala Met Val Pro Phe Gly Pro Tyr Trp
                115                 120                 125

Lys Phe Val Arg Lys Leu Ile Met Asn Asp Leu Leu Asn Ala Thr Thr
130                 135                 140

Val Asn Lys Leu Arg Pro Leu Arg Thr Gln Gln Ile Arg Lys Phe Leu
145                 150                 155                 160

Arg Ala Met Ala Gln Gly Ala Glu Ala Gln Lys Pro Leu Asp Leu Thr
                165                 170                 175

Glu Glu Leu Leu Lys Trp Thr Asn Ser Thr Ile Ser Met Met Met Leu
                180                 185                 190

Gly Glu Ala Glu Glu Ile Arg Asp Ile Ala Arg Glu Val Leu Lys Ile
                195                 200                 205

Phe Gly Glu Tyr Ser Leu Thr Asp Phe Ile Trp Pro Leu Lys His Leu
210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Glu Val Ser Gly Val Phe
                260                 265                 270

Leu Asp Thr Leu Leu Glu Phe Ala Glu Asp Glu Thr Met Glu Ile Lys
                275                 280                 285

Ile Thr Lys Asp His Ile Lys Gly Leu Val Val Asp Phe Phe Ser Ala
290                 295                 300

Gly Thr Asp Ser Thr Ala Val Ala Thr Glu Trp Ala Leu Ala Glu Leu
305                 310                 315                 320

Ile Asn Asn Pro Lys Val Leu Glu Lys Ala Arg Glu Glu Val Tyr Ser
                325                 330                 335

Val Val Gly Lys Asp Arg Leu Val Asp Glu Val Asp Thr Gln Asn Leu
                340                 345                 350

Pro Tyr Ile Arg Ala Ile Val Lys Glu Thr Phe Arg Met His Pro Pro
                355                 360                 365

Leu Pro Val Val Lys Arg Lys Cys Thr Glu Glu Cys Glu Ile Asn Gly
370                 375                 380

Tyr Val Ile Pro Glu Gly Ala Leu Ile Leu Phe Asn Val Trp Gln Val
385                 390                 395                 400

Gly Arg Asp Pro Lys Tyr Trp Asp Arg Pro Ser Glu Phe Arg Pro Glu
                405                 410                 415

Arg Phe Leu Glu Thr Gly Ala Glu Gly Glu Ala Arg Pro Leu Asp Leu
                420                 425                 430

Arg Gly Gln His Phe Gln Leu Leu Pro Phe Gly Ser Gly Arg Arg Met
                435                 440                 445

Cys Pro Gly Val Asn Leu Ala Thr Ser Gly Met Ala Thr Leu Leu Ala
450                 455                 460
```

```
Ser Leu Ile Gln Cys Phe Asp Leu Gln Val Leu Gly Pro Gln Gly Gln
465                 470                 475                 480

Ile Leu Lys Gly Gly Asp Ala Lys Val Ser Met Glu Glu Arg Ala Gly
                485                 490                 495

Leu Thr Val Pro Arg Ala His Ser Leu Val Cys Val Pro Leu Ala Arg
            500                 505                 510

Ile Gly Val Ala Ser Lys Leu Leu Ser
            515                 520
```

<210> SEQ ID NO 27
<211> LENGTH: 1566
<212> TYPE: DNA
<213> ORGANISM: Phaseolus aureus

<400> SEQUENCE: 27

| | | | | | |
|---|---|---|---|---|---|
| atgttgctgg | aacttgcact | tggtttattg | gttttggctc | tgtttctgca | cttgcgtccc | 60 |
| acacccactg | caaaatcaaa | agcacttcgc | catctcccaa | acccaccaag | cccaaagcct | 120 |
| cgtcttccct | tcataggaca | ccttcatctc | ttaaaagaca | aacttctcca | ctacgcactc | 180 |
| atcgacctct | ccaaaaaaca | tggtcccttca | ttctctctct | actttggctc | catgccaacc | 240 |
| gttgttgcct | ccacaccaga | attgttcaag | ctcttcctcc | aaacgcacga | ggcaacttcc | 300 |
| ttcaacacaa | ggttccaaac | ctcagccata | agacgcctca | cctatgatag | ctcagtggcc | 360 |
| atggttccct | tcggacctta | ctggaagttc | gtgaggaagc | tcatcatgaa | cgaccttctc | 420 |
| aacgccacca | ctgtaaacaa | gttgaggcct | ttgaggaccc | aacagatccg | caagttcctt | 480 |
| agggttatgg | cccaaggcgc | agaggcacag | aagccccttg | acttgaccga | ggagcttctg | 540 |
| aaaatggacca | acagcaccat | ctccatgatg | atgctcggcg | aggctgagga | gatcagagac | 600 |
| atcgctcgcg | aggttcttaa | gatctttggc | gaatacagcc | tcactgactt | catctggcca | 660 |
| ttgaagcatc | tcaaggttgg | aaagtatgag | aagaggatcg | acgacatctt | gaacaagttc | 720 |
| gaccctgtcg | ttgaaagagt | catcaagaag | cgccgtgaga | tcgtgaggag | gagaaagaac | 780 |
| ggagaggttg | ttgagggtga | ggtcagcggg | gttttccttg | acactttgct | tgaattcgct | 840 |
| gaggatgaga | ccacggagat | caaaatcacc | aaggaccaca | tcaagggtct | tgttgtcgac | 900 |
| tttttctcgg | caggaacaga | ctccacagcg | gtggcaacag | agtgggcatt | ggcagaactc | 960 |
| atcaacaatc | ctaaggtgtt | ggaaaaggct | cgtgaggagg | tctacagtgt | tgtgggaaag | 1020 |
| gacagacttg | tggacgaagt | tgacactcaa | aaccttcctt | acattagagc | aatcgtgaag | 1080 |
| gagacattcc | gcatgcaccc | gccactccca | gtggtcaaaa | gaaagtgcac | agaagagtgt | 1140 |
| gagattaatg | gatatgtgat | cccagaggga | gcattgattc | tcttcaatgt | atggcaagta | 1200 |
| ggaagagacc | ccaaatactg | ggacagacca | tcggagttcc | gtcctgagag | gttcctagag | 1260 |
| acagggctg | aagggggaagc | aaggcctctt | gatcttaggg | gacaacattt | tcaacttctc | 1320 |
| ccatttgggt | ctgggaggag | aatgtgccct | ggagtcaatc | tggctacttc | gggaatggca | 1380 |
| acacttcttg | catctcttat | tcagtgcttt | gacttgcaag | tgctgggtcc | acaaggacag | 1440 |
| atattgaagg | gtggtgacgc | caaagttagc | atggaagaga | gggccggcct | cactgttcca | 1500 |
| agggcacata | gtcttgtctg | tgttccactt | gcaaggatcg | gcgttgcatc | taaactcctt | 1560 |
| tcttaa | | | | | | 1566 |

<210> SEQ ID NO 28
<211> LENGTH: 521
<212> TYPE: PRT

<213> ORGANISM: Phaseolus aureus

<400> SEQUENCE: 28

```
Met Leu Leu Glu Leu Ala Leu Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Thr Ser Phe Asn Thr Arg Phe Gln Thr Ser Ala Ile Arg Arg
            100                 105                 110

Leu Thr Tyr Asp Ser Ser Val Ala Met Val Pro Phe Gly Pro Tyr Trp
        115                 120                 125

Lys Phe Val Arg Lys Leu Ile Met Asn Asp Leu Leu Asn Ala Thr Thr
    130                 135                 140

Val Asn Lys Leu Arg Pro Leu Arg Thr Gln Gln Ile Arg Lys Phe Leu
145                 150                 155                 160

Arg Val Met Ala Gln Gly Ala Glu Ala Gln Lys Pro Leu Asp Leu Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys His Leu
    210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Glu Val Ser Gly Val Phe
            260                 265                 270

Leu Asp Thr Leu Leu Glu Phe Ala Glu Asp Glu Thr Thr Glu Ile Lys
        275                 280                 285

Ile Thr Lys Asp His Ile Lys Gly Leu Val Val Asp Phe Phe Ser Ala
    290                 295                 300

Gly Thr Asp Ser Thr Ala Val Ala Thr Glu Trp Ala Leu Ala Glu Leu
305                 310                 315                 320

Ile Asn Asn Pro Lys Val Leu Glu Lys Ala Arg Glu Glu Val Tyr Ser
                325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
        355                 360                 365

Leu Pro Val Val Lys Arg Lys Cys Thr Glu Glu Cys Glu Ile Asn Gly
    370                 375                 380

Tyr Val Ile Pro Glu Gly Ala Leu Ile Leu Phe Asn Val Trp Gln Val
385                 390                 395                 400
```

```
Gly Arg Asp Pro Lys Tyr Trp Asp Arg Pro Ser Glu Phe Arg Pro Glu
                405                 410                 415

Arg Phe Leu Glu Thr Gly Ala Glu Gly Glu Ala Arg Pro Leu Asp Leu
            420                 425                 430

Arg Gly Gln His Phe Gln Leu Leu Pro Phe Gly Ser Gly Arg Arg Met
        435                 440                 445

Cys Pro Gly Val Asn Leu Ala Thr Ser Gly Met Ala Thr Leu Leu Ala
    450                 455                 460

Ser Leu Ile Gln Cys Phe Asp Leu Gln Val Leu Gly Pro Gln Gly Gln
465                 470                 475                 480

Ile Leu Lys Gly Gly Asp Ala Lys Val Ser Met Glu Glu Arg Ala Gly
                485                 490                 495

Leu Thr Val Pro Arg Ala His Ser Leu Val Cys Val Pro Leu Ala Arg
            500                 505                 510

Ile Gly Val Ala Ser Lys Leu Leu Ser
        515                 520
```

<210> SEQ ID NO 29
<211> LENGTH: 1566
<212> TYPE: DNA
<213> ORGANISM: Phaseolus aureus

<400> SEQUENCE: 29

```
atgttgctgg aacttgcact tggtttattg gttttggctc tgtttctgca cttgcgtccc      60
acacccactg caaaatcaaa agcacttcgc catctcccaa acccaccaag cccaaagcct     120
cgtcttccct tcataggaca ccttcatctc ttaaaagaca aacttctcca ctacgcactc     180
atcgacctct ccaaaaaaca tggtccctta ttctctctct actttggctc catgccaacc     240
gttgttgcct ccacaccaga attgttcaag ctcttcctcc aaacgcacga ggcaacttcc     300
ttcaacacaa ggttccaaac ctcagccata agacgcctca cctatgatag ctcagtggcc     360
atggttccct tcggacctta ctggaagttc gtgaggaagc tcatcatgaa cgaccttctc     420
aacgccacca ctgtaaacaa gttgaggcct tgaggaccc aacagatccg caagttcctt     480
agggttatgg cccaaggcgc agaggcacag aagcccttg acttgaccga ggagcttctg     540
aaatggacca acagcaccat ctccatgatg atgctcggcg aggctgagga gatcagagac     600
atcgctcgcg aggttcttaa gatctttggc gaatacagcc tcactgactt catctggcca     660
ttgaagcatc tcaaggttgg aaagtatgag aagaggatcg acgacatctt gaacaagttc     720
gaccctgtcg ttgaaagagt catcaagaag cgccgtgaga tcgtgaggag gagaaagaac     780
ggagaggttg ttgagggtga ggtcagcggg gttttccttg cactttgct tgaattcgct     840
gaggatgaga ccatggagat caaaatcacc aaggaccaca tcaagggtct tgttgtcgac     900
ttttctcgg caggaacaga ctccacagcg gaggcaacag agtgggcatt ggcagaactc     960
atcaacaatc taaggtgtt ggaaaaggct cgtgaggagg tctacagtgt tgtgggaaag    1020
gacagacttg tggacgaagt tgacactcaa aaccttcctt acattagagc aatcgtgaag    1080
gagacattcc gcatgcaccc gccactccca gtggtcaaaa gaaagtgcac agaagagtgt    1140
gagattaatg gatatgtgat cccagagga gcattgattc tcttcaatgt atggcaagta    1200
ggaagagacc ccaaatactg gacagacca tcggagttcc gtcctgagag gttcctagag    1260
acaggggctg aagggaagc aaggcctctt gatcttaggg acaacatttt caacttctcc    1320
ccatttgggt ctgggaggag aatgtgccct ggagtcaatc tggctacttc gggaatggca    1380
acacttcttg catctcttat tcagtgcttt gacttgcaag tgctgggtcc acaaggacag    1440
```

-continued

```
atattgaagg gtggtgacgc caaagttagc atggaagaga gagccggcct cactgttcca    1500
agggcacata gtcttgtctg tgttccactt gcaaggatcg gcgttgcatc taaactcctt    1560
tcttaa                                                                1566
```

<210> SEQ ID NO 30
<211> LENGTH: 521
<212> TYPE: PRT
<213> ORGANISM: Phaseolus aureus

<400> SEQUENCE: 30

```
Met Leu Leu Glu Leu Ala Leu Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Thr Ser Phe Asn Thr Arg Phe Gln Thr Ser Ala Ile Arg Arg
            100                 105                 110

Leu Thr Tyr Asp Ser Ser Val Ala Met Val Pro Phe Gly Pro Tyr Trp
        115                 120                 125

Lys Phe Val Arg Lys Leu Ile Met Asn Asp Leu Leu Asn Ala Thr Thr
130                 135                 140

Val Asn Lys Leu Arg Pro Leu Arg Thr Gln Gln Ile Arg Lys Phe Leu
145                 150                 155                 160

Arg Val Met Ala Gln Gly Ala Glu Ala Gln Lys Pro Leu Asp Leu Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys His Leu
    210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Glu Ile Val Arg
                245                 250                 255

Arg Arg Lys Asn Gly Glu Val Val Glu Gly Glu Val Ser Gly Val Phe
            260                 265                 270

Leu Asp Thr Leu Leu Glu Phe Ala Glu Asp Glu Thr Met Glu Ile Lys
        275                 280                 285

Ile Thr Lys Asp His Ile Lys Gly Leu Val Val Asp Phe Phe Ser Ala
    290                 295                 300

Gly Thr Asp Ser Thr Ala Glu Ala Thr Glu Trp Ala Leu Ala Glu Leu
305                 310                 315                 320

Ile Asn Asn Pro Lys Val Leu Glu Lys Ala Arg Glu Glu Val Tyr Ser
                325                 330                 335

Val Val Gly Lys Asp Arg Leu Val Asp Glu Val Asp Thr Gln Asn Leu
```

```
                    340              345              350
     Pro Tyr Ile Arg Ala Ile Val Lys Glu Thr Phe Arg Met His Pro Pro
              355                  360                  365
     Leu Pro Val Val Lys Arg Lys Cys Thr Glu Glu Cys Glu Ile Asn Gly
          370                  375                  380
     Tyr Val Ile Pro Glu Gly Ala Leu Ile Leu Phe Asn Val Trp Gln Val
     385                  390                  395                  400
     Gly Arg Asp Pro Lys Tyr Trp Asp Arg Pro Ser Glu Phe Arg Pro Glu
                      405                  410                  415
     Arg Phe Leu Glu Thr Gly Ala Glu Gly Glu Ala Arg Pro Leu Asp Leu
                  420                  425                  430
     Arg Gly Gln His Phe Gln Leu Leu Pro Phe Gly Ser Gly Arg Arg Met
              435                  440                  445
     Cys Pro Gly Val Asn Leu Ala Thr Ser Gly Met Ala Thr Leu Leu Ala
          450                  455                  460
     Ser Leu Ile Gln Cys Phe Asp Leu Gln Val Leu Gly Pro Gln Gly Gln
     465                  470                  475                  480
     Ile Leu Lys Gly Gly Asp Ala Lys Val Ser Met Glu Glu Arg Ala Gly
                      485                  490                  495
     Leu Thr Val Pro Arg Ala His Ser Leu Val Cys Val Pro Leu Ala Arg
                  500                  505                  510
     Ile Gly Val Ala Ser Lys Leu Leu Ser
              515                  520

<210> SEQ ID NO 31
<211> LENGTH: 1566
<212> TYPE: DNA
<213> ORGANISM: Trifolium pratense

<400> SEQUENCE: 31
atgttgctgg aacttgcact tggtttattg gttttggctc tgtttctgca cttgcgtccc      60
acacccactg caaaatcaaa agcacttcgc catctcccaa acccaccaag cccaaagcct     120
cgtcttccct tcataggaca ccttcatctc ttaaaagaca aacttctcca ctacgcactc     180
atcgacctct ccaaaaaaca tggtcccttta ttctctctct actttggctc catgccaacc     240
gttgttgcct ccacaccaga attgttcaag ctcttcctcc aaacgcacga ggcaacttcc     300
ttcaacacaa ggttccaaac ctcagccata agacgcctca cctatgatag ctcagtggcc     360
atggttccca tcggacctta ctggaagttc gtgaggaagc tcatcatgaa cgaccttctc     420
aacgccacca ctgtaaacaa gttgaggcct tgaggaccc aacagatccg caagttcctt     480
agggttatgg cccaaggcgc agaggcacag aagcccttg acttgaccga ggagcttctg     540
aaatggacca acagcaccat ctccatgatg atgctcggcg aggctgagga gatcagagac     600
atcgctcgcg aggttcttaa gatctttggc gaatacagcc tcactgactt catctggcca     660
ttgaagcatc tcaaggttgg aaagtatgag aagaggatcg acgacatctt gaacaagttc     720
gaccctgtcg ttgaaagagt catcaagaag cgccgtgaga tcgtgaggag agaaaagaac     780
ggagaggttg atgagggtga ggtcagcggg gttttccttg cacttttgct tgaattcgct     840
gaggatgaga ccacggagat caaaatcacc aaggaccaca tcaagggtct tgttgtcgac     900
tttttctcgg cagggacaga ctccacagcg gtggcaacag agtgggcatt ggcagaactc     960
atcaacaatc ctaaggtgtt ggaaaaggct cgtgaggagg tctacagtgt tgtgggaaag    1020
gacagacttg tggacgaagt tgacactcaa aaccttcctt acattagagc aatcgtgaag    1080
```

-continued

```
gagacattcc gcatgcaccc gccactccca gtggtcaaaa gaaagtgcac agaagagtgt    1140
gagattaatg gatatgtgat cccagaggga gcattgattc tcttcaatgt atggcaagta    1200
ggaagagacc ccaaatactg ggacagacca tcggagttcc gtcctgagag gttcctagag    1260 acagggctg  aagggaagc  aaggcctctt gatcttaggg gacaacattt tcaacttctc    1320
ccatttgggt ctgggaggag aatgtgccct ggagtcaatc tggctacttc gggaatggca    1380
acacttcttg catctcttat tcagtgcttt gacttgcaag tgctgggtcc acaaggacag    1440
atattgaagg gtggtgacgc caaagttagc atggaagaga gggccggcct cactgttcca    1500
agggcacata gtcttgtctg tgttccactt gcaaggatcg gcgttgcatc taaactcctt    1560
tcttaa                                                               1566
```

<210> SEQ ID NO 32
<211> LENGTH: 521
<212> TYPE: PRT
<213> ORGANISM: Trifolium pratense

<400> SEQUENCE: 32

```
Met Leu Leu Glu Leu Ala Leu Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Thr Ser Phe Asn Thr Arg Phe Gln Thr Ser Ala Ile Arg Arg
            100                 105                 110

Leu Thr Tyr Asp Ser Ser Val Ala Met Val Pro Ile Gly Pro Tyr Trp
        115                 120                 125

Lys Phe Val Arg Lys Leu Ile Met Asn Asp Leu Leu Asn Ala Thr Thr
    130                 135                 140

Val Asn Lys Leu Arg Pro Leu Arg Thr Gln Gln Ile Arg Lys Phe Leu
145                 150                 155                 160

Arg Val Met Ala Gln Gly Ala Glu Ala Gln Lys Pro Leu Asp Leu Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys His Leu
    210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Asp Glu Gly Glu Val Ser Gly Val Phe
            260                 265                 270

Leu Asp Thr Leu Leu Glu Phe Ala Glu Asp Glu Thr Thr Glu Ile Lys
        275                 280                 285
```

```
Ile Thr Lys Asp His Ile Lys Gly Leu Val Val Asp Phe Phe Ser Ala
    290                 295                 300
Gly Thr Asp Ser Thr Ala Val Ala Thr Glu Trp Ala Leu Ala Glu Leu
305                 310                 315                 320
Ile Asn Asn Pro Lys Val Leu Glu Lys Ala Arg Glu Glu Val Tyr Ser
                325                 330                 335
Val Val Gly Lys Asp Arg Leu Val Asp Glu Val Asp Thr Gln Asn Leu
            340                 345                 350
Pro Tyr Ile Arg Ala Ile Val Lys Glu Thr Phe Arg Met His Pro Pro
        355                 360                 365
Leu Pro Val Lys Arg Lys Cys Thr Glu Glu Cys Glu Ile Asn Gly
    370                 375                 380
Tyr Val Ile Pro Glu Gly Ala Leu Ile Leu Phe Asn Val Trp Gln Val
385                 390                 395                 400
Gly Arg Asp Pro Lys Tyr Trp Asp Arg Pro Ser Glu Phe Arg Pro Glu
                405                 410                 415
Arg Phe Leu Glu Thr Gly Ala Glu Gly Glu Ala Arg Pro Leu Asp Leu
            420                 425                 430
Arg Gly Gln His Phe Gln Leu Leu Pro Phe Gly Ser Gly Arg Arg Met
        435                 440                 445
Cys Pro Gly Val Asn Leu Ala Thr Ser Gly Met Ala Thr Leu Leu Ala
    450                 455                 460
Ser Leu Ile Gln Cys Phe Asp Leu Gln Val Leu Gly Pro Gln Gly Gln
465                 470                 475                 480
Ile Leu Lys Gly Gly Asp Ala Lys Val Ser Met Glu Glu Arg Ala Gly
                485                 490                 495
Leu Thr Val Pro Arg Ala His Ser Leu Val Cys Val Pro Leu Ala Arg
            500                 505                 510
Ile Gly Val Ala Ser Lys Leu Leu Ser
        515                 520

<210> SEQ ID NO 33
<211> LENGTH: 1566
<212> TYPE: DNA
<213> ORGANISM: Trifolium pratense

<400> SEQUENCE: 33
atgttgctgg aacttgcact tggtttattg gttttggctc tgtttctgca cttgcgtccc      60
acacccactg caaaatcaaa agcacttcgc catctcccaa acccaccaag cccaaagcct     120
cgtcttccct tcataggaca ccttcatctc ttaaaagaca aacttctcca ctacgcactc     180
atcgacctct ccaaaaaaca tggtccctta ttctctctct actttggctc catgccaacc     240
gttgttgcct ccacaccaga attgttcaag ctcttcctcc aaacgcacga ggcaacttcc     300
ttcaacacaa ggttccaaac ctcagccata agacgcctca cctatgatag ctcagtggcc     360
atggttccct tcggacctta ctggaagttc gtgaggaagc tcatcatgaa cgaccttctc     420
aacgccacca ctgtaaacaa gttgaggcct tgaggaccc aacagatccg caagttcctt     480
agggttatgg cccaaggcgc agaggcacag aagccccttg acttgaccga ggagcttctg     540
aaatggacca acagcaccat ctccatgatg atgctcggcg aggctgagga gatcagagac     600
atcgctcgcg aggttcttaa gatctttggc gaatacagcc tcactgactt catctggcca     660
ttgaagcatc tcaaggttgg aaagtatgag aagaggatcg acgacatctt gaacaagttc     720
gaccctgtcg ttgaaagagt catcaagaag cgccgtgaga tcgtgaggag gagaaagaac     780
```

```
ggagaggttg ttgagggtga ggtcagcggg gttttccttg acactttgct tgaattcgct    840
gaggatgaga ccacggagat caaaatcacc aaggaccaca tcaagggtct tgttgtcgac    900 ttttctcgg caggaacaga ctccacagcg gtggcaacag agtgggcatt ggcagaactc    960
atcaacaatc ctaaggtgtt ggaaaaggct cgtgaggagg tctacagtgt tgtgggaaag   1020
gacagacttg tggacgaagt tgacactcaa aaccttcctt acattagagc aatcgtgaag   1080
gagacattcc gcatgcaccc gccactccca gtggtcaaaa gaaagtgcac agaagagtgt   1140
gagattaatg gatatgtgat cccagaggga gcattgattc tcttcaatgt atggcaagta   1200
ggaagagacc ccaaatactg ggacagacca tcggagttcc gtcctgagag gttcctagag   1260 acagggctg aaggggaagc aaggcctctt gatcttaggg acaacatttt tcaacttctc   1320
ccatttgggt ctgggaggag aatgtgccct ggagtcaatc tggctacttc gggaatggca   1380
acacttcttg catctcttat tcagtgcttt gacttgcaag tgctgggtcc acaaggacag   1440
atattgaagg gtggtgacgc caaagttagc atggaagaga gggccggcct cactgttcca   1500
agggcacata gtcttgtctg tgttccactt gcaaggatcg gcgttgcatc taaactcctt   1560
tcttaa                                                              1566
```

<210> SEQ ID NO 34
<211> LENGTH: 521
<212> TYPE: PRT
<213> ORGANISM: Trifolium pratense

<400> SEQUENCE: 34

```
Met Leu Leu Glu Leu Ala Leu Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Thr Ser Phe Asn Thr Arg Phe Gln Thr Ser Ala Ile Arg Arg
            100                 105                 110

Leu Thr Tyr Asp Ser Ser Val Ala Met Val Pro Phe Gly Pro Tyr Trp
        115                 120                 125

Lys Phe Val Arg Lys Leu Ile Met Asn Asp Leu Leu Asn Ala Thr Thr
    130                 135                 140

Val Asn Lys Leu Arg Pro Leu Arg Thr Gln Gln Ile Arg Lys Phe Leu
145                 150                 155                 160

Arg Val Met Ala Gln Gly Ala Glu Ala Gln Lys Pro Leu Asp Leu Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys His Leu
    210                 215                 220
```

```
Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Glu Val Ser Gly Val Phe
            260                 265                 270

Leu Asp Thr Leu Leu Glu Phe Ala Glu Asp Glu Thr Thr Glu Ile Lys
        275                 280                 285

Ile Thr Lys Asp His Ile Lys Gly Leu Val Val Asp Phe Phe Ser Ala
    290                 295                 300

Gly Thr Asp Ser Thr Ala Val Ala Thr Glu Trp Ala Leu Ala Glu Leu
305                 310                 315                 320

Ile Asn Asn Pro Lys Val Leu Glu Lys Ala Arg Glu Glu Val Tyr Ser
                325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
        355                 360                 365

Leu Pro Val Val Lys Arg Lys Cys Thr Glu Glu Cys Glu Ile Asn Gly
370                 375                 380

Tyr Val Ile Pro Glu Gly Ala Leu Ile Leu Phe Asn Val Trp Gln Val
385                 390                 395                 400

Gly Arg Asp Pro Lys Tyr Trp Asp Arg Pro Ser Glu Phe Arg Pro Glu
                405                 410                 415

Arg Phe Leu Glu Thr Gly Ala Glu Gly Glu Ala Arg Pro Leu Asp Leu
            420                 425                 430

Arg Gly Gln His Phe Gln Leu Leu Pro Phe Gly Ser Gly Arg Arg Met
        435                 440                 445

Cys Pro Gly Val Asn Leu Ala Thr Ser Gly Met Ala Thr Leu Leu Ala
450                 455                 460

Ser Leu Ile Gln Cys Phe Asp Leu Gln Val Leu Gly Pro Gln Gly Gln
465                 470                 475                 480

Ile Leu Lys Gly Gly Asp Ala Lys Val Ser Met Glu Glu Arg Ala Gly
                485                 490                 495

Leu Thr Val Pro Arg Ala His Ser Leu Val Cys Val Pro Leu Ala Arg
            500                 505                 510

Ile Gly Val Ala Ser Lys Leu Leu Ser
        515                 520

<210> SEQ ID NO 35
<211> LENGTH: 1563
<212> TYPE: DNA
<213> ORGANISM: Pisum sativum

<400> SEQUENCE: 35
atgttgctgg aacttgcact tggtttgttt gtgttagctt tgtttctgca cttgcgtccc      60
acaccaagcg caaatcaaa agcacttcgc caccctccaa accctccaag cccaaagcct     120
cgtcttccct tcattggcca ccttcacctc ttaaaagata aacttctcca ctatgcactc     180
atcgatctct ccaaaaagca tggcccctta ttctctctct ccttcggctc catgccaacc     240
gtcgttgcct ccaccctga gttgttcaag ctcttcctcc aagcccacga ggcaacttcc     300
ttcagcacaa ggttccaaac ctctgccgta agacgcctca cttacgacaa ctctgtggcc     360
atggttccat tcggacctta ctggaagttc gtgaggaagc tcatcatgaa cgaccttctc     420
```

```
                                    -continued aacgccacca ccgtcaacga gctcaggcct ttgaggaccc aacagatccg caagttcctt     480
agggttatgg cccaaagcgc agaggcccag aagccccttg acgtcaccga ggagcttctc     540
aaatggacca acagcaccat ctccatgatg atgctcggcg aggctgagga gatcagagac     600
atcgctcgcg aggtccttaa gatcttcggc gaatacagcc tcactgactt catctggcct     660
ttgaagtatc tcaaggttgg aaagtatgag aagaggattg atgacatctt gaacaagttc     720
gaccctgtcg ttgaaagggt catcaagaag cgccgtgaga tcgtcagaag gagaaagaac     780
ggagaagttg ttgagggcga ggccagcggc gtcttcctcg acactttgct tgaattcgct     840
gaggacgaga ccatggagat caaaattacc aaggagcaaa tcaagggcct tgttgtcgac     900
tttttctctg cagggacaga ttccacagcg gtggcaacag agtgggcatt ggcagagctc     960
atcaacaatc ccaggggtgtt gcaaaaggct cgtgaggagg tctacagtgt tgtgggcaaa    1020
gatagactcg ttgacgaagt cgacactcaa aaccttcctt acattagggc cattgtgaag    1080
gagacattcc gaatgcaccc accactccca gtggtcaaaa gaaagtgcac agaagagtgt    1140
gagattaatg ggtatgtgat cccagaggga gcattggttc ttttcaatgt ttggcaagta    1200
ggaaaggacc ccaaatactg ggacagacca tcagaattcc gtcccgagag gttcttagaa    1260
actggcgctg aaggggaagc agggcctctt gatcttaggg gccagcattt ccaactcctc    1320
ccatttgggt ctgggaggag aatgtgccct ggtgtcaatt tggctacttc aggaatggca    1380
acacttcttg catctcttat ccaatgcttt gacctgcaag tgctgggccc tcaaggacaa    1440
atattgaaag gtgacgatgc caagttagc atggaagaga gagctggcct caccgttcca    1500
agggcacata gtctcgtttg tgttccactt gcaaggatcg gcgttgcatc taaactcctt    1560
tct                                                                  1563

<210> SEQ ID NO 36
<211> LENGTH: 521
<212> TYPE: PRT
<213> ORGANISM: Pisum sativum

<400> SEQUENCE: 36

Met Leu Leu Glu Leu Ala Leu Gly Leu Phe Val Leu Ala Leu Phe Leu
1               5                   10                  15

His Leu Arg Pro Thr Pro Ser Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Ser Phe Gly Ser Met Pro Thr
65                  70                  75                  80

Val Val Ala Ser Thr Pro Glu Leu Phe Lys Leu Phe Leu Gln Ala His
                85                  90                  95

Glu Ala Thr Ser Phe Ser Thr Arg Phe Gln Thr Ser Ala Val Arg Arg
            100                 105                 110

Leu Thr Tyr Asp Asn Ser Val Ala Met Val Pro Phe Gly Pro Tyr Trp
        115                 120                 125

Lys Phe Val Arg Lys Leu Ile Met Asn Asp Leu Leu Asn Ala Thr Thr
    130                 135                 140

Val Asn Glu Leu Arg Pro Leu Arg Thr Gln Gln Ile Arg Lys Phe Leu
145                 150                 155                 160

Arg Val Met Ala Gln Ser Ala Glu Ala Gln Lys Pro Leu Asp Val Thr
```

```
                165                 170                 175
Glu Glu Leu Leu Lys Trp Thr Asn Ser Thr Ile Ser Met Met Met Leu
            180                 185                 190
Gly Glu Ala Glu Glu Ile Arg Asp Ile Ala Arg Glu Val Leu Lys Ile
            195                 200                 205
Phe Gly Glu Tyr Ser Leu Thr Asp Phe Ile Trp Pro Leu Lys Tyr Leu
            210                 215                 220
Lys Val Gly Lys Tyr Glu Lys Arg Ile Asp Asp Ile Leu Asn Lys Phe
225                 230                 235                 240
Asp Pro Val Val Glu Arg Val Ile Lys Lys Arg Glu Ile Val Arg
                245                 250                 255
Arg Arg Lys Asn Gly Glu Val Val Glu Gly Glu Ala Ser Gly Val Phe
            260                 265                 270
Leu Asp Thr Leu Leu Glu Phe Ala Glu Asp Glu Thr Met Glu Ile Lys
            275                 280                 285
Ile Thr Lys Glu Gln Ile Lys Gly Leu Val Val Asp Phe Phe Ser Ala
            290                 295                 300
Gly Thr Asp Ser Thr Ala Val Ala Thr Glu Trp Ala Leu Ala Glu Leu
305                 310                 315                 320
Ile Asn Asn Pro Arg Val Leu Gln Lys Ala Arg Glu Glu Val Tyr Ser
                325                 330                 335
Val Val Gly Lys Asp Arg Leu Val Asp Glu Val Asp Thr Gln Asn Leu
            340                 345                 350
Pro Tyr Ile Arg Ala Ile Val Lys Glu Thr Phe Arg Met His Pro Pro
            355                 360                 365
Leu Pro Val Val Lys Arg Lys Cys Thr Glu Glu Cys Glu Ile Asn Gly
            370                 375                 380
Tyr Val Ile Pro Glu Gly Ala Leu Val Leu Phe Asn Val Trp Gln Val
385                 390                 395                 400
Gly Lys Asp Pro Lys Tyr Trp Asp Arg Pro Ser Glu Phe Arg Pro Glu
                405                 410                 415
Arg Phe Leu Glu Thr Gly Ala Glu Gly Glu Ala Gly Pro Leu Asp Leu
            420                 425                 430
Arg Gly Gln His Phe Gln Leu Leu Pro Phe Gly Ser Gly Arg Arg Met
            435                 440                 445
Cys Pro Gly Val Asn Leu Ala Thr Ser Gly Met Ala Thr Leu Leu Ala
            450                 455                 460
Ser Leu Ile Gln Cys Phe Asp Leu Gln Val Leu Gly Pro Gln Gly Gln
465                 470                 475                 480
Ile Leu Lys Gly Asp Asp Ala Lys Val Ser Met Glu Glu Arg Ala Gly
                485                 490                 495
Leu Thr Val Pro Arg Ala His Ser Leu Val Cys Val Pro Leu Ala Arg
            500                 505                 510
Ile Gly Val Ala Ser Lys Leu Leu Ser
            515                 520

<210> SEQ ID NO 37
<211> LENGTH: 1496
<212> TYPE: DNA
<213> ORGANISM: Trifolium repens

<400> SEQUENCE: 37
tctcacttgc gtcccacacc aagtgcaata tcaaaagcac ttcgccacct cccaaaccct      60
ccaagcccaa ggcctcgtct tcccttcatt ggccaccttc acctcttaaa agataaactt     120
```

-continued

```
ctccactatg cacccatcga tctctccaaa aagcatggcc ccttattctc tctctccttc      180
ggctccatgc caaccgtcgt tgcctccacc cctgagttgt tcaagctctt cctccaaacc      240
cacgaggcaa cttccttcaa cacaaggttc caaacctctg ccataagaca cctcacttac      300
gacaactctg tggccatggt tccattcgga ccttactgga agttcgtgag gaagctcatc      360
atgaacgacc ttctcaacgc caccaccgtc aacaagctca ggcctttgag acccaacag       420 atccgcaagt tccttagggt tatggcccaa agcgcagagg cccagaagcc ccttgacgtc      480
accgaggagc ttctcaaatg gaccaacagc accatctcca tgatgatgct cggcgaggct      540
gaggagatca gagacatcgc tcgcgaggtt cttaagatct tcggcgaata cagcctcact      600
gacttcatct ggcctttgaa gtacctcaag gttggaaagt atgagaagag gattgatgac      660
atcttgaaca agttcgaccc tgtcgttgaa agggtcatca agaagcgccg tgagatcgtc      720
agaaggagaa agaacggaga agttgttgag ggcgaggcca gcggcgtctt cctcgacact      780
ttgcttgaat tcgctgagga cgagaccatg gagatcaaaa ttaccaagga gcaaatcaag      840
ggccttgttg tcgactttt ctctgcaggg acagattcca cagcggtggt aacagagtgg       900
gcattggcag agctcatcaa caatcccagg gtgttgcaaa aggctcgtga ggaggtctac      960
agtgttgtgg gcaaagatag actcgttgac gaagttgaca ctcaaaacct tccttacatt     1020
agggccattg tgaaggagac attccgaatg cacccaccac tcccagtggt caaaagaaag     1080
tgcacagaag agtgtgagat taatgggtat gtgatcccag agggagcatt ggttcttttc     1140
aatgtttggc aagtaggaag ggaccccaaa tactgggaca gaccatcaga atcccgtccc     1200
gagaggttct tagaaactgg tgctgaaggg gaagcagggc tcttgatctt taggggccag     1260
catttccaac tcctcccatt tgggtctggg aggagaatgt gccctggtgt cagtttggct     1320
acttcaggaa tggcaacact tcttgcatct cttatccaat gctttgacct gcaagtgctg     1380
ggccctcaag gacaaatatt gaaggtgat gatgccaaag ttagcatgga agagagagct      1440
ggcctcacag ttccaagggc acatagtctc gtttgtgttc cacttgcaag gatcgg         1496
```

<210> SEQ ID NO 38
<211> LENGTH: 498
<212> TYPE: PRT
<213> ORGANISM: Trifolium repens

<400> SEQUENCE: 38

```
Ser His Leu Arg Pro Thr Pro Ser Ala Ile Ser Lys Ala Leu Arg His
1               5                   10                  15

Leu Pro Asn Pro Pro Ser Pro Arg Pro Arg Leu Pro Phe Ile Gly His
            20                  25                  30

Leu His Leu Leu Lys Asp Lys Leu Leu His Tyr Ala Pro Ile Asp Leu
        35                  40                  45

Ser Lys Lys His Gly Pro Leu Phe Ser Leu Ser Phe Gly Ser Met Pro
    50                  55                  60

Thr Val Ala Ser Thr Pro Glu Leu Phe Lys Leu Phe Leu Gln Thr
65                  70                  75                  80

His Glu Ala Thr Ser Phe Asn Thr Arg Phe Gln Thr Ser Ala Ile Arg
                85                  90                  95

His Leu Thr Tyr Asp Asn Ser Val Ala Met Val Pro Phe Gly Pro Tyr
            100                 105                 110

Trp Lys Phe Val Arg Lys Leu Ile Met Asn Asp Leu Leu Asn Ala Thr
        115                 120                 125
```

-continued

Thr Val Asn Lys Leu Arg Pro Leu Arg Thr Gln Gln Ile Arg Lys Phe
130                 135                 140

Leu Arg Val Met Ala Gln Ser Ala Glu Ala Gln Lys Pro Leu Asp Val
145                 150                 155                 160

Thr Glu Glu Leu Leu Lys Trp Thr Asn Ser Thr Ile Ser Met Met Met
            165                 170                 175

Leu Gly Glu Ala Glu Glu Ile Arg Asp Ile Ala Arg Glu Val Leu Lys
        180                 185                 190

Ile Phe Gly Glu Tyr Ser Leu Thr Asp Phe Ile Trp Pro Leu Lys Tyr
        195                 200                 205

Leu Lys Val Gly Lys Tyr Glu Lys Arg Ile Asp Asp Ile Leu Asn Lys
    210                 215                 220

Phe Asp Pro Val Val Glu Arg Val Ile Lys Arg Arg Glu Ile Val
225                 230                 235                 240

Arg Arg Arg Lys Asn Gly Glu Val Val Glu Gly Ala Ser Gly Val
                245                 250                 255

Phe Leu Asp Thr Leu Leu Glu Phe Ala Glu Asp Glu Thr Met Glu Ile
            260                 265                 270

Lys Ile Thr Lys Glu Gln Ile Lys Gly Leu Val Val Asp Phe Phe Ser
        275                 280                 285

Ala Gly Thr Asp Ser Thr Ala Val Val Thr Glu Trp Ala Leu Ala Glu
        290                 295                 300

Leu Ile Asn Asn Pro Arg Val Leu Gln Lys Ala Arg Glu Glu Val Tyr
305                 310                 315                 320

Ser Val Val Gly Lys Asp Arg Leu Val Asp Glu Val Asp Thr Gln Asn
                325                 330                 335

Leu Pro Tyr Ile Arg Ala Ile Val Lys Glu Thr Phe Arg Met His Pro
            340                 345                 350

Pro Leu Pro Val Val Lys Arg Lys Cys Thr Glu Glu Cys Glu Ile Asn
            355                 360                 365

Gly Tyr Val Ile Pro Glu Gly Ala Leu Val Leu Phe Asn Val Trp Gln
    370                 375                 380

Val Gly Arg Asp Pro Lys Tyr Trp Asp Arg Pro Ser Glu Ser Arg Pro
385                 390                 395                 400

Glu Arg Phe Leu Glu Thr Gly Ala Glu Gly Glu Ala Gly Pro Leu Asp
                405                 410                 415

Leu Arg Gly Gln His Phe Gln Leu Leu Pro Phe Gly Ser Gly Arg Arg
            420                 425                 430

Met Cys Pro Gly Val Ser Leu Ala Thr Ser Gly Met Ala Thr Leu Leu
        435                 440                 445

Ala Ser Leu Ile Gln Cys Phe Asp Leu Gln Val Leu Gly Pro Gln Gly
    450                 455                 460

Gln Ile Leu Lys Gly Asp Asp Ala Lys Val Ser Met Glu Glu Arg Ala
465                 470                 475                 480

Gly Leu Thr Val Pro Arg Ala His Ser Leu Val Cys Val Pro Leu Ala
                485                 490                 495

Arg Ile

<210> SEQ ID NO 39
<211> LENGTH: 1501
<212> TYPE: DNA
<213> ORGANISM: Trifolium repens

<400> SEQUENCE: 39

-continued

| | |
|---|---|
| tgtttctgca cttgcgtccc acacccactg caaaatcaaa agcacttcgc catctcccaa | 60 |
| acccaccaag cccaaagcct cgtcttccct tcataggaca ccttcatctc ttaaaagaca | 120 |
| aacttctcca ctacgcactc atcgacctct ccaaaaaaca tggtcccttta ttctctctct | 180 |
| actttggctc catgccaacc gttgttgcct ccacaccaga attgttcaag ctcttcctcc | 240 |
| aaacgcacga ggcaacttcc ttcaacacaa ggttccaaac ctcagccata agacgcctca | 300 |
| cctacgacaa ctctgtggcc atggttccat tcggacctta ctggaagttc gtgaggaagc | 360 |
| tcatcatgaa cgaccttctc aacgccacca ccgtcaacaa gctcaggcct ttgaggaccc | 420 |
| aacagatccg caagttcctt agggttatgg cccaaagcgc agaggcccag aagcccttg | 480 |
| acgtcaccga ggagcttctc aaatggacca acagcaccat ctccatgatg atgctcggcg | 540 |
| aggctgagga gatcagagac atcgctcgcg aggttcttaa gatcttcggc gaatacagcc | 600 |
| tcactgactt catctggcct ttgaagtatc tcaaggttgg aaagtatgag aagaggattg | 660 |
| atgacatctt gaacaagttc gaccctgtcg ttgaaagagt catcaagaag cgccgtgaga | 720 |
| tcgtcagaag gagaaagaac ggagaagttg ttgagggcga ggccagcggc gtcttcctcg | 780 |
| acactttgct tgaattcgct gaggacgaga ccatggagat caaaattacc aaggagcaaa | 840 |
| tcaagggcct tgttgtcgac ttttctctg caggacaga ttccacagcg gtggcaacag | 900 |
| agtgggcatt ggcagagctc atcaacaatc caaggtgtt gcaaaaggct cgtgaggagg | 960 |
| cctacagtgt tgtgggcaaa gatagactcg ttgacgaagt tgacactcaa aaccttcctt | 1020 |
| acattagggc cattgtgaag gagacattcc gaatgcaccc accactccca gtggtcaaaa | 1080 |
| gaaagtgcac agaagagtgt gggattaatg ggtatgtgat cccagaggga gcattggttc | 1140 |
| ttttcaatgt ttggcaagta ggaagggacc ccaaatactg ggacagacca tcagaattcc | 1200 |
| gtcccgagag gttcttagaa actggtgctg aagggaagc agggcctctt gatcttaggg | 1260 |
| gccagcattt ccaactcctc ccatttgggt ctgggaggag aatgtgccct ggtgtcaatt | 1320 |
| tggctacttc aggaatggca acacttcttg catctcttat ccaatgcttt gacctgcaag | 1380 |
| tgctgggccc tcaaggacaa atattgaaag gtgatgatgc caagttagc atggaagaga | 1440 |
| gagctggcct cacagttcca agggcacata gtctcgtttg tgttccactt gcaaggatcg | 1500 |
| g | 1501 |

<210> SEQ ID NO 40
<211> LENGTH: 499
<212> TYPE: PRT
<213> ORGANISM: Trifolium repens

<400> SEQUENCE: 40

Phe Leu His Leu Arg Pro Thr Pro Thr Ala Lys Ser Lys Ala Leu Arg
1               5                   10                  15

His Leu Pro Asn Pro Pro Ser Pro Lys Pro Arg Leu Pro Phe Ile Gly
            20                  25                  30

His Leu His Leu Leu Lys Asp Lys Leu Leu His Tyr Ala Leu Ile Asp
        35                  40                  45

Leu Ser Lys Lys His Gly Pro Leu Phe Ser Leu Tyr Phe Gly Ser Met
    50                  55                  60

Pro Thr Val Val Ala Ser Thr Pro Glu Leu Phe Lys Leu Phe Leu Gln
65                  70                  75                  80

Thr His Glu Ala Thr Ser Phe Asn Thr Arg Phe Gln Thr Ser Ala Ile
                85                  90                  95

Arg Arg Leu Thr Tyr Asp Asn Ser Val Ala Met Val Pro Phe Gly Pro

-continued

```
                100                 105                 110
Tyr Trp Lys Phe Val Arg Lys Leu Ile Met Asn Asp Leu Leu Asn Ala
            115                 120                 125

Thr Thr Val Asn Lys Leu Arg Pro Leu Arg Thr Gln Gln Ile Arg Lys
130                 135                 140

Phe Leu Arg Val Met Ala Gln Ser Ala Glu Ala Gln Lys Pro Leu Asp
145                 150                 155                 160

Val Thr Glu Glu Leu Leu Lys Trp Thr Asn Ser Thr Ile Ser Met Met
                165                 170                 175

Met Leu Gly Glu Ala Glu Ile Arg Asp Ile Ala Arg Glu Val Leu
            180                 185                 190

Lys Ile Phe Gly Glu Tyr Ser Leu Thr Asp Phe Ile Trp Pro Leu Lys
            195                 200                 205

Tyr Leu Lys Val Gly Lys Tyr Glu Lys Arg Ile Asp Asp Ile Leu Asn
            210                 215                 220

Lys Phe Asp Pro Val Val Glu Arg Val Ile Lys Lys Arg Arg Glu Ile
225                 230                 235                 240

Val Arg Arg Arg Lys Asn Gly Glu Val Val Glu Gly Glu Ala Ser Gly
                245                 250                 255

Val Phe Leu Asp Thr Leu Leu Glu Phe Ala Glu Asp Glu Thr Met Glu
            260                 265                 270

Ile Lys Ile Thr Lys Glu Gln Ile Lys Gly Leu Val Val Asp Phe Phe
            275                 280                 285

Ser Ala Gly Thr Asp Ser Thr Ala Val Ala Thr Glu Trp Ala Leu Ala
            290                 295                 300

Glu Leu Ile Asn Asn Pro Lys Val Leu Gln Lys Ala Arg Glu Glu Ala
305                 310                 315                 320

Tyr Ser Val Val Gly Lys Asp Arg Leu Val Asp Glu Val Asp Thr Gln
                325                 330                 335

Asn Leu Pro Tyr Ile Arg Ala Ile Val Lys Glu Thr Phe Arg Met His
            340                 345                 350

Pro Pro Leu Pro Val Val Lys Arg Lys Cys Thr Glu Glu Cys Gly Ile
            355                 360                 365

Asn Gly Tyr Val Ile Pro Glu Gly Ala Leu Val Leu Phe Asn Val Trp
            370                 375                 380

Gln Val Gly Arg Asp Pro Lys Tyr Trp Asp Arg Pro Ser Glu Phe Arg
385                 390                 395                 400

Pro Glu Arg Phe Leu Glu Thr Gly Ala Glu Gly Glu Ala Gly Pro Leu
                405                 410                 415

Asp Leu Arg Gly Gln His Phe Gln Leu Leu Pro Phe Gly Ser Gly Arg
            420                 425                 430

Arg Met Cys Pro Gly Val Asn Leu Ala Thr Ser Gly Met Ala Thr Leu
            435                 440                 445

Leu Ala Ser Leu Ile Gln Cys Phe Asp Leu Gln Val Leu Gly Pro Gln
            450                 455                 460

Gly Gln Ile Leu Lys Gly Asp Ala Lys Val Ser Met Glu Glu Arg
465                 470                 475                 480

Ala Gly Leu Thr Val Pro Arg Ala His Ser Leu Val Cys Val Pro Leu
                485                 490                 495

Ala Arg Ile
```

<210> SEQ ID NO 41
<211> LENGTH: 21

```
<212> TYPE: DNA
<213> ORGANISM: Artificial Sequence
<220> FEATURE:
<223> OTHER INFORMATION: PCR primer

<400> SEQUENCE: 41
ttgctggaac ttgcacttgg t                                              21

<210> SEQ ID NO 42
<211> LENGTH: 32
<212> TYPE: DNA
<213> ORGANISM: Artificial Sequence
<220> FEATURE:
<223> OTHER INFORMATION: PCR primer

<400> SEQUENCE: 42
gtatatgatg ggtaccttaa ttaagaaagg ag                                  32

<210> SEQ ID NO 43
<211> LENGTH: 26
<212> TYPE: DNA
<213> ORGANISM: Artificial Sequence
<220> FEATURE:
<223> OTHER INFORMATION: PCR primer

<400> SEQUENCE: 43
gacgcctcac ttacgacaac tctgtg                                         26

<210> SEQ ID NO 44
<211> LENGTH: 25
<212> TYPE: DNA
<213> ORGANISM: Artificial Sequence
<220> FEATURE:
<223> OTHER INFORMATION: PCR primer

<400> SEQUENCE: 44
cctctcggga cggaattctg atggt                                          25

<210> SEQ ID NO 45
<211> LENGTH: 25
<212> TYPE: DNA
<213> ORGANISM: Artificial Sequence
<220> FEATURE:
<223> OTHER INFORMATION: PCR primer

<400> SEQUENCE: 45
gcggtgcacg ggcggactct tcttc                                          25

<210> SEQ ID NO 46
<211> LENGTH: 25
<212> TYPE: DNA
<213> ORGANISM: Artificial Sequence
<220> FEATURE:
<223> OTHER INFORMATION: PCR primer

<400> SEQUENCE: 46
cgcccaatac gcaaaccgcc tctcc                                          25

<210> SEQ ID NO 47
<211> LENGTH: 1501
<212> TYPE: DNA
<213> ORGANISM: Beta vulgaris

<400> SEQUENCE: 47
tgtttctgca cttgcgtccc acacccactg caaaatcaaa agcacttcgc catctcccaa    60
```

| acccaccaag cccaaagcct cgtcttccct tcataggaca ccttcatctc ttaaaagaca | 120 |
| aacttctcca ctacgcactc atcgacctct ccaaaaaaca tggtcccctta ttctctctct | 180 |
| actttggctc catgccaacc gttgttgcct ccacaccaga attgttcaag ctcttcctcc | 240 |
| aaacgcacga ggcaacttcc ttcaacacaa ggttccaaac ctcagccata agacgcctca | 300 |
| cctatgatag ctcagtggcc atggttccct tcggacctta ctggaagttc gtgaggaagc | 360 |
| tcatcatgaa cgaccttctc aacgccacca ctgtaaacaa gttgaggcct ttgaggaccc | 420 |
| aacagatccg caagttcctt agggttatgg cccaaggcgc agaggcacag aagccccttg | 480 |
| acttgaccga ggagcttctg aaatggacca acagcaccat ctccatgatg atgctcggcg | 540 |
| aggctgagga gatcagagac atcgctcgcg aggttcttaa gatctttggc gaatacagcc | 600 |
| tcactgactt catctggcca ttgaagcatc tcaaggttgg aaagtatgag aagaggatcg | 660 |
| acgacatctt gaacaagttc gaccctgtcg ttgaaagagt catcaagaag cgccgtgaga | 720 |
| tcgtgaggag gagaaagaac ggagaggatg ttgagggtga ggtcagcggg gttttccttg | 780 |
| acactttgct tgaattcgct gaggatgaga ccatggagat caaaatcacc aaggaccaca | 840 |
| tcaagggtct tgttgtcgac tttttctcgg caggaacaga ctccacagcg gtggcaacag | 900 |
| agtgggcatt ggcagaactc atcaacaatc ctaaggtgtt ggaaaaggct cgtgaggagg | 960 |
| tctacagtgt tgtgggaaag gacagacttg tggacgaagt agacactcaa aaccttcctt | 1020 |
| acattagagc aatcgtgaag gagacattcc gcatgcaccc gccactccca gtggtcaaaa | 1080 |
| gaaagtgcat agaagagtgt gagattaatg gatatgtgat cccagaggga gcattgattc | 1140 |
| tcttcaatgt atggcaagta ggaagagacc ctaaatactg ggacagacca tcggagttcc | 1200 |
| gtcctgagag gttcctagag acaggggctg aaggggaagc aaggcttctt gatcttaggg | 1260 |
| gacaacattt tcaacttctc ccatttgggt ctgggaggag aatgtgccct ggagtcaatc | 1320 |
| tggctacttc gggaatggca acacttcttg catctcttat tcagtgctt gacttgcaag | 1380 |
| tgctgggtcc acaaggacag atattgaagg gtggtgacgc caaagttagc atggaagaga | 1440 |
| gagccggcct cactgttcca agggcacata gtcttgtctg tgttccactt gcaaggatcg | 1500 |
| g | 1501 |

<210> SEQ ID NO 48
<211> LENGTH: 499
<212> TYPE: PRT
<213> ORGANISM: Beta vulgaris

<400> SEQUENCE: 48

Phe Leu His Leu Arg Pro Thr Pro Thr Ala Lys Ser Lys Ala Leu Arg
1               5                   10                  15

His Leu Pro Asn Pro Pro Ser Pro Lys Pro Arg Leu Pro Phe Ile Gly
                20                  25                  30

His Leu His Leu Leu Lys Asp Lys Leu Leu His Tyr Ala Leu Ile Asp
            35                  40                  45

Leu Ser Lys Lys His Gly Pro Leu Phe Ser Leu Tyr Phe Gly Ser Met
        50                  55                  60

Pro Thr Val Val Ala Ser Thr Pro Glu Leu Phe Lys Leu Phe Leu Gln
65                  70                  75                  80

Thr His Glu Ala Thr Ser Phe Asn Thr Arg Phe Gln Thr Ser Ala Ile
                85                  90                  95

Arg Arg Leu Thr Tyr Asp Ser Ser Val Ala Met Val Pro Phe Gly Pro
            100                 105                 110

-continued

Tyr Trp Lys Phe Val Arg Lys Leu Ile Met Asn Asp Leu Leu Asn Ala
        115                 120                 125

Thr Thr Val Asn Lys Leu Arg Pro Leu Arg Thr Gln Gln Ile Arg Lys
130                 135                 140

Phe Leu Arg Val Met Ala Gln Gly Ala Glu Ala Gln Lys Pro Leu Asp
145                 150                 155                 160

Leu Thr Glu Glu Leu Leu Lys Trp Thr Asn Ser Thr Ile Ser Met Met
                165                 170                 175

Met Leu Gly Glu Ala Glu Glu Ile Arg Asp Ile Ala Arg Glu Val Leu
            180                 185                 190

Lys Ile Phe Gly Glu Tyr Ser Leu Thr Asp Phe Ile Trp Pro Leu Lys
        195                 200                 205

His Leu Lys Val Gly Lys Tyr Glu Lys Arg Ile Asp Asp Ile Leu Asn
    210                 215                 220

Lys Phe Asp Pro Val Val Glu Arg Val Ile Lys Lys Arg Arg Glu Ile
225                 230                 235                 240

Val Arg Arg Arg Lys Asn Gly Glu Asp Val Glu Gly Glu Val Ser Gly
                245                 250                 255

Val Phe Leu Asp Thr Leu Leu Glu Phe Ala Glu Asp Glu Thr Met Glu
            260                 265                 270

Ile Lys Ile Thr Lys Asp His Ile Lys Gly Leu Val Val Asp Phe Phe
        275                 280                 285

Ser Ala Gly Thr Asp Ser Thr Ala Val Ala Thr Glu Trp Ala Leu Ala
    290                 295                 300

Glu Leu Ile Asn Asn Pro Lys Val Leu Glu Lys Ala Arg Glu Glu Val
305                 310                 315                 320

Tyr Ser Val Val Gly Lys Asp Arg Leu Val Asp Glu Val Asp Thr Gln
                325                 330                 335

Asn Leu Pro Tyr Ile Arg Ala Ile Val Lys Glu Thr Phe Arg Met His
            340                 345                 350

Pro Pro Leu Pro Val Val Lys Arg Lys Cys Ile Glu Glu Cys Glu Ile
        355                 360                 365

Asn Gly Tyr Val Ile Pro Glu Gly Ala Leu Ile Leu Phe Asn Val Trp
    370                 375                 380

Gln Val Gly Arg Asp Pro Lys Tyr Trp Asp Arg Pro Ser Glu Phe Arg
385                 390                 395                 400

Pro Glu Arg Phe Leu Glu Thr Gly Ala Glu Gly Glu Ala Arg Leu Leu
                405                 410                 415

Asp Leu Arg Gly Gln His Phe Gln Leu Leu Pro Phe Gly Ser Gly Arg
            420                 425                 430

Arg Met Cys Pro Gly Val Asn Leu Ala Thr Ser Gly Met Ala Thr Leu
        435                 440                 445

Leu Ala Ser Leu Ile Gln Cys Phe Asp Leu Gln Val Leu Gly Pro Gln
    450                 455                 460

Gly Gln Ile Leu Lys Gly Gly Asp Ala Lys Val Ser Met Glu Glu Arg
465                 470                 475                 480

Ala Gly Leu Thr Val Pro Arg Ala His Ser Leu Val Cys Val Pro Leu
                485                 490                 495

Ala Arg Ile

<210> SEQ ID NO 49
<211> LENGTH: 30
<212> TYPE: DNA
<213> ORGANISM: Artificial Sequence

```
<220> FEATURE:
<223> OTHER INFORMATION: PCR primer

<400> SEQUENCE: 49
gaattcgcgg ccgctctaga actagtggat                                        30

<210> SEQ ID NO 50
<211> LENGTH: 30
<212> TYPE: DNA
<213> ORGANISM: Artificial Sequence
<220> FEATURE:
<223> OTHER INFORMATION: PCR primer

<400> SEQUENCE: 50
gaattcgcgg ccgcgaattg ggtaccgggc                                        30

<210> SEQ ID NO 51
<211> LENGTH: 27
<212> TYPE: DNA
<213> ORGANISM: Artificial Sequence
<220> FEATURE:
<223> OTHER INFORMATION: PCR primer

<400> SEQUENCE: 51
gcaaacgaag acaaatggga gatgata                                           27

<210> SEQ ID NO 52
<211> LENGTH: 1801
<212> TYPE: DNA
<213> ORGANISM: Glycine max
<220> FEATURE:
<221> NAME/KEY: Intron
<222> LOCATION: (895)..(1112)

<400> SEQUENCE: 52
ttgctggaac ttgcacttgg tttgtttgtg ttagctttgt ttctgcactt gcgtcccaca        60
ccaagtgcaa atcaaaagc acttcgccac ctcccaaacc ctccaagccc aaagcctcgt       120
cttcccttca ttggccacct tcacctctta aaagataaac ttctccacta tgcactcatc      180
gatctctcca aaaagcatgg ccccttattc tctctctcct tcggctccat gccaaccgtc      240
gttgcctcca cccctgagtt gttcaagctc ttcctccaaa cccacgaggc aacttccttc      300
aacacaaggt tccaaacctc tgccataaga cgcctcactt acgacaactc tgtggccatg      360
gttccattcg gaccttactg gaagttcgtg aggaagctca tcatgaacga ccttctcaac      420
gccaccaccg tcaacaagct caggcctttg aggacccaac agatccgcaa gttccttagg      480
gttatggccc aaagcgcaga ggcccagaag ccccttgacg tcaccgagga gcttctcaaa      540
tggaccaaca gcaccatctc catgatgatg ctcggcgagg ctgaggagat cagagacatc      600
gctcgcgagg ttcttaagat cttcggcgaa tacagcctca ctgacttcat ctggcctttg      660
aagtatctca aggttggaaa gtatgagaag aggattgatg acatcttgaa caagttcgac      720
cctgtcgttg aaagggtcat caagaagcgc cgtgagatcg tcagaaggag aaagaacgga      780
gaagttgttg agggcgaggc cagcggcgtc ttcctcgaca ctttgcttga attcgctgag      840
gacgagacca tggagatcaa aattaccaag gagcaaatca agggccttgt tgtcgtaagt      900
ttccttcttc tctcctactt tattactttc tttcattcat catatgtatt ggcattaaat      960
agtatactat atgagaaaat atgttacgca ctcacggtgt aaagatatgt ggtgtttttt     1020
taaaagaga tacagaagtt gcttttatgc atgtatgtta acgtatattt actcaagtgg     1080
aaactaatta attctcaatt ttgggtatgt aggactttt ctctgcaggg acagattcca     1140
```

-continued

```
cagcggtggc aacagagtgg gcattggcag agctcatcaa caatcccagg gtgttgcaaa      1200
aggctcgtga ggaggtctac agtgttgtgg gcaaagatag actcgttgac gaagttgaca      1260
ctcaaaacct tccttacatt agggccattg tgaaggagac attccgaatg cacccaccac      1320
tcccagtggt caaaagaaag tgcacagaag agtgtgagat taatgggtat gtgatcccag      1380
agggagcatt ggttcttttc aatgtttggc aagtaggaag ggaccccaaa tactgggaca      1440
gaccatcaga attccgtccc gagaggttct tagaaactgg tgctgaaggg gaagcagggc      1500
ctcttgatct taggggccag catttccaac tcctcccatt tgggtctggg aggagaatgt      1560
gccctggtgt caatttggct acttcaggaa tggcaacact tcttgcatct cttatccaat      1620
gctttgacct gcaagtgctg ggccctcaag gacaaatatt gaaggtgat gatgccaaag       1680 ttagcatgga agagagagct ggcctcacag ttccaagggc acatagtctc gtttgtgttc      1740
cacttgcaag gatcggcgtt gcatctaaac tcctttctta attaagggat ccatcatata      1800
c                                                                     1801
```

<210> SEQ ID NO 53
<211> LENGTH: 1900
<212> TYPE: DNA
<213> ORGANISM: Glycine max
<220> FEATURE:
<221> NAME/KEY: Intron
<222> LOCATION: (947)..(1082)

<400> SEQUENCE: 53

```
aattagcctc acaaaagcaa agatcaaaca aaccaaggac gagaacacga tgttgcttga      60
acttgcactt ggtttattgg ttttggctct gtttctgcac ttgcgtccca cacccactgc      120
aaaatcaaaa gcacttcgcc atctcccaaa cccaccaagc ccaaagcctc gtcttccctt      180
cataggacac cttcatctct taaaagacaa acttctccac tacgcactca tcgacctctc      240
caaaaaacat ggtcccttat tctctctcta ctttggctcc atgccaaccg ttgttgcctc      300
cacaccagaa ttgttcaagc tcttcctcca aacgcacgag gcaacttcct tcaacacaag      360
gttccaaacc tcagccataa gacgcctcac ctatgatagc tcagtggcca tggttccctt      420
cggaccttac tggaagttcg tgaggaagct catcatgaac gaccttccca acgccaccac      480
tgtaaacaag ttgaggcctt tgaggaccca acagacccgc aagttcctta gggttatggc      540
ccaaggcgca gaggcacaga gcccccttga cttgaccgag gagcttctga aatggaccaa      600
cagcaccatc tccatgatga tgctcggcga ggctgaggag atcagagaca tcgctcgcga      660
ggttcttaag atctttggcg aatacagcct cactgacttc atctggccat tgaagcatct      720
caaggttgga aagtatgaga agaggatcga cgacatcttg aacaagttcg accctgtcgt      780
tgaaagggtc atcaagaagc gccgtgagat cgtgaggagg agaaagaacg gagaggttgt      840
tgagggtgag gtcagcgggg ttttccttga cactttgctt gaattcgctg aggatgagac      900
catggagatc aaaatcacca aggaccacat cgagggtctt gttgtcgtga gtttcctgct      960
tcattcattg atcgaaatat gcagtatttt gttaacaaga gatcgagaat tgacatttat      1020
atattcatgt ggtggcaatt aattaacggt acgcattctt aatcgatatt gtgtatgtgc      1080
aggacttttt ctcggcagga acagactcca cagcggtggc aacagagtgg gcattggcag      1140
aactcatcaa caatcctaag gtgttggaaa aggctcgtga ggaggtctac agtgttgtgg      1200
gaaaggacag acttgtggac gaagttgaca ctcaaaacct tccttacatt agagcaatcg      1260
tgaaggagac attccgcatg cacccgccac tcccagtggt caaaagaaag tgcacagaag      1320
```

-continued

```
agtgtgagat taatggatat gtgatcccag agggagcatt gattctcttc aatgtatggc      1380
aagtaggaag agaccccaaa tactgggaca gaccatcgga gttccgtcct gagaggttcc      1440
tagagacagg ggctgaaggg gaagcagggc ctcttgatct tagggacaa catttttcaac      1500 ttctcccatt tgggtctggg aggagaatgt gccctggagt caatctggct acttcgggaa      1560
tggcaacact tcttgcatct cttattcagt gcttcgactt gcaagtgctg ggtccacaag      1620
gacagatatt gaagggtggt gacgccaaag ttagcatgga agagagagcc ggcctcactg      1680
ttccaagggc acatagtctt gtctgtgttc cacttgcaag gatcggcgtt gcatctaaac      1740
tcctttctta attaagatca tcgtcatcat catcatatat aatatttact ttttgtgtgt      1800
tgataatcat catttcaata aggtctcgtt catctacttt ttatgaagta tataagccct      1860
tccatgcaca ttgtatcatc tcccatttgt cttcgtttgc                             1900

<210> SEQ ID NO 54
<211> LENGTH: 1501
<212> TYPE: DNA
<213> ORGANISM: Lupinus albus

<400> SEQUENCE: 54
tgtttctgca cttgcgtccc acacccactg caaaatcaaa agcacttcgc catctcccaa        60
acccaccaag cccaaagcct cgtcttccct tcataggaca ccttcatctc ttaaaagaca       120
aacttctcca ctacgcactc atcgacctct ccaaaaaaca tggtccctta ttctctctct       180
actttggctc catgccaacc gttgttgcct ccacaccaga attgttcaag ctcttcctcc       240
aaacgcacga ggcaacttcc ttcaacacaa ggttccaaac ctcagccata agacgcctca       300
cctatgatag ctcagtggcc agggttccct tcggacctta ctggaagttc gtgaggaagc       360
tcatcatgaa cgaccttctt aacgccacca ctgtaaacaa gttgaggcct ttgaggaccc       420
aacagatccg caagttcctt agggttatgg cccaaggcgc agaggcacag aagccccttg       480
acttgaccga ggagcttctg aaatggacca acagcaccat ctccatgatg atgctcggcg       540
aggctgagga gatcagagac atcgctcgcg aggttcttaa gatctttggc gaatacagcc       600
tcactgactt catctggcca ttgaagcatc tcaaggttgg aaagtatgag aagaggatcg       660
acgacatctt gaacaagttc gaccctgtcg ttgaaaagagt catcaagaag cgccgtgaga       720
tcgtgaggag gagaaagaac ggagaggttg ttgagggtga ggtcagcggg gttctccttg       780
acactttgct tgaattcgct gaggatgaga ccatggagat caaaatcacc aaggaccaca       840
tcaagggtct tgttgtcgac tttttctcgg caggaacaga ctccacagcg gtggcaacag       900
agtgggcatt ggcagaactc atcaacaatc taaggtgtt ggaaagggct cgtgaggagg       960
tctacagtgt tgtgggaaag gacagacttg tggacgaagt tgacactcaa aaccttcctt      1020
acattagagc aatcgtgaag gagacattcc gcatgcaccc gccactccca gtggtcaaaa      1080
gaaagtgcac agaagagtgt gagattaatg gatatgtgat cccagaggga gcattgattc      1140
tcttcaatgt atggcaagta ggaagagacc ccaaatactg ggacagacca tcggagttcc      1200
gtcctgagag gttcctagag acagaggctg aaggggaagc aaggcctctt gatcttaggg      1260
gacaacattt tcaacttctc ccatttgggt ctggggaggag aatgtgccct ggagtcattc      1320
tggctacttc gggaatggca acacttcttg catctcttat tcagtgcttt gacttgcaag      1380
tgctgggtcc acaaggacag atattgaagg gtgtgacgc caaagttagc atggaagaga       1440
gagccggcct cactgttcca agggcacata gtcttgtctg tgttccactt gcaaggatcg      1500
```

-continued g                                                                                                        1501

<210> SEQ ID NO 55
<211> LENGTH: 499
<212> TYPE: PRT
<213> ORGANISM: Lupinus albus

<400> SEQUENCE: 55

Phe Leu His Leu Arg Pro Thr Pro Thr Ala Lys Ser Lys Ala Leu Arg
1               5                   10                  15

His Leu Pro Asn Pro Pro Ser Pro Lys Pro Arg Leu Pro Phe Ile Gly
            20                  25                  30

His Leu His Leu Leu Lys Asp Lys Leu Leu His Tyr Ala Leu Ile Asp
        35                  40                  45

Leu Ser Lys Lys His Gly Pro Leu Phe Ser Leu Tyr Phe Gly Ser Met
    50                  55                  60

Pro Thr Val Val Ala Ser Thr Pro Glu Leu Phe Lys Leu Phe Leu Gln
65                  70                  75                  80

Thr His Glu Ala Thr Ser Phe Asn Thr Arg Phe Gln Thr Ser Ala Ile
                85                  90                  95

Arg Arg Leu Thr Tyr Asp Ser Ser Val Ala Arg Val Pro Phe Gly Pro
            100                 105                 110

Tyr Trp Lys Phe Val Arg Lys Leu Ile Met Asn Asp Leu Leu Asn Ala
        115                 120                 125

Thr Thr Val Asn Lys Leu Arg Pro Leu Arg Thr Gln Gln Ile Arg Lys
    130                 135                 140

Phe Leu Arg Val Met Ala Gln Gly Ala Glu Ala Gln Lys Pro Leu Asp
145                 150                 155                 160

Leu Thr Glu Glu Leu Leu Lys Trp Thr Asn Ser Thr Ile Ser Met Met
                165                 170                 175

Met Leu Gly Glu Ala Glu Ile Arg Asp Ile Ala Arg Glu Val Leu
            180                 185                 190

Lys Ile Phe Gly Glu Tyr Ser Leu Thr Asp Phe Ile Trp Pro Leu Lys
        195                 200                 205

His Leu Lys Val Gly Lys Tyr Glu Lys Arg Ile Asp Asp Ile Leu Asn
    210                 215                 220

Lys Phe Asp Pro Val Val Glu Arg Val Ile Lys Lys Arg Arg Glu Ile
225                 230                 235                 240

Val Arg Arg Arg Lys Asn Gly Glu Val Val Glu Gly Glu Val Ser Gly
                245                 250                 255

Val Leu Leu Asp Thr Leu Leu Glu Phe Ala Glu Asp Glu Thr Met Glu
            260                 265                 270

Ile Lys Ile Thr Lys Asp His Ile Lys Gly Leu Val Val Asp Phe Phe
        275                 280                 285

Ser Ala Gly Thr Asp Ser Thr Ala Val Ala Thr Glu Trp Ala Leu Ala
    290                 295                 300

Glu Leu Ile Asn Asn Pro Lys Val Leu Glu Arg Ala Arg Glu Glu Val
305                 310                 315                 320

Tyr Ser Val Val Gly Lys Asp Arg Leu Val Asp Glu Val Asp Thr Gln
                325                 330                 335

Asn Leu Pro Tyr Ile Arg Ala Ile Val Lys Glu Thr Phe Arg Met His
            340                 345                 350

Pro Pro Leu Pro Val Val Lys Arg Lys Cys Thr Glu Glu Cys Glu Ile
        355                 360                 365

```
Asn Gly Tyr Val Ile Pro Glu Gly Ala Leu Ile Leu Phe Asn Val Trp
    370                 375                 380
Gln Val Gly Arg Asp Pro Lys Tyr Trp Asp Arg Pro Ser Glu Phe Arg
385                 390                 395                 400
Pro Glu Arg Phe Leu Glu Thr Glu Ala Glu Gly Glu Ala Arg Pro Leu
                405                 410                 415
Asp Leu Arg Gly Gln His Phe Gln Leu Leu Pro Phe Gly Ser Gly Arg
            420                 425                 430
Arg Met Cys Pro Gly Val Ile Leu Ala Thr Ser Gly Met Ala Thr Leu
        435                 440                 445
Leu Ala Ser Leu Ile Gln Cys Phe Asp Leu Gln Val Leu Gly Pro Gln
    450                 455                 460
Gly Gln Ile Leu Lys Gly Gly Asp Ala Lys Val Ser Met Glu Glu Arg
465                 470                 475                 480
Ala Gly Leu Thr Val Pro Arg Ala His Ser Leu Val Cys Val Pro Leu
                485                 490                 495
Ala Arg Ile

<210> SEQ ID NO 56
<211> LENGTH: 1501
<212> TYPE: DNA
<213> ORGANISM: Medicago sativa

<400> SEQUENCE: 56
tgtttctgca cttgcgtccc acacccactg caaaatcaaa agcacttcgc catctcccaa      60
acccaccaag cccaaagcct cgtcttccct tcataggaca ccttcatctc ttaaaagaca     120
aacttctcca ctacgcactc atcgacctct ccaaaaaaca tggtccctta ttctctctct     180
actttggctc catgccaacc gttgttgcct ccacaccaga attgttcaag ctcttccttc     240
aaacgcacga ggcaacttcc ttcaacacaa ggttccaaac ctcagccata agacgcctca     300
cctatgatag ctcagtggcc atggctccct tcggacctta ctggaagttc gtgaggaagc     360
tcatcatgaa cgaccttctc aacgccacca ctgtaaacaa gttgaggcct ttgaggaccc     420
aacagatccg caagttcctt agggttatgg cccaaggcgc agaggcacag aagccccttg     480
acttgaccga ggagcttctg aaatggacca acagcaccac ctccatgatg atgctcggcg     540
aggctgagga gatcagagac atcgcccgcg aggttcttaa gatctttggc gaatacagcc     600
tcactgactt catccggcca ttgaagcatc tcaaggttgg aaagtatgag aagaggatcg     660
acgacatctt gaacaagttc gaccctgtcg ttgaaagagt catcaagaag cgccgtgaga     720
tcgtgaggag gagaaagaac ggagaggttg ttgagggtga ggtcagcggg gttttccttg     780
acactttgct tgaattcgct gaggatgaga ccacggagat caaaatcacc aaggaccaca     840
tcaagggtct tgttgtcgac ttttttctcgg caggaacaga ctccacagcg gtggcaacag     900
agtgggcatt ggcagaactc atcaacaatc taaggtgtt ggaaaaggct cgtgaggagg     960
tctacagtgt tgtgggaaag gacagacttg tggacgaagt tgacactcaa aaccttcctt    1020
acattagagc aatcgtgaag gagacattcc gcatgcaccc gccactccca gtggtcaaaa    1080
gaaagtgcac agaagagtgt gagattaatg gatatgtgat cccagaggga gcattgattc    1140
tcttcaatgt atggcaagta ggaagagact ccaaatactg ggacagacca tcggagttcc    1200
gtcctgagag gttcctagag acaggggctg aaggggaagc aaggcctctt gatcttaggg    1260
gacaacattt tcaacttctc ccatttgggt ctggggagag aatgtgccct ggagtcaatc    1320
tggctacttc gggaatggca acacttcttg catctcttat tcagtgcttt gacttgcaag    1380
```

-continued

```
tgctgggtcc acaaggacag atattgaagg gtggtgacgc caaagttagc atggaagaga    1440
gggccggcct cactgttcca aggcacata gtcttgtctg tgttccactt gcaaggatcg    1500
g                                                                   1501
```

<210> SEQ ID NO 57
<211> LENGTH: 499
<212> TYPE: PRT
<213> ORGANISM: Medicago sativa

<400> SEQUENCE: 57

```
Phe Leu His Leu Arg Pro Thr Pro Thr Ala Lys Ser Lys Ala Leu Arg
1               5                   10                  15

His Leu Pro Asn Pro Pro Ser Pro Lys Pro Arg Leu Pro Phe Ile Gly
            20                  25                  30

His Leu His Leu Leu Lys Asp Lys Leu Leu His Tyr Ala Leu Ile Asp
        35                  40                  45

Leu Ser Lys Lys His Gly Pro Leu Phe Ser Leu Tyr Phe Gly Ser Met
    50                  55                  60

Pro Thr Val Val Ala Ser Thr Pro Glu Leu Phe Lys Leu Phe Leu Gln
65                  70                  75                  80

Thr His Glu Ala Thr Ser Phe Asn Thr Arg Phe Gln Thr Ser Ala Ile
                85                  90                  95

Arg Arg Leu Thr Tyr Asp Ser Ser Val Ala Met Ala Pro Phe Gly Pro
            100                 105                 110

Tyr Trp Lys Phe Val Arg Lys Leu Ile Met Asn Asp Leu Leu Asn Ala
        115                 120                 125

Thr Thr Val Asn Lys Leu Arg Pro Leu Arg Thr Gln Gln Ile Arg Lys
    130                 135                 140

Phe Leu Arg Val Met Ala Gln Gly Ala Glu Ala Gln Lys Pro Leu Asp
145                 150                 155                 160

Leu Thr Glu Glu Leu Leu Lys Trp Thr Asn Ser Thr Thr Ser Met Met
                165                 170                 175

Met Leu Gly Glu Ala Glu Glu Ile Arg Asp Ile Ala Arg Glu Val Leu
            180                 185                 190

Lys Ile Phe Gly Glu Tyr Ser Leu Thr Asp Phe Ile Arg Pro Leu Lys
        195                 200                 205

His Leu Lys Val Gly Lys Tyr Glu Lys Arg Ile Asp Asp Ile Leu Asn
    210                 215                 220

Lys Phe Asp Pro Val Val Glu Arg Val Ile Lys Lys Arg Arg Glu Ile
225                 230                 235                 240

Val Arg Arg Arg Lys Asn Gly Glu Val Val Glu Gly Glu Val Ser Gly
                245                 250                 255

Val Phe Leu Asp Thr Leu Leu Glu Phe Ala Glu Asp Glu Thr Thr Glu
            260                 265                 270

Ile Lys Ile Thr Lys Asp His Ile Lys Gly Leu Val Val Asp Phe Phe
        275                 280                 285

Ser Ala Gly Thr Asp Ser Thr Ala Val Ala Thr Glu Trp Ala Leu Ala
    290                 295                 300

Glu Leu Ile Asn Asn Pro Lys Val Leu Glu Lys Ala Arg Glu Glu Val
305                 310                 315                 320

Tyr Ser Val Val Gly Lys Asp Arg Leu Val Asp Glu Val Asp Thr Gln
                325                 330                 335

Asn Leu Pro Tyr Ile Arg Ala Ile Val Lys Glu Thr Phe Arg Met His
```

```
                    340                 345                 350
Pro Pro Leu Pro Val Val Lys Arg Lys Cys Thr Glu Glu Cys Glu Ile
            355                 360                 365
Asn Gly Tyr Val Ile Pro Glu Gly Ala Leu Ile Leu Phe Asn Val Trp
        370                 375                 380
Gln Val Gly Arg Asp Ser Lys Tyr Trp Asp Arg Pro Ser Glu Phe Arg
385                 390                 395                 400
Pro Glu Arg Phe Leu Glu Thr Gly Ala Glu Gly Ala Arg Pro Leu
                405                 410                 415
Asp Leu Arg Gly Gln His Phe Gln Leu Leu Pro Phe Gly Ser Gly Arg
            420                 425                 430
Arg Met Cys Pro Gly Val Asn Leu Ala Thr Ser Gly Met Ala Thr Leu
            435                 440                 445
Leu Ala Ser Leu Ile Gln Cys Phe Asp Leu Gln Val Leu Gly Pro Gln
            450                 455                 460
Gly Gln Ile Leu Lys Gly Gly Asp Ala Lys Val Ser Met Glu Glu Arg
465                 470                 475                 480
Ala Gly Leu Thr Val Pro Arg Ala His Ser Leu Val Cys Val Pro Leu
                485                 490                 495
Ala Arg Ile
```

<210> SEQ ID NO 58
<211> LENGTH: 1501
<212> TYPE: DNA
<213> ORGANISM: Medicago sativa

<400> SEQUENCE: 58

| | | | | | |
|---|---|---|---|---|---|
| tgtttctgca | cttgcgtccc | acacccactg | caaaatcaaa | agcacttcgc | catctcccaa | 60 |
| acccaccaag | cccaaagcct | cgtcttccct | tcataggaca | ccttcatctc | ttaaaagaca | 120 |
| aacttctcca | ctacgcactc | atcgacctct | ccaaaaaaca | tggtccctta | ttctctctct | 180 |
| actttggctc | catgccaacc | gttgttgcct | ccacaccaga | attgttcaag | ctcttcctcc | 240 |
| aaacgcacga | ggcaacttcc | ttcaacacaa | ggttccaaac | ctcagccata | agacgcctca | 300 |
| cctatgatag | ctcagtggcc | atggttccct | tcggacctta | ctggaagttc | gtgaggaagc | 360 |
| tcatcatgaa | cgaccttctc | aacgccacca | ctgtaaacaa | gttgaggcct | ttgaggaccc | 420 |
| aacagatccg | caagctcctt | agggttatgg | cccaaggcgc | agaggcacag | aagccccttg | 480 |
| acttgaccga | ggagcttctg | aaatggacca | acagcaccat | ctccatgatg | atgctcggcg | 540 |
| aggctgagga | gatcagagac | atcgctcgcg | aggttcttaa | gatcttttggc | gaatacagcc | 600 |
| tcactgactt | catctggcca | ttgaagcatc | tcaaggttgg | aaagtatgag | aagaggatcg | 660 |
| acgacatctt | gaacaagttc | gaccctgtcg | ttgaaagagt | catcaagaag | cgccgtgaga | 720 |
| tcgtgaggag | gagaaagaac | ggagaggtta | ttgagggtga | ggtcagcggg | gttttccttg | 780 |
| acactttgct | tgaattcgct | gaggatgaga | ccacggagat | caaaatcacc | aaggaccaca | 840 |
| tcaagggtct | tgttgtcgac | ttttttctcgg | caggaacaga | ctccacagcg | gtggcaacag | 900 |
| agtgggcatt | ggcagaactc | atcaacaatc | ctaaggtgtt | ggagaaggct | cgtgaggagg | 960 |
| tctacagtgt | tgtgggaaag | gacagacttg | tggacgaagt | tgacactcaa | aaccttcctt | 1020 |
| acattagagc | aatcgtgaag | gagacattcc | gcatgcaccc | gccactccca | gtggtcaaaa | 1080 |
| gaaagtgcac | agaagagtgt | gagattaatg | gatatgtgat | cccagaggga | gcattgattc | 1140 |
| tcttcaatgt | atggcaagta | ggaagagacc | ccaaatactg | ggacagacca | tcggagttcc | 1200 |

-continued

```
gtcctgagag gttcctagag acaggggctg aaggggaagc aaggcctctt gatcttaggg      1260
gacaacattt tcaacttctc ccatttgggt ctgggaggag aatgtgccct ggagtcaatc      1320
tggctacttc gggaatggca acacttcttg catctcttat tcagtgcttt gacttgcaag      1380
tgctgggtcc acaaggacag atattgaagg gtggtgacgc caaagttagc atggaagaga      1440
gggccggcct cactgttcca aggcacata gtcttgtctg tgttccactt gcaaggatcg       1500
g                                                                      1501
```

<210> SEQ ID NO 59
<211> LENGTH: 499
<212> TYPE: PRT
<213> ORGANISM: Medicago sativa

<400> SEQUENCE: 59

```
Phe Leu His Leu Arg Pro Thr Pro Thr Ala Lys Ser Lys Ala Leu Arg
1               5                   10                  15

His Leu Pro Asn Pro Pro Ser Pro Lys Pro Arg Leu Pro Phe Ile Gly
            20                  25                  30

His Leu His Leu Leu Lys Asp Lys Leu Leu His Tyr Ala Leu Ile Asp
        35                  40                  45

Leu Ser Lys Lys His Gly Pro Leu Phe Ser Leu Tyr Phe Gly Ser Met
    50                  55                  60

Pro Thr Val Val Ala Ser Thr Pro Glu Leu Phe Lys Leu Phe Leu Gln
65                  70                  75                  80

Thr His Glu Ala Thr Ser Phe Asn Thr Arg Phe Gln Thr Ser Ala Ile
                85                  90                  95

Arg Arg Leu Thr Tyr Asp Ser Ser Val Ala Met Val Pro Phe Gly Pro
            100                 105                 110

Tyr Trp Lys Phe Val Arg Lys Leu Ile Met Asn Asp Leu Leu Asn Ala
        115                 120                 125

Thr Thr Val Asn Lys Leu Arg Pro Leu Arg Thr Gln Gln Ile Arg Lys
    130                 135                 140

Leu Leu Arg Val Met Ala Gln Gly Ala Glu Ala Gln Lys Pro Leu Asp
145                 150                 155                 160

Leu Thr Glu Glu Leu Leu Lys Trp Thr Asn Ser Thr Ile Ser Met Met
                165                 170                 175

Met Leu Gly Glu Ala Glu Ile Arg Asp Ile Ala Arg Glu Val Leu
            180                 185                 190

Lys Ile Phe Gly Glu Tyr Ser Leu Thr Asp Phe Ile Trp Pro Leu Lys
        195                 200                 205

His Leu Lys Val Gly Lys Tyr Glu Lys Arg Ile Asp Asp Ile Leu Asn
    210                 215                 220

Lys Phe Asp Pro Val Val Glu Arg Val Ile Lys Arg Arg Glu Ile
225                 230                 235                 240

Val Arg Arg Lys Asn Gly Glu Val Ile Glu Gly Glu Val Ser Gly
                245                 250                 255

Val Phe Leu Asp Thr Leu Leu Glu Phe Ala Glu Asp Glu Thr Thr Glu
            260                 265                 270

Ile Lys Ile Thr Lys Asp His Ile Lys Gly Leu Val Val Asp Phe Phe
        275                 280                 285

Ser Ala Gly Thr Asp Ser Thr Ala Val Ala Thr Glu Trp Ala Leu Ala
    290                 295                 300

Glu Leu Ile Asn Asn Pro Lys Val Leu Glu Lys Ala Arg Glu Glu Val
305                 310                 315                 320
```

```
Tyr Ser Val Val Gly Lys Asp Arg Leu Val Asp Glu Val Asp Thr Gln
            325                 330                 335
Asn Leu Pro Tyr Ile Arg Ala Ile Val Lys Glu Thr Phe Arg Met His
            340                 345                 350
Pro Pro Leu Pro Val Val Lys Arg Lys Cys Thr Glu Glu Cys Glu Ile
            355                 360                 365
Asn Gly Tyr Val Ile Pro Glu Gly Ala Leu Ile Leu Phe Asn Val Trp
            370                 375                 380
Gln Val Gly Arg Asp Pro Lys Tyr Trp Asp Arg Pro Ser Glu Phe Arg
385                 390                 395                 400
Pro Glu Arg Phe Leu Glu Thr Gly Ala Glu Gly Ala Arg Pro Leu
                405                 410                 415
Asp Leu Arg Gly Gln His Phe Gln Leu Leu Pro Phe Gly Ser Gly Arg
                420                 425                 430
Arg Met Cys Pro Gly Val Asn Leu Ala Thr Ser Gly Met Ala Thr Leu
                435                 440                 445
Leu Ala Ser Leu Ile Gln Cys Phe Asp Leu Gln Val Leu Gly Pro Gln
                450                 455                 460
Gly Gln Ile Leu Lys Gly Gly Asp Ala Lys Val Ser Met Glu Glu Arg
465                 470                 475                 480
Ala Gly Leu Thr Val Pro Arg Ala His Ser Leu Val Cys Val Pro Leu
                485                 490                 495
Ala Arg Ile

<210> SEQ ID NO 60
<211> LENGTH: 1497
<212> TYPE: DNA
<213> ORGANISM: Beta vulgaris

<400> SEQUENCE: 60
tctgcacttg cgtcccacac ccactgcaaa atcaaaagca cttcgccatc tcccaaaccc      60
accaagccca aagcctcgtc ttcccttcat aggacacctt catctcttaa aagcaaaact     120
tctccactac gcactcatcg acctctccaa aaaacatggt cccttattct ctcactactt     180
tggctccatg ccaaccgttg ttgcctccac accagaattg ttcaagctct tcctccaaac     240
gaacgaggca acttccttca acacaaggtt ccaaacctca gccataagac gcctcaccta     300
tgatagctca gtggccatgg ttcccttcgg accttactgg aagttcgtga ggaagctcat     360
catgaacgac cttctcaacg ccaccactgt aaacaagttg aggcctttga ggacccaaca     420
gatccgcaag ttccttaggg ctatggccca aggcgcagag gcacggaagc cccttgactt     480
gaccgaggag cttctgaaat gggccaacag caccatctcc atgatgatgc tcggcgaggc     540
tgaggagatc agagacatcg ctcgcgaggt tcttaagatc tttggcgaat acagcctcac     600
tgacttcatc tggccattga agcatctcaa ggttggaaag tatgagaaga ggatcgacga     660
catcttgaac aagttcgacc ctgtcgttga aagagtcatc aagaagcgcc gtgagatcgt     720
gaggaggaga aagaacggag aggttgttga gggtgaggtc agcggggttt tccttgacac     780
tttgcttgaa ttcgctgagg atgagaccat ggagatcaaa atcaccaagg accacaccaa     840
gggtcttgtt gtcgacttct tctcggcagg aacagactcc acagcggtgg caacagagtg     900
ggcattggca gaactcatca acaatcctaa ggtgttggaa aaggctcgtg aggaggtcta     960
cagtgttgtg ggaaaggaca gacttgtgga cgaagttgac actcaaaacc ttccttacat    1020
tagagcaatc gtgaaggaga cattccgcat gcacccgcca ctcccagtgg tcaaaagaaa    1080
```

```
gtgcacagaa gagtgtgaga ttaatggata tgtgatccca gagggagcat tgattcccct    1140
caatgtatgg caagtaggaa gagaccccaa atactgggac agaccatcgg agttccgtcc    1200
tgagaggttc ctagagacag gggctgaagg ggaagcaagg cctcttgatc ttaggggaca    1260 acatttcaa cttctcccat ttgggtctgg gaggagaatg tgccctggag tcaatctggc    1320
tacttcggga acggcaacac ttcttgcatc tcttattcag tgctttgact tgcaagtgct    1380
gggtccacag ggacagatat tgaagggtgg tgacgccaaa gttagcatgg aagagagagc    1440
cggcctcact gttccaaggg cacatagtct tgtctgtgtt ccacttgcaa ggatcgg      1497
```

<210> SEQ ID NO 61
<211> LENGTH: 498
<212> TYPE: PRT
<213> ORGANISM: Beta vulgaris

<400> SEQUENCE: 61

```
Leu His Leu Arg Pro Thr Pro Thr Ala Lys Ser Lys Ala Leu Arg His
1               5                   10                  15

Leu Pro Asn Pro Pro Ser Pro Lys Pro Arg Leu Pro Phe Ile Gly His
            20                  25                  30

Leu His Leu Leu Lys Asp Lys Leu Leu His Tyr Ala Leu Ile Asp Leu
        35                  40                  45

Ser Lys Lys His Gly Pro Leu Phe Ser His Tyr Phe Gly Ser Met Pro
    50                  55                  60

Thr Val Val Ala Ser Thr Pro Glu Leu Phe Lys Leu Phe Leu Gln Thr
65                  70                  75                  80

Asn Glu Ala Thr Ser Phe Asn Thr Arg Phe Gln Thr Ser Ala Ile Arg
                85                  90                  95

Arg Leu Thr Tyr Asp Ser Ser Val Ala Met Val Pro Phe Gly Pro Tyr
            100                 105                 110

Trp Lys Phe Val Arg Lys Leu Ile Met Asn Asp Leu Leu Asn Ala Thr
        115                 120                 125

Thr Val Asn Lys Leu Arg Pro Leu Arg Thr Gln Gln Ile Arg Lys Phe
    130                 135                 140

Leu Arg Ala Met Ala Gln Gly Ala Glu Ala Arg Lys Pro Leu Asp Leu
145                 150                 155                 160

Thr Glu Glu Leu Leu Lys Trp Ala Asn Ser Thr Ile Ser Met Met Met
                165                 170                 175

Leu Gly Glu Ala Glu Glu Ile Arg Asp Ile Ala Arg Glu Val Leu Lys
            180                 185                 190

Ile Phe Gly Glu Tyr Ser Leu Thr Asp Phe Ile Trp Pro Leu Lys His
        195                 200                 205

Leu Lys Val Gly Lys Tyr Glu Lys Arg Ile Asp Ile Leu Asn Lys
    210                 215                 220

Phe Asp Pro Val Val Glu Arg Val Ile Lys Arg Arg Glu Ile Val
225                 230                 235                 240

Arg Arg Arg Lys Asn Gly Glu Val Val Glu Gly Val Ser Gly Val
                245                 250                 255

Phe Leu Asp Thr Leu Leu Glu Phe Ala Glu Asp Glu Thr Met Glu Ile
            260                 265                 270

Lys Ile Thr Lys Asp His Thr Lys Gly Leu Val Val Asp Phe Phe Ser
        275                 280                 285

Ala Gly Thr Asp Ser Thr Ala Val Ala Thr Glu Trp Ala Leu Ala Glu
    290                 295                 300
```

-continued

```
Leu Ile Asn Asn Pro Lys Val Leu Glu Lys Ala Arg Glu Val Tyr
305                 310                 315                 320

Ser Val Val Gly Lys Asp Arg Leu Val Asp Glu Val Asp Thr Gln Asn
            325                 330                 335

Leu Pro Tyr Ile Arg Ala Ile Val Lys Glu Thr Phe Arg Met His Pro
            340                 345                 350

Pro Leu Pro Val Val Lys Arg Lys Cys Thr Glu Cys Glu Ile Asn
    355                 360                 365

Gly Tyr Val Ile Pro Glu Gly Ala Leu Ile Pro Phe Asn Val Trp Gln
370                 375                 380

Val Gly Arg Asp Pro Lys Tyr Trp Asp Arg Pro Ser Glu Phe Arg Pro
385                 390                 395                 400

Glu Arg Phe Leu Glu Thr Gly Ala Glu Gly Ala Arg Pro Leu Asp
            405                 410                 415

Leu Arg Gly Gln His Phe Gln Leu Leu Pro Phe Gly Ser Gly Arg Arg
            420                 425                 430

Met Cys Pro Gly Val Asn Leu Ala Thr Ser Gly Thr Ala Thr Leu Leu
            435                 440                 445

Ala Ser Leu Ile Gln Cys Phe Asp Leu Gln Val Leu Gly Pro Gln Gly
    450                 455                 460

Gln Ile Leu Lys Gly Gly Asp Ala Lys Val Ser Met Glu Glu Arg Ala
465                 470                 475                 480

Gly Leu Thr Val Pro Arg Ala His Ser Leu Val Cys Val Pro Leu Ala
            485                 490                 495

Arg Ile

<210> SEQ ID NO 62
<211> LENGTH: 22
<212> TYPE: DNA
<213> ORGANISM: Artificial Sequence
<220> FEATURE:
<223> OTHER INFORMATION: PCR primer

<400> SEQUENCE: 62
gttaccatgg ctgctgctat tg                                              22

<210> SEQ ID NO 63
<211> LENGTH: 24
<212> TYPE: DNA
<213> ORGANISM: Artificial Sequence
<220> FEATURE:
<223> OTHER INFORMATION: PCR primer

<400> SEQUENCE: 63
ttaaacgtaa aatgaaacaa gagg                                            24

<210> SEQ ID NO 64
<211> LENGTH: 26
<212> TYPE: DNA
<213> ORGANISM: Artificial Sequence
<220> FEATURE:
<223> OTHER INFORMATION: PCR primer

<400> SEQUENCE: 64
gacacttcga cactgctgct gcttat                                          26

<210> SEQ ID NO 65
<211> LENGTH: 25
<212> TYPE: DNA
```

-continued

```
<213> ORGANISM: Artificial Sequence
<220> FEATURE:
<223> OTHER INFORMATION: PCR primer

<400> SEQUENCE: 65
tctcaaactc acctgggcta tggat                                          25

<210> SEQ ID NO 66
<211> LENGTH: 521
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (10)..(10)
<223> OTHER INFORMATION: Xaa= Phe or Leu
<220> FEATURE:
<221> NAME/KEY: MISC_FEATURE
<222> LOCATION: (16)..(16)
<223> OTHER INFORMATION: Xaa=Ser or Leu
<220> FEATURE:
<221> NAME/KEY: MISC_FEATURE
<222> LOCATION: (23)..(23)
<223> OTHER INFORMATION: Xaa=Ser or Thr
<220> FEATURE:
<221> NAME/KEY: MISC_FEATURE
<222> LOCATION: (25)..(25)
<223> OTHER INFORMATION: Xaa=Ile or Lys
<220> FEATURE:
<221> NAME/KEY: MISC_FEATURE
<222> LOCATION: (39)..(39)
<223> OTHER INFORMATION: Xaa=Lys or Arg
<220> FEATURE:
<221> NAME/KEY: MISC_FEATURE
<222> LOCATION: (48)..(48)
<223> OTHER INFORMATION: Xaa=Pro or Leu
<220> FEATURE:
<221> NAME/KEY: MISC_FEATURE
<222> LOCATION: (60)..(60)
<223> OTHER INFORMATION: Xaa=Pro or Leu
<220> FEATURE:
<221> NAME/KEY: MISC_FEATURE
<222> LOCATION: (73)..(73)
<223> OTHER INFORMATION: Xaa=Leu or His
<220> FEATURE:
<221> NAME/KEY: MISC_FEATURE
<222> LOCATION: (74)..(74)
<223> OTHER INFORMATION: Xaa=Ser or Tyr
<220> FEATURE:
<221> NAME/KEY: MISC_FEATURE
<222> LOCATION: (95)..(95)
<223> OTHER INFORMATION: Xaa=Ala or Thr
<220> FEATURE:
<221> NAME/KEY: MISC_FEATURE
<222> LOCATION: (96)..(96)
<223> OTHER INFORMATION: Xaa=Asn or His
<220> FEATURE:
<221> NAME/KEY: MISC_FEATURE
<222> LOCATION: (102)..(102)
<223> OTHER INFORMATION: Xaa=Asn or Ser
<220> FEATURE:
<221> NAME/KEY: MISC_FEATURE
<222> LOCATION: (110)..(110)
<223> OTHER INFORMATION: Xaa=Ile, Val, or Thr
<220> FEATURE:
<221> NAME/KEY: MISC_FEATURE
<222> LOCATION: (112)..(112)
<223> OTHER INFORMATION: Xaa=Arg or His
<220> FEATURE:
<221> NAME/KEY: MISC_FEATURE
<222> LOCATION: (117)..(117)
<223> OTHER INFORMATION: Xaa=Asn or Ser
<220> FEATURE:
<221> NAME/KEY: MISC_FEATURE
<222> LOCATION: (118)..(118)
<223> OTHER INFORMATION: Xaa=Ser or Leu
```

```
<220> FEATURE:
<221> NAME/KEY: MISC_FEATURE
<222> LOCATION: (121)..(121)
<223> OTHER INFORMATION: Xaa=Met or Arg
<220> FEATURE:
<221> NAME/KEY: MISC_FEATURE
<222> LOCATION: (122)..(122)
<223> OTHER INFORMATION: Xaa=Ala or Val
<220> FEATURE:
<221> NAME/KEY: MISC_FEATURE
<222> LOCATION: (124)..(124)
<223> OTHER INFORMATION: Xaa=Phe or Ile
<220> FEATURE:
<221> NAME/KEY: MISC_FEATURE
<222> LOCATION: (129)..(129)
<223> OTHER INFORMATION: Xaa=Lys or Arg
<220> FEATURE:
<221> NAME/KEY: MISC_FEATURE
<222> LOCATION: (147)..(147)
<223> OTHER INFORMATION: Xaa=Lys or Glu
<220> FEATURE:
<221> NAME/KEY: MISC_FEATURE
<222> LOCATION: (159)..(159)
<223> OTHER INFORMATION: Xaa=Leu or Phe
<220> FEATURE:
<221> NAME/KEY: MISC_FEATURE
<222> LOCATION: (162)..(162)
<223> OTHER INFORMATION: Xaa=Ala or Val
<220> FEATURE:
<221> NAME/KEY: MISC_FEATURE
<222> LOCATION: (166)..(166)
<223> OTHER INFORMATION: Xaa=Ser or Gly
<220> FEATURE:
<221> NAME/KEY: MISC_FEATURE
<222> LOCATION: (170)..(170)
<223> OTHER INFORMATION: Xaa=Gln or Arg
<220> FEATURE:
<221> NAME/KEY: MISC_FEATURE
<222> LOCATION: (175)..(175)
<223> OTHER INFORMATION: Xaa=Val or Leu
<220> FEATURE:
<221> NAME/KEY: MISC_FEATURE
<222> LOCATION: (183)..(183)
<223> OTHER INFORMATION: Xaa=Ala or Thr
<220> FEATURE:
<221> NAME/KEY: MISC_FEATURE
<222> LOCATION: (187)..(187)
<223> OTHER INFORMATION: Xaa=Thr or Ile
<220> FEATURE:
<221> NAME/KEY: MISC_FEATURE
<222> LOCATION: (191)..(191)
<223> OTHER INFORMATION: Xaa=Met or Val
<220> FEATURE:
<221> NAME/KEY: MISC_FEATURE
<222> LOCATION: (209)..(209)
<223> OTHER INFORMATION: Xaa=Phe or Tyr
<220> FEATURE:
<221> NAME/KEY: MISC_FEATURE
<222> LOCATION: (219)..(219)
<223> OTHER INFORMATION: Xaa=Arg or Trp
<220> FEATURE:
<221> NAME/KEY: MISC_FEATURE
<222> LOCATION: (223)..(223)
<223> OTHER INFORMATION: Xaa=Tyr or His
<220> FEATURE:
<221> NAME/KEY: MISC_FEATURE
<222> LOCATION: (253)..(253)
<223> OTHER INFORMATION: Xaa=Gly or Glu
<220> FEATURE:
<221> NAME/KEY: MISC_FEATURE
<222> LOCATION: (259)..(259)
<223> OTHER INFORMATION: Xaa=Lys or Glu
<220> FEATURE:
<221> NAME/KEY: MISC_FEATURE
<222> LOCATION: (263)..(263)
<223> OTHER INFORMATION: Xaa=Val or Asp
<220> FEATURE:
<221> NAME/KEY: MISC_FEATURE
<222> LOCATION: (264)..(264)
```

-continued

```
<223> OTHER INFORMATION: Xaa=Val, Asp, or Ile
<220> FEATURE:
<221> NAME/KEY: MISC_FEATURE
<222> LOCATION: (268)..(268)
<223> OTHER INFORMATION: Xaa=Ala or Val
<220> FEATURE:
<221> NAME/KEY: MISC_FEATURE
<222> LOCATION: (272)..(272)
<223> OTHER INFORMATION: Xaa=Phe or Leu
<220> FEATURE:
<221> NAME/KEY: MISC_FEATURE
<222> LOCATION: (285)..(285)
<223> OTHER INFORMATION: Xaa=Thr or Met
<220> FEATURE:
<221> NAME/KEY: MISC_FEATURE
<222> LOCATION: (292)..(292)
<223> OTHER INFORMATION: Xaa=ANY AMINO ACID
<220> FEATURE:
<221> NAME/KEY: MISC_FEATURE
<222> LOCATION: (293)..(293)
<223> OTHER INFORMATION: Xaa=ANY AMINO ACID
<220> FEATURE:
<221> NAME/KEY: MISC_FEATURE
<222> LOCATION: (294)..(294)
<223> OTHER INFORMATION: Xaa=Thr or Ile
<220> FEATURE:
<221> NAME/KEY: MISC_FEATURE
<222> LOCATION: (301)..(301)
<223> OTHER INFORMATION: Xaa=Phe or Leu
<220> FEATURE:
<221> NAME/KEY: MISC_FEATURE
<222> LOCATION: (306)..(306)
<223> OTHER INFORMATION: Xaa=Thr or Ile
<220> FEATURE:
<221> NAME/KEY: MISC_FEATURE
<222> LOCATION: (311)..(311)
<223> OTHER INFORMATION: Xaa=Val or Glu
<220> FEATURE:
<221> NAME/KEY: MISC_FEATURE
<222> LOCATION: (312)..(312)
<223> OTHER INFORMATION: Xaa=Val or Ala
<220> FEATURE:
<221> NAME/KEY: MISC_FEATURE
<222> LOCATION: (325)..(325)
<223> OTHER INFORMATION: Xaa=Arg or Lys
<220> FEATURE:
<221> NAME/KEY: MISC_FEATURE
<222> LOCATION: (328)..(328)
<223> OTHER INFORMATION: Xaa=Gln or Glu
<220> FEATURE:
<221> NAME/KEY: MISC_FEATURE
<222> LOCATION: (329)..(329)
<223> OTHER INFORMATION: Xaa=ANY AMINO ACID
<220> FEATURE:
<221> NAME/KEY: MISC_FEATURE
<222> LOCATION: (334)..(334)
<223> OTHER INFORMATION: Xaa=Val or Ala
<220> FEATURE:
<221> NAME/KEY: MISC_FEATURE
<222> LOCATION: (342)..(342)
<223> OTHER INFORMATION: Xaa=Arg or Ile
<220> FEATURE:
<221> NAME/KEY: MISC_FEATURE
<222> LOCATION: (377)..(377)
<223> OTHER INFORMATION: Xaa=Thr or Ile
<220> FEATURE:
<221> NAME/KEY: MISC_FEATURE
<222> LOCATION: (381)..(381)
<223> OTHER INFORMATION: Xaa=Glu or Gly
<220> FEATURE:
<221> NAME/KEY: MISC_FEATURE
<222> LOCATION: (385)..(385)
<223> OTHER INFORMATION: Xaa=Tyr, His, or Cys
<220> FEATURE:
<221> NAME/KEY: MISC_FEATURE
<222> LOCATION: (387)..(387)
<223> OTHER INFORMATION: Xaa=Ile or Thr
<220> FEATURE:
<221> NAME/KEY: MISC_FEATURE
```

```
<222> LOCATION: (393)..(393)
<223> OTHER INFORMATION: Xaa=Val or Ile
<220> FEATURE:
<221> NAME/KEY: MISC_FEATURE
<222> LOCATION: (394)..(394)
<223> OTHER INFORMATION: Xaa=Leu or Pro
<220> FEATURE:
<221> NAME/KEY: MISC_FEATURE
<222> LOCATION: (402)..(402)
<223> OTHER INFORMATION: Xaa=Arg or Lys
<220> FEATURE:
<221> NAME/KEY: MISC_FEATURE
<222> LOCATION: (404)..(404)
<223> OTHER INFORMATION: Xaa=Ser or Pro
<220> FEATURE:
<221> NAME/KEY: MISC_FEATURE
<222> LOCATION: (413)..(413)
<223> OTHER INFORMATION: Xaa=Ser or Phe
<220> FEATURE:
<221> NAME/KEY: MISC_FEATURE
<222> LOCATION: (422)..(422)
<223> OTHER INFORMATION: Xaa=Glu or Gly
<220> FEATURE:
<221> NAME/KEY: MISC_FEATURE
<222> LOCATION: (428)..(428)
<223> OTHER INFORMATION: Xaa=Gly or Arg
<220> FEATURE:
<221> NAME/KEY: MISC_FEATURE
<222> LOCATION: (429)..(429)
<223> OTHER INFORMATION: Xaa=Pro or Leu
<220> FEATURE:
<221> NAME/KEY: MISC_FEATURE
<222> LOCATION: (435)..(435)
<223> OTHER INFORMATION: Xaa=Gln or Arg
<220> FEATURE:
<221> NAME/KEY: MISC_FEATURE
<222> LOCATION: (447)..(447)
<223> OTHER INFORMATION: Xaa=Arg or Gly
<220> FEATURE:
<221> NAME/KEY: MISC_FEATURE
<222> LOCATION: (453)..(453)
<223> OTHER INFORMATION: Xaa=Asn, Ser, or Ile
<220> FEATURE:
<221> NAME/KEY: MISC_FEATURE
<222> LOCATION: (459)..(459)
<223> OTHER INFORMATION: Xaa=Met or Thr
<220> FEATURE:
<221> NAME/KEY: MISC_FEATURE
<222> LOCATION: (485)..(485)
<223> OTHER INFORMATION: Xaa=Asp or Gly

<400> SEQUENCE: 66

Met Leu Leu Glu Leu Ala Leu Gly Leu Xaa Val Leu Ala Leu Phe Xaa
1               5                   10                  15

His Leu Arg Pro Thr Pro Xaa Ala Xaa Ser Lys Ala Leu Arg His Leu
            20                  25                  30

Pro Asn Pro Pro Ser Pro Xaa Pro Arg Leu Pro Phe Ile Gly His Xaa
        35                  40                  45

His Leu Leu Lys Asp Lys Leu Leu His Tyr Ala Xaa Ile Asp Leu Ser
    50                  55                  60

Lys Lys His Gly Pro Leu Phe Ser Xaa Xaa Phe Gly Ser Met Pro Thr
65                  70                  75                  80

Val Val Ala Ser Thr Pro Glu Leu Phe Lys Leu Phe Leu Gln Xaa Xaa
                85                  90                  95

Glu Ala Thr Ser Phe Xaa Thr Arg Phe Gln Thr Ser Ala Xaa Arg Xaa
            100                 105                 110

Leu Thr Tyr Asp Xaa Xaa Val Ala Xaa Xaa Pro Xaa Gly Pro Tyr Trp
        115                 120                 125

Xaa Phe Val Arg Lys Leu Ile Met Asn Asp Leu Leu Asn Ala Thr Thr
130                 135                 140
```

```
Val Asn Xaa Leu Arg Pro Leu Arg Thr Gln Gln Ile Arg Lys Xaa Leu
145                 150                 155                 160

Arg Xaa Met Ala Gln Xaa Ala Glu Ala Xaa Lys Pro Leu Asp Xaa Thr
            165                 170                 175

Glu Glu Leu Leu Lys Trp Xaa Asn Ser Thr Xaa Ser Met Met Xaa Leu
            180                 185                 190

Gly Glu Ala Glu Glu Ile Arg Asp Ile Ala Arg Glu Val Leu Lys Ile
            195                 200                 205

Xaa Gly Glu Tyr Ser Leu Thr Asp Phe Ile Xaa Pro Leu Lys Xaa Leu
    210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Xaa Ile Val Arg
                245                 250                 255

Arg Arg Xaa Asn Gly Glu Xaa Xaa Glu Gly Glu Xaa Ser Gly Val Xaa
            260                 265                 270

Leu Asp Thr Leu Leu Glu Phe Ala Glu Asp Glu Thr Xaa Glu Ile Lys
        275                 280                 285

Ile Thr Lys Xaa Xaa Xaa Lys Gly Leu Val Val Asp Xaa Phe Ser Ala
    290                 295                 300

Gly Xaa Asp Ser Thr Ala Xaa Xaa Thr Glu Trp Ala Leu Ala Glu Leu
305                 310                 315                 320

Ile Asn Asn Pro Xaa Val Leu Xaa Xaa Ala Arg Glu Glu Xaa Tyr Ser
                325                 330                 335

Val Val Gly Lys Asp Xaa Leu Val Asp Glu Val Asp Thr Gln Asn Leu
            340                 345                 350

Pro Tyr Ile Arg Ala Ile Val Lys Glu Thr Phe Arg Met His Pro Pro
        355                 360                 365

Leu Pro Val Val Lys Arg Lys Cys Xaa Glu Glu Cys Xaa Ile Asn Gly
370                 375                 380

Xaa Val Xaa Pro Glu Gly Ala Leu Xaa Xaa Phe Asn Val Trp Gln Val
385                 390                 395                 400

Gly Xaa Asp Xaa Lys Tyr Trp Asp Arg Pro Ser Glu Xaa Arg Pro Glu
        405                 410                 415

Arg Phe Leu Glu Thr Xaa Ala Glu Gly Glu Ala Xaa Xaa Leu Asp Leu
            420                 425                 430

Arg Gly Xaa His Phe Gln Leu Leu Pro Phe Gly Ser Gly Arg Xaa Met
            435                 440                 445

Cys Pro Gly Val Xaa Leu Ala Thr Ser Gly Xaa Ala Thr Leu Leu Ala
    450                 455                 460

Ser Leu Ile Gln Cys Phe Asp Leu Gln Val Leu Gly Pro Gln Gly Gln
465                 470                 475                 480

Ile Leu Lys Gly Xaa Asp Ala Lys Val Ser Met Glu Glu Arg Ala Gly
            485                 490                 495

Leu Thr Val Pro Arg Ala His Ser Leu Val Cys Val Pro Leu Ala Arg
            500                 505                 510

Ile Gly Val Ala Ser Lys Leu Leu Ser
            515                 520
```

NUCLEIC ACID SEQUENCES ENCODING ISOFLAVONE SYNTHASE

This application claims the benefit of U.S. Provisional Application No. 60/117,769, filed Jan. 27, 1999, U.S. Provisional Application No. 60/144,783, filed Jul. 20, 1999, and U.S. Provisional Application No. 60/156,094, filed Sep. 24, 1999.

FIELD OF THE INVENTION

This invention is in the field of plant molecular biology. More specifically, this invention pertains to nucleic acid sequences encoding isoflavone synthase and their use in producing isoflavones.

BACKGROUND OF THE INVENTION

Isoflavonoids represent a class of secondary metabolites produced in legumes by a branch of the phenylpropanoid pathway and include such compounds as isoflavones, isoflavanones, rotenoids, pterocarpans, isoflavans, quinone derivatives, 3-aryl-4-hydroxy-coumarins, 3-arylcoumarins, isoflav-3-enes, coumestans, alpha-methyldeoxybenzoins, 2-arylbenzofurans, isoflavanol, coumaronochromone and the like. In plants, these compounds are known to be involved in interactions with other organisms and to participate in the defense responses of legumes against phytopathogenic microorganisms (Dewick, P. M. (1993) in The Flavonoids, Advances in Research Since 1986, Harborne, J. B. Ed., pp. 117–238, Chapman and Hall, London). Isoflavonoid-derived compounds also are involved in symbiotic relationships between roots and rhizobial bacteria which eventually result in nodulation and nitrogen-fixation (Phillips, D. A. (1992) in *Recent Advances in Phytochemistry.* Vol. 26, pp 201–231, Stafford, H. A. and Ibrahim, R. K., Eds, Pleneum Press, New York), and overall they have been shown to act as antibiotics, repellents, attractants, and signal compounds (Barz, W. and Welle, R. (1992) *Phenolic Metabolism in Plants, pg* 139–164, Ed by H. A. Stafford and R. K. Ibrahim, Plenum Press, New York).

Isoflavonoids have also been reported to have physiological activity in animal and human studies. For example, it has been reported that the isoflavones found in soybean seeds possess antihemolytic (Naim, M., et al. (1976) *J. Agric. Food Chem.* 24:1174–1177), antifungal (Naim, M., et al. (1974) *J. Agr. Food Chem.* 22:806–810), estrogenic (Price, K. R. and Fenwick, G. R. (1985) *Food Addit. Contam.* 2:73–106), tumor-suppressing (Messina, M. and Barnes, S. (1991) *J. Natl. Cancer Inst.* 83:541–546; Peterson, G., et al. (1991) *Biochem. Biophys. Res. Commun.* 179:661–667), hypolipidemic (Mathur, K., et al. (1964) *J. Nutr.* 84:201–204), and serum cholesterol-lowering (Sharma, R. D. (1979) *Lipids* 14:535–540) effects. These epidemiological studies indicate that isoflavones in soybean protein products, when taken as a dietary supplement, may produce many significant health benefits.

Free isoflavones rarely accumulate to high levels in soybeans. Instead they are usually conjugated to carbohydrates or organic acids. Soybean seeds contain three types of isoflavones in four different forms: the aglycones, daidzein, genistein and glycitein; the glucosides, daidzin, genistin and glycitin; the acetylgucosides, 6"-O-acetyldaidzin, 6"-O-acetylgenistin and 6"-O-acetylglycitin; and the malonylglucosides, 6"-O-malonyldaidzin, 6"-O-malonylgenistin and 6"-O-malonylglycitin. In accordance with the present invention, all of these compounds are included in the term isoflavonoids. The content of isoflavonoids in soybean seeds is quite variable and is affected by both genetics and environmental conditions such as growing location and temperature during seed fill (Tsukamoto, C., et al. (1995) *J. Agric. Food Chem.* 43:1184–1192; Wang, H. and Murphy, P. A. (1994) *J. Agric. Food Chem.* 42:1674–1677). In addition, isoflavonoid content in legumes can be stress-induced by pathogenic attack, wounding, high UV light exposure and pollution (Dixon, R. A. and Paiva, N. L. (1995) *Plant Cell* 7:1085–1097).

The biosynthetic pathway for isoflavonoids in soybean and their relationship with several other classes of phenylpropanoids is presented in FIG. 1. Many of the enzymes involved in the synthesis of isoflavonoids in legumes have been identified and many of the genes in the pathway have been cloned. These include three P450-dependent monooxygenases, cinnamate 4-hydoxylase (Potts, J. R. M., et al. (1974) *J. Biol. Chem.* 249:5019–5026), isoflavone 2'-hydroxylase (Akashi, T. et al. (1998) *Biochem. Biophys. Res. Commun.* 251:67–70), and dihydroxypterocarpan 6a-hydroxylase (Schopfer, C. R., et. al. (1998) *FEBS Lett.* 432: 182–186). However, to date the gene encoding isoflavone synthase, the first step in the phenylpropanoid branch that commits metabolic intermediates to the synthesis of isoflavonoids, has been neither identified nor cloned from any species. In this central reaction, 2S-flavanone is converted into an isoflavonoid such as genistein and daidzein. The enzymatic reaction for this oxidative aryl migration step was first reported by Hagmann, M. L. and Grisebach, H. ((1984) *FEBS Lett.* 175.199–202). The reaction involves a P450 monoxygenase-mediated conversion of the 2S-flavanone to a 2-hydroxyisoflavanone, followed by conversion to the isoflavonoid. This last step is possibly mediated by a soluble dehydratase (Kochs, G. and Grisenbach, H. (1985) *Eur. J. Biochem.* 155:311–318). However, the 2-hydroxyisoflavanone intermediate was described as unstable and could convert directly to genistein.

Cytochrome P450-dependant monooxygenases comprise a large group of heme-containing enzymes, most of which catalyze NADPH- and $O_2$-dependant hydroxylation reactions. Most of these enzymes do not use NADPH directly, but rely upon an interaction with a flavoprotein known as a P450 reductase that transfers electrons from the cofactor to the P450. Cloning of plant P450s by traditional protein purification strategies has been difficult, as these membrane-bound proteins are often very unstable and are typically present in low abundance. PCR-based cloning strategies using sequence homologies between P450s has increased dramatically the number of P450 genes cloned. However, the in vivo activity of many of these cloned genes remains unknown and they are classified simply as P450s, and are grouped into families based solely on sequence homology (Chapple, C. (1998) *Annu. Rev. Plant Physiol. Plant Mol. Bio.* 49:311–343). Proteins that are greater than 55% identical are designated as members of the same subfamily, while P450s that are 97% identical, or greater, are assumed to be allelic variants of the same gene (Chapple, C. (1998) *Annu. Rev. Plant Physiol. Plant Mol. Bio.* 49:311–343).

Efforts to determine in vivo activities of existing P450 clones are increasing. Most efforts involve expressing genes or cDNAs for P450s in yeast or insect cell systems, and then screening for a particular activity. For example, isoflavone 2'-hydroxylase (Akashi, T., et al. (1998) *Biochem. Biophys. Res. Commun.* 251:67–70) and dihydroxypterocarpan 6a-hydroxylase (Schopfer, C. R., et al. (1998) *FEBS Letters* 432:182–186) were identified in this manner.

The physiological activities associated with isoflavonoids in both plants and humans makes the manipulation of their contents in crop plants highly desirable. For example, increasing levels of isoflavonoid in soybean seeds would increase the efficiency of extraction and lower the cost of isoflavone-related products sold today for use in either reduction of serum cholesterol or in estrogen replacement therapy. Decreasing levels of isoflavonoid in soybean seeds would be beneficial for production of soy-based infant formulas where the estrogenic effects of isoflavonoid are undesirable. Raising levels of isoflavonoid phytoalexins in vegetative plant tissue could increase plant defenses to pathogen attack, thereby improving plant disease resistance and lowering pesticide use rates. Manipulation of isoflavonoid levels in roots could lead to improved nodulation and increased efficiencies of nitrogen fixation. To date, however, it has proven difficult to develop soybean or other plant lines with consistently high levels of isoflavonoid. Because isoflavone synthase is the central reaction in pathways producing isoflavonoids, identification of this functional gene is extremely important, and its manipulation via molecular techniques is expected to allow production of soybeans and other plants with high, stable levels of isoflavonoid. Introduction of the isoflavone synthase gene in non-legume crop species including, but not limited to, corn, wheat, rice, sunflower, and canola could lead to synthesis of isoflavonoids. The expression of isoflavonoids would confer to these species disease resistance and/or properties which produce human/livestock health benefits.

Substrates for isoflavone synthase may be limiting for synthesizing very high levels of isoflavonoids in soybean, or for synthesizing isoflavonoids in non-legumes. It is desirable to increase the flux of metabolites through the phenylpropanoid pathway to provide additional amounts of substrate to those occurring naturally. Different stress conditions such as UV irradiation, phosphate starvation, prolonged exposure to cold, and chemical (such as herbicide) treatment can cause activation of the phenylpropanoid pathway. While these treatments may produce the desired substrate availability, it is more desirable to have a genetic means of activating the phenylpropanoid pathway. It is known that expression of genes encoding certain transcription factors can regulate the expression of various genes that encode enzymes of the phenylpropanoid pathway. These include, but are not limited to, the C1 myb-type transcription factor of maize and the AmMyb305 of *Antirrhinum majus*. The C1 myb-type transcription factor of maize, in conjunction with the myc-type transcription factor R, activates chalcone synthase and chalcone isomerase genes (Grotewold, E., et al. (1998) *Plant Cell* 10:721–740). The Antirrhinum majus AmMyb305 activates the phenylalanine ammonia lyase promoter (Sablowski, R. W., et al. (1994) *EMBO J.* 13:128–137). Transcription factors such as these may be expressed in host plant cells to activate expression of genes in the phenylpropanoid pathway thereby increasing the encoded enzyme activities and the flux of compounds through the pathway. Increases in the precursors to substrates of isoflavone synthase would enhance the production of isoflavonoids.

SUMMARY OF THE INVENTION

The instant invention relates to isolated nucleic acid sequences encoding isoflavone synthase. In addition, this invention relates to nucleic acid sequences that are complementary to nucleic acid sequences encoding isoflavone synthase. The nucleic acid sequences may be of genomic or cDNA origin and may contain introns.

In another embodiment, the instant invention relates to chimeric genes encoding isoflavone synthase or to chimeric genes that comprise nucleic acid sequences that are complementary to the nucleic acid sequences encoding the enzyme, operably linked to suitable regulatory sequences, wherein expression of the chimeric genes results in production of levels of isoflavone synthase in transformed host cells that are altered (i.e., increased or decreased) from the levels produced in untransformed host cells.

In a further embodiment, the instant invention concerns a transformed host cell comprising in its genome a chimeric gene encoding an isoflavone synthase that is operably linked to suitable regulatory sequences. Expression of the chimeric gene results in production of altered levels of the enzyme in the transformed host cell. The transformed host cell can be of eukaryotic or prokaryotic origin, and includes cells derived from higher plants and microorganisms. The invention also includes transformed plants that arise from transformed host cells of higher plants, and seeds derived from such transformed plants.

An additional embodiment of the instant invention concerns a method of altering the level of expression of a plant isoflavone synthase in a transformed host cell comprising transforming a host cell with a chimeric gene comprising a nucleic acid sequence (cDNA or genomic DNA) encoding an isoflavone synthase operably linked to suitable regulatory sequences and growing the transformed host cell under conditions that are suitable for expression of the chimeric gene wherein expression of the chimeric gene results in production of altered levels of isoflavone synthase in the transformed host cell. The altered levels of isoflavone synthase may be higher due to overexpression, or may be lower due to cosuppression or anti sense suppression.

A further embodiment of the instant invention is a method for increasing the amount of one or more isoflavonoids in a host cell. The method comprising the steps of transforming a host cell with a chimeric gene comprising a nucleic acid sequence encoding an isoflavone synthase operably linked to suitable regulatory sequences and growing the transformed host cell under conditions that are suitable for expression of the chimeric gene wherein expression of the chimeric gene results in production of an amount of isoflavonoids in the transformed host cell that is greater than the amount of isoflavonoids that are produced in a cell that is not transformed with the chimeric gene.

A further embodiment of the instant invention is a method for decreasing the amount of one or more isoflavonoids in a host cell. The method comprising the steps of transforming a host cell with a chimeric gene comprising a nucleic acid sequence encoding all or a substantial portion of an isoflavone synthase operably linked to suitable regulatory sequences and growing the transformed host cell under conditions that are suitable for expression of the chimeric gene wherein expression of the chimeric gene results in production of an amount of isoflavonoids in the transformed host cell that is less than the amount of isoflavonoids that are produced in a cell that is not transformed with the chimeric gene. The invention also includes transformed plants that arise from transformed host cells of higher plants, and seeds derived from such transformed plants.

An additional embodiment of the instant invention concerns a method for obtaining a nucleic acid sequence encoding all or substantially all of an amino acid sequence encoding isoflavone synthase.

A still further embodiment of the instant invention concerns a transformed host cell comprising a chimeric gene encoding isoflavone synthase and at least one chimeric gene encoding a transcription factor that can regulate expression of one or more genes in the phenylpropanoid pathway. The invention also includes transformed plants that arise from transformed host cells of higher plants, and seeds derived from such transformed plants.

A further embodiment is a method of increasing the amount of one or more isoflavonoids in a host cell comprising transforming a host cell with a chimeric gene having a nucleic acid sequence encoding an isoflavone synthase operably linked to suitable regulatory sequences and with at least one chimeric gene having a nucleic acid sequence encoding a transcription factor that regulates expression of genes in the phenylpropanoid pathway, and growing the transformed host cell under conditions that are suitable for expression of the chimeric genes wherein expression of the chimeric genes result in production of an amount of one or more isoflavonoids in the transformed host cell that is greater than the amount of the isoflavonoids that are produced in a cell that is not transformed with the chimeric genes. The invention also includes transformed plants that arise from transformed host cells of higher plants, and seeds derived from such transformed plants.

Yet a further embodiment of the present invention is a method of altering the level of isoflavonoids in a plant cell that is transformed with a chimeric isoflavone synthase gene comprising exposing said cell to a phenylpropanoid pathway-altering agent. The phenylpropanoid pathway-altering agent may be a transcription factor or stress, for example. Stress includes and is not limited to ultraviolet light, temperature, pressure, phosphate level, and herbicide treatment. The transcription factors may be a C1 myb-type transcription factor of maize and a myc-type transcription factor R, or a chimera containing the maize R region between the C1 DNA binding domain and the C1 activation domain.

Biological Deposit

The following transformed yeast strain and vector plasmid have been deposited with the American Type Culture Collection (ATCC), 10801 University Boulevard, Manassas, Va. 20110-2209, and bears the following designation, accession number and date of deposit.

| Yeast Strain | Accession Number | Date of Deposit |
| --- | --- | --- |
| Isoflavone Synthase GM1 | ATCC 203606 | Jan. 27, 1999 |
| Plasmid DP7951 | ATCC PTA-371 | Jul. 20, 1999 |

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 depicts the phenylpropanoid metabolic pathway, and illustrates particularly the biosynthesis of isoflavonoids.

FIGS. 2A and B presents the results of HPLC analyses of naringenin standards.

FIG. 2A presents the absorption spectra recorded at 260 nm and FIG. 2B presents the absorption spectra recorded at 280 nm.

FIGS. 3A and B presents the results of HPLC analyses of genistein standards. FIG. 3A presents the absorption spectra recorded at 260 nm and FIG. 3B presents the absorption spectra recorded at 280 nm.

FIGS. 4A and B presents the results of HPLC analyses of genistein and naringenin from microsomes derived from elicitor-treated soybean hypocotyls. Absorption spectra was recorded at 260 nm (FIG. 4A) and 280 nm (FIG. 4B). Naringenin and genistein peaks are indicated.

FIGS. 5A and B presents the results of HPLC analyses of genistein and naringenin from microsomes derived from non-treated soybean hypocotyls. Absorption spectra was recorded at 260 nm (FIG. 5A) and 280 nm (FIG. 5B). Naringenin and genistein peaks are indicated.

FIGS. 6A and B presents the results of HPLC analyses of genistein and naringenin from microsomes derived from elicitor-treated soybean cell suspension cultures. Absorption spectra was recorded at 260 nm (FIG. 6A) and 280 nm (FIG. 6B). Naringenin and genistein peaks are indicated.

FIGS. 7A and B presents the results of HPLC analyses of genistein and naringenin from microsomes derived from non-treated soybean cell suspension cultures. Absorption spectra was recorded at 260 nm (FIG. 7A) and 280 nm (FIG. 7B). Naringenin peak is indicated.

FIGS. 8A and B presents the results of HPLC analyses of genistein and naringenin in 75 µg of yeast microsomal proteins prior to incubation in the presence of NADPH cofactor (negative control). Absorption spectra was recorded at 260 nm (FIG. 8A) and 280 nm (FIG. 8B).

FIGS. 9A and B presents the results of HPLC analyses of genistein and naringenin in 75 µg of yeast microsomal proteins after 1 h incubation in the presence of NADPH cofactor. Absorption spectra was recorded at 260 nm (FIG. 9A) and 280 nm (FIG. 9B).

FIGS. 10A and B presents the results of HPLC analyses of genistein and naringenin in 75 µg of yeast microsomal proteins after 2 h incubation in the presence of NADPH cofactor. Absorption spectra was recorded at 260 nm (FIG. 10A) and 280 nm (FIG. 10B).

FIG. 11A and B presents the results of HPLC analyses of genistein and naringenin in 75 µg of yeast microsomal proteins after 3 h incubation in the presence of NADPH cofactor. Absorption spectra was recorded at 260 nm (FIG. 11A) and 280 nm (FIG. 11B).

FIG. 12A and B presents the results of HPLC analyses of genistein and naringenin in 75 µg of yeast microsomal proteins after 4 h incubation in the presence of NADPH cofactor. Absorption spectra was recorded at 260 nm (FIG. 12A) and 280 nm (FIG. 12B).

FIGS. 13A and B presents the results of HPLC analyses of genistein and naringenin in 75 µg of yeast microsomal proteins after 14 h incubation in the presence of NADPH cofactor. Absorption spectra was recorded at 260 nm (FIG. 13A) and 280 nm (FIG. 13B).

FIGS. 14A and B presents the results of HPLC analyses of genistein and naringenin in 75 µg of yeast microsomal proteins after 40 minutes incubation in the presence of NADPH cofactor. Absorption spectra was recorded at 260 nm (FIG. 14A) and 280 nm (FIG. 14B).

FIG. 15A and B presents the results of HPLC analyses of genistein and naringenin in 150 µg of yeast microsomal proteins after 40 minutes incubation in the presence of NADPH cofactor. Absorption spectra was recorded at 260 nm (FIG. 15A) and 280 nm (FIG. 15B).

FIGS. 16A and B presents the results of HPLC analyses of genistein and naringenin in 75 µg of yeast microsomal proteins after 4 h incubation in the absence of NADPH cofactor. Absorption spectra was recorded at 260 nm (FIG. 16A) and 280 nm (FIG. 16B).

FIGS. 17A and B presents a comparison of the absorption spectra recorded by a diode array detector of a genistein standard (FIG. 17A; with an HPLC retention time of 3.128), and a reference spectrum (FIG. 17B).

FIGS. 18A and B presents a comparison of the absorption spectra recorded by a diode array detector of the newly synthesized peak located at the retention time of 3.131 in the HPLC analysis of yeast microsomes incubated for 14 h in the presence of NADPH on FIG. 18A and the reference spectrum on FIG. 18B.

FIG. 19A, B, C, D and E presents the electropositive mass spectrum obtained for the peaks observed by HPLC analysis of yeast microsome samples incubated with liquiritigenin.

FIG. 19A corresponds to the peak at 273.2 m/z, FIG. 19B corresponds to the peak at 271 m/z, FIG. 19C corresponds to "peak 2", FIG. 19D corresponds to liquiritigenin standard (the substrate), and FIG. 19E corresponds to daidzein standard (the product).

Figure 25:
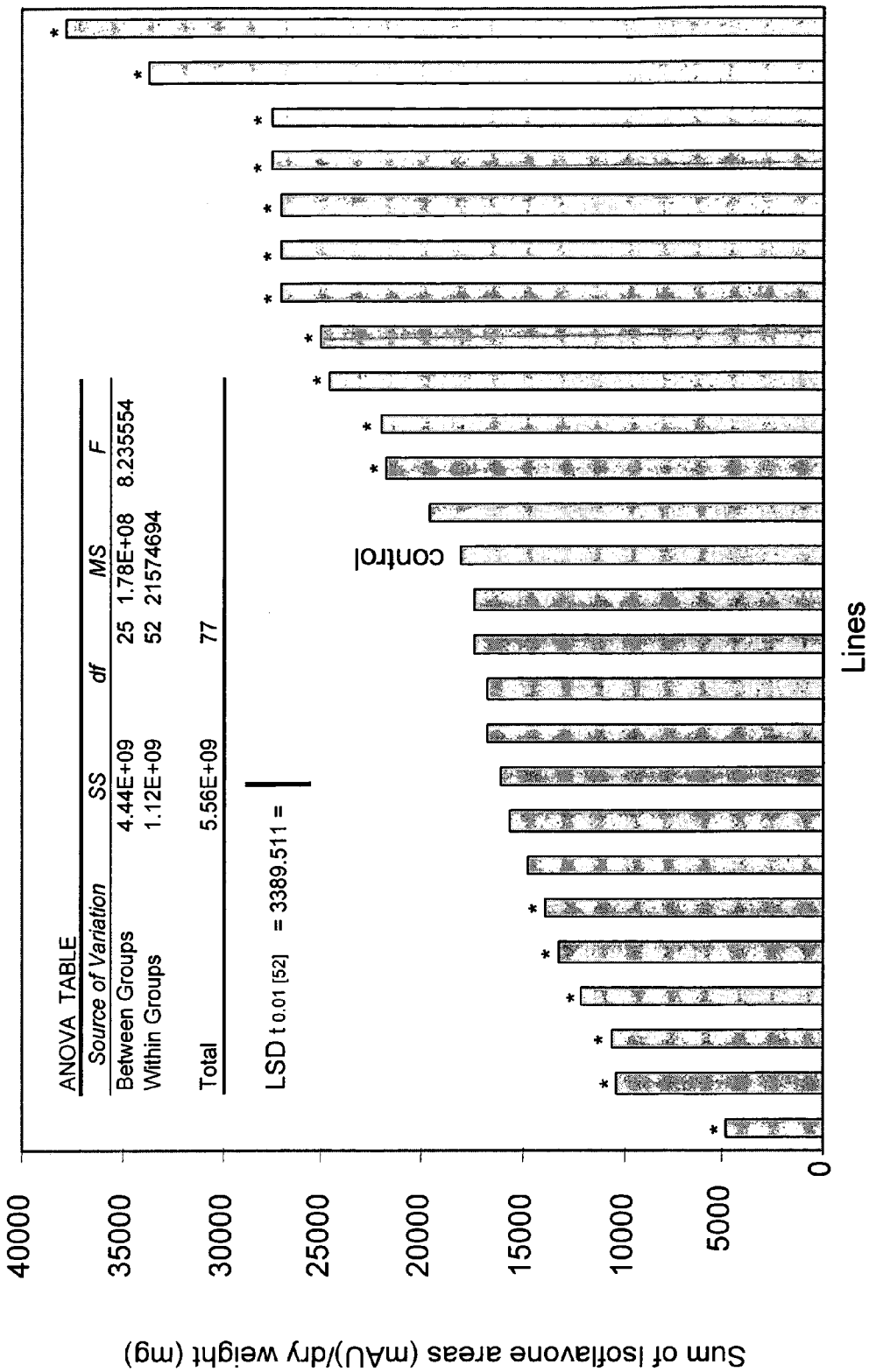

FIG. 25 depicts the distribution of the isoflavonoid content of 25 transgenic lines transformed with the isoflavone synthase sequence from clone sgs1c.pk006.o20 and a control line. Bars represent the mean of three analyses for each line. The result of single factor ANOVA is presented along with the least significant difference (LSD) at $P \leq 0.01$. The asterisk above the bars represents those lines with mean isoflavonoid concentrations significantly lower than control (bars 1 through 6), or those lines with mean isoflavonoid concentrations significantly greater than control (bars 15 through 25) based on the LSD test at $P \leq 0.01$.

Figure 26:
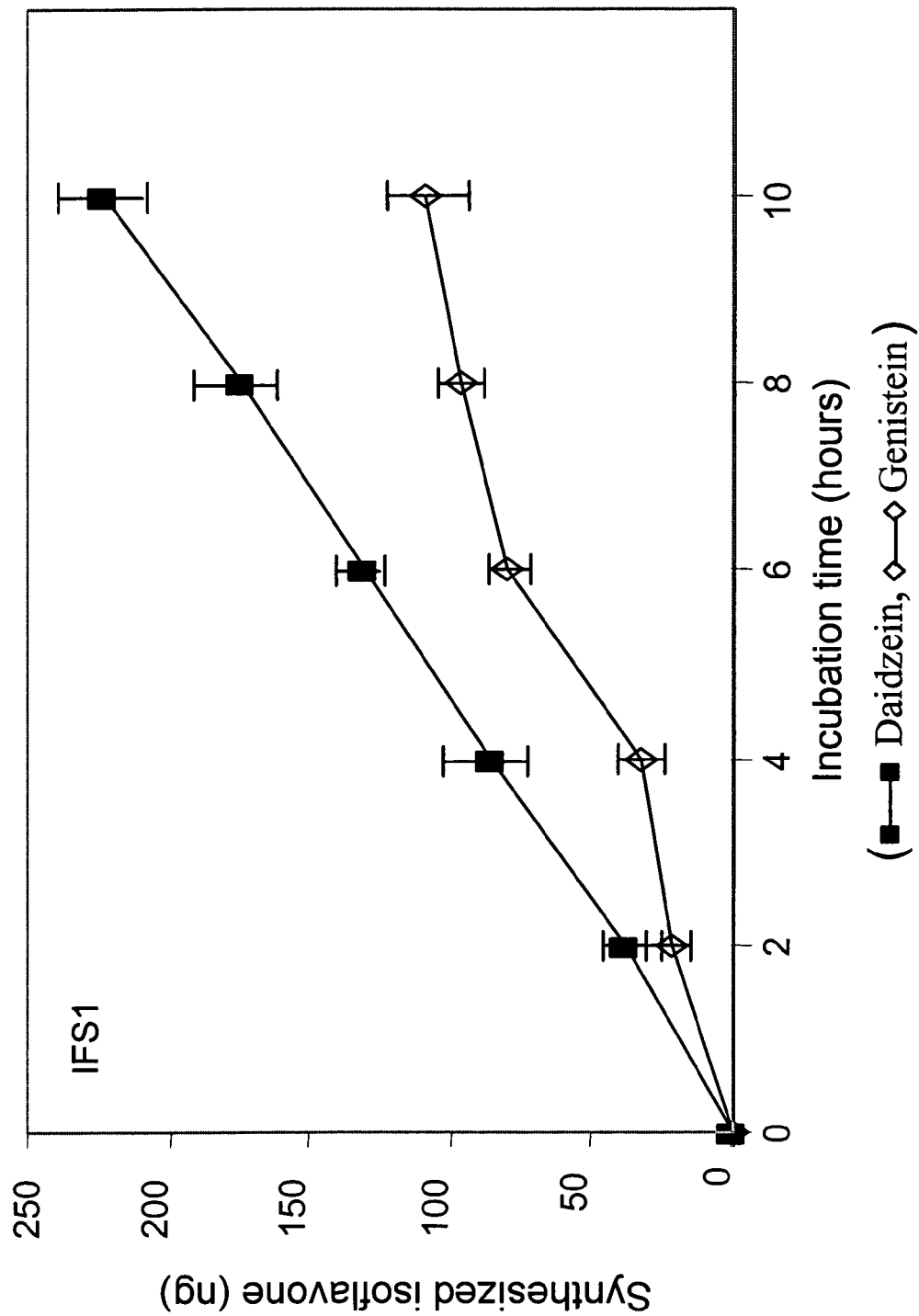

FIG. 26 depicts the comparison of the rates of genistein and daidzein synthesis by microsomes of the yeast transformant GM1. Samples representing incubation periods of 2, 4, 6, 8 and 10 h were analyzed by HPLC and the peak areas for genistein and daidzein were quantitated by calibration with authentic genistein and daidzein standards. Assays were repeated three times and the average amount of isoflavonoid synthesized at each time point was plotted, with vertical lines representing error bars.

Figure 27:
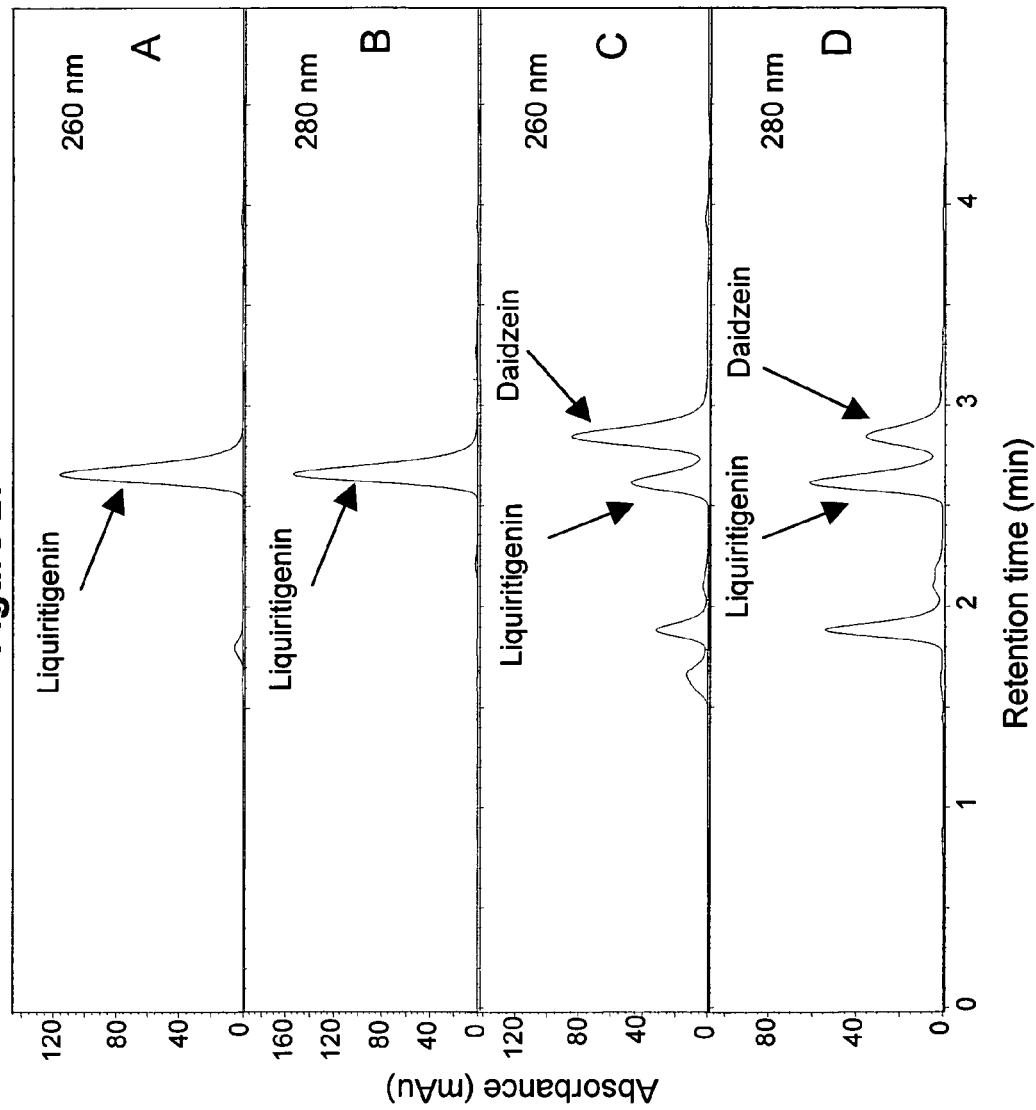

FIG. 27 presents the results of HPLC analyses of daidzein and liquiritigenin in extracts from BMS cells before incubation in the presence of NADPH cofactor (Panels A and B) and after 10 h incubation in the presence of NADPH cofactor (Panels C and D). Absorption spectra was recorded at 260 nm (Panels A and C) and 280 nm (Panels B and D).

Figure 28:
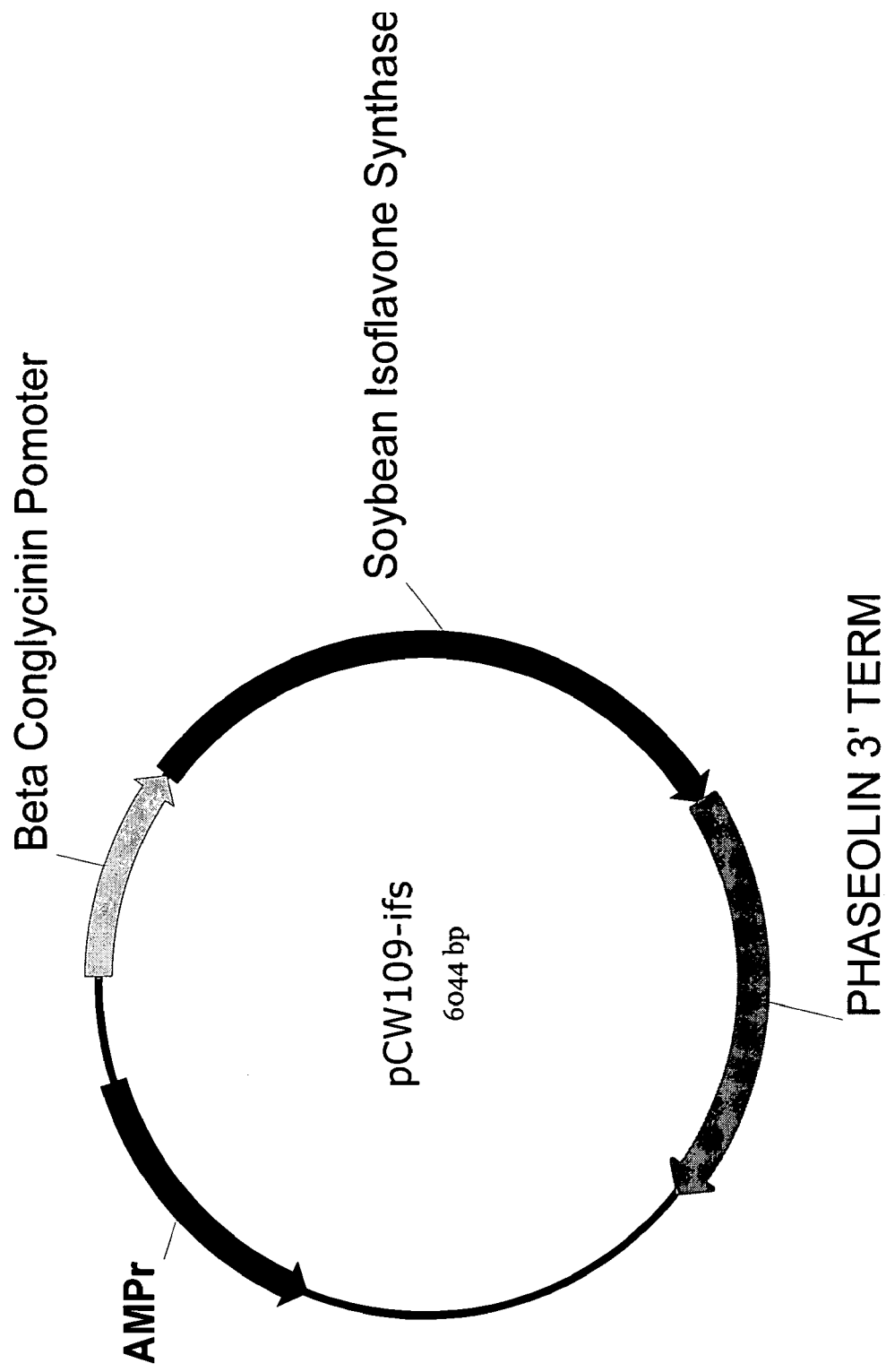

FIG. 28 depicts the plasmid map of pCW109—IFS.

The following sequence descriptions and Sequences Listing attached hereto comply with the rules governing nucleotide and/or amino acid sequence disclosures in patent applications as set forth in 37 C.F.R. §1.821–1.825. The Sequence Listing contains the one letter code for nucleotide sequence characters and the three letter codes for amino acids as defined in conformity with the IUPAC-IUB standards described in Nucleic Acids Research 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. § 1.822.

SEQ ID NO:1 is the nucleotide sequence comprising the soybean cDNA insert in clone sgs1c.pk006.o20 encoding an enzymatically active isoflavone synthase.

SEQ ID NO:2 is the deduced amino acid sequence of an enzymatically active soybean isoflavone synthase derived from the nucleotide sequence of SEQ ID NO:1.

SEQ ID NO:3 is the nucleotide sequence of an oligonucleotide primer used in the construction of yeast strain WHT1.

SEQ ID NO:4 is the nucleotide sequence of an oligonucleotide primer used in the construction of the yeast strain WHT1.

SEQ ID NO:5 is the nucleotide sequence of an oligonucleotide primer used to amplify the cDNA insert from clone sgs1c.pk006.o20.

SEQ ID NO:6 is the nucleotide sequence of an oligonucleotide primer used to amplify the cDNA insert from clone sgs1c.pk006.o20.

SEQ ID NO:7 is the nucleotide sequence of an oligonucleotide primer used for PCR amplification of the soybean clone with sequence corresponding to the one found in NCBI General Identifier No. 2739005. This oligonucleotide sequence corresponds to nucleotides 3 to 26 of the NCBI sequence.

SEQ ID NO:8 is the nucleotide sequence of an oligonucleotide primer used for PCR amplification of the soybean clone with sequence corresponding to the one found in NCBI General Identifier No. 2739005. This oligonucleotide sequence corresponds to the complement of nucleotides 1798 to 1824 of the NCBI sequence.

SEQ ID NO:9 is the nucleotide sequence of an enzymatically active soybean isoflavone synthase having an NCBI General Identifier No. 2739005.

SEQ ID NO:10 is the deduced amino acid sequence of an enzymatically active soybean isoflavone synthase derived from of SEQ ID NO:9 and having an NCBI General Identifier No. 2739006.

SEQ ID NO:11 is the nucleotide sequence of an oligonucleotide primer used for PCR amplification of the isoflavone synthase genes from mung bean, red clover, white clover, lentil, hairy vetch, alfalfa, lupine and snow pea.

SEQ ID NO:12 is the nucleotide sequence of an oligonucleotide primer used for PCR amplification of the isoflavone synthase genes from mung bean, red clover, white clover, lentil, hairy vetch, alfalfa, lupine and snow pea.

SEQ ID NO:13 is the nucleotide sequence of an oligonucleotide primer used in the second round of PCR amplification of the white clover, lentil, hairy vetch, alfalfa and lupine isoflavone synthase genes.

SEQ ID NO:14 is the nucleotide sequence of an oligonucleotide primer used in the second round of PCR amplification of the white clover, lentil, hairy vetch, alfalfa and lupine isoflavone synthase genes.

SEQ ID NO:15 is the nucleotide sequence comprising the alfalfa cDNA insert in clone alfalfa1 encoding an almost entire alfalfa isoflavone synthase.

SEQ ID NO:16 is the deduced amino acid sequence of an almost entire alfalfa isoflavone synthase derived from the nucleotide sequence of SEQ ID NO:15. SEQ ID NO:17 is the nucleotide sequence comprising the hairy vetch cDNA insert in clone hairy vetch1 encoding an almost entire hairy vetch isoflavone synthase.

SEQ ID NO:18 is the deduced amino acid sequence of an almost entire hairy vetch isoflavone synthase derived from the nucleotide sequence of SEQ ID NO:17.

SEQ ID NO:19 is the nucleotide sequence comprising the lentil cDNA insert in clone lentil1 encoding an almost entire lentil isoflavone synthase.

SEQ ID NO:20 is the deduced amino acid sequence of an almost entire lentil isoflavone synthase derived from the nucleotide sequence of SEQ ID NO:19.

SEQ ID NO:21 is the nucleotide sequence comprising the lentil cDNA insert in clone lentil2 encoding an almost entire lentil isoflavone synthase.

SEQ ID NO:22 is the deduced amino acid sequence of an almost entire lentil isoflavone synthase derived from the nucleotide sequence of SEQ ID NO:21.

SEQ ID NO:23 is the nucleotide sequence comprising the mung bean cDNA insert in clone mung bean1 encoding an entire mung bean isoflavone synthase.

SEQ ID NO:24 is the deduced amino acid sequence of an entire mung bean isoflavone synthase derived from SEQ ID NO:23.

SEQ ID NO:25 is the nucleotide sequence comprising the mung bean cDNA insert in clone mung bean2 encoding an entire mung bean isoflavone synthase.

SEQ ID NO:26 is the deduced amino acid sequence of an entire mung bean isoflavone synthase derived from SEQ ID NO:25.

SEQ ID NO:27 is the nucleotide sequence comprising the mung bean cDNA insert in clone mung bean3 encoding an entire mung bean isoflavone synthase.

SEQ ID NO:28 is the deduced amino acid sequence of an entire mung bean isoflavone synthase derived from SEQ ID NO:27.

SEQ ID NO:29 is the nucleotide sequence comprising the mung bean cDNA insert in clone mung bean4 encoding an entire mung bean isoflavone synthase.

SEQ ID NO:30 is the deduced amino acid sequence of an entire mung bean isoflavone synthase derived from SEQ ID NO:29.

SEQ ID NO:31 is the nucleotide sequence comprising the red clover cDNA insert in clone red clover1 encoding an entire red clover isoflavone synthase.

SEQ ID NO:32 is the deduced amino acid sequence of an entire red clover isoflavone synthase derived from SEQ ID NO:31.

SEQ ID NO:33 is the nucleotide sequence comprising the red clover cDNA insert in clone red clover2 encoding an entire red clover isoflavone synthase.

SEQ ID NO:34 is the deduced amino acid sequence of an entire red clover isoflavone synthase derived from SEQ ID NO:33.

SEQ ID NO:35 is the nucleotide sequence comprising the snow pea cDNA insert in clone snow pea1 encoding an entire snow pea isoflavone synthase.

SEQ ID NO:36 is the deduced amino acid sequence of an entire snow pea isoflavone synthase derived from SEQ ID NO:37.

SEQ ID NO:37 is the nucleotide sequence comprising the white clover cDNA insert in clone white clover1 encoding an almost entire white clover isoflavone synthase.

SEQ ID NO:38 is the deduced amino acid sequence of an almost entire white clover isoflavone synthase derived from SEQ ID NO:37.

SEQ ID NO:39 is the nucleotide sequence comprising the white clover cDNA insert in clone white clover2 encoding an almost entire white clover isoflavone synthase.

SEQ ID NO:40 is the deduced amino acid sequence of an almost entire white clover isoflavone synthase derived from SEQ ID NO:39.

SEQ ID NO:41 is the nucleotide sequence of an oligonucleotide primer used for PCR amplification of the isoflavone synthase coding region in clone sgs1c.pk006.o20.

SEQ ID NO:42 is the nucleotide sequence of an oligonucleotide primer used for PCR amplification of the isoflavone synthase coding region in clone sgs1c.pk006.o20.

SEQ ID NO:43 is the nucleotide sequence of an oligonucleotide primer used to determine the transcription of the soybean isoflavone synthase in transgenic tobacco.

SEQ ID NO:44 is the nucleotide sequence of an oligonucleotide primer used to determine the transcription of the soybean isoflavone synthase in transgenic tobacco.

SEQ ID NO:45 is the nucleotide sequence of an oligonucleotide primer to the maize R coding region used to amplify genomic DNA to determine the presence of a chimera containing the maize R region between the region encoding the C1 DNA binding domain and the C1 activation domain (CRC) in transgenic corn cells.

SEQ ID NO:46 is the nucleotide sequence of an oligonucleotide primer to the 3' untranslated region from potato protease inhibitor II gene used to amplify genomic DNA to determine the presence of CRC in transgenic corn cells.

SEQ ID NO:47 is the nucleotide sequence comprising the sugarbeet cDNA insert in clone sugarbeet2, encoding an almost entire sugarbeet isoflavone synthase.

SEQ ID NO:48 is the deduced amino acid sequence of an almost entire sugarbeet isoflavone synthase derived from SEQ ID NO:47.

SEQ ID NO:49 is the nucleotide sequence of an oligonucleotide primer used for the PCR amplification of the soybean isoflavone synthase coding region in clone sgs1c.pk006.o20.

SEQ ID NO:50 is the nucleotide sequence of an oligonucleotide primer used for the PCR amplification of the soybean isoflavone synthase coding region in clone sgs1c.pk006.o20.

SEQ ID NO:51 is the nucleotide sequence of an oligonucleotide primer used to amplify the genomic sequence comprising the isoflavone synthase in clone sgs1c.pk006.o20.

SEQ ID NO:52 is the nucleotide sequence of a genomic fragment encoding the isoflavone synthase in clone sgs1c.pk006.o20.

SEQ ID NO:53 is the nucleotide sequence of a genomic fragment encoding the CYP93C1 isoflavone synthase.

SEQ ID NO:54 is the nucleotide sequence comprising the lupine cDNA insert in clone lupine 1 encoding an entire lupine isoflavone synthase.

SEQ ID NO:55 is the deduced amino acid sequence of an entire lupine isoflavone synthase derived from SEQ ID NO:54.

SEQ ID NO:56 is the nucleotide sequence comprising the alfalfa cDNA insert in clone alfalfa2 encoding an almost entire alfalfa isoflavone synthase.

SEQ ID NO:57 is the amino acid sequence of an almost entire alfalfa isoflavone synthase derived from SEQ ID NO:56.

SEQ ID NO:58 is the nucleotide sequence comprising the alfalfa cDNA insert in clone alfalfa3 encoding an almost entire alfalfa isoflavone synthase.

SEQ ID NO:59 is the amino acid sequence of an almost entire alfalfa isoflavone synthase derived from SEQ ID NO:58.

SEQ ID NO:60 is the nucleotide sequence comprising the sugarbeet cDNA insert in clone sugarbeet1, encoding an almost entire sugarbeet isoflavone synthase.

SEQ ID NO:61 is the deduced amino acid sequence of an almost entire sugarbeet isoflavone synthase derived from SEQ ID NO:60.

SEQ ID NO:62 is the nucleotide sequence of an oligonucleotide primer used for the PCR amplification of the soybean chalcone reductase coding region in clone src3c.pk009.e4.

SEQ ID NO:63 is the nucleotide sequence of an oligonucleotide primer used for the PCR amplification of the soybean chalcone reductase coding region in clone src3c.pk009.e4.

SEQ ID NO:64 is the nucleotide sequence of an oligonucleotide primer used for the PCR amplification of the soybean chalcone reductase present in monocot cells.

SEQ ID NO:65 is the nucleotide sequence of an oligonucleotide primer used for the PCR amplification of the soybean chalcone reductase present in monocot cells.

SEQ ID NO:66 is the amino acid sequence of the consensus sequence produced by the Megalign Program using the Clustal method and the amino acid sequences depicted in SEQ ID NOs:2, 16, 18, 20, 22, 24, 26, 28, 30, 32, 34, 36, 38, 40, 48, 55, 57, 59, and 61.

DETAILED DESCRIPTION OF THE INVENTION

The instant invention discloses nucleotide and amino acid sequences for isoflavone synthases from legumes such as soybean, alfalfa, lupine, hairy vetch, lentil, mung bean, red clover, snow pea, and white clover and non-legumes such as sugarbeet. As the enzyme that catalyzes the first step of the isoflavonoid branch of the phenylpropanoid pathway (see FIG. 1), altering the level of this enzyme may be useful for changing isoflavonoid content.

Plant P450 enzymes catalyze a diverse range of reactions, including molecular transformations in primary metabolism, and in the metabolism and detoxification of xenobiotics. Although tentative identification of any given gene or conceptual translation product as a P450 is relatively simple based on its similarity to other known P450s, the assignment of actual catalytic function cannot necessarily be inferred from nucleic acid or protein sequence information alone. The instant disclosure demonstrates and teaches the identification of a cDNA from soybean that encodes isoflavone synthase based on the ability of the encoded polypeptide to convert the normal substrate for the reaction, 2S-flavanone, to genistein. Demonstration of activity has been accomplished in subcellular fractions of a yeast strain, WHT1, which has been specifically altered to also express a P450 reductase from *Helianthus tuberosum*. In this manner, and using the materials identified and described herein, other nucleic acid sequences from soybean and from other plants that are predicted to encode P450s may be tested to determine whether any of those P450's possess isoflavone synthase activity.

"The isoflavonoids are biogeneticaly related to the flavonoids but constitute a distinctly separate class in that they contain a rearranged C15 skeleton and may be regarded as derivatives of 3-phenylchroman." Isoflavonoids. Dewick, P. M. (1982) in The Flavonoids: Advances in Research, Harborne, J. B. and Mabry, T. J., Ed., pp 535–640, Chapman and Hall Ltd, New York. Oxidative rearrangement of a flavanone precursor with a 2,3-aryl shift yields an isoflavonoid. Isoflavones are the most abundant of the natural isoflavonoid derivatives, with over 160 isoflavone aglycones being recognized.

In the context of this disclosure, a number of terms shall be utilized. As used herein, a "nucleic acid sequence" is a polymer of RNA or DNA that is single- or double-stranded, optionally containing synthetic, non-natural or altered nucleotide bases. A nucleic acid sequence in the form of a polymer of DNA may be comprised of one or more segments of cDNA, genomic DNA or synthetic DNA.

As used herein, "substantially similar" refers to nucleic acid sequences wherein changes in one or more nucleotide bases results in substitution of one or more amino acids, but do not affect the functional properties of the polypeptide encoded by the nucleotide sequence. "Substantially similar" also refers to nucleic acid sequences wherein changes in one or more nucleotide bases does not affect the ability of the nucleic acid sequence to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid sequence which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid sequences may also be characterized by their ability to hybridize. Estimates of such homology are provided by either DNA-DNA or DNA-RNA hybridization under conditions of stringency as is well understood by those skilled in the art (Hames and Higgins, Eds. (1985) *Nucleic Acid Hybridisation*, IRL Press, Oxford, U.K.). Stringency conditions can be adjusted to screen for moderately similar sequences, such as homologous sequences from distantly related organisms, to highly similar sequences, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid sequences of the instant invention may also be characterized by their percent identity to the nucleic acid sequences disclosed herein, as determined by algorithms commonly employed by those skilled in this art. Preferred are those nucleic acid sequences whose sequences are at least about 85% identical and more preferably at least about 90% identical to the nucleotide sequences reported herein. More preferred are nucleic acid sequences that are at least about 90% identical and more preferably at least about 95% identical to the nucleotide sequences reported herein. More preferred are nucleic acid sequences that are 95% identical to the nucleotide sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 2, GAP PENALTY=5, WINDOW=4 and DIAGONALS SAVED=4.

Substantially similar nucleic acid sequences of the instant invention may also be characterized by the percent identity of the amino acid sequences that they encode to the amino acid sequences disclosed herein, as determined by algorithms commonly employed by those skilled in this art. Preferred are those nucleic acid sequences whose nucleotide sequences encode amino acid sequences that are at least about 95% identical and even more preferably at least about 98% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY-3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid sequence comprising the primers. Accordingly, a "substantial portion" of a nucleotide sequence comprises a nucleotide sequence that will afford specific identification and/or isolation of a nucleic acid sequence comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid sequence comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid sequence for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid sequences which may then be enzymatically assembled to construct the entire desired nucleic acid sequence. "Chemically synthesized", as related to nucleic acid sequence, means that the component nucleotides were assembled in vitro. Manual chemical synthesis of nucleic acid sequences may be accomplished using well established procedures, or automated chemical synthesis can be performed using one of a number of commercially available machines. Accordingly, the nucleic acid sequences can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid sequence that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity. It may be an innate element of the promoter or a heterologous element inserted to enhance the level and/or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid sequence to be expressed in most cell types at most times are commonly referred to as "constitutive promoters". "Organ-specific" or "development-specific" promoters are those that direct gene expression almost exclusively in specific organs, such as leaves or seeds, or at specific development stages in an organ, such as in early or late embryogenesis, respectively. New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid sequences of different lengths may have identical promoter activity.

The expression of foreign genes in plants is well established (De Blaere et al. (1987) *Meth. Enzymol.* 143:277–291). Proper level of expression of mRNAs may require the use of different chimeric genes utilizing different promoters. Such chimeric genes can be transferred into host plants either together in a single expression vector or sequentially using more than one vector. Expression in plants will use regulatory sequences functional in such plants.

The origin of the promoter chosen to drive the expression of the coding sequence is not critical as long as it has sufficient transcriptional activity to accomplish the invention by expressing translatable mRNA for the desired protein genes in the desired host tissue.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid sequences on a single nucleic acid sequence so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid sequence of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Transformation" refers to the transfer of a nucleic acid sequence into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Sambrook").

A nucleic acid sequence encoding a soybean isoflavone synthase was isolated and identified from a cDNA library. Nucleic acid sequences encoding three alfalfa, one hairy vetch, one snow pea, one lupine, two lentil, two red clover, two white clover, two sugarbeet, and four mung bean isoflavone synthases have been isolated-using RT-PCR. Nucleic acid sequences encoding two soybean isoflavone synthases have been isolated from genomic DNA. The nucleic acid sequences of the instant invention may be used to isolate cDNAs and genes encoding homologous enzymes from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other isoflavone synthase proteins, either as cDNAs or genomic DNAs, could be isolated directly by using all or a portion of the instant nucleic acid sequence as a DNA hybridization probe to screen libraries from any desired plant employing methodology well known to those skilled in the art. Specific oligonucleotide probes based upon the instant nucleic acid sequence can be designed and synthesized by methods known in the art (Sambrook). Moreover, the entire sequence can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full-length cDNA or genomic fragments under conditions of appropriate stringency.

In addition, two short segments of the instant nucleic acid sequences may be used in polymerase chain reaction protocols to amplify longer nucleic acid sequences encoding homologous genes from DNA or RNA. The polymerase chain reaction may also be performed on a library of cloned nucleic acid sequences wherein the sequence of one primer is derived from the instant nucleic acid sequences, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA sequences can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36: 1; Sambrook).

The nucleic acid sequence of the instant invention may be used to create transgenic plants and transgenic seeds in which expression of nucleic acid sequences (or their complements) encoding the disclosed enzyme result in levels of the corresponding endogenous enzyme that are higher or lower than normal. Alternatively, expression of the instant nucleic acid sequence may result in the production of the encoded enzyme in cell types or developmental stages in which they are not normally found. Either strategy would have the effect of altering the level of isoflavonoids.

For example, overexpression of isoflavone synthase may result in an increase in isoflavonoid content in legumes. Increased isoflavonoid content in legumes has been shown to be associated with beneficial health effects in humans. In contrast, certain soy food products would benefit from lower levels of isoflavonoid due to adverse effects on flavor.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

The nucleic acid sequence of the instant invention may be used to create transgenic plants that have increased expression of the disclosed enzyme and that are additionally transformed with a chimeric gene encoding a transcription factor that regulates expression of one or more genes in the phenylpropanoid pathway. The chimeric transcription factor gene has regulatory sequences such that its expression is coordinated with that of the isoflavone synthase gene developmentally and preferably within the same cell type. This combination of expression of isoflavone synthase and transcription factor regulating phenylpropanoid pathway genes has the effect of enhancing the level of isoflavonoid synthesis due to increased levels of substrates for isoflavone synthase. The chimeric transcription factor gene regulates expression of at least one gene in the phenylpropanoid pathway. While not intending to be bound by any theory or theories of operation it is believed to regulate as many as two, three or four genes in the phenylpropanoid pathway.

For example, a plant cell that does not naturally produce isoflavonoids and does not have an active phenylpropanoid pathway would not produce the substrates for isoflavone synthase to convert to isoflavonoids. Activation of the phenylpropanoid pathway in the desired cells or at the desired developmental stage would provide these substrates allowing the synthesis of isoflavonoids.

The present invention is also directed to a method of altering the level of isoflavonoids in a cell comprising exposing said cell to a phenylpropanoid pathway altering agent. The cell may be a plant cell such as a monocot, including and not limited to corn, or a dicot, such as soybean, for example. A phenylpropanoid pathway altering agent may be any agent that results in an increase or decrease in the level of expression of an enzyme in the phenylpropanoid pathway, such as isoflavone synthase, phenylalanine ammonia lyase, chalcone synthase, among others. Such phenylpropanoid pathway altering agents include and are not limited to a transcription factor and stress. Transcription factors include and are not limited to chimeric transcription factors, a chimera containing the maize R region between the region encoding the C1 DNA binding domain and the C1 activation domain (CRC) for example. Stresses to a plant cell include ultraviolet light, temperature, pressure, chemicals including and not limited to herbicides, and phosphate level. Phosphate levels may be increased or decreased such that decreasing phosphate levels may result in phosphate starvation.

It may also be desirable to reduce or eliminate expression of genes encoding the instant polypeptides in plants for some applications. In order to accomplish this, a chimeric gene designed for co-suppression of the instant polypeptide can be constructed by linking a gene or gene sequence encoding that polypeptide to plant promoter sequences. Alternatively, a chimeric gene designed to express antisense RNA for all or part of the instant nucleic acid sequence can be constructed by linking the gene or gene sequence in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant isoflavone synthases (or portions of the enzymes) may be produced in heterologous host cells, particularly in the cells of microbial hosts, and can be used to prepare antibodies to the enzymes by methods well known to those skilled in the art. The antibodies are useful for detecting the enzymes in situ in cells or in vitro in cell extracts. Preferred heterologous host cells for production of isoflavone synthase are yeast hosts. Yeast expression systems and expression vectors containing regulatory sequences that direct high level expression of foreign proteins are well known to those skilled in the art. Any of these could be used to construct chimeric genes for production of the instant isoflavone synthase. These chimeric genes could then be introduced into appropriate hosts via transformation to provide high level expression of the enzymes. An example of a vector for high level expression of the instant isoflavone synthase in a yeast host is provided (Example 5).

All or a substantial portion of the nucleic acid sequences of the instant invention may also be used as probes for genetically and physically mapping the genes that they are a part of, and as markers for traits linked to those genes. Such information may be useful in plant breeding in order to develop lines with desired phenotypes. For example, the instant nucleic acid sequences may be used as restriction sequence length polymorphism (RFLP) markers. Southern blots (Maniatis) of restriction-digested plant genomic DNA may be probed with the nucleic acid sequences of the instant invention. The resulting banding patterns may then be subjected to genetic analyses using computer programs such as MapMaker (Lander et al. (1987) *Genomics* 1:174–181) in order to construct a genetic map. In addition, the nucleic acid sequences of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The physiological activities associated with isoflavonoids in both plants and humans makes the manipulation of their contents in crop plants highly desirable. For example, increasing levels of isoflavonoids in soybean seeds would increase the efficiency of extraction and lower the cost of isoflavonoid-related products sold. Decreasing levels of isoflavonoids in soybean seeds would be beneficial for production of soy-based infant formulas where the estrogenic effects of isoflavonoids are undesirable. Decreasing levels of isoflavonoids may also increase palatability of soy foods. Raising levels of isoflavonoid phytoalexins in vegetative plant tissue could increase plant defenses to pathogen attack, thereby improving resistance and lowering the need for pesticide use. Manipulation of isoflavonoid levels in roots could lead to improved nodulation and increased efficiencies of nitrogen fixation. To date, however, it has proven difficult to develop soybean or other plant lines with consistently high levels of isoflavonoids.

Identification of the functional isoflavone synthase gene is extremely important because isoflavone synthase catalyzes the central reaction in pathways producing isoflavonoids. Manipulation of the isoflavone synthase gene via molecular techniques is expected to allow production of soybeans and other plants with high, stable levels of isoflavonoids. Introduction of the isoflavone synthase gene in non-legume crop species including, but not limited to, corn, wheat, rice, sunflower, and canola could lead to synthesis of isoflavonoids in these species. Synthesis of isoflavonoids would 1) confer disease resistance to the crops and/or 2) produce crops which would benefit human and/or livestock health.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Microsome Preparation from Elicitor-Treated Soybean Hypocotyls and Elicitor-Treated Cell Suspension Culture Elicitor Treatment of Soybean Seeds Soybean seeds were placed on a bed of vermiculite (5 to 6 cm thick) and covered with a layer of vermiculite about 2 cm thick. Seeds were germinated for five days in a growth chamber until the average length of hypocotyls reached to about 3 to 4 cm. The growth chamber was kept at a cycle that consisted of a 14 h light period at 25° C. and a 10 h dark period at 21° C. Illumination was supplied from cool white fluorescent and incandescent lamps that provide a photon flux density of 450 $\mu Em^{-2}s^{-1}$. Soybean hypocotyls were pulled out from the vermiculite bed and were placed on wet paper towels. The soybean hypocotyls were divided into two groups: one of the groups was treated with elicitor and the other was not treated.

Elicitor treatment was conducted as follows. The epidermal surfaces of the hypocotyls were opened using a razor blade. The incisions were approximately 2 cm long and 1 to 2 mm deep; one was made on each hypocotyl. Fungal-derived elicitors were prepared by the method of Sharp et al. (Sharp, J. K. et al. (1984) *J. Biol. Chem.* 259:11312–11320). Twenty micrograms of acidified fungal elicitors were dissolved in 20 $\mu$L of 10 mM $KH_2PO_4$, and were then applied to the wound of a hypocotyl The treated hypocotyls were incubated for 15 h in the dark at room temperature and 100% humidity. At the end of the incubation period, the hypocotyls were sectioned closely below the cotyledonal node and were immediately frozen in liquid nitrogen and stored at −76° C. until used. Non-elicitor-treated hypocotyls were handled in the same manner as were elicitor-treated hypocotyls, except for wounding and elicitor application. The non-treated hypocotyls were used as a negative control of isoflavone synthase induction.

Elicitor Treatment of Soybean Cell Suspension Culture

Soybean suspension cell cultures were grown at 25° C. in 250 mL flasks that were tightly covered with two layers of aluminum foil to prevent illumination. Cells were grown in 35 mL of Murashige and Skoog medium (Gibco BRL) supplemented with 0.75 mg/L 2,4-dichlorophenoxyacetic acid and 0.55 mg/mL 6-benzyl aminopurine. Cells were diluted (1:3 ratio) into fresh medium every 7 days and elicitor treatment was conducted 3 days after cell dilution. One hundred fifty milligrams of the same fungal elicitor used to treat the hypocotyls was dissolved in 15 mL of 10 mM $KH_2PO_4$ and was filter sterilized. Five milligrams of sterile fungal elicitor dissolved in 333 µL 10 mM $KH_2PO_4$ was added per flask. Cells were harvested 15 h after addition of elicitor. The same suspension culture conditions were used before and after elicitor treatment. Cells were recovered using a Nalgene PES filter unit (0.2 µm) followed by 3 minutes of air flow. Filtered cells were immediately frozen in liquid nitrogen and kept at −76° C. until used. Non-elicitor-treated cells were handled in the same manner, except for the addition of elicitor.

Microsome Preparation from Soybean Hypocotyls and Suspension-Cultured Cells

For preparation of the crude extracts, 3 to 5 g of previously frozen, elicitor-treated and non-treated soybean hypocotyls and elicitor-treated and non-treated suspension cultured cells were ground in liquid nitrogen using a pre-chilled pestle and mortar. The powder was added to 25 mL of extraction buffer (buffer A: 0.1 M Tris-HCl, pH 7.5, 14 mM β-mercaptoethanol, 20% (w/v) sucrose and 0.8 g of Dowex 1X2 resin (mesh 200–400)), and the slurry was stirred for 20 to 30 minutes in an ice-water bath. The slurry was transferred to Nalgene Oak Ridge tubes and centrifuged at 8000 g for 10 minutes at 4° C. The supernate was carefully transferred into 13 mL polyallomer tubes which fit into a Sorvall TH641 rotor and centrifuged at 160,000 g for 40 minutes to 2 h at 4° C. The precipitated microsomes were washed twice with the storage buffer (buffer B: 80 mM $KH_2PO_4$, pH 8.5, 14 mM β-mercaptoethanol, 30% (v/v) glycerol) and resuspended with storage buffer. The microsomal pellet was gently homogenized by hand using a disposable plastic pestle, and the suspension was divided into several aliquots which were frozen on dry-ice. Bradford protein micro assays were used to quantify the protein content of the microsomal preparations (Bio-Rad, Richmond, Calif.). Two microliters of a microsome preparation were diluted with 198 µL of distilled water. Forty microliters of this dilution was mixed with 10 µL of Bio-Rad protein assay solution in a microtiter plate, and the total protein concentration was determined by reading the sample in a kinetic microplate reader (Molecular Devices Inc.), according to the manufacturer's instructions (Bio-Rad). Microsomes were stored at −76° C. until used.

Example 2

Development of Isoflavone Synthase Assay

An assay to measure isoflavone synthase activity was developed using either of the two substrates of isoflavone synthase, (±) naringenin (4',5,7-trihydroxyflavanone; Sigma, N-5893) or liquiritigenin monohydrate (4',7-dihydroxyflavanone; Indofine, 02–1150S), dissolved in 80% ethanol. The reaction mixture was prepared at room temperature and consisted of 100 µM naringenin or liquiritigenin, 80 mM $K_2HPO_4$, 0.5 mM glutathione (Sigma, G-4251), 20% w/v sucrose, and 30 to 150 µg of microsome preparation. The reaction mixtures were preincubated for 5 minutes without NADPH (synthesis of genistein and daidzein requires NADPH as a co-factor). The volume of microsomes and substrate added to any one reaction did not exceed 5% and 1%, respectively, of the total reaction volume. A typical reaction volume was 250 µL. The reaction was started by the addition of 40 nmol of NADPH per each 100 µL of final reaction volume. The pH of the reaction mixture was 8.0 before the addition of the substrate, NADPH and microsomes.

Microsomes were thawed, an aliquot removed and the remaining sample was immediately frozen on dry ice and stored in the freezer. The reactions using microsomes prepared from soybean elicitor-treated hypocotyls were run for incubation periods of up to 24 h, while the reactions using the yeast microsomes were allowed to run for incubation periods of up to 14 h. Following incubation, 200 µL of ethyl acetate was added directly to the mixture and the mixture was shaken for 1 minute using a vortex mixer. Separation of the organic phase was accelerated by centrifugation for 2 minutes at 4° C. The organic phase was removed and analyzed.

Qualitative and quantitative analyses were performed using a Hewlett Packard 1100 series HPLC and a Hewlett-Packard/Micromass LC/MS. Samples were assayed on a Hewlett Packard 1100 series HPLC system using either a Li-Chrospher 100 RP-18 column (5 µm) or a Phenomenex Luna 3u C18 (2) column (150×4.6 mm). Using either column, samples from in vitro microsome assays in ethyl acetate, were isocratically separated for 5 minutes employing 65% methanol as the mobile phase. The second column was used for plant samples where the ethyl acetate was evaporated and the samples resuspended in 80% methanol. In these cases separation used a 10 minutes linear gradient from 20% methanol/80% 10 mM ammonium acetate, pH 8.3 to 100% methanol using a flow rate of 0.8 ml per minute. Genistein and daidzein were monitored by the absorbance at 260 nm and naringenin and liquiritigenin were monitored by the absorbance at 280 nm. Peak areas were converted to nanograms using, as standards for calibration, authentic naringenin, liquiritigenin, genistein, and daidzein (Indofine Chemical Company, Inc., Somerville, N.J.) dissolved in ethanol.

Analyses using LC/MS employed 10 µL of the ethyl acetate phase that had been first evaporated with nitrogen gas and resuspended in 100 µL of 25% acetonitrile in water. These samples were analyzed by a Hewlett-Packard/Micromass LC/MS instrument. A twenty-five microliter sample was run on a Zorbax Eclipse XDB-C8 reverse-phase column (3×150 mm, 3.5 micron) isocratically with 25% of solvent B in solvent A. Solvent A was 0.1% formic acid in water, and solvent B was 0.1% formic acid in acetonitrile. Mass spectrometry was carried out by electro-spray scanning from 200–400 m/e, using +60 volt cone voltage. The diode array signals were monitored between 200–400 nm in both instruments.

The genistein and liquiritigenin signals observed in the in vitro assay samples were verified by comparisons of retention time, diode array detected absorption spectra and mass spectrometry data to the standards. FIG. 2 presents the results of HPLC analyses of naringenin standards and FIG. 3 presents the results of HPLC analyses of genistein standards.

Incubations in the absence of an essential component required for isoflavone synthase-catalyzed synthesis of isoflavonoid (e.g., NADPH, naringenin, liquiritigenin, or microsomes) were performed as negative controls.

Positive control samples consisting of soybean microsomes which were prepared from elicitor-treated hypocotyls and suspension culture cells were used to establish the in vitro assay system. Optimization of this in vitro assay system was critical for validation of the yeast expression system for functional cloning. We observed positive results (i.e., the synthesis of genistein) in assays that used either the microsomes of elicitor-treated soybean hypocotyls (FIG. 4) or those obtained from elicitor-treated cell suspension cultures (FIG. 6). We observed about six times higher specific enzyme activities of isoflavone synthase in the microsomes of elicitor-treated hypocotyls and cell cultures (FIG. 4 and FIG. 6, respectively) than in the microsomes obtained from non-treated hypocotyls and cell cultures (FIG. 5 and FIG. 7, respectively).

Example 3

Composition of Soybean cDNA Library, Isolation and Sequencing of cDNA Clone

A cDNA library was prepared using mRNAs from soybean seeds that had been allowed to germinate for 4 hours. The library was prepared in Uni-ZAP™ XR vector according to the manufacturer's protocol (Stratagene Cloning Systems, La Jolla, Calif.). Conversion of the Uni-ZAP™ XR library into a plasmid library was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al. (1991) *Science* 252: 1651–1656). The resulting ESTs were analyzed using a Perkin Elmer Model 377 fluorescent sequencer.

Example 4

Identification and Characterization of a cDNA Clone for Isoflavone Synthase

ESTs encoding candidate isoflavone synthases were identified by conducting BLAST (Basic Local Alignment Search Tool; Altschul, S. F., et al., (1993) *J. Mol. Biol.* 215: 403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 3 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI.

The insert in cDNA clone sgs1c.pk006.o20 was identified as a candidate isoflavone synthase gene by a BLAST search against the NCBI database. The 5' sequence of this insert was determined to be related to *Glycine max* cytochrome P450 monooxygenase CYP93C1p (CYP93C1) mRNA, the complete coding sequence of which may be found as NCBI General Identifier No. 2739005. The CYP93C1p cDNA sequence was obtained using random isolation and screening to identify soybean P450s involved in herbicide metabolism (Siminszky B., et al. (1999) *Proc. Natl. Acad. Sci. U.S.A.* 96:1750–1755). Isoflavone synthase catalyzes in soybeans the oxidation of 7,4'dihydroxyflavanone (liquiritigenein) or 5,7,4'trihydroxyflananone (naringenin) to daidzein or genistein respectively. Earlier published work (Kochs and Griesbach (1986) *Eur. J. Biochem* 155:311–318; Hashim et al. (1990) *FEBS* 271:219–222) suggested that the enzyme that catalyzes this reaction is a cytochrome P450. Accordingly, in order to confirm the identity of the polypeptide encoded by the insert in cDNA clone sgs1c.pk006.o20 as an isoflavone synthase, the polypeptide encoded by this insert was evaluated for its ability to catalyze the formation of genistein from naringenin.

The ability of the cDNA insert in clone sgs1c.pk006.o20 to encode an isoflavone synthase was evaluated by expression of the encoded polypeptide in an engineered yeast (*Saccharomyces cerivisae*) strain. Microsomes prepared from the engineered yeast strain transformed with a plasmid encoding the putative isoflavone synthase were assayed for their ability to mediate the synthesis of genistein in the presence of substrate (naringenin).

Yeast strain W303-1B was used as the starting material and modified by homologous recombination. The coding sequence of the P450 reductase HT1 isolated from *Helianthus tuberosus* (NCBI General Identifier No. 1359894) was inserted into the integrative plasmid pYeDP110 (Pompon, D. et al. (1996) *Meth. Enz.* 272:51–64). Insertion was achieved after PCR amplification for addition of Bam HI and Eco RI restriction sites 5' and 3' of the coding region, respectively, using the primers listed as SEQ ID NO:3 and SEQ ID NO:4.

```
5'-CGGGATCCATGCAACCGGAAACCGTCG-3'        [SEQ ID NO:3]

5'-CCGGAATTCTCACCAAACATCACGGAGGTATC-3'   [SEQ ID NO:4]
```

Transformation of W303-1B with the linearized plasmid led to homologous recombination with the promoter and terminator sequences of the endogenous yeast reductase (CPR1) resulting in the disruption of the CPR1 gene and replacement with the URA3 gene and HT1 under the control of the galactose-inducible promoter GAL10-CYC1. The resulting strain is designated WHT1.

Plasmid DNA (200 ng) from cDNA clone sgs1c.pk006.o20 was used as template for PCR with primers that are homologous to the vector sequences flanking the cDNA cloning site (SEQ ID NO:5 and SEQ ID NO:6).

```
5'-TCAAGGAGAAAAAACCCCGGATCCATGTTGCTGGAACTTGCACTTGG-3'  [SEQ ID NO:5]

5'-GGCCAGTGAATTGTAATACGACTCACTATAGGGCG-3'              [SEQ ID NO:6]
```

Amplification was performed using the GC melt kit (Clontech) with a 1 M final concentration of GC melt reagent. Amplification took place in a Perkin Elmer 9700 thermocycler for 30 cycles as follows: 94° C. for 30 seconds, 60° C. for 30 seconds, and 72° C. for 1 minute. The amplified insert was then incubated with a modified pRS315 plasmid (NCBI General Identifier No. 984798; Sikorski, R. S. and Hieter, P. (1989) *Genetics* 122:19–27) that had been digested with Not I and Spe I. Plasmid pRS315 had been previously modified by the insertion of a bidirectional gal1/10 promoter between the Xho I and Hind III sites. The plasmid was then transformed into the WHT1 yeast strain using standard procedures. The insert recombines though gap repair to form the desired plasmid (Hua, S. B., et al. (1997) *Plasmid* 38:91–96.). The resulting transformed yeast strain is named Isoflavone Synthase GM1 (hereinafter referred to as "GM1"), and bears ATCC Accession No. 203606.

Yeast microsomes were prepared according to the methods of Pompon et al. (Pompon, D., et al. (1996) *Meth. Enz.* 272:51–64). Briefly, a yeast colony was grown overnight (to saturation) in SG (-Leucine) medium at 30° C. with good aeration. A 1:50 dilution of this culture was made into 500 mL of YPGE medium with adenine supplementation and allowed to grow at 30° C. with good aeration to an $OD_{600}$ of 1.6 (24–30 h). Fifty mL of 20% galactose was added, and the culture was allowed to grow overnight at 30° C. The cells were recovered by centrifugation at 5,500 rpm for five minutes in a Sorvall GS-3 rotor. The cell pellet was resuspended in 80 mL of TEK buffer (0.1 M KCl in TE) and left at room temperature for five minutes. The cells were recovered by centrifugation as described above. The cell pellet was resuspended in 5 mL of TES-B (0.6M sorbitol in TE), and glass beads (0.5 mm diameter) were gently added until they reached the surface of the suspension. The cells were disrupted by shaking up and down for five minutes, with an agitation frequency of at least once every 0.5 second. Five mL of TES-B were added to the crude extract, and the beads were washed with some agitation. The supernatant was withdrawn and saved. The wash was repeated twice and the liquid fractions were pooled. The combined fractions were clarified by spinning at 11,000 rpm in a Sorvall SS34 rotor. The pellet was discarded and the microsomes were precipitated by the addition of NaCl to a final concentration of 0.15 M. PEG 4000 was added to a final concentration of 0.1 g/mL. The mixture was incubated on ice for at least 15 minutes, and the microsomal fraction was recovered by at 8,500 rpm for 10 minutes in an SS34 rotor. The pellets were resuspended in TEG (glycerol, 20% by volume, in TE) at a concentration of 20–40 mgs of protein per mL at which point they may be stored at −70° C. for months without any detectable loss of activity.

Example 5

Demonstration of Functional Expression of Isoflavone Synthase in Yeast

The synthesis of genistein or daidzein from either naringenin or liquiritigenin was observed in an in vitro assay that was mediated by yeast microsomes prepared from the yeast transformant GM1 expressing the polypeptide encoded by the insert in soybean cDNA clone sgs1c.pk006.o20. Samples were prepared and run on a LiChrospher 100 RP-18 column (5 μm) or a Phenomenex Luna 3u C18 (2) column (150×4.6 mm) as described in Example 2. Peaks in the yeast microsome assay samples were identified as being genistein or daidzein by their HPLC retention time and absorption spectrum. The retention time and the absorption spectrum of the peak found in the expected location of genistein was identical to the retention time and spectrum of authentic genistein (compare FIGS. 3 and 4, FIGS. 17 and 18). The daidzein peak also had identical retention time and absorption spectrum to the standard. More direct evidence was obtained using LC/MS. Data for daidzein is shown in FIG. 19. The molecular weights of the materials corresponding to the expected genistein and daidzein peaks from the yeast microsome assay samples were 270.32 and 255.2, respectively. The molecular weights of authentic genistein and daidzein are 270.23 and 255.2, respectively.

The synthesis of genistein in yeast microsomes obtained from the yeast strain Isoflavone Synthase GM1 was monitored over the course of incubation with the substrate naringenin. Samples representing incubation periods of 0 minutes and 1, 2, 3, 4 and 14 h were analyzed. Results are presented in FIGS. 8 through 13. A simultaneous increase of genistein, the product, and decrease of naringenin, the substrate of isoflavone synthase, was observed. A detectable amount of genistein was synthesized as early as 40 minutes (FIG. 14). Incubation of microsomes with either naringenin or liquiritigenin as substrate shows an increase in accumulation of genistein and daidzein (the product) over ten hours as seen in FIG. 26.

Genistein synthesis corresponds quantitatively with the amount of input GM1 microsomes (FIG. 14 and FIG. 15). The genistein peak in the assay using GM1 as a source was about 10 times higher than the peak observed from soybean microsome prepared from elicitor-treated hypocotyls (compare FIG. 4 and FIG. 13). Genistein synthesis by yeast microsomes using GM1 also demonstrated an absolute requirement for NADPH. Without the cofactor, the reaction mixture did not synthesize any detectable genistein over a 4-h incubation (FIG. 16).

An unidentified peak, designated "peak 2," with a retention time of 1.59, was also detected during monitoring of reactions catalyzed by yeast microsomes at 280 nm (see FIG. 9 to FIG. 15). This peak was not significant in negative controls (FIG. 8 and FIG. 16). Koch and Grisebach proposed a hypothesis for the synthesis of an intermediate during the conversion of naringenin to genistein (Kochs, G. and Grisenbach, H. (1985) *Eur. J. Biochem.* 155:311–318). This proposal stated that the oxidative aryl migration required to convert naringenin to genistein proceeds via a cytochrome P450 monooxygenase-mediated conversion of the 2S-flavanone to a 2-hydroxyisoflavone, followed by dehydration to the isoflavonoid, possibly mediated by a soluble dehydratase. The 2-hydroxyisoflavone intermediate was described as unstable and could spontaneously convert to genistein. In electrospray LC/MS the most prominent peak in the spectrum of "peak 2" is at m/z=289, consistent with it being the $[MH]^+$ form of the proposed hydroxylated intermediate. The height of "peak 2" detected in the 4 h incubation sample was bigger than that for "peak 2" in the 14 h incubation sample. That sample showed the largest genistein peak among the microsome assays that were performed. It is suspected that "peak 2" may represent this proposed intermediate that may be formed transiently during the synthesis of genistein by isoflavone synthase. A similar intermediate (at m/z=273) was also detected in the conversion of liquiritigenin to daidzein (FIG. 19).

To compare the rates of genistein and daidzein synthesis by microsomes of the yeast transformant GM1, samples representing incubation periods of 2, 4, 6, 8 and 10 h were analyzed. The peak areas for genistein and daidzein were quantitated by calibration with authentic genistein and daidzein standards. Assays were repeated three times and the average amount of isoflavonoid synthesized at each time point was plotted, with vertical lines representing error bars (FIG. 26).

Example 6

Identification of CYP93C1 as a Soybean Isoflavone Synthase

The sequence of the mRNA encoding CYP93C1, a cytochrome P450 monooxygenase, is found in the NCBI database having General Identifier No. 2739005. The function of the protein encoded by this mRNA has yet to be identified. The cDNA insert in clone sgs1c.pk006.o20 encodes an isoflavone synthase and has sequence similarities with CYP93C1. To determine whether CYP93C1 encodes a functional isoflavone synthase, cDNA was prepared and cloned into the yeast vector pRS315-gal and transformed into yeast strain WHT1 to assay for its ability to produce genistein. The CYP93C1 mRNA was amplified from RNA isolated from soybean tissue (cv. S1990) infected with the fungal pathogen *Sclerotinia slerotiorum* using RT-PCR. Fungal infection causes an increase in the amount of isoflavonoid produced and thus the amount of isoflavone synthase transcript was increased in the infected tissue. Soybean plants were infected 45 days after planting seeds and were harvested two days later. Total RNA was prepared using the TRIzol Reagent following the manufacturer's instructions (Gibco BRL) and 1 µg of the resulting total RNA was converted into a first strand cDNA using the Superscript™ Preamplification system and using oligodT as the reverse transcription primer. One microliter of first strand cDNA was amplified by PCR using the primers listed as SEQ ID NO:7 and SEQ ID NO:8:

```
5'-AAAATTAGCCTCACAAAAGCAAAG-3'        [SEQ ID NO:7]

5'-ATATAAGGATTGATAGTTTATAGTAGG-3'     [SEQ ID NO:8]
```

The nucleotide sequence in SEQ ID NO:7 corresponds to nucleotides 3 to 26 of the sequence found in NCBI General Identifier No. 2739005. The nucleotide sequence in SEQ ID NO:8 corresponds to the complement of nucleotides 1798 to 1824 of the sequence found in NCBI General Identifier No. 2739005. Amplification was performed on a Perkin Elmer Applied Biosystems GeneAmp PCR System using the Advantage-GC cDNA polymerase mix (Clontech), following the manufacturer's instructions, with a 1 M final concentration of GC melt reagent. Previous to amplification, the mixture was incubated at 94° C. for 5 minutes. Amplification was performed using 30 cycles of: 94° C. for 30 seconds, 53° C. for 30 seconds and 72° C. for 2 minutes. Following amplification, the mixture was incubated at 72° C. for 7 minutes. The amplified product was then cloned into pCR2.1 using "The Original TA Cloning Kit" (Invitrogen). Plasmid DNA was purified using QIAFilter cartridges (Qiagen Inc) according to the manufacturer's instructions. Sequence was generated on an ABI Automatic sequencer using dye terminator technology and using a combination of vector and insert-specific primers. Sequence editing was performed using DNAStar (DNASTAR, Inc.). The sequence generated represents coverage at least two times in each direction. The sequence of the resulting clone, presented in SEQ ID NO:9, was identical with that of CYP93C1 (NCBI General Identifier No. 2739005); the deduced amino acid sequence of this cDNA is shown in SEQ ID NO:10.

The above plasmid was then cloned into the yeast vector pRS315-gal using gap repair as described in Example 4. Standard procedures were used to transform the resulting plasmid into the WHT1 yeast strain. Microsomes were prepared from the WHT1 yeast strain containing the soybean CYP93C1 sequence and assayed for the production of genistein and daidzein as described in Example 5. The resulting microsomes exhibited isoflavone synthase activities. To compare the rates of genistein and daidzein synthesis by microsomes of the yeast transformant containing the soybean CYP93C1 sequence, samples representing incubation periods of 2, 4, 6, 8 and 10 h were analyzed. The peak areas for genistein and daidzein were quantitated by calibration with authentic genistein and daidzein standards as prepared in Example 2. Daidzein and genistein accumulated linearly over the time course.

Example 7

Amplification and Identification of Isoflavone Synthase From Other Legume Species Nucleic acid sequences encoding isoflavone synthases from lupine, mung bean, snow pea, alfalfa, red clover, white clover, hairy vetch and lentil were derived from total RNA prepared from young seedlings. Mung bean sprouts and snow pea sprouts were obtained from the local grocery store. Seeds for alfalfa, red clover, white clover, hairy vetch, and lentil were obtained from Pinetree Garden Seeds while seeds for lupine (cv Russell Mix) were obtained from Botanical Interests, Inc. Seedlings were germinated in a controlled temperature growth chamber (14 h light at 25° C. and 10 h dark at 21° C.) and harvested after approximately two weeks except for lupine, which was harvested after approximately three weeks. Total RNA was prepared using TRIzol Reagent (Gibco BRL) according to the manufacturer's instructions. For each plant, a first strand cDNA was prepared from 1 µg total RNA using the Superscript™ Preamplification System (Gibco BRL) following the manufacturer's instructions. OligodT was used as the reverse transcription primer in all cases except white clover where random hexamers were used.

Amplification was performed on a Perkin-Elmer Applied Biosystems GeneAmp PCR System 9700PCR using Advantage-GC cDNA polymerase mix (Clontech) according to the manufacturer's instructions and with a final concentration of GC melt reagent equal to 1 M. Amplification was preceded in all cases by incubation at 94° C. for 5 minutes and was followed by incubation at 72° C. for 7 minutes. Two sets of primers were used for PCR amplification. Primer set one is composed of SEQ ID NO:11 and SEQ ID NO:12 and primer set two is composed of SEQ ID NO:13 and SEQ ID NO:14:

```
5'-ATGTTGCTGGAACTTGCACTT-3'      [SEQ ID NO:11]

5'-TTAAGAAAGGAGTTTAGATGCAACG-3'  [SEQ ID NO:12]

5'-TGTTTCTGCACTTGCGTCCCAC-3'     [SEQ ID NO:13]

5'-CCGATCCTTGCAAGTGGAACAC-3'     [SEQ ID NO:14]
```

The initial amplification of all samples was done using 1 µL of first strand cDNA and primer set one (SEQ ID NO:11 and SEQ ID NO:12). Amplification of mung bean was performed using 30 cycles of 94° C. for 30 seconds, 48° C. for 30 seconds and 72° C. for 2 minutes. Amplification of red clover was performed using 30 cycles of 94° C. for 30 seconds, 50° C. for 30 seconds and 72° C. for 1 minute. Amplification of white clover, lentil, hairy vetch, alfalfa and lupine was carried out in two steps. The first amplification reaction was performed using 30 cycles of 94° C. for 30 seconds, 50° C. for 30 seconds and 72° C. for one minute. A second amplification reaction was done with 1 μL of the resulting product and primer set two (SEQ ID NO:13 and SEQ ID NO:14) using 30 cycles of 94° C. for 30 seconds, 50.5° C. for 30 seconds and 72° C. for one minute. Amplification of snow pea was performed in three different PCR reactions. The first reaction was performed using 30 cycles of 94° C. 30 seconds, 50.5° C. for 30 seconds and 72° C. for one minute. One microliter from the resulting product was used for a second amplification reaction using primer set one and 30 cycles of 94° C. for 30 seconds, 60° C. for 30 seconds and 72° C. for one minute. The resulting reaction was analyzed on a 1% agarose gel and the band at the expected size was gel purified using the QIAquick Gel Extraction Kit (Qiagen). The purified DNA was resuspended in 30 μL of water and 1 μL was used as a template for a third PCR reaction using primer set one with 30 cycles of 94° C. for 30 seconds, 60° C. for 30 seconds and 72° C. for 90 seconds.

The resulting mung bean, red clover and snow pea PCR sequences were cloned into pCR2.1 using "The Original TA Cloning Kit" (Invitrogen). The resulting white clover, lentil, hairy vetch, alfalfa and lupine PCR sequences were cloned into pCR2.1 using TOPO™ TA Cloning Kit (Invitrogen). Plasmid DNA was purified using QIAFilter cartridges (Qiagen Inc) or Wizard Plus Minipreps DNA Purification System (Promega) following the manufacturer's instructions. Sequence was generated on an ABI Automatic sequencer using dye terminator technology and using a combination of vector and insert-specific primers. Sequence editing was performed using DNAStar (DNASTAR, Inc.). All sequences represent coverage at least two times in both directions.

The nucleotide sequence of comprising the cDNA insert in clone alfalfa 1 is shown in SEQ ID NO:15; the deduced amino acid sequence of this DNA is shown in SEQ ID NO:16. The nucleotide sequence comprising the cDNA insert in clone alfalfa 2 is shown in SEQ ID NO:57; the deduced amino acid sequence of this DNA is shown in SEQ ID NO:58. The nucleotide sequence comprising the cDNA insert in clone alfalfa 3 is shown in SEQ ID NO:59; the deduced amino acid sequence of this DNA is shown in SEQ ID NO:60. The nucleotide sequence comprising the cDNA insert in clone hairy vetch 1 is shown in SEQ ID NO:17; the deduced amino acid sequence of this DNA is shown in SEQ ID NO:18. The nucleotide sequence comprising the cDNA insert in clone lentil 1 is shown in SEQ ID NO:19; the deduced amino acid sequence of this DNA is shown in SEQ ID NO:20. The nucleotide sequence comprising the cDNA insert in clone lentil 2 is shown in SEQ ID NO:21; the deduced amino acid sequence of this DNA is shown in SEQ ID NO:22. The nucleotide sequence comprising the cDNA insert in clone mung bean 1 is shown in SEQ ID NO:23; the deduced amino acid sequence of this DNA is shown in SEQ ID NO:24. The nucleotide sequence comprising the cDNA insert in clone mung bean 2 is shown in SEQ ID NO:25; the deduced amino acid sequence of this DNA is shown in SEQ ID NO:26. The nucleotide sequence comprising the cDNA insert in clone mung bean 3 is shown in SEQ ID NO:27; the deduced amino acid sequence of this DNA is shown in SEQ ID NO:28. The nucleotide sequence comprising the cDNA insert in clone mung bean 4 is shown in SEQ ID NO:29; the deduced amino acid sequence of this DNA is shown in SEQ ID NO:30. The nucleotide sequence comprising the cDNA insert in clone red clover 1 is shown in SEQ ID NO:31; the deduced amino acid sequence of this DNA is shown in SEQ ID NO:32. The nucleotide sequence comprising the cDNA insert in clone red clover 2 is shown in SEQ ID NO:33; the deduced amino acid sequence of this DNA is shown in SEQ ID NO:34. The nucleotide sequence comprising the cDNA insert in clone snow pea 1 is shown in SEQ ID NO:35; the deduced amino acid sequence of this DNA is shown in SEQ ID NO:36. The nucleotide sequence comprising the cDNA insert in clone white clover 1 is shown in SEQ ID NO:37; the deduced amino acid sequence of this DNA is shown in SEQ ID NO:38. The nucleotide sequence comprising the cDNA insert in clone white clover 2 is shown in SEQ ID NO:39; the deduced amino acid sequence of this DNA is shown in SEQ ID NO:40. The nucleotide sequence comprising the cDNA insert in clone lupine 1 is shown in SEQ ID NO:54; the deduced amino acid sequence of this DNA is shown in SEQ ID NO:55.

Plasmids corresponding to mung bean 2, red clover 2 and snow pea 1 were amplified and the plant-specific DNA (corresponding to SEQ ID NO:25, SEQ ID NO:33 and SEQ ID NO:35) were transferred to the yeast vector pRS315-gal following the gap repair method explained in Example 4 to produce the yeast expression strains isoflavone synthase VR2, isoflavone synthase TP2, and isoflavone synthase PS1, respectively. The eight amino acids at the amino- and carboxy-terminus correspond to those translated from the primers used in PCR amplification and not necessarily belong to the endogenous genes. Microsomes were isolated from the resulting yeast WHT1 strains containing the mung bean, red clover or snow pea genes, and assayed for isoflavone synthase activity as described in Example 5, with minor modifications. After incubation for 16 hours, 200 μL of ethyl acetate was added to recover the isoflavonoids from the assay solution, the ethyl acetate was evaporated under nitrogen using a heating module evaporation system and the sample resuspended in 200 μL of 80% methanol. A 10 μL sample of this solution was injected into a Phenomenex Luna 3μ C18 (2) column (size: 150×4.6 mm. The samples were eluted over 10 minutes using an increasing methanol gradient (from 20% methanol/80% 100 mM ammonium acetate buffer (pH 5.9) to 100% methanol (v/v)) at a flow rate of 1 mL per minute. The levels of genistein and naringenin in the eluted samples were monitored through the absorption spectrum at 260 and 290 nm. The genistein signal was verified by comparisons of retention time, diode array detected absorption spectra. As seen in Table 1, microsomes from all three strains produced genistein and therefore exhibited isoflavone synthase activity.

TABLE 1

Genistein Synthesis Using in vitro Yeast Assay System

| Yeast expression strain | Genistein Synthesized |
| --- | --- |
| Isoflavone Synthase VR2 | 1298 ng |
| Isoflavone Synthase TP2 | 59 ng |
| Isoflavone Synthase PS1 | 19 ng |
| pRS315-gal | Not detectable |

Example 8

Amplification and Identification of Isoflavone Synthase From Non-Legume Species

Isoflavonoids are most often found in the legumes, although there are occasional examples of isoflavonoids in non-legume plants (Dewick, P. M., Isoflavonoids in The Flavonoids: Advances in Research edited by J. B. Harborne and T. J. Mabry pp. 535–640). To obtain isoflavone synthases with greater molecular diversity, isoflavone synthase genes from *Beta vulgaris* (sugarbeet) were cloned and their activity tested. Sugarbeet, a member of the family Chenopodiaceae, is one of the few non-legume species to have been shown to have isoflavonoids present (Geigert, et al. (1973) *Tetrahedron*. 29:2703–2706).

Sugarbeet seeds were germinated in a growth chamber as described in Example 7 (14 h light at 25° C. and 10 h dark at 21° C.) and harvested after two weeks. Total RNA was prepared using TRIzol Reagent (Gibco BRL) according to the manufacturer's instructions. First strand cDNA was prepared from 1 μg total RNA using the Superscript™ Preamplification System (Gibco BRL) following the manufacturer's instructions with OligodT as the reverse transcription primer.

Amplification was carried out in two steps. The first amplification reaction was performed using 1 μL of first strand cDNA and primer set one (SEQ ID NO:11 and SEQ ID NO:12) with 30 cycles of 94° C. for 30 seconds, 50° C. for 30 seconds and 72° C. for one minute. A second amplification reaction was done with 1 μL of the resulting product with primer set two (SEQ ID NO:13 and SEQ ID NO:14) and using 30 cycles of 94° C. for 30 seconds, 50.5° C. for 30 seconds and 72° C. for one minute. The resulting PCR sequence was cloned into pCR2.1 using TOPO™ TA Cloning Kit (Invitrogen). Plasmid DNA was purified using QIAFilter cartridges (Qiagen Inc) or Wizard Plus Minipreps DNA Purification System (Promega) following the manufacturer's instructions. Sequence was generated on an ABI Automatic sequencer using dye terminator technology and using a combination of vector and insert-specific primers. Sequence editing was performed using DNAStar (DNASTAR, Inc.). All sequences represent coverage at least two times in both directions. The nucleotide sequence comprising the cDNA insert in clone sugarbeet 2 is shown in SEQ ID NO:47; the deduced amino acid sequence of this DNA is shown in SEQ ID NO:48. The nucleotide sequence comprising the cDNA insert in clone sugarbeet 1 is shown in SEQ ID NO:60; the deduced amino acid sequence of this DNA is shown in SEQ ID NO:61.

The data in Table 2 summarizes the relationship of the isoflavone synthase nucleotide and amino acid sequences disclosed herein. Reported are the percent identity of the nucleotide sequences set forth in SEQ ID NOs:9, 15, 17, 19, 21, 23, 25, 27, 29, 31, 33, 35, 37, 39, 47 and 54 to instant soybean isoflavone synthase sequence set forth in SEQ ID NO:1. In addition, the percent identity of the amino acid sequences deduced from the instant nucleotide sequences as set forth in SEQ ID NOs:10, 16, 18, 20, 22, 24, 26, 28, 30, 32, 34, 36 38, 40, 48 and 55 are compared to the amino acid sequence set forth in SEQ ID NO:2.

TABLE 2

Percent Identity of Nucleotide Coding Sequences and Amino Acid Sequences of Polypeptides Homologous to Isoflavone Synthase

| SEQ ID NO. | | | length | Percent Identity to SEQ ID NO: 1/2 | |
|---|---|---|---|---|---|
| nt | aa | Crop | (nts)* | nucleotides (nt) | amino acids (aa) |
| 9 | 10 | Soybean | 1824 | 85.9 | 96.7 |
| 15 | 16 | Alfalfa1 | 1501 | 99.5 | 99.0** |
| 56 | 57 | Alfalfa2 | 1501 | 92.2 | 96.2** |
| 58 | 59 | Alfalfa3 | 1501 | 92.3 | 96.6** |
| 17 | 18 | Hairy vetch | 1501 | 92.3 | 96.2** |
| 19 | 20 | Lentil1 | 1501 | 97.9 | 98.8** |
| 21 | 22 | Lentil2 | 1501 | 92.3 | 96.4** |
| 23 | 24 | Mung bean1 | 1566 | 92.5 | 96.7 |
| 25 | 26 | Mung bean2 | 1566 | 92.5 | 96.7 |
| 27 | 28 | Mung bean3 | 1566 | 92.6 | 96.7 |
| 29 | 30 | Mung bean4 | 1566 | 92.7 | 96.7 |
| 31 | 32 | Red clover | 1566 | 92.5 | 96.4 |
| 33 | 34 | Red clover | 1566 | 92.6 | 96.7 |
| 35 | 36 | Snow pea | 1563 | 99.3 | 99.0 |
| 37 | 38 | White clover1 | 1496 | 99.3 | 98.4** |
| 39 | 40 | White clover2 | 1501 | 98.3 | 99.0** |
| 60 | 61 | Sugarbeet1 | 1497 | 91.9 | 95.6** |
| 47 | 48 | Sugarbeet2 | 1501 | 92.3 | 96.6** |
| 54 | 55 | Lupine | 1501 | 92.2 | 96.2** |

*SEQ ID NO: 1 contains 1756 nucleotides.
**These sequences are 22 amino acids shorter because the primers used for PCR were derived from the soybean sequence.

The data presented in Table 2 indicates that the nucleotide and amino acid sequences encoding the various isoflavone synthases are highly conserved among divergent species. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10).

A consensus sequence was determined by aligning the amino acid sequences of the present invention using the Clustal method of alignment and this sequence is shown in SEQ ID NO:66. Amino acids not conserved are indicated by Xaa. These are:

| | |
|---|---|
| $Xaa_{10}$ | Phe or Leu |
| $Xaa_{16}$ | Ser or Leu |
| $Xaa_{23}$ | Ser or Thr |
| $Xaa_{25}$ | Ile or Lys |
| $Xaa_{39}$ | Lys or Arg |
| $Xaa_{48}$ | Pro or Leu |
| $Xaa_{60}$ | Pro or Leu |
| $Xaa_{73}$ | Leu or His |
| $Xaa_{74}$ | Ser or Tyr |
| $Xaa_{95}$ | Ala or Thr |
| $Xaa_{96}$ | Asn or His |
| $Xaa_{102}$ | Asn or Ser |
| $Xaa_{110}$ | Ile, Val, or Thr |
| $Xaa_{112}$ | Arg or His |
| $Xaa_{117}$ | Asn or Ser |
| $Xaa_{118}$ | Ser or Leu |
| $Xaa_{121}$ | Met or Arg |
| $Xaa_{122}$ | Ala or Val |
| $Xaa_{124}$ | Phe or Ile |
| $Xaa_{129}$ | Lys or Arg |
| $Xaa_{147}$ | Lys or Glu |
| $Xaa_{159}$ | Leu or Phe |
| $Xaa_{162}$ | Ala or Val |
| $Xaa_{166}$ | Ser or Gly |
| $Xaa_{170}$ | Gln or Arg |
| $Xaa_{175}$ | Val or Leu |
| $Xaa_{183}$ | Ala or Thr |
| $Xaa_{187}$ | Thr or Ile |
| $Xaa_{191}$ | Met or Val |

-continued

| | |
|---|---|
| Xaa209 | Phe or Tyr |
| Xaa219 | Arg or Trp |
| Xaa223 | Tyr or His |

5'-TTGCTGGAACTTGCACTTGGT-3'    [SEQ ID NO:41]

5'-GTATATGATGGGTACCTTAATTAAGAAAGGAG-3'    [SEQ ID NO:42]

-continued

| | |
|---|---|
| Xaa253 | Gly or Glu |
| Xaa259 | Lys or Glu |
| Xaa263 | Val or Asp |
| Xaa264 | Val, Asp, or Ile |
| Xaa268 | Ala or Val |
| Xaa272 | Phe or Leu |
| Xaa285 | Thr or Met |
| Xaa292 | Any amino acid |
| Xaa293 | Any amino acid |
| Xaa294 | Thr, or Ile |
| Xaa301 | Phe or Leu |
| Xaa306 | Thr or Ile |
| Xaa311 | Val or Glu |
| Xaa312 | Val or Ala |
| Xaa325 | Arg or Lys |
| Xaa328 | Gln or Glu |
| Xaa329 | Any amino acid |
| Xaa334 | Val or Ala |
| Xaa342 | Arg or Ile |
| Xaa377 | Thr or Ile |
| Xaa381 | Glu or Gly |
| Xaa385 | Tyr, His, or Cys |
| Xaa387 | Ile or Thr |
| Xaa393 | Val or Ile |
| Xaa394 | Leu or Pro |
| Xaa402 | Arg or Lys |
| Xaa404 | Ser or Pro |
| Xaa413 | Ser or Phe |
| Xaa422 | Glu or Gly |
| Xaa428 | Gly or Arg |
| Xaa429 | Pro or Leu |
| Xaa435 | Gln or Arg |
| Xaa447 | Arg or Gly |
| Xaa453 | Asn, Ser, or Ile |
| Xaa459 | Met or Thr, and |
| Xaa485 | Asp or Gly |

To verify that the similarity between the isoflavone synthase nucleotide sequences from soybean and from sugarbeet were not due to artifacts of PCR, a nucleic acid sequence containing the soybean isoflavone synthase set forth in SEQ ID NO:1 was used as a probe for Southern blot analysis against sugarbeet genomic DNA. Hybridization was done overnight at 65° C. in 6×SSC, 5× Denhardts. Filters were washed 2 times in 2×SSC, 1% SDS at room temperature and 2 times in 0.2×SSC, 0.5% SDS at 65° C. Hybridizing bands were detected indicating that sugarbeet does contain genes with high homology to the soybean isoflavone synthase sequence.

Example 9

Preparation of Transgenic Tobacco with Chimeric Isoflavone Synthase Gene

Figure 20:
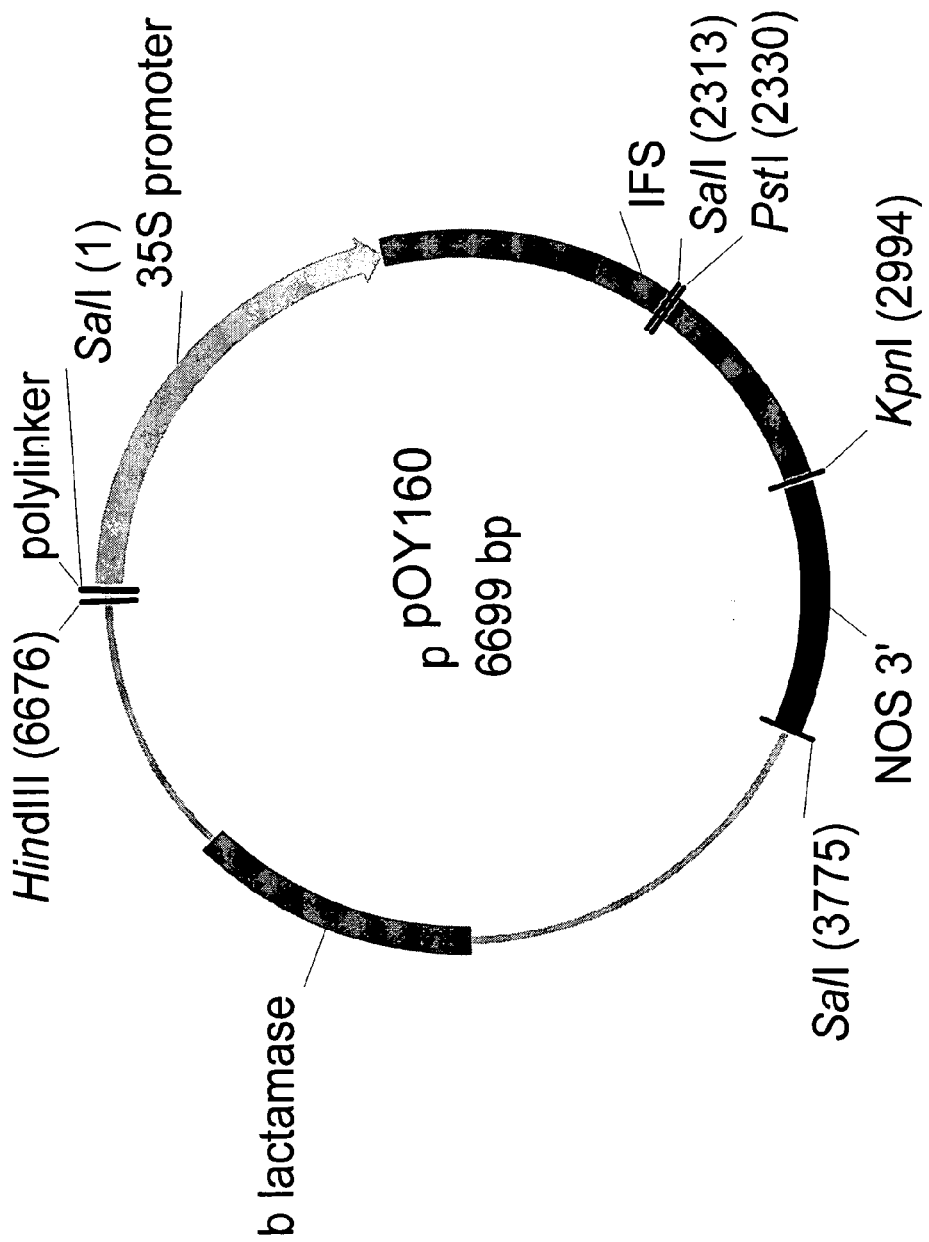
FIG. 20 depicts the plasmid map of pOY160.

The ability to obtain isoflavone synthase activity by expressing the gene from soybean clone sgs1c.pk006.o20 in other plants was tested by preparing transgenic tobacco plants expressing the isoflavone synthase gene and assaying for genistein production. The 1.6 Kb isoflavone synthase coding region from clone sgs1c.pk006.o20 (SEQ ID NO:1) was amplified using a standard PCR reaction in a GeneAmp PCR System with the primers shown in SEQ ID NO:41 and SEQ ID NO:42:

The resulting DNA sequence (IFS) contains from the second codon to the stop codon of the soybean isoflavone synthase gene sequence followed by a Kpn I site. The following three sequences (in 5' to 3' order) were assembled in pUC18 vector (New England Biolabs) to yield plasmid pOY160 (depicted in FIG. 20):

35S/cabL, a promoter sequence comprising 1.3 Kb from the cauliflower mosaic virus (CaMV) 35S promoter extending to 8 bp downstream from the transcription start site followed by a 60 bp leader sequence derived from the chlorophyll a/b binding protein gene 22L (Harpster M. H. et al. (1988) *Mol. Gen. Genet.* 212: 182–190);

IFS, the isoflavone synthase gene fragment generated by PCR amplification using the primers from SEQ ID NO:41 and SEQ ID NO:42.

Nos3'; an 800 bp fragment which contains the polyadenylation signal sequence from the nopaline synthase gene (Depicker A. et al. (19820 *J. Mol. Appl. Genet.* 1:561–573).

The 5' end of IFS was ligated to Nco I-digested, filled-in, 35S/cabL. The 3' end of IFS was digested with Kpn I and ligated to Kpn I-digested Nos3'.

The following three fragments were ligated to create plasmid pOY204:

1) The Hind III/Pst I fragment comprising the 35S/cabL-5'IFS from pOY160,

2) The Pst I/Sal I fragment comprising the 3'IFS-Nos3' from pOY160,

3) The Hind III/Sal I fragment from vector pPZP211.

The vector pPZP211 contains an npt II gene fragment under the control of the 35S CaMV promoter conferring kanamycin resistance as the plant selectable marker (Hajdukiewicz P. et al. (1994) *Plant Mol. Biol.* 25:989–994).

The plasmid pOY204 was transformed into the *Agrobacterium tumefaciens* strain LBA4404 and was subsequently introduced into *Nicotiana tobaccum* by leaf disc co-cultivation following standard procedures (De Blaere et al. 1987 *Meth. Enzymol.* 143:277). The leaf discs were incubated for three weeks on selection medium (MS salts with vitamins (Gibco BRL), 1 mg/L 6-benzylaminopurine (BA), 100 mg/L kanamycin, and 500 mg/L Claforan). The regenerating plants were transferred to rooting medium (selection medium without BA) for another two weeks. Transformed plants were identified by the appearance of roots in this selection media. Following standard protocols, DNA samples were prepared from six randomly-selected shoots and used as templates for PCR using the primers from SEQ ID NO:41 and SEQ ID NO:42. Verification of the presence of the isoflavone synthase coding region in the genome of the tested tobacco shoots was done by separating the reaction product using a 1% agarose gel and staining with ethidium bromide. The expected 1.6 Kb fragment was obtained as the reaction product in all the transgenic tobacco shoots and not in the untransformed tobacco controls.

Transcription of Soybean Isoflavone Synthase in Transgenic Tobacco Shoots

Transcription of the isoflavone synthase gene in the transgenic tobacco shoots was confirmed using RT-PCR. Total steady-state plant RNA was extracted from four randomly-selected tobacco shoots resulting from transformation with pOY204 using the RNeasy Plant Mini Kit (Qiagen) following standard protocols. RT-PCR amplification was performed using "The SuperScript One Step RT-PCR Kit" (Gibco BRL) with the primers:

5'-GACGCCTCACTTACGACAACTCTGTG-3'  [SEQ ID NO:43]

5'-CCTCTCGGGACGGAATTCTGATGGT-3'  [SEQ ID NO:44]

After incubation at 50° C. for 45 minutes, amplification was carried out using 37 cycles of 93° C. for 30 seconds, 64° C. for 30 seconds and 72° C. for 1 minute. The resulting DNA was separated on a 1% agarose gel. Samples from the putative isoflavone synthase-containing tobacco showed an 840 bp band not seen in the sample from the untransformed tobacco control.

Example 10

Expression of Soybean Isoflavone Synthase in Transgenic Tobacco

Activity of Soybean Isoflavone Synthase in Tobacco Shoots

The activity of the soybean isoflavone synthase in the transgenic tobacco was determined by analyzing shoots for the presence of genistein. Approximately one gram of tissue from shoots of five-week-old rooting transformants and from untransformed tobacco plants were ground in liquid nitrogen and extracted for 20 minutes at room temperature using 110 mL of 80% ethanol. After filtration through Acrodisc CR-PTFE syringe filters (Gelman Sciences), 3 mL from each extraction solution were concentrated to 1 mL by evaporation under nitrogen gas flow using a 50° C. heating block. To hydrolyze any malonyl or glucosyl-derivatized compounds present, 3 mL of 1 N HCl were added and the samples incubated at 95° C. for 2 h followed by extraction using 1 mL ethyl acetate. Five hundred μL of the ethyl acetate phase were dried under nitrogen and resuspended in 20 μL chloroform. The presence of genistein in the samples was determined by gas chromatography/mass spectroscopy (GC/MS) analysis.

Before injection into a Hewlett Packard 6890 gas chromatograph, the hydroxyl groups in the samples were derivatized to trimethylsilylate by the addition of 100 μL of BSTFA (N, O-bis(trimethylsilyl)-trifluoroacetamide; Supelco) and incubation at 37° C. for 1 h. The samples were dried under nitrogen gas and re-dissolved in 20 μL chloroform immediately before manual injection into the gas chromatograph. Two μL of sample were manually injected onto a 15 meter dry bed GC capillary column (J&W, Jones Chromatography, Mid Glamorgan, UK) through an injector port operated in the split mode (5:1). The initial oven temperature was set at 200° C. and the column was set at a linear temperature gradient from 200° C. to 300° C. in 20 minutes with a helium gas flow rate of 1.5 mL/minute. The mass spectrum was monitored using a Hewlett Packard 5973 mass-selective detector at an ionization potential of 70 eV. The mass ions identified from the cracking pattern of pure genistein treated as mentioned above are 414 and 399 m/z. These peaks represent the products of partially derivatized genistein, the form obtained following the above procedure. Twenty nine of thirty three tobacco transformants analyzed by gas chromatography had an identifiable genistein peak at 8.7 minutes. The presence of genistein in these peaks was confirmed by the detection of peaks at 414 and 399 m/z in the mass spectra. These results confirmed that the soybean isoflavone synthase coding region is expressed in tobacco plants under control of the 35S CaMV promoter and causes novel production of genistein in tobacco shoot tissue.

Presence of Genistein in Tobacco Flowers

Flowers from the tobacco transformants were assayed for the presence of genistein. Extracts were prepared as described above, except that after hydrolysis, the dried ethyl acetate extracts were resuspended in 1 mL of 80% methanol. The HPLC protocol was the same as in Example 2 using a Phenomenex Luna 3u C18 (2) column (150×4.6 mm). As compared to extracts from wild type plants, the transformant flowers contained two additional large peaks in the HPLC profile. One of these peaks was identified as genistein while the other is unknown. Detection of the large genistein peak in the HPLC profile of the tobacco flower extracts indicated that there was a much higher amount of genistein present in the tobacco flowers than in the tobacco shoots, since the genistein in the shoot samples was only detectable by GC/MS. The prevalence of genistein in the flowers relates to the expression of the anthocyanin biosynthetic pathway, which is active in the flowers as indicated by the pink flower color. An active anthocyanin pathway produces the naringenin substrate for isoflavone synthase.

Example 11

Expression of Soybean Isoflavone Synthase in Transgenic *Arabidopsis*

*Arabidopsis thaliana* was transformed with the plasmid pOY204 via in planta vacuum infiltration following standard protocols (Bechtold et al. (1993) *CR Life Sciences* 316: 1194–1199). Briefly, three-week-old *Arabidopsis thaliana* ectotype WS plants were submerged in 500 mL of *Agrobacterium*, strain GV3101 harboring pOY204, suspended in basic MS media (Gibco BRL) and vacuum was applied repeatedly for 10 minutes. The infiltrated plants were allowed to set seeds for another three weeks. The harvested seeds were surface-sterilized, then germinated and grown for three weeks on plates containing 75 mg/L kanamycin. Approximately 120 green healthy plants were recovered in the first round of screening and were transferred to soil for two more weeks. The plants at this stage had green immature pods and few leaves. Extracts were prepared and analyzed by HPLC and GC/MS as described in Example 2, except that after hydrolysis, the dried ethyl acetate extracts were resuspended in 1 mL of 80% methanol. Five of twelve randomly-selected *Arabidopsis* transformants analyzed by HPLC had an identifiable genistein peak at 8.7 minutes. GC MS analysis confirmed the presence of genistein in these peaks by detection of the characteristic peaks at 414 and 399 m/z in the mass spectra. These results show that the soybean isoflavone synthase gene is functional in the *Arabidopsis* plants and genistein is produced.

Example 12

Enhancing Isoflavonoid Levels in Transgenic *Arabidopsis*

To determine whether activation of the phenylpropanoid pathway results in increased accumulation of isoflavonoids in IFS-transformed *Arabidopsis*, the pathway was activated by UV light treatments. Homozygous *Arabidopsis* transformants of line A109-4, which synthesize genistein, were identified through germination on kanamycin-containing medium by first selecting a transformant that segregated kanamycin resistance in a 3:1 ratio. A resistant progeny from this generation that then produced 100% resistant progeny was identified as a homozygote. Plants from this population and wild type *Arabidopsis* plants were transferred to 2-inch pots 10 days after germination and grown for 10 more days. Plants were placed directly under 366 nm UV light for 16 h (46 mWatt/cm$^2$, using an UVL-56 BLAK-Ray Lamp from UV Products, Inc., San Gabriel, Calif.). Control plants were placed under the same described environment except for the UV illumination. The above ground parts of *Arabidopsis* plants were pulverized in liquid nitrogen to fine powder immediately after UV treatment. The tissues were extracted with 10 mL 80% methanol per 1 gram of fresh weight. The genistein content from tissue extracts of UV-treated and untreated plants was determined by HPLC using a Phenomenex Luna 3u (2) column (150×4.6 mm) and a mobil phase linear gradient which goes in 15 minutes from 20% methanol, 80% 10 mM ammonium acetate, pH 8.3 to 100% methanol followed by 100% methanol for 5 minutes as described in Example 2. Aliquots from the same extracts were also assayed for anthocyanin accumulation using photospectrometry as described by Bariola, P. A., et. al. ((1999) *Plant Physiol.* 119:331–342). Briefly, one mL of extract was mixed with one mL of 0.5% (v/v) HCl followed by the addition of two mL of chloroform and vortexing for ten seconds. The mixture was allowed to separate to two phases at room temperature. The absorbance of the aqueous phase was assayed at 530 nm and 657 nm. The anthocyanin content was calculated by subtracting the absorbance value at 657 from the absorbance value at 530 and normalizing to fresh weight. As seen in Table 3, the anthocyanin content and genistein level in IFS-transformed *Arabidopsis* varies with UV treatment (The average and standard deviations of four independent plants from each group are shown).

TABLE 3

Anthocyanin Content and Genistein Levels in Transgenic *Arabidopsis* Plants

| Sample | Anthocyanin (A530-A657) | | Genistein (by HPLC) (mAu/25 uL) | |
|---|---|---|---|---|
| | Control | UV | Control | UV |
| Control Plants (no IFS gene) | 0.0463 ± 0.0148 | 0.0591 ± 0.0202 | 0 | 0 |
| A109-4 (35S-IFS) | 0.0339 ± 0.0100 | 0.0368 ± 0.0116 | 121 ± 41 | 303 ± 58 |

Anthocyanins are products of one branch of the phenylpropanoid pathway, and the level of their accumulation is an indication of the activity of this pathway. As seen in the table above, genistein was not detectable and the anthocyanin levels increased by about 28% after UV treatment in the control plants. In plants expressing IFS the anthocyanin levels were not significantly increased while the genistein levels more than doubled. A duplication of this experiment also showed an increase in genistein level (anthocyanin levels without UV treatment: 0.1426+/−0.0245; and with UV treatment: 0.1463+/−0.0145 (units as described above); genistein without UV treatment: 602+/−94; and with UV treatment: 857+/−46 (units as described above)). In this case the level of anthocyanins in non-treated plants was much higher, probably due to insect infestation. The level of genistein was higher in non-treated plants and the increase with UV treatment was not as large as in the first experiment. These results demonstrate that activation of the phenylpropanoid pathway, in this case by stress treatment (UV or insect infestation), results in an increased level of genistein accumulation in transformants expressing isoflavone synthase.

Example 13

Expression of Soybean Isoflavone Synthase in Monocot Cells

The ability to obtain isoflavone synthase activity in monocot cells was tested by transforming the soybean gene from clone sgs1c.pk006.o20 into corn suspension cells and assaying for genistein production. The soybean isoflavone synthase gene was cloned in a vector for expression in monocot cells and its activity determined by the expression of genistein in corn. A chimeric isoflavone synthase gene plasmid was prepared (pOY206) using the pGEM9Zf cloning vector (Promega) for expression of the instant isoflavone synthase in monocots. The following fragments were inserted between two copies of the 3 Kb SAR fragment (the A element, originally located between 8.7 and 11.7 kb upstream of the chicken lysozyme gene coding region (Loc P. V. and Stratling W. H. (1988) *EMBO J.* 7:655–664):

1. the 35S/cabL promoter fragment from Example 9,
2. a 490 bp fragment containing the sixth intron from the maize Adh1 gene (Mascarenhas, D. et al. (1990) *Plant Mol. Biol.* 15:913–920) and ending with an Nco I site,
3. IFS, the isoflavone synthase fragment from Example 9.
4. a 285 bp fragment containing the polyadenylation signal sequence from the nopaline synthase gene (Depicker A. et al. (1982) *J. Mol. Appl. Genet.* 1:561–573).

Gene Combinations Used for Corn Cell Transformation

Figure 21:
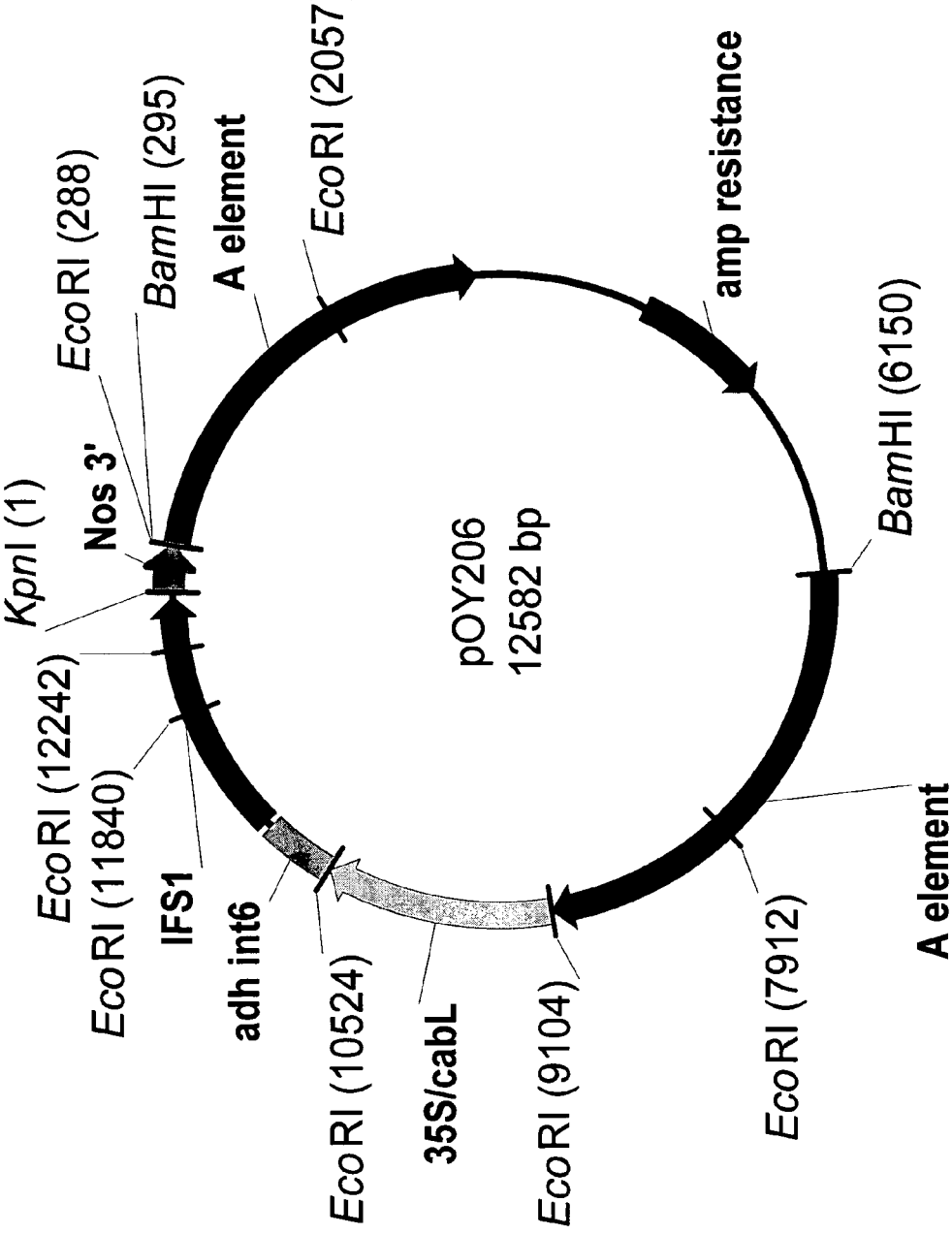
FIG. 21 depicts the plasmid map of pOY206.

The plasmid pOY206 (FIG. 21) containing the chimeric isoflavone synthase gene for expression in monocots was transformed into corn cells in conjunction with plasmid pDETRIC. Plasmid pDETRIC contains the bar gene from *Streptomyces hygroscopicus* that confers resistance to the herbicide glufosinate (Thompson et al. (1987) *EMBO J.* 6:2519). In the pDETRIC plasmid the bar gene is under the control of the CaMV 35S promoter, its translation-initiation codon has been changed from GTG to ATG for proper translation initiation in plants (De Block et al. (1987) *EMBO J.* 6:2513), and uses the *Agrobacterium tumefaciens* octopine synthase polyadenylation signal.

Figure 22:
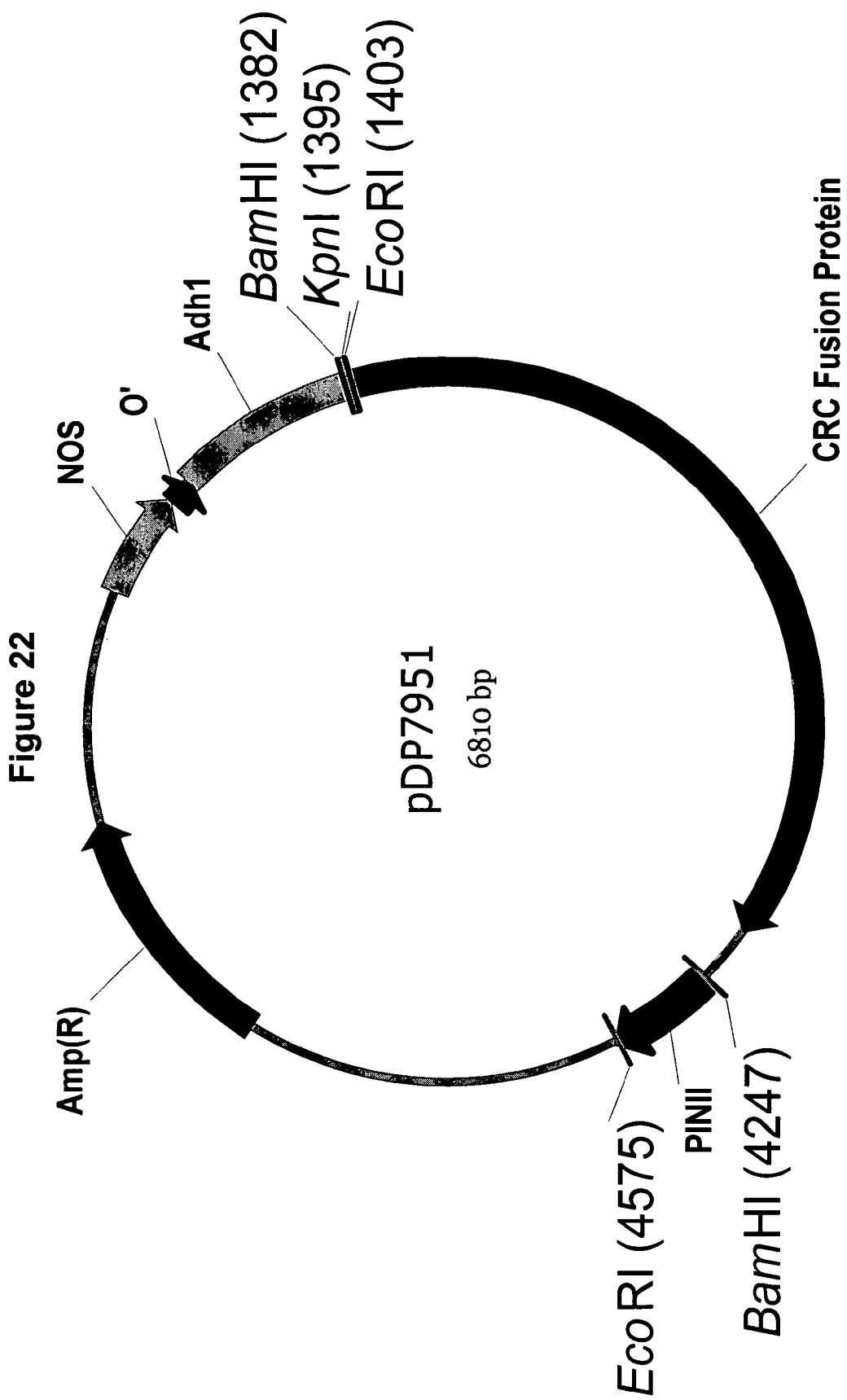
FIG. 22 depicts the plasmid map of pDP7951, having an ATCC accession No. PTA-371.

Since the phenylpropanoid pathway is not active in corn suspension cells a third plasmid containing a gene encoding a transcription factor that activates the phenylpropanoid pathway was, in some cases, bombarded into the corn cells in conjunction with isoflavone synthase gene. This plasmid, pDP7951 (depicted in FIG. 22 and bearing ATCC accession number PTA-371), contains in the 5'-3' orientation:

the *Agrobacterium* nopaline synthase gene promoter region, a tobacco mosaic virus (TMV) omega enhancer sequence, the fifth intron from the maize adh1 gene, CRC (a chimera containing the maize R region between the region encoding the C1 DNA binding domain and the C1 activation domain), the potato protease inhibitor II polyadenylation signal sequence.

Figure 23:
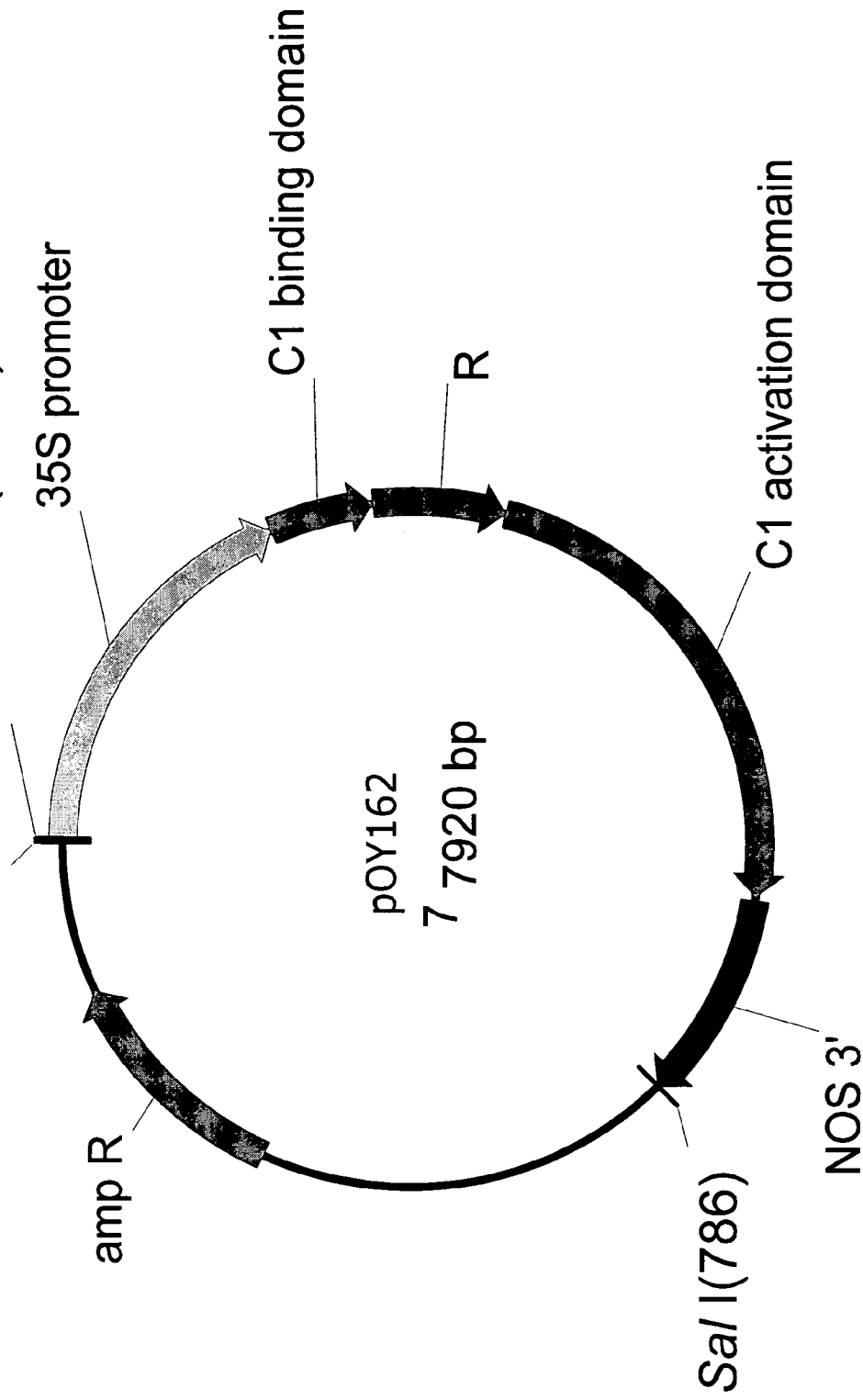
FIG. 23 depicts the plasmid map of pOY162.

Additionally, a chimeric gene consisting of the CRC coding region expressed from the CaMV 35S promoter was prepared and used in corn cell transformations. The Sma I fragment of DP7951 containing CRC was ligated to Nco I and Kpn I ends that had been blunt ended with Mung bean nuclease (New England Biolabs) to create the chimeric gene: 35S/cabL-IFS-Nos3'. This plasmid is called pOY162, and its restriction enzyme map is shown in FIG. 23.

Transformation of monocot cells

Black Mexican Sweet (BMS) suspension culture is a commonly used, corn-derived, monocot cell line. Cultures were maintained in MS2D medium (MS salts with vitamins (Gibco BRL), 20 g/L sucrose, 2 mg/L 2,4-dichlorophenoxyacetic acid, pH 5.8), incubated with shaking (125 rpm) at 26° C. in the dark, and subcultured with fresh medium every five days.

Transformations were performed by microprojectile bombardment using a DuPont Biolistic PDS 1000/He system (Klein T. M. et al. (1987) *Nature* 327:70–73). Gold particles (0.6 microns) were coated with mixtures of plasmid DNAs as indicated in Table 4:

TABLE 4

Plasmid Groups used in Maize Transformations

| Group | Plasmids |
|---|---|
| 1 | 3 µg pDETRIC + 6 µg pOY206 |
| 2 | 3 µg pDETRIC + 6 µg pOY206 + 6 µg pDP7951 |
| 3 | 3 µg pDETRIC + 6 µg pDP7951 |
| 4 | 3 µg pDETRIC + 6 µg pOY206 + 6 µg pOY162 |

Two days after subculture, BMS suspension culture aliquots (6 mL each), were evenly distributed over Whatman#1 filter disks, transferred onto solid MS2D medium (MS2D, 7 g/L agar) and incubated at 26° C. overnight. Filter disks containing the BMS cells were positioned approximately 3.5 inches away from the retaining screen and bombarded twice. Membrane rupture pressure was set at 1,100 psi and the chamber was evacuated to −28 inches of mercury. Bombarded tissues were incubated for four days at 26° C. in the dark and then transferred to MS2D selection medium (solid MS2D medium containing 3 mg/L Bialaphos). Resistant tissue was transferred to fresh MS2D selection medium after seven weeks and tissue was harvested for analysis two weeks later.

Analysis of Transformed Corn Cells for Synthesis of Anthocyanins and Genistein

All control tissue and BMS lines transformed with group 1 were white in color. Approximately half of the Bialaphos-selected resistant tissue that grew in plates bombarded with groups containing CRC (groups 2 and 3) showed the wild type white color, while the other half showed various degrees of red coloration, a visual indication of anthocyanin accumulation. The red phenotype indicates that expression of CRC in these lines is sufficient to transcriptionally activate the expression of genes in the phenylpropanoid pathway leading to anthocyanin synthesis and accumulation (Grotewold E. et al. (1998) *Plant Cell* 10:721–740). Presence of the isoflavone synthase gene in these tissues was confirmed by the appearance of the appropriate sized fragments when performing PCR on genomic DNA using primers from SEQ ID NO:43 and SEQ ID NO:44. The presence of the CRC coding region in these tissues was verified by the production of an appropriate fragment when performing PCR on genomic DNA using the primers from SEQ ID NO:45 (to the R region) and SEQ ID NO:46 (to the 3' untranslated region from potato protease inhibitor II gene).

5'-GCGGTGCACGGGCGGACTCTTCTTC-3'    [SEQ ID NO:45]

5'-CGCCCAATACGCAAACCGCCTCTCC-3'    [SEQ ID NO:46]

Tissue from 25 lines transformed with Group 1, 5 white lines resulting from transformation with Group 2, 7 red lines transformed with Group 2, 6 white lines transformed with Group 3, and 6 red lines transformed with Group 3 was harvested and analyzed for the presence of genistein using HPLC and GC-MS. Extracts were prepared and analyzed as described in Example 2. The genistein HPLC peak and the identifying 414 and 399 m/z MS peaks were detected in the extracts from all seven red lines transformed with Group 2 while no genistein was detected in any of the white lines transformed with the same plasmids. Lines transformed with Group 3 did not have genistein whether they were red or white. Sixteen lines transformed with Group 4 also produced genistein. A summary of these results is shown in Table 5.

TABLE 5

Genistein Synthesis in Transformed BMS Tissue

| Group | No. | Tissue Color | Naringenin Produced | Genistein Produced |
|---|---|---|---|---|
| 1 | 25 | White | NO | NO |
| 2 | 5 | White | NO | NO |
| 2 | 7 | Red | YES | YES |
| 3 | 6 | White | NO | NO |
| 3 | 6 | Red | YES | NO |
| 4 | 16 | Red | YES | YES |

The synthesis of genistein in BMS lines transformed with a soybean isoflavone synthase-containing construct indicated that the soybean protein was expressed and was functional in monocot cells. Genistein was only produced in cell lines producing naringenin indicating that the soybean isoflavone synthase gene was only effective in the presence of an activated phenylpropanoid pathway. The intermediate naringenin in the phenylpropanoid pathway provided the substrate for isoflavone synthase to produce genistein.

Example 14

Synthesis of Daidzein in Monocot Cells

Figure 1:
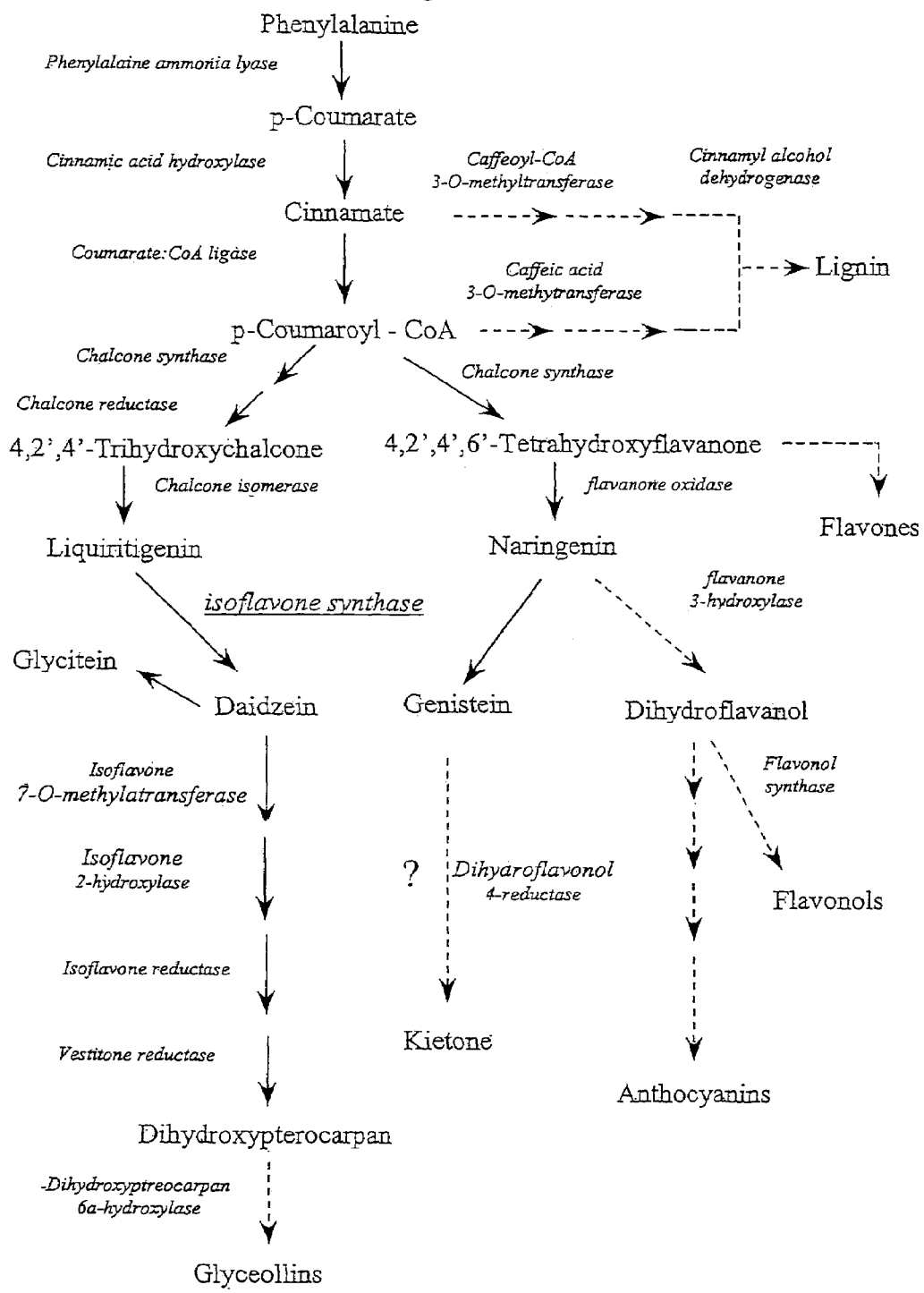

The activity of chalcone reductase determines the relative levels of substrates available for isoflavone synthase to produce genistein or daidzein (see FIG. 1). Chalcone reductase reduces 4,2',4',6'-tetrahydroxychalcone to 4,2',4'-trihydroxychalcone, thus producing liquiritigenin as the substrate for isoflavone synthase to produce daidzein. Chalcone reductases are present in legumes, but have not been found in most non-legume plants including *Arabidopsis*, tobacco, and corn. To produce daidzein in non-legume plants, a plasmid DNA containing a soybean chalcone reductase gene was introduced into corn suspension cells by microprojectile bombardment, together with a selection marker, CRC, and IFS constructs as described in Example 13.

A soybean cDNA clone encoding chalcone reductase was identified by homology to known chalcone reductase genes of alfalfa (Ballance and Dixon (1995) *Plant Phys.* 107: 1027–1028). The cDNA library was prepared using mRNAs from eight-day-old soybean roots inoculated with cyst Nematode for four days, and sequenced as described in Example 3. BLAST analysis was performed as described in Example 4. The DNA containing the entire coding region from the identified clone, src3c.pk009.e4, was amplified using PCR with the primers shown in SEQ ID NO:62 and SEQ ID NO:63

```
5'-GTTACCATGGCTGCTGCTATTG-3'        [SEQ ID NO:62]

5'-TTAAACGTAAAATGAAACAAGAGG-3'      [SEQ ID NO:63]
```

The 5' primer had an Nco I site at the start of the coding region. The 1.3 kb PCR product was subcloned into the pTOPO2.1 vector (Invitrogen Inc., Carlsbad, Calif.). The 1.3 kb coding region fragment was excised as a Nco I/Kpn I fragment, using the Nco I site and the Kpn I site from the vector. This fragment was isolated and ligated between the 35S/CabL promoter and Nos 3' polyadenylation signal sequence in the pUC 18 vector as described in Example 9, to produce plasmid pCHR40, which was used in the BMS transformation experiments.

Transformation of corn suspension cells was done as described in Example 13, using pDETRIC, pCHR40, pOY206 and pOY162. Selection and culturing were as described in Example 13. Each selected line was assayed for the presence of the IFS and CRC genes using PCR as in Example 13. The presence of the CHR gene was determined by the appearance of a 0.6 kb fragment when performing PCR on the tissues using the primers shown in SEQ ID NO:64 and SEQ ID NO:65:

```
5'-GACACTTCGACACTGCTGCTGCTTAT-3'    [SEQ ID NO:64]

5'-TCTCAAACTCACCTGGGCTATGGAT-3'     [SEQ ID NO:65]
```

Of 32 lines screened, five carried all three transgenes. Extracts were prepared, as described in Example 13, from these 32 lines and a control line that carries the CRC and IFS genes, but not the CHR gene. All of the extracts were treated with 1 N HCl to hydrolyze all possible oligosaccharide derivatives as described in Example 10. HPLC and GC-MS were performed as described in Examples 2 and 10. One out of the five lines was shown to produce daidzein. In the HPLC assay, in addition to the peaks of naringenin and genistein, a small peak occurred at the same retention time as the daidzein standard (9.6 min) (FIGS. 27C and D). This peak was not present in the control samples (FIGS. 27A and B). In the GC-MS assay, the daidzein-specific cracking pattern was found at the same retention time as the standard (8.0 min). All of the major ions of the daidzein spectrum were present (m/z: 398, 383, 218, 97). This example shows that introduction of the soybean chalcone reductase gene into corn cells together with the isoflavone synthase and CRC genes results in the production of both daidzein and genistein.

Example 15

Alteration of Isoflavonoid Levels-in Soybean Somatic Embryos

The ability to change the levels of isoflavonoids by overexpressing the gene from soybean clone sgs1c.pk006.o20 in soybean somatic embryos was tested by preparing transgenic soybean somatic embryos and assaying the isoflavonoid levels. The entire insert from clone sgs1c.pk006.o20 (SEQ ID NO:1) was amplified in a standard PCR reaction on a Perkin Elmer Applied Biosystems GeneAmp PCR System using Pfu polymerase (Stratagene) with the primers shown in SEQ ID NO:49 and SEQ ID NO:50:

```
5'-GAATTCGCGGCCGCTCTAGAACTAGTGGAT-3' [SEQ ID NO:49]

5'-GAATTCGCGGCCGCGAATTGGGTACCGGGC-3' [SEQ ID NO:50]
```

Figure 24:
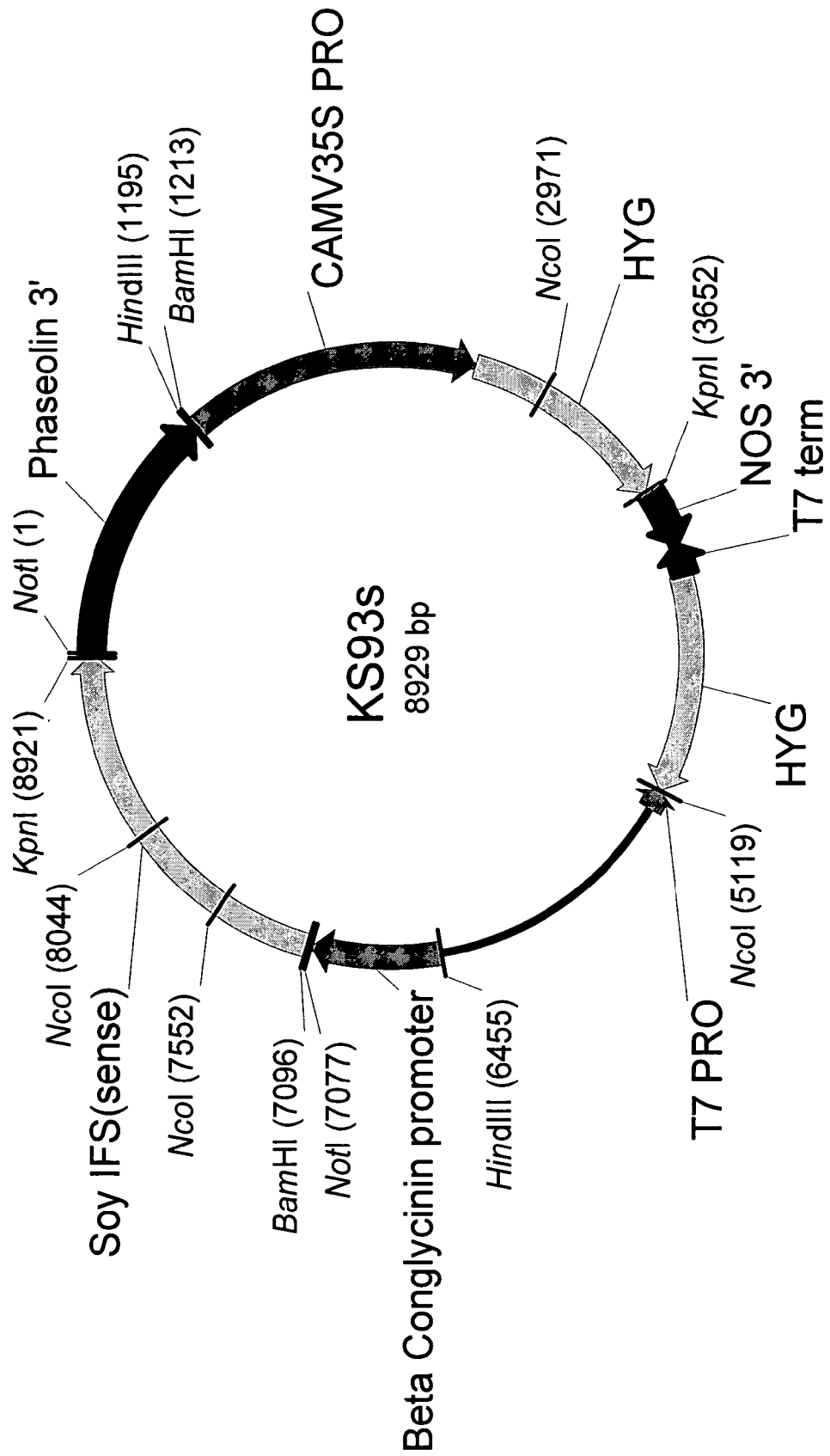
FIG. 24 depicts the plasmid map of pKS93s.

The resulting fragment is bound by Not I sites in the primer sequences and contains a 5' leader sequence, the coding region for isoflavone synthase, the untranslated 3' region from SEQ ID NO:1, and a stretch of 18 A residues at the 3' end. This fragment was digested with Not I and ligated to Not I-digested and phosphatase-treated pKS67. The plasmid pKS67 was prepared by replacing in pRB20 (described in U.S. Pat. No. 5,846,784) the 800 bp Nos 3' fragment, described in Example 9, with the 285 bp Nos 3' fragment, described in Example 12. Clones were screened for the sense orientation of the isoflavone synthase insert fragment by digestion with Bam HI. The resulting plasmid pKS93s, shown in FIG. 24, has the beta-conglycinin promoter operably linked to the fragment encoding isoflavone synthase followed by the Nos 3'end. Plasmid pKS93s contains a T7 promoter/HPT/T7 terminator cassette for expression of the HPT enzyme in certain strains of *E. coli*, such as NovaBlue (DE3) (from Novagen), that are lysogenic for lambda DE3 (which carries the T7 RNA Polymerase gene under lacV5 control). Plasmid pK93s also contains the 35S/HPT/NOS 3' cassette for constitutive expression of the HPT enzyme in plants. These two expression systems allow selection for growth in the presence of hygromycin to be used as a means of identifying cells that contain plasmid DNA sequences in both bacterial and plant systems.

Transformation of Soybean Somatic Embryo Cultures

The following stock solutions and media were used for transformation and propagation of soybean somatic embryos:

| Stock Solutions | | |
|---|---|---|
| | (g/L) | Media |
| MS Sulfate 100× stock | | 5B55 (per Liter) |
| | | 10 mL of each MS stock |
| $MgSO_4 \cdot 7H_2O$ | 37.0 | 1 mL of B5 Vitamin stock |
| $MnSO_4 \cdot H_2O$ | 1.69 | 0.8 g $NH_4NO_3$ |
| $ZnSO_4 \cdot 7H_2O$ | 0.86 | 3.033 g $KNO_3$ |
| $CuSO_4 \cdot 5H_2O$ | 0.0025 | 1 mL 2,4-D (10 mg/mb stock) |

-continued

| Stock Solutions | | |
|---|---|---|
| | (g/L) | Media |
| MS Halides 100× stock | | 0.667 g asparagine pH 5.7 |
| CaCl$_2$.2H$_2$O | 44.0 | SB103 (per Liter) |
| KI | 0.083 | 1 pk. Murashige & Skoog salt mixture* |
| CoCl$_2$.6H$_2$O | 0.00125 | 60 g maltose |
| KH$_2$PO$_4$ | 17.0 | 2 g gelrite |
| H$_3$BO$_3$ | 0.62 | pH 5.7 |
| Na$_2$MoO$_4$.2H$_2$O | 0.025 | SB148 (per Liter) |
| Na$_2$EDTA | 3.724 | 1 pk. Murashige & Skoog salt mixture* |
| FeSO$_4$.7H$_2$O | 2.784 | 60 g maltose |
| B5 Vitamin stock | | 1 mL B5 vitamin stock |
| myo-inositol | 100.0 | 7 g agarose |
| nicotinic acid | 1.0 | pH 5.7 |
| pyridoxine HCl | 1.0 | |
| thiamine | 10.0 | |

*(Gibco BRL)

Soybean embryonic suspension cultures were maintained in 35 mL liquid media (SB55) on a rotary shaker (150 rpm) at 28° C. with a mix of fluorescent and incandescent lights providing a 16 h day 8 h night cycle. Cultures were subcultured every 2 to 3 weeks by inoculating approximately 35 mg of tissue into 35 mL of fresh liquid media.

Soybean embryonic suspension cultures were transformed with pKS93s by the method of particle gun bombardment (see Klein et al. (1987) Nature 327:70–73) using a DuPont Biolistic PDS1000/He instrument. Five µL of pKS93s plasmid DNA (1 g/L), 50 µL CaCl$_2$ (2.5 M), and 20 µL spermidine (0.1 M) were added to 50 µL of a 60 mg/mL 1 mm gold particle suspension. The particle preparation was agitated for 3 minutes, spun in a microfuge for 10 seconds and the supernate removed. The DNA-coated particles were then washed once with 400 µL of 70% ethanol and resuspended in 40 µL of anhydrous ethanol. The DNA/particle suspension was sonicated three times for 1 second each. Five µL of the DNA-coated gold particles were then loaded on each macro carrier disk.

Approximately 300 to 400 mg of two-week-old suspension culture was placed in an empty 60 mm×15 mm petri dish and the residual liquid removed from the tissue using a pipette. The tissue was placed about 3.5 inches away from the retaining screen and bombarded twice. Membrane rupture pressure was set at 1100 psi and the chamber was evacuated to −28 inches of Hg. Two plates were bombarded, and following bombardment, the tissue was divided in half, placed back into liquid media, and cultured as described above.

Fifteen days after bombardment, the liquid media was exchanged with fresh SB55 containing 50 mg/mL hygromycin. The selective media was refreshed weekly. Six weeks after bombardment, green, transformed tissue was isolated and inoculated into flasks to generate new transformed embryonic suspension cultures.

Transformed embryonic clusters were removed from liquid culture media and placed on a solid agar media, SB103, containing 0.5% charcoal to begin maturation. After 1 week, embryos were transferred to SB103 media minus charcoal. After 5 weeks on SB103 media, maturing embryos were separated and placed onto SB148 media. During maturation embryos were kept at 26° C. with a mix of fluorescent and incandescent lights providing a 16 h day 8 h night cycle. After 3 weeks on SB148 media, embryos were analyzed for the expression of the isoflavonoids. Each embryonic cluster gave rise to 5 to 20 somatic embryos.

Non-transformed somatic embryos were cultured by the same method as used for the transformed somatic embryos.

Analysis of Transformed Somatic Embryos

At the end of the 8$^{th}$ week on SB103 medium somatic embryos were harvested from 12 independently transformed lines. Somatic embryos were collected individually and stored in 96-well plates at −80° until lyophilized. Somatic embryos were lyophilized for 24 hours. Three to five lyophilized somatic embryos were pooled in a micro centrifuge tube and the dry weight was measured three times. Three samples of dried embryos were assayed for each transformed line. An 80% methanol solution was added to the lyophilized somatic embryos and the samples incubated for 24 h in the dark at room temperature to extract isoflavonoids. The 80% methanol solution was filtered through a Costar nylon membrane microcentrifuge filter with 0.22 µm pore size (Sigma).

For HPLC analysis of the extracts, twenty µl of the 80% methanol sample was applied to a Phenomenex Luna 3µ C18 (2) column (size: 150×4.6 mm). Separation occurred during the gradient elution of 10 mM ammonium buffer, pH 8.35 (solvent A) and methanol (solvent B) as the mobile phase. Continuous increasing of solvent B in solvent A, from 20 to 100% for 10 min was employed. Standards for the isoflavonoids daidzin, daidzein, glycitin, glycitein, genistin, genistein, liquiritigenin and naringenin were prepared by the gradual addition of 80% methanol to each powder. The peaks and spectra corresponding to daidzein, glycitin and genistein conjugated with malonylated glucosides were determined by LC/MS. Isoflaovonoids were monitored through the absorption spectra at 260 and 280 nm. The isoflavonoid signals observed in the soybean somatic embryo samples were verified by comparisons of the retention times and diode array detected absorption spectra with those of the standards. The areas of all peaks corresponding to the isoflaovones in a sample were added and divided by the dry weight of that sample. These dry weight based normalized area sums were used for statistical analysis.

An analysis of variance test (ANOVA; Steel, R. G. D. and Torrie, J. H. (1996) Principles and Procedures of Statistics: A Biometrical Approach (McGraw-Hill Series in Probability and Statistics, New York) was conducted using Microsoft Excel 97 (Microsoft). Data were analyzed as a single factor design with single gene transformation as the main effect. Experimental units were the sum of peak areas of identified isoflavonoids normalized to dry weight. The mean square from the ANOVA was used to calculate the least significant difference (LSD) for each comparison. The sum of isoflavonoid peak areas of samples from a non-transformed control line were compared with those of 25 independent pKS93s-transformed, hygromycin resistant lines. FIG. 25 shows a graph depicting the distribution of the sum of isoflavone area per mg of dry weight of soybean somatic embryos transgenic for the isoflavone synthase gene and a control line. The results are depicted in the graph in ascending order of the amount of total isoflavones produced. Some lines, such as the ones represented in bars 7 through 14, contained approximately the same levels of isoflavones as the control line. While most of the lines showed intermediate increases or decreases in the amounts of isoflavones produced, there are clear examples of lines having markedly increased or decreased amounts of isoflavones. For example, bar 25 represents a line which expresses 208% as much isoflavones as the control line, bar 24 represents a line which expresses 184% as much isoflavones as the control line, and bar 1 represents a line which produces only 25% of the isoflavones as the control line. These differences in the amounts of isoflavones produced may be caused by the position of the transgene in the chromosome, the number of copies of the gene that are integrated in the chromosome, DNA methylation, gene silencing, etc. These results indicate that transgenic expression of isoflavone synthase affords the ability to manipulate isoflavonoid levels as desired for a particular application; i.e., transformants may be chosen for advancement that have large changes in isoflavonoid levels (i.e., very high as in IS 19 or very low as in IS6) or more subtle changes in the content of isoflavonoids.

Example 16

Amplification and Analysis of Soybean Genomic Isoflavone Synthase DNA

Genomic sequences encoding isoflavone synthase may be used to express isoflavone synthase as well as the cDNA sequences. Therefore the genomic sequences containing the coding regions for the soybean isoflavone synthase genes were isolated.

Soybean genomic DNA was prepared from *Glycine max* cv. Wye following standard protocols (DNeasy Plant Maxi Kit, Qiagen, Valencia, Calif.). Using this DNA as template, a genomic DNA fragment including the sequence corresponding to the soybean insert in sgs1c.pk006.o20 was produced by PCR with the primers listed as SEQ ID NO:41 and SEQ ID NO:42. A genomic DNA fragment including the sequence of CYP93C1 was produced with the primers listed as SEQ ID NO:7 and SEQ ID NO:51:

```
5'-AAAATTAGCCTCACAAAAGCAAAG-3'    [SEQ ID NO:7]

5'-GCAAACGAAGACAAATGGGAGATGATA-3' [SEQ ID NO:51]
```

Amplification was performed on a Perkin Elmer Applied Biosystems GeneAmp PCR System using the Expand™ Hi fidelity PCR system from Boehringer Mannheim (Indianapolis, Ind.). These PCR fragments were cloned into the pCR2.1 vector (Invitrogen) and sequenced as described in Example 6. The nucleotide sequence of the genomic fragment comprising the isoflavone synthase sequence from clone sgs1c.pk006.o20 is given in SEQ ID NO:52. The nucleotide sequence of the genomic fragment comprising the isoflavone synthase sequence of CYP93C1 is given in SEQ ID NO:53. Both genes were found to contain one intron. The splice junction for both introns is within the codon for amino acid 300. The intron sequence in SEQ ID NO:52 corresponds to nucleotides 895 to 1112 (217 nucleotides), while the intron sequence in SEQ ID NO:53 corresponds to nucleotides 947 to 1082 (135 nucleotides) in SEQ ID NO:53. Alignment of the intron nucleotide sequences using the Clustal method of alignment and the default parameters (KTUPLE 2, GAP PENALTY=5, WINDOW=4 and DIAGONALS SAVED=4) shows that the intron sequences are 46.3% identical.

Example 17

Alteration of Isoflavonoid Levels in Soybean Plants

The ability to alter the isoflavonoid levels in transgenic soybean plants expressing the gene from soybean clone sgs1c.pk006.o20 was tested by transforming somatic embryo cultures with a vector containing the gene, allowing the plant to regenerate, and meassuring the levels of isoflavonoids produced. In addition, the soybean IFS gene was transformed in conjunction with the CRC gene.

Construction of Vectors for Transformation of *Glycine max*

A vector containing a chimeric isoflavone synthase gene was constructed as follows. The 1.6 Kb isoflavone synthase coding region from clone sgs1c.pk006.o20 (SEQ ID NO:1) was amplified using a standard PCR reaction in a GeneAmp PCR System using Pfu polymerase (Stratagene) with the primers shown in SEQ ID NO:41 and SEQ ID NO:42 as in Example 9. The plasmid pCW109 (World Patent Publication No. WO94/11516) was digested with Nco I. The resulting DNA fragments were treated with T4 DNA polymerase in the presence of dATP; dCTP, dGTP and dTTP to obtain blunt ends followed by digestion with Kpn I. The ligation of these two DNA fragments created the plasmid pCW109—IFS, shown in FIG. 28, which has operably linked:

the beta-conglycinin promoter the isoflavone synthase coding region the phaseolin 3' end The 3.2 Kb fragment containing the beta-conglycinin/P-IFS-phaseolin 3' chimeric gene was purified from pCW109-IFS as a Hind III fragment and ligated with Hind III-digested and phosphatase-treated pZBL 102. pZBL102 is derived from pKS18HH (described in U.S. Pat. No. 5,846,784) by replacing the long Nos 3' fragment in pKS18HH with the short Nos 3' fragment described in Example 13. The Sal I site between the two hygromycin phosphotransferase coding regions was deleted, and a Not I site was added between the Hind III and Sal I sites 5' to the 35S promoter of the 35S—HPT gene.

The resulting plasmid, named pWSJ001, has a T7 promoter/HPT/T7 terminator cassette for expression of the HPT enzyme in certain strains of *E. coli* that are lysogenic for lambda DE3. The lambda DE3 carries the T7 RNA Polymerase gene under lacV5 control and is found in commercially available *E. coli* strains such as NovaBlue (DE3) (from Novagen). Plasmid pWSJ001 also contains the 35S/ HPT/NOS 3' cassette for constitutive expression of the HPT enzyme in plants. These two expression systems allow selection for growth in the presence of hygromycin to be used as a means of identifying cells that contain plasmid DNA sequences in both bacterial and plant systems.

A vector containing a chimeric CRC gene was constructed as follows. The plasmid pDP7951 of Example 13, FIG. 22, was digested with SmaI and the fragment containing the CRC coding region was purified. This CRC fragment was ligated to a modified vector containing the sequences of pCW109 (World Patent Publication No. WO94/11516) with the substitution of a phaseolin promoter fragment extending to 410 and including leader sequences to +77 (Slightom et al., 1991 Plant Mol Biol Man B16:1) instead of the beta-conglycinin promoter. Modification included digestion with NcoI and S1 nuclease treatment followed by religation to remove the ATG sequence of the NcoI site that follows the promoter fragment. The vector was then digested with KpnI and the ends filled in so that the SmaI CRC fragment was inserted in a blunt-end ligation. From the resulting plasmid, the HindIII fragment containing the phaseolin promoter-CRC-phaseolin 3' chimeric gene was isolated and ligated with HindIII digested pZBL 102 (described above). The resulting plasmid was called pOY203.

Transformation Of Somatic Soybean Embryo Cultures and Regeneration Of Soybean Plants Soybean embryogenic suspension cultures were transformed with pWSJ001 or pWSJ001 in conjunction with pOY203 by the method of particle gun bombardment as in Example 15. Besides the media used for the soybean somatic embryo cultures described in Example 15, the following media were used:

| Media |
|---|
| SBP6 |
| SB55 with only 0.5 mL 2,4-D |
| SB71-1 (per liter) |
| B5 salts |
| 1 ml B5 vitamin stock |
| 30 g sucrose |
| 750 mg MgCl2 |
| 2 g gelrite |
| pH 5.7 |

Eleven days post bombardment, the liquid media was exchanged with fresh SB55 containing 50 mg/mL hygromycin. The selective media was refreshed weekly. Seven weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Thus each new line was treated as independent transformation event. These suspensions can then be maintained as suspensions of embryos clustered in an immature developmental stage through subculture or regenerated into whole plants by maturation and germination of individual somatic embryos.

Transformed embryogenic clusters were removed from liquid culture and placed on a solid agar media (SB103) containing no hormones or antibiotics. Embryos were cultured for eight weeks at 26° C. with mixed florescent and incandescent lights on a 16:8 h day/night schedule. During this period, individual embryos were removed from the clusters and analyzed at various stages of embryo development. Selected lines were assayed by PCR for the presence of the an additional IFS gene using the primers shown in SEQ ID NO:43 and SEQ ID NO:44. Separation of the PCR products on an agarose gel yielded a 1062 bp fragment indicative of the endogenous IFS gene (i.e., containing introns) and an 845 bp fragment in the embryos containing the transgene IFS. Somatic embryos become suitable for germination after eight weeks and were then removed from the maturation medium and dried in empty petri dishes for 1 to 5 days. The dried embryos were then planted in SB71-1 medium where they were allowed to germinate under the same lighting and germination conditions described above. Germinated embryos were transferred to sterile soil and grown to maturity. Seed were harvested.

Seed from IFS-transformed and IFS+CRC-transformed soybean plants are analyzed for isoflavonoid levels. Extracts are prepared and analyzed by HPLC as described in Example 15 except that a 150 to 200 mg chip of soybean seed is used for the analysis. Seeds with statistically significant variation in the level of isoflavonoid concentration are further analyzed.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated nucleic acid encoding a polypeptide with isoflavone synthase activity having the amino acid sequence set forth in SEQ ID NO:66.

2. A chimeric polynucleotide comprising the nucleic acid of claim 1 operably linked to at least one regulatory sequence.

3. An isolated transformed host cell comprising the chimeric polynucleotide of claim 2.

4. The transformed host cell of claim 3 further comprising a second chimeric polynucleotide comprising a nucleic acid encoding a polypeptide that regulates expression of at least one enzyme of the phenylpropanoid pathway.

5. The transformed host cell of claim 4 wherein the second chimeric polynucleotide encodes a polypeptide comprising the maize C1 DNA binding domain, the maize transcription factor R, and the maize C1 activation domain.

6. The transformed host cell of claim 3 wherein the host cell is a eukaryotic cell.

7. The eukaryotic cell of claim 6 wherein the cell is a yeast cell.

8. The eukaryotic cell of claim 6 wherein the cell is a plant cell.

9. The plant cell of claim 8 wherein the cell is a soybean cell.

10. The plant cell of claim 8 wherein the cell is a corn cell.

11. A method of altering the level of expression of isoflavone synthase in a host cell comprising:

(a) transforming a host cell with the chimeric polynucleotide of claim 2 or transforming the host cell with the chimeric polynucleotide of claim 2 and with a second chimeric polynucleotide comprising a nucleic acid sequence encoding a polypeptide that regulates expression of at least one enzyme of the phenylpropanoid pathway; and (b) growing the transformed host cell produced in step (a) under conditions that are suitable for expression of the chimeric polynucleotide wherein expression of the chimeric polynucleotide results in production of altered levels of isoflavone synthase in the transformed host cell.

12. The method of claim 11 wherein the host cell is a eukaryotic cell.

13. The method of claim 12 wherein the eukaryotic cell is a yeast cell.

14. The method of claim 12 wherein the eukaryotic cell is a plant cell.

15. The method of claim 14 wherein the plant cell is a soybean cell.

16. The method of claim 14 wherein the plant cell is a corn cell.

17. The isolated nucleic acid of claim 1 where $Xaa_{10}$ is Phe
$Xaa_{16}$ is Leu
$Xaa_{23}$ is Ser
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Ser
$Xaa_{95}$ is Thr
$Xaa_{96}$ is His
$Xaa_{102}$ is Asn
$Xaa_{110}$ is Ile
$Xaa_{112}$ is Arg
$Xaa_{117}$ is Asn
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Val
$Xaa_{166}$ is Ser
$Xaa_{170}$ is Gln
$Xaa_{175}$ is Val
$Xaa_{183}$ is Thr
$Xaa_{187}$ is Ile
$Xaa_{191}$ is Met
$Xaa_{209}$ is Phe
$Xaa_{219}$ is Trp
$Xaa_{223}$ is Tyr
$Xaa_{253}$ is Glu
$Xaa_{259}$ is Lys
$Xaa_{263}$ is Val
$Xaa_{264}$ is Val
$Xaa_{268}$ is Ala
$Xaa_{272}$ is Phe
$Xaa_{285}$ is Met
$Xaa_{294}$ is Ile
$Xaa_{301}$ is Phe
$Xaa_{306}$ is Thr
$Xaa_{311}$ is Val
$Xaa_{312}$ is Ala
$Xaa_{325}$ is Arg
$Xaa_{328}$ is Gln
$Xaa_{334}$ is Val
$Xaa_{342}$ is Arg
$Xaa_{377}$ is Thr
$Xaa_{381}$ is Glu
$Xaa_{385}$ is Tyr
$Xaa_{387}$ is Ile
$Xaa_{393}$ is Val
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Gly
$Xaa_{429}$ is Pro
$Xaa_{435}$ is Gln
$Xaa_{447}$ is Arg
$Xaa_{453}$ is Asn
$Xaa_{459}$ is Met, and
$Xaa_{485}$ is Asp.

18. The isolated nucleic acid of claim 1 where $Xaa_{16}$ is Leu
$Xaa_{23}$ is Ser
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Ser
$Xaa_{95}$ is Thr
$Xaa_{96}$ is His
$Xaa_{102}$ is Asn
$Xaa_{110}$ is Thr
$Xaa_{112}$ is Arg
$Xaa_{117}$ is Asn
$Xaa_{118}$ is Ser
$Xaa_{121}$ is Met $Xaa_{122}$ is Val
$Xaa_{124}$ is Phe
$Xaa_{129}$ is Arg
$Xaa_{147}$ is Lys
$Xaa_{159}$ is Phe
$Xaa_{162}$ is Val
$Xaa_{166}$ is Ser
$Xaa_{170}$ is Gln
$Xaa_{175}$ is Val
$Xaa_{183}$ is Thr
$Xaa_{187}$ is Ile
$Xaa_{191}$ is Met
$Xaa_{209}$ is Phe
$Xaa_{219}$ is Trp
$Xaa_{223}$ is Tyr
$Xaa_{253}$ is Gly
$Xaa_{259}$ is Glu
$Xaa_{263}$ is Val
$Xaa_{264}$ is Val
$Xaa_{268}$ is Ala
$Xaa_{272}$ is Phe
$Xaa_{285}$ is Met
$Xaa_{294}$ is Ile
$Xaa_{301}$ is Leu
$Xaa_{306}$ is Thr
$Xaa_{311}$ is Val
$Xaa_{312}$ is Ala
$Xaa_{325}$ is Arg
$Xaa_{328}$ is Gln
$Xaa_{334}$ is Val
$Xaa_{342}$ is Arg
$Xaa_{377}$ is Thr
$Xaa_{381}$ is Glu
$Xaa_{385}$ is Tyr
$Xaa_{387}$ is Ile
$Xaa_{393}$ is Val
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Gly
$Xaa_{429}$ is Pro
$Xaa_{435}$ is Gln
$Xaa_{447}$ is Arg
$Xaa_{453}$ is Asn
$Xaa_{459}$ is Met, and
$Xaa_{485}$ is Asp.

19. The isolated nucleic acid of claim 1 where
$Xaa_{16}$ is Leu
$Xaa_{23}$ is Thr
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Tyr
$Xaa_{95}$ is Thr
$Xaa_{96}$ is His
$Xaa_{102}$ is Asn
$Xaa_{110}$ is Ile
$Xaa_{112}$ is Arg
$Xaa_{117}$ is Ser
$Xaa_{118}$ is Leu
$Xaa_{121}$ is Met
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Val
$Xaa_{166}$ is Gly
$Xaa_{170}$ is Gln
$Xaa_{175}$ is Leu
$Xaa_{183}$ is Thr
$Xaa_{187}$ is Ile
$Xaa_{191}$ is Met
$Xaa_{209}$ is Tyr
$Xaa_{219}$ is Trp
$Xaa_{223}$ is His
$Xaa_{253}$ is Glu
$Xaa_{259}$ is Lys
$Xaa_{263}$ is Val
$Xaa_{264}$ is Val
$Xaa_{268}$ is Val
$Xaa_{272}$ is Phe
$Xaa_{285}$ is Thr
$Xaa_{294}$ is Ile
$Xaa_{301}$ is Phe
$Xaa_{306}$ is Ile
$Xaa_{311}$ is Val
$Xaa_{312}$ is Ala
$Xaa_{325}$ is Lys
$Xaa_{328}$ is Glu
$Xaa_{334}$ is Val
$Xaa_{342}$ is Arg
$Xaa_{377}$ is Thr
$Xaa_{381}$ is Glu
$Xaa_{385}$ is Tyr
$Xaa_{387}$ is Ile
$Xaa_{393}$ is Ile
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Arg
$Xaa_{429}$ is Pro
$Xaa_{435}$ is Gln
$Xaa_{447}$ is Gly
$Xaa_{453}$ is Asn
$Xaa_{459}$ is Met, and
$Xaa_{485}$ is Gly.

20. The isolated nucleic acid of claim 1 where
$Xaa_{16}$ is Leu
$Xaa_{23}$ is Thr
$Xaa_{25}$ is Lys
$Xaa_{39}$ is Lys
$Xaa_{48}$ is Pro
$Xaa_{60}$ is Leu
$Xaa_{73}$ is Leu
$Xaa_{74}$ is Tyr
$Xaa_{95}$ is Thr
$Xaa_{96}$ is His
$Xaa_{102}$ is Asn
$Xaa_{110}$ is Ile
$Xaa_{112}$ is Arg
$Xaa_{117}$ is Ser
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Lys $Xaa_{159}$ is Phe
$Xaa_{162}$ is Val
$Xaa_{166}$ is Ser
$Xaa_{170}$ is Gln
$Xaa_{175}$ is Val
$Xaa_{183}$ is Thr
$Xaa_{187}$ is Ile
$Xaa_{191}$ is Met
$Xaa_{209}$ is Phe
$Xaa_{219}$ is Trp
$Xaa_{223}$ is Tyr
$Xaa_{253}$ is Glu
$Xaa_{259}$ is Lys
$Xaa_{263}$ is Val
$Xaa_{264}$ is Val
$Xaa_{268}$ is Ala
$Xaa_{272}$ is Phe
$Xaa_{285}$ is Met
$Xaa_{294}$ is Ile
$Xaa_{301}$ is Phe
$Xaa_{306}$ is Thr
$Xaa_{311}$ is Val
$Xaa_{312}$ is Ala
$Xaa_{325}$ is Arg
$Xaa_{328}$ is Gln
$Xaa_{334}$ is Val
$Xaa_{342}$ is Ile
$Xaa_{377}$ is Thr
$Xaa_{381}$ is Glu
$Xaa_{385}$ is His
$Xaa_{387}$ is Ile
$Xaa_{393}$ is Val
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Gly
$Xaa_{429}$ is Pro
$Xaa_{435}$ is Gln
$Xaa_{447}$ is Arg
$Xaa_{453}$ is Asn
$Xaa_{459}$ is Met, and
$Xaa_{485}$ is Asp.

21. The isolated nucleic acid of claim 1 where
$Xaa_{16}$ is Leu
$Xaa_{23}$ is Thr
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Tyr
$Xaa_{95}$ is Thr
$Xaa_{96}$ is His
$Xaa_{102}$ is Asn
$Xaa_{110}$ is Ile
$Xaa_{112}$ is Arg
$Xaa_{117}$ is Ser
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Val
$Xaa_{166}$ is Gly
$Xaa_{170}$ is Gln
$Xaa_{175}$ is Leu
$Xaa_{183}$ is Thr
$Xaa_{187}$ is Ile
$Xaa_{191}$ is Val
$Xaa_{209}$ is Phe
$Xaa_{219}$ is Trp
$Xaa_{223}$ is His
$Xaa_{253}$ is Glu
$Xaa_{259}$ is Lys
$Xaa_{263}$ is Val
$Xaa_{264}$ is Val
$Xaa_{268}$ is Val
$Xaa_{272}$ is Phe
$Xaa_{285}$ is Met
$Xaa_{294}$ is Ile
$Xaa_{301}$ is Phe
$Xaa_{306}$ is Thr
$Xaa_{311}$ is Val
$Xaa_{312}$ is Ala
$Xaa_{325}$ is Lys
$Xaa_{328}$ is Glu
$Xaa_{334}$ is Val
$Xaa_{342}$ is Arg
$Xaa_{377}$ is Thr
$Xaa_{381}$ is Glu
$Xaa_{385}$ is Cys
$Xaa_{387}$ is Thr
$Xaa_{393}$ is Ile
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Arg
$Xaa_{429}$ is Leu
$Xaa_{435}$ is Arg
$Xaa_{447}$ is Arg
$Xaa_{453}$ is Asn
$Xaa_{459}$ is Met, and
$Xaa_{485}$ is Gly.

22. The isolated nucleic acid of claim 1 where
$Xaa_{10}$ is Leu
$Xaa_{16}$ is Leu
$Xaa_{23}$ is Thr
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Tyr
$Xaa_{95}$ is Thr
$Xaa_{96}$ is His
$Xaa_{102}$ is Asn
$Xaa_{110}$ is Ile
$Xaa_{112}$ is Arg
$Xaa_{117}$ is Ser
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Val
$Xaa_{166}$ is Gly $Xaa_{170}$ is Gln
$Xaa_{175}$ is Leu
$Xaa_{183}$ is Thr
$Xaa_{187}$ is Ile
$Xaa_{191}$ is Met
$Xaa_{209}$ is Phe
$Xaa_{219}$ is Trp
$Xaa_{223}$ is His
$Xaa_{253}$ is Glu
$Xaa_{259}$ is Lys
$Xaa_{263}$ is Val
$Xaa_{264}$ is Val
$Xaa_{268}$ is Val
$Xaa_{272}$ is Phe
$Xaa_{285}$ is Met
$Xaa_{294}$ is Ile
$Xaa_{301}$ is Phe
$Xaa_{306}$ is Thr
$Xaa_{311}$ is Val
$Xaa_{312}$ is Ala
$Xaa_{325}$ is Lys
$Xaa_{328}$ is Glu
$Xaa_{334}$ is Ala
$Xaa_{342}$ is Arg
$Xaa_{377}$ is Thr
$Xaa_{381}$ is Glu
$Xaa_{385}$ is Tyr
$Xaa_{387}$ is Ile
$Xaa_{393}$ is Ile
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Arg
$Xaa_{429}$ is Pro
$Xaa_{435}$ is Gln
$Xaa_{447}$ is Arg
$Xaa_{453}$ is Asn
$Xaa_{459}$ is Met, and
$Xaa_{485}$ is Gly.

23. The isolated nucleic acid of claim 1 where
$Xaa_{10}$ is Leu
$Xaa_{16}$ is Leu
$Xaa_{23}$ is Thr
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Tyr
$Xaa_{95}$ is Thr
$Xaa_{96}$ is His
$Xaa_{102}$ is Asn
$Xaa_{110}$ is Ile
$Xaa_{112}$ is Arg
$Xaa_{117}$ is Ser
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Ala
$Xaa_{166}$ is Gly
$Xaa_{170}$ is Gln
$Xaa_{175}$ is Leu
$Xaa_{183}$ is Thr
$Xaa_{187}$ is Ile
$Xaa_{191}$ is Met
$Xaa_{209}$ is Phe
$Xaa_{219}$ is Trp
$Xaa_{223}$ is His
$Xaa_{253}$ is Glu
$Xaa_{259}$ is Lys
$Xaa_{263}$ is Val
$Xaa_{264}$ is Val
$Xaa_{268}$ is Val
$Xaa_{272}$ is Phe
$Xaa_{285}$ is Met
$Xaa_{294}$ is Ile
$Xaa_{301}$ is Phe
$Xaa_{306}$ is Thr
$Xaa_{311}$ is Val
$Xaa_{312}$ is Ala
$Xaa_{325}$ is Lys
$Xaa_{328}$ is Glu
$Xaa_{334}$ is Val
$Xaa_{342}$ is Arg
$Xaa_{377}$ is Thr
$Xaa_{381}$ is Glu
$Xaa_{385}$ is Tyr
$Xaa_{387}$ is Ile
$Xaa_{393}$ is Ile
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Arg
$Xaa_{429}$ is Pro
$Xaa_{435}$ is Gln
$Xaa_{447}$ is Arg
$Xaa_{453}$ is Asn
$Xaa_{459}$ is Met, and
$Xaa_{485}$ is Gly.

24. The isolated nucleic acid of claim 1 where
$Xaa_{10}$ is Leu
$Xaa_{16}$ is Leu
$Xaa_{23}$ is Thr
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Tyr
$Xaa_{95}$ is Thr
$Xaa_{96}$ is His
$Xaa_{102}$ is Asn
$Xaa_{110}$ is Iler
$Xaa_{112}$ is Arg
$Xaa_{117}$ is Ser
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Val
$Xaa_{166}$ is Gly
$Xaa_{170}$ is Gln
$Xaa_{175}$ is Leu Xaa$_{183}$ is Thr
Xaa$_{187}$ is Ile
Xaa$_{191}$ is Met
Xaa$_{209}$ is Phe
Xaa$_{219}$ is Trp
Xaa$_{223}$ is His
Xaa$_{253}$ is Glu
Xaa$_{259}$ is Lys
Xaa$_{263}$ is Val
Xaa$_{264}$ is Val
Xaa$_{268}$ is Val
Xaa$_{272}$ is Phe
Xaa$_{285}$ is Thr
Xaa$_{294}$ is Ile
Xaa$_{301}$ is Phe
Xaa$_{306}$ is Thr
Xaa$_{311}$ is Val
Xaa$_{312}$ is Ala
Xaa$_{325}$ is Lys
Xaa$_{328}$ is Glu
Xaa$_{334}$ is Val
Xaa$_{342}$ is Arg
Xaa$_{377}$ is Thr
Xaa$_{381}$ is Glu
Xaa$_{385}$ is Tyr
Xaa$_{387}$ is Ile
Xaa$_{393}$ is Ile
Xaa$_{394}$ is Leu
Xaa$_{402}$ is Arg
Xaa$_{404}$ is Pro
Xaa$_{413}$ is Phe
Xaa$_{422}$ is Gly
Xaa$_{428}$ is Arg
Xaa$_{429}$ is Pro
Xaa$_{435}$ is Gln
Xaa$_{447}$ is Arg
Xaa$_{453}$ is Asn
Xaa$_{459}$ is Met, and
Xaa$_{485}$ is Gly.

25. The isolated nucleic acid of claim 1 where
Xaa$_{10}$ is Leu
Xaa$_{16}$ is Leu
Xaa$_{23}$ is Thr
Xaa$_{25}$ is Lys
Xaa$_{39}$ is Lys
Xaa$_{48}$ is Leu
Xaa$_{60}$ is Leu
Xaa$_{73}$ is Leu
Xaa$_{74}$ is Tyr
Xaa$_{95}$ is Thr
Xaa$_{96}$ is His
Xaa$_{102}$ is Asn
Xaa$_{110}$ is Ile
Xaa$_{112}$ is Arg
Xaa$_{117}$ is Ser
Xaa$_{118}$ is Ser
Xaa$_{121}$ is Met
Xaa$_{122}$ is Val
Xaa$_{124}$ is Phe
Xaa$_{129}$ is Lys
Xaa$_{147}$ is Lys
Xaa$_{159}$ is Phe
Xaa$_{162}$ is Val
Xaa$_{166}$ is Gly
Xaa$_{170}$ is Gln
Xaa$_{175}$ is Leu
Xaa$_{183}$ is Thr
Xaa$_{187}$ is Ile
Xaa$_{191}$ is Met
Xaa$_{209}$ is Phe
Xaa$_{219}$ is Trp
Xaa$_{223}$ is His
Xaa$_{253}$ is Glu
Xaa$_{259}$ is Lys
Xaa$_{263}$ is Val
Xaa$_{264}$ is Val
Xaa$_{268}$ is Val
Xaa$_{272}$ is Phe
Xaa$_{285}$ is Met
Xaa$_{294}$ is Ile
Xaa$_{301}$ is Phe
Xaa$_{306}$ is Thr
Xaa$_{311}$ is Glu
Xaa$_{312}$ is Ala
Xaa$_{325}$ is Lys
Xaa$_{328}$ is Glu
Xaa$_{334}$ is Val
Xaa$_{342}$ is Arg
Xaa$_{377}$ is Thr
Xaa$_{381}$ is Glu
Xaa$_{385}$ is Tyr
Xaa$_{387}$ is Ile
Xaa$_{393}$ is Ile
Xaa$_{394}$ is Leu
Xaa$_{402}$ is Arg
Xaa$_{404}$ is Pro
Xaa$_{413}$ is Phe
Xaa$_{422}$ is Gly
Xaa$_{428}$ is Arg
Xaa$_{429}$ is Pro
Xaa$_{435}$ is Gln
Xaa$_{447}$ is Arg
Xaa$_{453}$ is Asn
Xaa$_{459}$ is Met, and
Xaa$_{485}$ is Gly.

26. The isolated nucleic acid of claim 1 where
Xaa$_{10}$ is Leu
Xaa$_{16}$ is Leu
Xaa$_{23}$ is Thr
Xaa$_{25}$ is Lys
Xaa$_{39}$ is Lys
Xaa$_{48}$ is Leu
Xaa$_{60}$ is Leu
Xaa$_{73}$ is Leu
Xaa$_{74}$ is Tyr
Xaa$_{95}$ is Thr
Xaa$_{96}$ is His
Xaa$_{102}$ is Asn
Xaa$_{110}$ is Ile
Xaa$_{112}$ is Arg
Xaa$_{117}$ is Ser
Xaa$_{118}$ is Ser
Xaa$_{121}$ is Met
Xaa$_{122}$ is Val
Xaa$_{124}$ is Ile
Xaa$_{129}$ is Lys
Xaa$_{147}$ is Lys
Xaa$_{159}$ is Phe
Xaa$_{162}$ is Val
Xaa$_{166}$ is Gly
Xaa$_{170}$ is Gln
Xaa$_{175}$ is Leu
Xaa$_{183}$ is Thr
Xaa$_{187}$ is Ile $Xaa_{191}$ is Met
$Xaa_{209}$ is Phe
$Xaa_{219}$ is Trp
$Xaa_{223}$ is His
$Xaa_{253}$ is Glu
$Xaa_{259}$ is Lys
$Xaa_{263}$ is Val
$Xaa_{264}$ is Asp
$Xaa_{268}$ is Val
$Xaa_{272}$ is Phe
$Xaa_{285}$ is Thr
$Xaa_{294}$ is Ile
$Xaa_{301}$ is Phe
$Xaa_{306}$ is Thr
$Xaa_{311}$ is Val
$Xaa_{312}$ is Ala
$Xaa_{325}$ is Lys
$Xaa_{328}$ is Glu
$Xaa_{334}$ is Val
$Xaa_{342}$ is Arg
$Xaa_{377}$ is Thr
$Xaa_{381}$ is Glu
$Xaa_{385}$ is Tyr
$Xaa_{387}$ is Ile
$Xaa_{393}$ is Ile
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Arg
$Xaa_{429}$ is Pro
$Xaa_{435}$ is Gln
$Xaa_{447}$ is Arg
$Xaa_{453}$ is Asn
$Xaa_{459}$ is Met
$Xaa_{485}$ is Gly.

27. The isolated nucleic acid of claim 1 where
$Xaa_{10}$ is Leu
$Xaa_{16}$ is Leu
$Xaa_{23}$ is Thr
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Tyr
$Xaa_{95}$ is Thr
$Xaa_{96}$ is His
$Xaa_{102}$ is Asn
$Xaa_{110}$ is Ile
$Xaa_{112}$ is Arg
$Xaa_{117}$ is Ser
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Val
$Xaa_{166}$ is Gly
$Xaa_{170}$ is Gln
$Xaa_{175}$ is Leu
$Xaa_{183}$ is Thr
$Xaa_{187}$ is Ile
$Xaa_{191}$ is Met
$Xaa_{209}$ is Phe
$Xaa_{219}$ is Trp
$Xaa_{223}$ is His
$Xaa_{253}$ is Glu
$Xaa_{259}$ is Lys
$Xaa_{263}$ is Val
$Xaa_{264}$ is Val
$Xaa_{268}$ is Val
$Xaa_{272}$ is Phe
$Xaa_{285}$ is Thr
$Xaa_{294}$ is Ile
$Xaa_{301}$ is Phe
$Xaa_{306}$ is Thr
$Xaa_{311}$ is Val
$Xaa_{312}$ is Ala
$Xaa_{325}$ is Lys
$Xaa_{328}$ is Glu
$Xaa_{334}$ is Val
$Xaa_{342}$ is Arg
$Xaa_{377}$ is Thr
$Xaa_{381}$ is Glu
$Xaa_{385}$ is Tyr
$Xaa_{387}$ is Ile
$Xaa_{393}$ is Ile
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Arg
$Xaa_{429}$ is Pro
$Xaa_{435}$ is Gln
$Xaa_{447}$ is Arg
$Xaa_{453}$ is Asn
$Xaa_{459}$ is Met, and
$Xaa_{485}$ is Gly.

28. The isolated nucleic acid of claim 1 where
$Xaa_{10}$ is Phe
$Xaa_{16}$ is Leu
$Xaa_{23}$ is Ser
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Ser
$Xaa_{95}$ is Ala
$Xaa_{96}$ is His
$Xaa_{102}$ is Ser
$Xaa_{110}$ is Val
$Xaa_{112}$ is Arg
$Xaa_{117}$ is Asn
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Glu
$Xaa_{159}$ is Phe
$Xaa_{162}$ is Val
$Xaa_{166}$ is Ser
$Xaa_{170}$ is Gln
$Xaa_{175}$ is Val
$Xaa_{183}$ is Thr
$Xaa_{187}$ is Ile
$Xaa_{191}$ is Met
$Xaa_{209}$ is Phe $Xaa_{219}$ is Trp
$Xaa_{223}$ is Tyr
$Xaa_{253}$ is Glu
$Xaa_{259}$ is Lys
$Xaa_{263}$ is Val
$Xaa_{264}$ is Val
$Xaa_{268}$ is Ala
$Xaa_{272}$ is Phe
$Xaa_{285}$ is Met
$Xaa_{294}$ is Ile
$Xaa_{301}$ is Phe
$Xaa_{306}$ is Thr
$Xaa_{311}$ is Val
$Xaa_{312}$ is Ala
$Xaa_{325}$ is Arg
$Xaa_{328}$ is Gln
$Xaa_{334}$ is Val
$Xaa_{342}$ is Arg
$Xaa_{377}$ is Thr
$Xaa_{381}$ is Glu
$Xaa_{385}$ is Tyr
$Xaa_{387}$ is Ile
$Xaa_{393}$ is Val
$Xaa_{394}$ is Leu
$Xaa_{402}$ is Lys
$Xaa_{404}$ is Pro
$Xaa_{413}$ is Phe
$Xaa_{422}$ is Gly
$Xaa_{428}$ is Gly
$Xaa_{429}$ is Pro
$Xaa_{435}$ is Gln
$Xaa_{447}$ is Arg
$Xaa_{453}$ is Asn
$Xaa_{459}$ is Met, and
$Xaa_{485}$ is Asp.

29. The isolated nucleic acid of claim 1 where
$Xaa_{16}$ is Ser
$Xaa_{23}$ is Ser
$Xaa_{25}$ is Ile
$Xaa_{39}$ is Arg
$Xaa_{48}$ is Leu
$Xaa_{60}$ is Pro
$Xaa_{73}$ is Leu
$Xaa_{74}$ is Ser
$Xaa_{95}$ is Thr
$Xaa_{96}$ is His
$Xaa_{102}$ is Asn
$Xaa_{110}$ is Ile
$Xaa_{112}$ is His
$Xaa_{117}$ is Asn
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Val
$Xaa_{166}$ is Ser
$Xaa_{170}$ is Gln
$Xaa_{175}$ is Val
$Xaa_{183}$ is Thr
$Xaa_{187}$ is Ile
$Xaa_{191}$ is Met
$Xaa_{209}$ is Phe
$Xaa_{219}$ is Trp
$Xaa_{223}$ is Tyr
$Xaa_{253}$ is Glu
$Xaa_{259}$ is Lys
$Xaa_{263}$ is Val
$Xaa_{264}$ is Val
$Xaa_{268}$ is Ala
$Xaa_{272}$ is Phe
$Xaa_{285}$ is Met
$Xaa_{294}$ is Ile
$Xaa_{301}$ is Phe
$Xaa_{306}$ is Thr
$Xaa_{311}$ is Val
$Xaa_{312}$ is Val
$Xaa_{325}$ is Arg
$Xaa_{328}$ is Gln
$Xaa_{334}$ is Val
$Xaa_{342}$ is Arg
$Xaa_{377}$ is Thr
$Xaa_{381}$ is Glu
$Xaa_{385}$ is Tyr
$Xaa_{387}$ is Ile
$Xaa_{393}$ is Val
$Xaa_{394}$ is Leu
$Xaa_{402}$ is Arg
$Xaa_{404}$ is Pro
$Xaa_{413}$ is Ser
$Xaa_{422}$ is Gly
$Xaa_{428}$ is Gly
$Xaa_{429}$ is Pro
$Xaa_{435}$ is Gln
$Xaa_{447}$ is Arg
$Xaa_{453}$ is Ser
$Xaa_{459}$ is Met, and
$Xaa_{485}$ is Asp.

30. The isolated nucleic acid of claim 1 where
$Xaa_{16}$ is Leu
$Xaa_{23}$ is Thr
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Tyr
$Xaa_{95}$ is Thr
$Xaa_{96}$ is His
$Xaa_{102}$ is Asn
$Xaa_{110}$ is Ile
$Xaa_{112}$ is Arg
$Xaa_{117}$ is Ser
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Val
$Xaa_{166}$ is Ser
$Xaa_{170}$ is Gln
$Xaa_{175}$ is Val
$Xaa_{183}$ is Thr
$Xaa_{187}$ is Ile
$Xaa_{191}$ is Met
$Xaa_{209}$ is Phe
$Xaa_{219}$ is Trp
$Xaa_{223}$ is Tyr
$Xaa_{253}$ is Glu
$Xaa_{259}$ is Lys $Xaa_{263}$ is Val
$Xaa_{264}$ is Val
$Xaa_{268}$ is Ala
$Xaa_{272}$ is Phe
$Xaa_{285}$ is Met
$Xaa_{294}$ is Ile
$Xaa_{301}$ is Phe
$Xaa_{306}$ is Thr
$Xaa_{311}$ is Val
$Xaa_{312}$ is Val
$Xaa_{325}$ is Lys
$Xaa_{328}$ is Gln
$Xaa_{334}$ is Ala
$Xaa_{342}$ is Arg
$Xaa_{377}$ is Thr
$Xaa_{381}$ is Gly
$Xaa_{385}$ is Tyr
$Xaa_{387}$ is Ile
$Xaa_{393}$ is Val
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Gly
$Xaa_{429}$ is Pro
$Xaa_{435}$ is Gin
$Xaa_{447}$ is Arg
$Xaa_{453}$ is Asn
$Xaa_{459}$ is Met, and
$Xaa_{485}$ is Asp.

31. The isolated nucleic acid of claim 1 where
$Xaa_{16}$ is Leu
$Xaa_{23}$ is Thr
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Tyr
$Xaa_{95}$ is Thr
$Xaa_{96}$ is His
$Xaa_{102}$ is Asn
$Xaa_{110}$ is Ile
$Xaa_{112}$ is Arg
$Xaa_{117}$ is Ser
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Val
$Xaa_{166}$ is Gly
$Xaa_{170}$ is Gln
$Xaa_{175}$ is Leu
$Xaa_{183}$ is Thr
$Xaa_{187}$ is Ile
$Xaa_{191}$ is Met
$Xaa_{209}$ is Phe
$Xaa_{219}$ is Trp
$Xaa_{223}$ is His
$Xaa_{253}$ is Glu
$Xaa_{259}$ is Lys
$Xaa_{263}$ is Asp
$Xaa_{264}$ is Val
$Xaa_{268}$ is Val
$Xaa_{272}$ is Phe
$Xaa_{285}$ is Met
$Xaa_{294}$ is Ile
$Xaa_{301}$ is Phe
$Xaa_{306}$ is Thr
$Xaa_{311}$ is Val
$Xaa_{312}$ is Ala
$Xaa_{325}$ is Lys
$Xaa_{328}$ is Glu
$Xaa_{334}$ is Val
$Xaa_{342}$ is Arg
$Xaa_{377}$ is Ile
$Xaa_{381}$ is Glu
$Xaa_{385}$ is Tyr
$Xaa_{387}$ is Ile
$Xaa_{393}$ is Ile
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Arg
$Xaa_{429}$ is Leu
$Xaa_{435}$ is Gln
$Xaa_{447}$ is Arg
$Xaa_{453}$ is Asn
$Xaa_{459}$ is Met, and
$Xaa_{485}$ is Gly.

32. The isolated nucleic acid of claim 1 where
$Xaa_{10}$ is Phe or Leu
$Xaa_{16}$ is Leu
$Xaa_{23}$ is Thr
$Xaa_{25}$ is Lys
$Xaa_{39}$ is Lys
$Xaa_{48}$ is Leu
$Xaa_{60}$ is Leu
$Xaa_{73}$ is Leu
$Xaa_{74}$ is Tyr
$Xaa_{95}$ is Thr
$Xaa_{96}$ is His
$Xaa_{102}$ is Asn
$Xaa_{110}$ is Ile
$Xaa_{112}$ is Arg
$Xaa_{117}$ is Ser
$Xaa_{118}$ is Ser
$Xaa_{121}$ is Arg
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Val
$Xaa_{166}$ is Gly
$Xaa_{170}$ is Gln
$Xaa_{175}$ is Leu
$Xaa_{183}$ is Thr
$Xaa_{187}$ is Ile
$Xaa_{191}$ is Met
$Xaa_{209}$ is Phe
$Xaa_{219}$ is Trp
$Xaa_{223}$ is His
$Xaa_{253}$ is Glu
$Xaa_{259}$ is Lys
$Xaa_{263}$ is Val
$Xaa_{264}$ is Val
$Xaa_{268}$ is Val Xaa₂₇₂ is Leu
Xaa₂₈₅ is Met
Xaa₂₉₄ is Ile
Xaa₃₀₁ is Phe
Xaa₃₀₆ is Thr
Xaa₃₁₁ is Val
Xaa₃₁₂ is Ala
Xaa₃₂₅ is Lys
Xaa₃₂₈ is Glu
Xaa₃₃₄ is Val
Xaa₃₄₂ is Arg
Xaa₃₇₇ is Thr
Xaa₃₈₁ is Glu
Xaa₃₈₅ is Tyr
Xaa₃₈₇ is Ile
Xaa₃₉₃ is Ile
Xaa₃₉₄ is Leu
Xaa₄₀₂ is Arg
Xaa₄₀₄ is Pro
Xaa₄₁₃ is Phe
Xaa₄₂₂ is Glu
Xaa₄₂₈ is Arg
Xaa₄₂₉ is Pro
Xaa₄₃₅ is Gln
Xaa₄₄₇ is Arg
Xaa₄₅₃ is Ile
Xaa₄₅₉ is Met, and
Xaa₄₈₅ is Gly.

33. The isolated nucleic acid of claim 1 where
Xaa₁₆ is Leu
Xaa₂₃ is Thr
Xaa₂₅ is Lys
Xaa₃₉ is Lys
Xaa₄₈ is Leu
Xaa₆₀ is Leu
Xaa₇₃ is Leu
Xaa₇₄ is Tyr
Xaa₉₅ is Thr
Xaa₉₆ is His
Xaa₁₀₂ is Asn
Xaa₁₁₀ is Ile
Xaa₁₁₂ is Arg
Xaa₁₁₇ is Ser
Xaa₁₁₈ is Ser
Xaa₁₂₁ is Met
Xaa₁₂₂ is Ala
Xaa₁₂₄ is Phe
Xaa₁₂₉ is Lys
Xaa₁₄₇ is Lys
Xaa₁₅₉ is Phe
Xaa₁₆₂ is Val
Xaa₁₆₆ is Gly
Xaa₁₇₀ is Gln
Xaa₁₇₅ is Leu
Xaa₁₈₃ is Thr
Xaa₁₈₇ is Thr
Xaa₁₉₁ is Met
Xaa₂₀₉ is Phe
Xaa₂₁₉ is Arg
Xaa₂₂₃ is His
Xaa₂₅₃ is Glu
Xaa₂₅₉ is Lys
Xaa₂₆₃ is Val
Xaa₂₆₄ is Val
Xaa₂₆₈ is Phe
Xaa₂₇₂ is Thr
Xaa₂₈₅ is Thr Xaa₂₉₄ is Ile
Xaa₃₀₁ is Phe
Xaa₃₀₆ is Thr
Xaa₃₁₁ is Val
Xaa₃₁₂ is Ala
Xaa₃₂₅ is Lys
Xaa₃₂₈ is Glu
Xaa₃₃₄ is Val
Xaa₃₄₂ is Arg
Xaa₃₇₇ is Thr
Xaa₃₈₁ is Glu
Xaa₃₈₅ is Tyr
Xaa₃₈₇ is Ile
Xaa₃₉₃ is Ile
Xaa₃₉₄ is Leu
Xaa₄₀₂ is Arg
Xaa₄₀₄ is Ser
Xaa₄₁₃ is Phe
Xaa₄₂₂ is Gly
Xaa₄₂₈ is Arg
Xaa₄₂₉ is Pro
Xaa₄₃₅ is Gln
Xaa₄₄₇ is Arg
Xaa₄₅₃ is Asn
Xaa₄₅₉ is Met, and
Xaa₄₈₅ is Gly.

34. The isolated nucleic acid of claim 1 where
Xaa₁₆ is Leu
Xaa₂₃ is Thr
Xaa₂₅ is Lys
Xaa₃₉ is Lys
Xaa₄₈ is Leu
Xaa₆₀ is Leu
Xaa₇₃ is Leu
Xaa₇₄ is Tyr
Xaa₉₅ is Thr
Xaa₉₆ is His
Xaa₁₀₂ is Asn
Xaa₁₁₀ is Ile
Xaa₁₁₂ is Arg
Xaa₁₁₇ is Ser
Xaa₁₁₈ is Ser
Xaa₁₂₁ is Met
Xaa₁₂₂ is Val
Xaa₁₂₄ is Phe
Xaa₁₂₉ is Lys
Xaa₁₄₇ is Lys
Xaa₁₅₉ is Leu
Xaa₁₆₂ is Val
Xaa₁₆₆ is Gly
Xaa₁₇₀ is Gln
Xaa₁₇₅ is Leu
Xaa₁₈₃ is Thr
Xaa₁₈₇ is Ile
Xaa₁₉₁ is Met
Xaa₂₀₉ is Phe
Xaa₂₁₉ is Trp
Xaa₂₂₃ is His
Xaa₂₅₃ is Glu
Xaa₂₅₉ is Lys
Xaa₂₆₃ is Val
Xaa₂₆₄ is Ile
Xaa₂₆₈ is Val
Xaa₂₇₂ is Phe
Xaa₂₈₅ is Thr
Xaa₂₉₄ is Ile
Xaa₃₀₁ is Phe $Xaa_{306}$ is Thr
$Xaa_{311}$ is Val
$Xaa_{312}$ is Ala
$Xaa_{325}$ is Lys
$Xaa_{328}$ is Glu
$Xaa_{334}$ is Val
$Xaa_{342}$ is Arg
$Xaa_{377}$ is Thr
$Xaa_{381}$ is Glu
$Xaa_{385}$ is Tyr
$Xaa_{387}$ is Ile
$Xaa_{393}$ is Ile
$Xaa_{394}$ is Leu
$Xaa_{402}$ is Arg
$Xaa_{404}$ is Pro
$Xaa_{413}$ is Phe
$Xaa_{422}$ is Gly
$Xaa_{428}$ is Arg
$Xaa_{429}$ is Pro
$Xaa_{435}$ is Gln
$Xaa_{447}$ is Arg
$Xaa_{453}$ is Asn
$Xaa_{459}$ is Met, and
$Xaa_{485}$ is Gly.

35. The isolated nucleic acid of claim 1 where
$Xaa_{16}$ is Leu
$Xaa_{23}$ is Thr
$Xaa_{25}$ is Lys
$Xaa_{39}$ is Lys
$Xaa_{48}$ is Leu
$Xaa_{60}$ is Leu
$Xaa_{73}$ is His
$Xaa_{74}$ is Tyr
$Xaa_{95}$ is Thr
$Xaa_{96}$ is Asn
$Xaa_{102}$ is Asn
$Xaa_{110}$ is Ile
$Xaa_{112}$ is Arg
$Xaa_{117}$ is Ser
$Xaa_{118}$ is Ser
$Xaa_{121}$ is Met
$Xaa_{122}$ is Val
$Xaa_{124}$ is Phe
$Xaa_{129}$ is Lys
$Xaa_{147}$ is Lys
$Xaa_{159}$ is Phe
$Xaa_{162}$ is Ala
$Xaa_{166}$ is Gly
$Xaa_{170}$ is Arg
$Xaa_{175}$ is Leu
$Xaa_{183}$ is Ala
$Xaa_{187}$ is Ile
$Xaa_{191}$ is Met
$Xaa_{209}$ is Phe
$Xaa_{219}$ is Trp
$Xaa_{223}$ is His
$Xaa_{253}$ is Glu
$Xaa_{259}$ is Lys
$Xaa_{263}$ is Val
$Xaa_{264}$ is Val
$Xaa_{268}$ is Val
$Xaa_{272}$ is Phe
$Xaa_{285}$ is Met
$Xaa_{294}$ is Thr
$Xaa_{301}$ is Phe
$Xaa_{306}$ is Thr
$Xaa_{311}$ is Val
$Xaa_{312}$ is Ala
$Xaa_{325}$ is Lys
$Xaa_{328}$ is Glu
$Xaa_{334}$ is Val
$Xaa_{342}$ is Arg
$Xaa_{377}$ is Thr
$Xaa_{381}$ is Glu
$Xaa_{385}$ is Tyr
$Xaa_{387}$ is Ile
$Xaa_{393}$ is Ile
$Xaa_{394}$ is Pro
$Xaa_{402}$ is Arg
$Xaa_{404}$ is Pro
$Xaa_{413}$ is Phe
$Xaa_{422}$ is Gly
$Xaa_{428}$ is Arg
$Xaa_{429}$ is Pro
$Xaa_{435}$ is Gln
$Xaa_{447}$ is Arg
$Xaa_{453}$ is Asn
$Xaa_{459}$ is Thr, and
$Xaa_{485}$ is Gly.

* * * * *